United States Patent
Boer et al.

(10) Patent No.: US 10,947,515 B2
(45) Date of Patent: *Mar. 16, 2021

(54) UDP-GLYCOSYLTRANSFERASES

(71) Applicant: DSM IP ASSETS B.V., Heerlen (NL)

(72) Inventors: Viktor Marius Boer, Echt (NL);
Johannes Gustaaf Ernst Van Leeuwen, Echt (NL); Priscilla Zwartjens, Echt (NL); Catharina Petronella Antonia Maria Kolen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/777,427

(22) Filed: Jan. 30, 2020

(65) Prior Publication Data

US 2020/0224180 A1 Jul. 16, 2020

Related U.S. Application Data

(62) Division of application No. 15/558,133, filed as application No. PCT/EP2016/055734 on Mar. 16, 2016, now Pat. No. 10,604,743.

(Continued)

(51) Int. Cl.
*C12N 1/14* (2006.01)
*C12N 1/16* (2006.01)
(Continued)

(52) U.S. Cl.
CPC ............ *C12N 9/1048* (2013.01); *A23L 2/60* (2013.01); *A23L 27/36* (2016.08); *C12N 1/14* (2013.01);
(Continued)

(58) Field of Classification Search
None
See application file for complete search history.

(56) References Cited

U.S. PATENT DOCUMENTS

| 4,590,160 A | 5/1986 | Nishihashi et al. |
| 5,204,253 A | 4/1993 | Sanford et al. |
| (Continued) | | |

FOREIGN PATENT DOCUMENTS

| CN | 101720910 A | 6/2010 |
| CN | 102216313 A | 10/2011 |
| (Continued) | | |

OTHER PUBLICATIONS

Csernetics et al. "Expression of three isoprenoid biosynthesis genes and their effects on the carotenoid production of the zygomycete Mucor circinelloides", Fungal Genetics and Biology, No. 24 (2011) pp. 696-703.

(Continued)

*Primary Examiner* — Richard C Ekstrom
(74) *Attorney, Agent, or Firm* — McBee Moore & Vanik IP, LLC

(57) ABSTRACT

The present invention relates to a recombinant host comprising a recombinant nucleic acid sequence encoding a polypeptide having at least about: a. 85% identity to the amino acid sequence set forth in SEQ ID NO: 1; b. 85% identity to the amino acid sequence set forth in SEQ ID NO: 3; c. 85% identity to the amino acid sequence set forth in SEQ ID NO: 6; d. 85% identity to the amino acid sequence set forth in SEQ ID NO: 9; e. 85% identity to the amino acid sequence set forth in SEQ ID NO: 11; f. 85% identity to the amino acid sequence set forth in SEQ ID NO: 14; g. 85% identity to the amino acid sequence set forth in SEQ ID NO: 17; h. 85% identity to the amino acid sequence set forth in SEQ ID NO: 20; i. 85% identity to the amino acid sequence (Continued)

set forth in SEQ ID NO: 22; or j. 85% identity to the amino acid sequence set forth in SEQ ID NO: 25.

19 Claims, 32 Drawing Sheets

Specification includes a Sequence Listing.

Related U.S. Application Data

(60) Provisional application No. 62/133,606, filed on Mar. 16, 2015.

(51) Int. Cl.
*C12P 5/00* (2006.01)
*C12P 19/56* (2006.01)
*C12N 9/10* (2006.01)
*A23L 27/30* (2016.01)
*A23L 2/60* (2006.01)
*C12N 1/20* (2006.01)

(52) U.S. Cl.
CPC ............. *C12N 1/16* (2013.01); *C12N 1/20* (2013.01); *C12N 9/1051* (2013.01); *C12P 5/007* (2013.01); *C12P 19/56* (2013.01); *C12Y 204/01017* (2013.01)

(56) References Cited

U.S. PATENT DOCUMENTS

| | | |
|---|---|---|
| 5,306,862 A | 4/1994 | Chappell et al. |
| 5,460,949 A | 10/1995 | Saunders et al. |
| 5,538,880 A | 7/1996 | Lundquist et al. |
| 5,876,988 A | 3/1999 | Selten et al. |
| 6,013,863 A | 1/2000 | Lundquist et al. |
| 6,215,051 B1 | 4/2001 | Yu et al. |
| 6,255,557 B1 | 7/2001 | Brandle |
| 6,284,493 B1 | 9/2001 | Roth |
| 6,284,506 B1 | 9/2001 | Hoshino et al. |
| 6,329,571 B1 | 12/2001 | Hiei |
| 6,432,672 B1 | 8/2002 | Selten et al. |
| 6,586,202 B2 | 6/2003 | Hoshino et al. |
| 6,660,507 B2 | 12/2003 | Cheng et al. |
| 6,806,076 B1 | 10/2004 | Miyake et al. |
| 6,969,595 B2 | 11/2005 | Brzostowicz et al. |
| 7,034,140 B2 | 4/2006 | Bramucci et al. |
| 7,056,717 B2 | 6/2006 | Cheng et al. |
| 7,098,000 B2 | 8/2006 | Cheng et al. |
| 7,129,392 B2 | 10/2006 | Hahn et al. |
| 7,132,268 B2 | 11/2006 | Miyake et al. |
| 7,172,886 B2 | 2/2007 | Keasling et al. |
| 7,183,089 B2 | 2/2007 | Keasling et al. |
| 7,186,891 B1 | 3/2007 | Chappell et al. |
| 7,208,298 B2 | 4/2007 | Miyake et al. |
| 7,335,815 B2 | 2/2008 | Boronat et al. |
| 7,364,885 B2 | 4/2008 | Miyake et al. |
| 7,422,884 B2 | 9/2008 | Bai et al. |
| 7,514,597 B2 | 4/2009 | Nakamura et al. |
| 7,569,389 B2 | 8/2009 | Feldmann et al. |
| 7,622,284 B2 | 11/2009 | Op et al. |
| 7,692,065 B2 | 4/2010 | Harper et al. |
| 7,838,287 B2 | 11/2010 | Goldsmith et al. |
| 7,923,541 B2 | 4/2011 | Yang et al. |
| 7,927,851 B2 | 4/2011 | Brandle et al. |
| 7,943,366 B2 | 5/2011 | Rajgarhia et al. |
| 7,981,647 B2 | 7/2011 | Berry et al. |
| 8,034,591 B2 | 10/2011 | Winkler et al. |
| 8,129,171 B2 | 3/2012 | Boles et al. |
| 9,562,251 B2 | 2/2017 | Hansen et al. |
| 9,738,890 B2 | 8/2017 | Roubos et al. |
| 10,604,743 B2 * | 3/2020 | Boer .............. C12N 1/16 |
| 2002/0142408 A1 | 10/2002 | Dicosimo et al. |
| 2003/0033626 A1 | 2/2003 | Hahn et al. |
| 2003/0148416 A1 | 8/2003 | Berry et al. |
| 2003/0148479 A1 | 8/2003 | Keasling et al. |
| 2003/0190734 A1 | 10/2003 | Hoshino et al. |
| 2003/0219798 A1 | 11/2003 | Gokarn et al. |
| 2004/0010815 A1 | 1/2004 | Lange et al. |
| 2004/0072311 A1 | 4/2004 | Dicosimo et al. |
| 2004/0078846 A1 | 4/2004 | Desouza et al. |
| 2004/0176570 A1 | 9/2004 | Bacher et al. |
| 2004/0194162 A1 | 9/2004 | Hahn et al. |
| 2005/0003474 A1 | 1/2005 | Desouza et al. |
| 2005/0032169 A1 | 2/2005 | Miyake et al. |
| 2005/0142648 A1 | 6/2005 | Boles et al. |
| 2006/0014264 A1 | 1/2006 | Sauer et al. |
| 2006/0079476 A1 | 4/2006 | Keasling et al. |
| 2006/0083838 A1 | 4/2006 | Jackson et al. |
| 2006/0127972 A1 | 6/2006 | Nieboer et al. |
| 2007/0004000 A1 | 1/2007 | Miyake et al. |
| 2007/0077616 A1 | 4/2007 | Keasling et al. |
| 2007/0099261 A1 | 5/2007 | Keasling et al. |
| 2007/0118916 A1 | 5/2007 | Puzio et al. |
| 2007/0128311 A1 | 6/2007 | Prakash et al. |
| 2007/0166782 A1 | 7/2007 | Keasling et al. |
| 2007/0202579 A1 | 8/2007 | Berry et al. |
| 2007/0238157 A1 | 10/2007 | Millis et al. |
| 2007/0238159 A1 | 10/2007 | Millis et al. |
| 2007/0238160 A1 | 10/2007 | Millis et al. |
| 2007/0254354 A1 | 10/2007 | Millis et al. |
| 2007/0269857 A1 | 11/2007 | Miyake et al. |
| 2007/0286850 A1 | 12/2007 | Bai et al. |
| 2008/0064063 A1 | 3/2008 | Brandle et al. |
| 2008/0081358 A1 | 4/2008 | Viitanen et al. |
| 2008/0131926 A1 | 6/2008 | Miyake et al. |
| 2008/0261280 A1 | 10/2008 | Hahn et al. |
| 2008/0271205 A1 | 10/2008 | Yamaguchi et al. |
| 2008/0286870 A1 | 11/2008 | Viitanen et al. |
| 2008/0292775 A1 | 11/2008 | Prakash et al. |
| 2008/0318227 A1 | 12/2008 | Bacher et al. |
| 2009/0004724 A1 | 1/2009 | Keasling et al. |
| 2009/0047718 A1 | 2/2009 | Blaschek et al. |
| 2009/0055974 A1 | 2/2009 | Tanksley et al. |
| 2009/0074935 A1 | 3/2009 | Lee |
| 2009/0143308 A1 | 6/2009 | Monk et al. |
| 2009/0286262 A1 | 11/2009 | Slack |
| 2010/0112156 A1 | 5/2010 | Abelyan et al. |
| 2010/0120096 A1 | 5/2010 | Kitaoka et al. |
| 2010/0221801 A1 | 9/2010 | Van Dyk |
| 2010/0297722 A1 | 11/2010 | Anterola et al. |
| 2010/0316782 A1 | 12/2010 | Shi et al. |
| 2011/0087011 A1 | 4/2011 | Chiang et al. |
| 2011/0092684 A1 | 4/2011 | Abelyan et al. |
| 2011/0126318 A1 | 5/2011 | Allen et al. |
| 2011/0160311 A1 | 6/2011 | Prakash et al. |
| 2012/0021111 A1 | 1/2012 | Pfister et al. |
| 2012/0083593 A1 | 4/2012 | Liu et al. |
| 2012/0164678 A1 | 6/2012 | Stephanopoulos et al. |
| 2012/0178169 A1 | 7/2012 | Voytas et al. |
| 2013/0076280 A1 | 3/2013 | Yoo |
| 2013/0137138 A1 | 5/2013 | Hansen |
| 2014/0303036 A1 | 10/2014 | Roubos et al. |
| 2014/0329281 A1 | 11/2014 | Houghton-Larsen et al. |
| 2014/0357588 A1 | 12/2014 | Markosyan et al. |
| 2015/0031868 A1 | 1/2015 | Lehmann et al. |
| 2015/0037892 A1 | 2/2015 | Wiessenhaan et al. |
| 2015/0128306 A1 | 5/2015 | Ono |
| 2015/0159188 A1 | 6/2015 | Ono et al. |
| 2015/0218533 A1 | 8/2015 | Ono |
| 2015/0252401 A1 | 9/2015 | Wang et al. |
| 2015/0342234 A1 | 12/2015 | Hicks et al. |
| 2016/0010133 A1 | 1/2016 | Park et al. |
| 2016/0102331 A1 | 4/2016 | Boer et al. |
| 2016/0153017 A1 | 6/2016 | Van Der Hoeven et al. |
| 2016/0177360 A1 | 6/2016 | Boer et al. |
| 2016/0186225 A1 | 6/2016 | Mikkelsen et al. |
| 2016/0213039 A1 | 7/2016 | Kumar et al. |
| 2016/0251635 A1 | 9/2016 | Mao et al. |
| 2017/0218419 A1 | 8/2017 | Kishore et al. |
| 2017/0275666 A1 | 9/2017 | Prakash et al. |
| 2017/0314011 A1 | 11/2017 | Roubos et al. |

(56) References Cited

U.S. PATENT DOCUMENTS

| | | | |
|---|---|---|---|
| 2017/0332673 A1 | 11/2017 | Philippe et al. | |
| 2018/0073050 A1 | 3/2018 | Boer et al. | |

FOREIGN PATENT DOCUMENTS

| | | | |
|---|---|---|---|
| CN | 103179850 A | 6/2013 | |
| CN | 103397064 A | 11/2013 | |
| CN | 103732753 A | 4/2014 | |
| CN | 104845990 A | 8/2015 | |
| EP | 0955363 A2 | 11/1999 | |
| EP | 1072683 A1 | 1/2001 | |
| EP | 1171610 A1 | 1/2002 | |
| EP | 1198575 A1 | 4/2002 | |
| EP | 1383864 A1 | 1/2004 | |
| EP | 1392824 A2 | 3/2004 | |
| EP | 1499708 B1 | 1/2006 | |
| EP | 1897951 A2 | 3/2008 | |
| EP | 1947189 A2 | 7/2008 | |
| EP | 2575432 A1 | 4/2013 | |
| EP | 2902410 A1 | 8/2015 | |
| JP | 58-149697 A | 9/1983 | |
| JP | 03-277275 A | 12/1991 | |
| JP | 05-115298 A | 5/1993 | |
| JP | 10-001408 A | 1/1998 | |
| JP | 2009-034080 A | 2/2009 | |
| KR | 2015-0000258 A | 1/2015 | |
| WO | 00/36081 A2 | 6/2000 | |
| WO | 00/37663 A2 | 6/2000 | |
| WO | 00/37671 A2 | 6/2000 | |
| WO | 00/63389 A1 | 10/2000 | |
| WO | 00/63400 A2 | 10/2000 | |
| WO | 01/11055 A1 | 2/2001 | |
| WO | 01/12828 A1 | 2/2001 | |
| WO | 01/83769 A2 | 11/2001 | |
| WO | 01/94561 A2 | 12/2001 | |
| WO | 02/20728 A2 | 3/2002 | |
| WO | 02/20815 A2 | 3/2002 | |
| WO | 02/24865 A2 | 3/2002 | |
| WO | 02/26933 A2 | 4/2002 | |
| WO | 02/55709 A2 | 7/2002 | |
| WO | 02/99095 A2 | 12/2002 | |
| WO | 03/08540 A2 | 1/2003 | |
| WO | 03/062430 A1 | 7/2003 | |
| WO | 2004/029255 A2 | 4/2004 | |
| WO | 2004/099381 A2 | 11/2004 | |
| WO | 2005/079183 A2 | 8/2005 | |
| WO | 2006/009434 A1 | 1/2006 | |
| WO | 2006/016395 A1 | 2/2006 | |
| WO | 2006/093289 A1 | 9/2006 | |
| WO | 2006/096392 A2 | 9/2006 | |
| WO | 2006096130 A1 | 9/2006 | |
| WO | 2007/136847 A2 | 11/2007 | |
| WO | 2008/008256 A2 | 1/2008 | |
| WO | 2008/034648 A1 | 3/2008 | |
| WO | 2008/039499 A2 | 4/2008 | |
| WO | 2008/051349 A2 | 5/2008 | |
| WO | 2008/091547 A2 | 7/2008 | |
| WO | 2009/005704 A1 | 1/2009 | |
| WO | 2009/071277 A1 | 6/2009 | |
| WO | 2009/086049 A2 | 7/2009 | |
| WO | 2009/105612 A2 | 8/2009 | |
| WO | 2009/108680 A2 | 9/2009 | |
| WO | 2009/111513 A1 | 9/2009 | |
| WO | 2009/140394 A1 | 11/2009 | |
| WO | 2010/021001 A2 | 2/2010 | |
| WO | 2010/038911 A1 | 4/2010 | |
| WO | 2010/044960 A1 | 4/2010 | |
| WO | 2010/142305 A1 | 12/2010 | |
| WO | 2010/146463 A2 | 12/2010 | |
| WO | 2011/028671 A1 | 3/2011 | |
| WO | 2011/037959 A1 | 3/2011 | |
| WO | 2011/046423 A1 | 4/2011 | |
| WO | 2011/056834 A | 5/2011 | |
| WO | 2011/060057 A1 | 5/2011 | |
| WO | 2011/140329 A1 | 11/2011 | |
| WO | 2011/151326 A2 | 12/2011 | |
| WO | 2011/153144 A1 | 12/2011 | |
| WO | 2011/153378 A1 | 12/2011 | |
| WO | 2012/075030 A1 | 6/2012 | |
| WO | 2013/007657 A1 | 1/2013 | |
| WO | 2013/019050 A2 | 2/2013 | |
| WO | 2013/021261 A2 | 2/2013 | |
| WO | 2013/022989 A2 | 2/2013 | |
| WO | 2013/076280 A1 | 5/2013 | |
| WO | 2013/076577 A1 | 5/2013 | |
| WO | 2013/096420 A1 | 6/2013 | |
| WO | 2013/102793 A2 | 7/2013 | |
| WO | 2013/110673 A1 | 8/2013 | |
| WO | 2013/135728 A1 | 9/2013 | |
| WO | 2013/144257 A1 | 10/2013 | |
| WO | 2013/176738 A1 | 11/2013 | |
| WO | 2014/086890 A1 | 6/2014 | |
| WO | 2014/122227 A2 | 8/2014 | |
| WO | 2014/122328 A1 | 8/2014 | |
| WO | 2014/191580 A1 | 12/2014 | |
| WO | 2014/193934 A1 | 12/2014 | |
| WO | 2014/195944 A1 | 12/2014 | |
| WO | 2014191581 A2 | 12/2014 | |
| WO | 2015/007748 A1 | 1/2015 | |
| WO | 2015/011209 A1 | 1/2015 | |
| WO | 2015/014959 A1 | 2/2015 | |
| WO | 2015/014969 A1 | 2/2015 | |
| WO | 2015/016393 A1 | 2/2015 | |
| WO | 2015/028324 A2 | 3/2015 | |
| WO | 2015/051454 A1 | 4/2015 | |
| WO | 2015/132411 A2 | 9/2015 | |
| WO | 2016/023844 A1 | 2/2016 | |
| WO | 2016/038095 A2 | 3/2016 | |
| WO | 2016/120486 | 8/2016 | |
| WO | 2017/025362 A1 | 2/2017 | |

OTHER PUBLICATIONS

Velayos et al. "Expression of the care gene, encoding geranylgeranyl pyrophosphate synthase, is up-regulated by blue light in Mucor circinelloides", Curr Genet (2003) vol. 43, pp. 112-120.

Database Geneseq [Online] (Mar. 12, 2015), "S. Rebaudiana Derived Polypeptide (UGT2 4) Seq:106.", XP-002760405, retrieved from EBI accession No. GSP:BBU04074, Database accession No. BBU04074 L: Sequence information for W02015007743; sequence.

Database Geneseq [Online] (Sep. 12, 2013), "Stevia Rebaudiana UGT2 gene, Seq: 87.", XP002757289, retrieved from EBI accession No. GSN:BAR69149 Database accession No. BAR69149, L: Sequence Information for W02013/110673; sequence.

Database Geneseq [Online] (Sep. 12, 2013), "Stevia Rebaudiana UGT2 protein, Seq: 88.", XP002757288, retrieved from EBI accession No. GSP:BAR69150, Database accession No. BAR69150 L: Sequence Information for W02013/110673; sequence.

Database Geneseq [Online] (Apr. 11, 2013), "Stevia rebaudiana UGT 91d2e polypeptide, Seq ID:5.", XP002757294, retrieved from EBI accession No. GSP:BAK52046, Database accession No. BAK52046 L: Sequence information for W02013/022989; sequence.

Database Geneseq [Online] (Jan. 29, 2015-01-29), "Stevia rebaudiana UDP-glycosyltransferase (UGT) protein (UGT2 la) Seq 88.", XP002757290, retrieved from EBI accession No. GSP:BBQ97923 Database accession No. BBQ97923 L: Sequence Information for W02014/191580; sequence.

Database Geneseq [Online] (Jan. 29, 2015), "S. rebaudiana UDP-glycosyltransferase (UGT) protein (UGT2 lb), Seq 100.", XP002757291, retrieved from EBI accession No. GSP:BBQ97935, Database accession No. BBQ97935 L: Sequence Information for W02014/191580; sequence.

Database Geneseq [Online] (Jan. 29, 2015), "Stevia rebaudiana UGT2 protein, Seq: 88.", XP002757293, retrieved from EBI accession No. GSRBBR03844 Database accession No. BBR03844 L: Sequence Information for W02014/191581; sequence.

Database Geneseq [Online] (Mar. 26, 2015), "Stevia rebaudiana UDP-glycosyltransferase (UGT) protein, Seq ID 100.", XP002757292, retrieved from EBI accession No. GSP:BBU39053 Database accession No. BBU39053 L: Sequence information for W02015/014969; sequence.

(56) References Cited

OTHER PUBLICATIONS

Praveen Guleria et al: "Insights into Steviol Glycoside Biosynthesis Pathway Enzymes Through Structural Homology Modeling", American Journal of Biochemistry and Molecular Biology, vol. 3, No. 1, (Oct. 4, 2012), pp. 1-19, XF055270235.
Praveen Guleria et al: "Agrobacterium Mediated Transient Gene Silencing (AMTS) in Stevia rebaudiana: insights into Steviol Glycoside Biosynthesis Pathway", Flos One, vol. 8, No. 9, (Sep. 4, 2013), p. e74731, XP055269932.
Gueldener, Ulrich et al., "A new efficient gene disruption cassette for repeated use in budding yeast", Nucleic Acids Research, 1996, pp. 2519-2524, vol. 24, No. 13.
Lambert, Jolanda M. et al., "Cre-lox-Based System for Multiple Gene Deletions and Selectable-Marker Removal in Lactobacillus plantarum", Applied and Environmental Microbiology, Feb. 2007, pp. 1126-1135, vol. 73, No. 4.
GenBank Accession No. NM_116512, dated Jan. 22, 2014 (3 pages).
GenBank Accession No. NP_001105097, dated Aug. 4, 2015 (2 pages).
GenBank Accession No. NP_013636.1 (YML075C), dated Jul. 16, 2015 (3 pages).
GenBank Accession No. NP_194183, dated Jan. 22, 2014 (4 pages).
GenBank Accession No. NP_195399, dated Jan. 22, 2014 (3 pages).
GenBank Accession No. NP_197872.1, dated Jan. 22, 2014 (2 pages).
GenBank Accession No. Q9UVY5.1, dated Apr. 1, 2015 (3 pages).
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
Geuns Jan M.C., "Stevioside," Phytochemistry 64(5):913-21 (2003).
Giaever et al., "The yeast deletion collection: a decade of functional genomics," Genetics 197(2):451-65 (Jun. 2014).
Gietz et al., "High-efficiency yeast transformation using the LiAc/ SS carrier DNA/PEG method," Nat Protoc. 2(1):31-4 (2007).
Girvan et al., "Flavocytochrome P450 BM3 mutant W1046A is a NADH-dependent fatty acid hydroxylase: implications for the mechanism of electron transfer in the P450 BM3 dimer," Arch Biochem Biophys. 507(1):75-85 (Mar. 2011).
Gloster, Tracey M. "Advances in understanding glycosyltransferases from a structural perspective," Curr Opin Struct Biol. 28:131-41 (2014).
Goralczyk, "Compounds from Stevia for Improving and Maintaining Mental Performance," Stevia World Forum, Feb. 24-25, 2010, 17 pages.
Gossen et al., "Studying gene function in eukaryotes by conditional gene inactivation," Ann Rev Genet. 36:153-73 (2002).
Gritz et al., "Plasmid-encoded hygromycin B resistance: the sequence of hygromycin B phosphotransferase gene and its expression in *Escherichia coli* and *Saccharomyces cerevisiae*," Gene 25(2-3):179-88 (Nov. 1983).
Gunel et al., "Metabolic Engineering for Production of Geranylgeranyl Pyrophosphate Synthase in Non-Carotenogenic Yeast Schizosaccharomyces Pombe," Biotechnol. & Biotechnol. Eq. 20(3):76-82 (2006).
Guo et al., "Protein tolerance to random amino acid change", Proceedings of the National Academy of Sciences USA, vol. 101, No. 25, pp. 9205-9210 (2004).
Hallstrom et al., "Divergent transcriptional control of multidrug resistance genes in *Saccharomyces cerevisiae*," J. Biol. Chem. 273(4):2098-104 (Jan. 1998).

Hansen et al., "De novo biosynthesis of vanillin in fission yeast (*Schizosaccharomyces pombe*) and baker's yeast (*Saccharomyces cerevisiae*)," Appl Environ Microbiol. 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).
Hellfritsch et al., "Human psychometric and taste receptor responses to steviol glycosides," J. Agric. Food Chem. 60(27):6782-93 (Jul. 2012).
Humphrey et al., "Spatial organisation of four enzymes from Stevia rebaudiana that are involved in steviol glycoside synthesis," Plant Mol Bio. 61(1-2):47-62 (2006).
Husar et al., Overexpression of the UGT73C6 alters brassinosteriod glucoside formation in *Arabidopsis thaliana*, BMC Plant Biology, 11:1-14 (2011).
Iandolino et al., "High-Quality RNA, cDNA, and Derived EST Libraries From Grapevine (*Vitis vinifera* L.)," Plant Mol Biol Reporter 22:269-78 (2004).
International Preliminary Report on Patentability received for PCT Patent Application No. PCT/EP2016/055734, dated Sep. 28, 2017, 18 pages.
International Search Report and Written Opinion received for PCT Patent Application No. PCT/EP2016/055734, dated Aug. 23, 2016, 26 pages.
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosynthesis: baxane 13 alpha-hydroxylase is a cytochrome P450-dependent monooxygenase," Proc Natl Acad Sci U S A 98(24):13595-600 (2001).
Jewett et al. "An integrated cell-free metabolic platform for protein production and synthetic biology," Mol Syst Biol. 4:220 (2008).
Johnstone et al., "Cloning an *Aspergillus nidulans* developmental gene by transformation," EMBO J. 4(5):1307-11 (1985).
Katzmann et al., "Expression of an ATP-binding cassette transporter-encoding gene (YOR1) is required for oligomycin resistance in *Saccharomyces cerevisiae*," Mol. Cell Biol. 15(12):6875-83 (Dec. 1995).
Kawai et al., "Transformation of *Saccharomyces cerevisiae* and other fungi: methods and possible underlying mechanism," Bioeng Bugs. 1(6):395-403 (2010).
Khan et al., "Physical and chemical mutagenesis in Stevia rebaudiana: variant generation with higher UGT expression and glycosidic profile but with low photosynthetic capabilities," Acta Physiologiae Plantarum 38(1) (2016).
Khoury et al., "Computational design of Candida boidinii xylose reductase for altered cofactor specificity," Protein Sci. 18(10):2125-38 (Oct. 2009).
Kim et al., ""Hydroxylation of ent-Kaurenoic Acid to Steviol in Stevia rebaudiana Bertoni-Purification and Partial Characterization of the Enzyme,"" Arch Biochem Biophys. 332(2):223-30 (1996).
Kim et al., "Characterization of ent-kaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10),806-11 (2000).
Kumar et al., "A comprehensive analysis of fifteen genes of steviol glycosides biosynthesis pathway in *Stevia rebaudiana* (Bertoni)," Gene 492:276-84 (Epub Oct. 20, 2011).
Kusama et al., "Transglucosylation into stevioside by the enzyme system from *Streptomyces* sp.," Agric. Biol. Chem. 50(10):2445-51 (Oct. 1986).
Li et al., "Crystal structure of Medicago truncatula UGT85H2—insights into the structural basis of a multifunctional (iso)flavonoid glycosyltransferase," J Mol Biol. 370(5):951-63 (2007).

(56) References Cited

OTHER PUBLICATIONS

Li et al., "Phylogenetic analysis of the UDP-glycosyltransferase multigene family of *Arabidopsis thaliana*," J Biol Chem. 276(6):4338-43 (2001).
Li et al., "Systematic Mutational Analysis of Peptide Inhibition of the p53-MDM2/MDMX," J Mol Biol. 398(2)200-13 (2010).
Li et al., "High-density cultivation of oleaginous yeast Rhodosporidium toruloides Y4 in fed-batch culture," Enzyme and Microbial Technology 41(3):312-7 (Aug. 2007).
Lin et al., "Arrestin-related ubiquitin-ligase adaptors regulate endocytosis and protein turnover at the cell surface," Cell 135(4):714-25 (2008).
Liu et al., "Biosynthesis of Rebaudioside A by Whole Cell of Recombinant *Saccharomyces cerevisiae*," Food and Fermentation Industries, 38(7) : 6-10 (2012) (Abstract translation).
Liu et al., "Functional and biochemical characterization of *Escherichia coli* sugar efflux transporters" Journal of Biological Chemistry, 274(33):22977-84 (Aug. 1999).
Liu et al., "Preparation of high-activity whole cell biocatalysts by permeabilization of recombinant yeasts with alcohol," J Biosci Bioeng. 89(6):554-8 (2000).
Louveau, Thomas et al., "Predicting the substrate specificity of a glycosyltransferase implicated in the production of phenolic volatiles in tomato fruit", Febs Journal, Jan. 17, 2011, pp. 390-400, vol. 278, No. 2.
Ma "Part 1. Molecular Cloning and Functional Analysis of UDPG Glucosyltransferase Gene. Part 2. Molecular Cloning, Sequence Analysis and Evolution of Actin and EF1a Genes in Stevia Rebaudiana." Chinese Doctor and Master Dissertations Full-Text Database, Agricultural Technology Part, vol. 2; pp. 1-74 (2004).
Ma et al., "Molecular cloning and characterization of Stevia Rebaudiana UDP-glucosyltransferase," Acta Biologiae Experimentalis Sinica 36(2):123-9 (2003).
Madan et al., "*Stevia rebaudiana* (Bert.) Bertoni—A Review," Indian Journal of Natural Products and Resources 1(3):267-86 (2010).
Madhav et al., "Functional and structural variation of uridine diphosphate glycosyltransferase (UGT) gene of *Stevia rebaudiana*—UGTSr involved in the synthesis of rebaudioside A," Plant Physiol. Biochem. 63:245-53 (Feb. 2013).
Mahe et al., "The ATP Binding Cassette Transporters Pdr5 and Snq2 of *Saccharomyces cerevisiae* Can Mediate Transport of Steriods via in Vivo", JBC, 271(41):25167-25172. (Oct. 1996).
Malonek et al., "The NADPH-cytochrome P450 Reductase Gene from *Gibberalla fujikuroi* is Essential for Gibberellin Biosynthesis," J Bio Chem. 279(24):25075-84 (2004).
Mantovaneli et al., "The effect of temperature and flow rate on the clarification of the aqueous stevia-extract in a fixed-bed column with zeolites," Braz J Chem Eng. 21(3):449-58 (2004).
Mao et al., "Produce steviol glycosides in engineered yeast", 2015 Synthetic Biology: Engineering, Evolution & Design (SEED), Poster Abstract (Jun. 2015).
Martin et al., "Ice2p is important for the distribution and structure of the cortical ER network in *Saccharomyces cerevisiae*," J Cell Sci. 118(Pt 1):65-77 (Oct. 2006).
Masada et al., "An efficient chemoenzymatic production of small molecule glucosides with in situ UDP-glucose recycling," FEBS Lett. 581(13):2562-6 (2007).
Mattanovich et al., "Recombinant protein production in yeasts," Methods Mol Biol. 824:329-58 (2012).
Megeji et al., "Introducing Stevia rebaudiana, a natural zero-calorie sweetener," Current Science 88(5):801-4 (2005).
Mikayama et al., "Molecular cloning and functional expression of a cDNA encoding glycosylation-inhibiting factor," Proc Natl Acad Sci U S A. 90(21):10056-60 (1993).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Morita et al., "Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2"-O-glucosyltransferase, due to 4-bp insertions in the gene," Plant J. 42(3):353-63 (2005).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in *Saccharomyces cerevisiae*," Microb Cell Fact. 8:45 (2009).
Nagalakshmi et al., "The transcriptional landscape of the yeast genome defined by RNA sequencing," Science 320(5881 ): 1344-9 (2008).
Nagatoshi et al., "UGT75L6 and UGT94E5 mediate sequential glucosylation of crocetin to crocin in Gardenia jasminoides", FEBS Letters, 586:1055-1061 (2012).
Naglak et al., "Rapid protein release from *Escherichia coli* by chemical permeabilization under fermentation conditions," Biotechnol Bioeng. 39(7):732-40 (1991).
Nagy et al., "Role of the yeast ABC transporter Yor1p in cadmium detoxification," Biochimie 88(11):1665-71 (Jun. 2006).
Nakagiri et al., "cDNA cloning, functional expression and characterization of ent-copalyl diphosphate synthase from *Scoparia dulcis* L.," Plant Sci. 169:760-7 (2005).
NCBI Crocetin glucoside Solanum lycopersicum, Crocetin glucoside glucosyltransferase-like [Solanum lycopersicum], Nov. 19, 2014, Accession No. XP 004249995.
NCBI Reference Sequence XP 009770958.1, "Crocetin glucoside glucosyltransferase-like [Nicotiana sylvestris]", Oct. 21, 2014.
NCBI Reference Sequence XP 009795814.1, "Crocetin Glucoside glucosyltransferase-like [Nicotiana sylvestris]", Oct. 21, 2014.
NCBI Reference Sequence XP 009796593.1, "Crocetin glucoside glucosyltransferas-like [Nicotiana sylvestris]", Oct. 21, 2014.
Nelson et al., "P450 superfamily: update on new sequences, gene mapping, accession numbers and nomenclature," Pharmacogenetics 6:1-42 (1996).
Newman et al., "High-level production of amorpha-4,11-diene in a two-phase partitioning bioreactor of metabolically engineered *Escherichia coli*," Biotechnol Bioeng 95(4):684-91 (2006).
Ni et al., "Outer membrane mutation effects on UDP-glucose permeability and whole-cell catalysis rate," Appl Microbiol Biotechnol. 73(2):384-93 (2006).
Nicaud, "Yarrowia lipolytica," Yeast 29(10):409-18 (Oct. 2012).
Nielsen et al., "Efficient PCR-based gene targeting with a recyclable marker for Aspergillus nidulans," Fungal Genet Biol. 43(1):54-64 (2006).
Nikaido et al., "Mechanisms of RND multidrug efflux pumps," Biochim. Biophys. Acta. 1794(5):769-81 (May 2009).
Nikko et al. "Arrestin-like proteins mediate ubiquitination and endocytosis of the yeast metal transporter Smf1," EMBO Rep. 9(12):1216-21 (2008).
Nikko et al., "Arrestin-mediated endocytosis of yeast plasma membrane transporters," Traffic 10(12):1856-67 (2009).
Nour-Eldin et al., "User cloning and User fusion: the ideal cloning techniques for small and big laboratories," Methods Mol Biol. 643:185-200 (2010).
Office Action received for European Application No. 16710728, dated Aug. 14, 2018, 11 pages.
Ohta et al., "Characterization of Novel Steviol Glycosides from Leaves of *Stevia rebaudiana* Morita," J. Applied Glycosides 57(3):199-209 (Mar. 2010).
Ohta et al., MassBank Accession No. FU000299 (May 2016).
Ohta et al., MassBank Accession No. FU000332 (May 2016).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka et al., "Reconstruction of de novo pathway for synthesis of UDP-glucuronic acid and UDP-xylose from intrinsic UDP-glucose in *Saccharomyces cerevisiae*," FEBS J. 273(12)2645-57 (2006).

(56) References Cited

OTHER PUBLICATIONS

Ooyen et al., "Heterologous protein production in the yeast Kluyveromyces lactis," FEMS Yeast Res. 6(3):381-92 (May 2006).
Flores et al., "Permeabilization of yeast cells (Kluyveromyces lactis) with organic solvents," Enzyme Microb Technol. 16(4):340-6 (1994).
Fowler et al., "Effects of Dimethylsulfoxide on the Lactose Operon in *Escherichia coli*," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Garber et al., "Computational methods for transcriptome annotation and quantification using RNA-seq," Nat Methods 8(6):469-77 (2011).
GenBank Accession No. AAB62280, dated Jul. 2, 1997 (2 pages).
GenBank Accession No. AAB87091, dated Mar. 22, 2000 (2 pages).
GenBank Accession No. AAC28895.1, dated Aug. 6, 1998 (2 pages).
GenBank Accession No. AAC39505, dated Jul. 26, 1998 (1 page).
GenBank Accession No. AAF61439.1, dated Sep. 25, 2000 (2 pages).
GenBank Accession No. AAM53963.1, dated Jun. 17, 2002 (2 pages).
GenBank Accession No. AAR06912, dated Dec. 28, 2004 (2 pages).
GenBank Accession No. AAS07253.1, dated Jan. 31, 2004 (3 pages).
GenBank Accession No. AAT93110.1, dated Apr. 24, 2007 (2 pages).
GenBank Accession No. ABA42921, dated Jun. 21, 2006 (1 page).
GenBank Accession No. ABC98596, dated Jan. 31, 2014 (2 pages.).
GenBank Accession No. ABD60225, dated May 28, 2008 (2 pages).
GenBank Accession No. ABD92926, dated Oct. 10, 2007 (2 pages).
GenBank Accession No. AC133334, dated Jan. 31, 2004 (44 pages).
GenBank Accession No. ACD93722, dated Jun. 10, 2008 (1 page).
GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AEE36246, dated Oct. 6, 2014 (3 pages).
GenBank Accession No. AF034774, dated Apr. 17, 1998 (2 pages).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).
GenBank Accession No. AY345982.1, dated Dec. 28, 2004 (2 pages).
GenBank Accession No. AY562490, dated May 23, 2006 (3 pages).
GenBank Accession No. AZF53544, dated Apr. 14, 2011 (2 pages).
GenBank Accession No. BAA43200, dated Mar. 13, 1999 (2 pages).
GenBank Accession No. BAB59027, dated Jan. 30, 2002 (1 page).
GenBank Accession No. BAF61135, dated May 9, 2007 (2 pages).
GenBank Accession No. BAG30962, dated Nov. 12, 2012 (2 pages).
GenBank Accession No. BC153262, dated Oct. 4, 2007 (3 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. CAA75568, dated Nov. 14, 2006 (2 pages).
GenBank Accession No. CAA76703, dated Nov. 14, 2006 (1 page).
GenBank Accession No. CAE09055, dated Nov. 14, 2006 (2 pages).
GenBank Accession No. CAG41604, dated Feb. 6, 2015 (2 pages).
GenBank Accession No. DQ269454.4, dated May 28, 2008 (2 pages).
GenBank Accession No. DQ398871.3, dated May 28, 2008 (2 pages).
GenBank Accession No. EDY51667, dated Sep. 2, 2008 (2 pages).
GenBank Accession No. EU263989, dated Jun. 11, 2008 (2 pages).
GenBank Accession No. EU722415.1, dated Jun. 10, 2008 (2 pages).
GenBank Accession No. EU751291.1, dated Jun. 24, 2008 (2 pages).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73(13):4342-50 (2007).
Wallin, "Steviol Glycosides," Chem. Tech Assessment—63rd JECFA, pp. 1-5 (2004).
Wallin, "Steviol Glycosides," Chem. Tech Assessment—69th JECFA, pp. 1-7 (2007).
Wallner et al., "Can correct protein models be identified?," Protein Sci. 12(5):1073-86 (May 2003).
Wanchao et al., "Advances on the Steviol Glycoside Biosynthesis and Its Key Enzymes," Biotechnology Bulletin, Feb. 2008 (English Abstract Translation).
Wang et al., "Efficient enzymatic production of rebaudioside A from stevioside", Bioscience, Biotechnology, and Biochemistry, 80:67-73 (Aug. 2015).
Wang et al., "Characterics of the tomato nuclear genome as determined by sequencing undermethylated EcoRI digested fragments," Theoretical and Applied Genetics, 112(1):72-84 (2005).
Wang et al., "Design and construction of artificial biological systems for complex natural products biosynthesis," Chinese Journal of Biotechnology, 29(8):1146-60 (2013).
Wang et al., "Pathway mining-based integration of critical enzyme parts for de novo biosynthesis of steviolglycoside sweetener in *Escherichia coli*", Cell Research, 26:258-261 (Sep. 2015).
Wang et al., "RNA-Seq: a revolutionary tool for transcriptomics," Nat Rev Genet. 10(1):57-63 (2009).
Wang, "Structure, mechanism and engineering of plant natural product glycosyltransferases," FEBS Letters 583(20):3303-9 (2009).
Warth et al., "Hydrophilic interaction liquid chromatography coupled with tandem mass spectrometry for the quantification of uridine diphosphate-glucose, uridine diphosphate-glucuronic acid, deoxynivalenol and its glucoside: In-house validation and application to wheat," Journal of Chromatography A, 1423, pp. 183-189 (2015).
Wilhelm et al., "Defining transcribed regions using RNA-seq," Nature Protocols 5:255-66 (2010).
Xu et al., "Generation of hepatitis B virus PreS2-S antigen in Hansenula polymorpha," Virol Sin. 29(6):403-9 (Dec. 2014).
Yadav et al., "A review on the improvement of stevia [Stevia rebaudiana (Bertoni)]," Can J Plant Sci. 91:1-27 (2011).
Yadav et al., "Steviol Glycosides from Stevia: Biosynthesis Pathway Review and their Application in Foods and Medicine", CritRev. 52(11):988-998 (2012).
Yang et al., Base substitution mutations in uridinediphosphate-dependent glycosyltransferase 76G1 gene of Stevia rebaudiana causes the low levels of rebaudioside A: mutations in UGT76G1, a key gene of steviol glycosides synthesis, Plant Physiol Biochem. 80:220-5 (2014).
Yang Quanhua et.al., "Analysis of the Chemical constituents of Stevia rebaudiana and its sweetness," Journal of Beijing University of Chemical Technology, vol. 39, No. 2., p. 28-32 (2012) (English Abstract).
Yao et al., "A genetic linkage map for Stevia rebaudiana," Genome 42:657-61 (1999).
Yazaki, "ABC transporters involved in the transport of plant secondary metabolites," FEBS Lett. 580(4):1183-91 (Feb. 2006).
Yu et al., "Bioconversion of ethyl 4-chloro-3-oxobutanoate by permeabilized fresh brewer's yeast cells in the presence of allyl bromide," J Ind Microbiol Biotechnol. 34(2)151-6 (2007).
Yuan et al., "Kinetics and activation parameters for oxidations of styrene by Compounds I from the cytochrome P450(BM-3) (CYP102A1) heme domain and from CYP119," Biochemistry 48(38):9140-6 (Sep. 2009).

(56) References Cited

OTHER PUBLICATIONS

Zheng et al. "An efficient one-step site-directed and site-saturation mutagenesis protocol," Nucleic Acids Res. 32(14):e115 (Aug. 2004).
Zhu et al., "A multi-omic map of the lipid-producing yeast Rhodosporidium toruloides," Nature Commun. 3:1112 (Oct. 2012).
Abraham et al., "Permeabilization of baker's yeast with N-lauroyl sarcosine," J Ind Microbial Biotechnol. 35(8):799-804 (2008).
Ageitos et al., "Oily yeasts as oleaginous cell factories," Appl Microbiol Biotechnol. 90(4):1219-27 (May 2011).
Agrawal Pawan K., "NMR spectroscopy in the structural elucidation of oligosaccharides and glycosides," Phytochemistry 31(10):3307-30 (1992).
Ajikumar et al., "Terpenoids: opportunities for biosynthesis of natural product drugs using engineered microorganisms," Molecular Pharmaceuticals 5(2):167-90 (2008).
Alakomi et al., "Lactic acid permeabilizes gram-negative bacteria by disrupting the outer membrane," Appl Environ Microbiol. 66(5):2001-5 (2000).
Ali et al., "Biochemical investigation during different stages of in vitro propagation of Stevia rebaudiana," Pak J Bot. 42(4):2827-37 (2010).
Altschul et al., Basic Local Alignment Search Tool, J. Mol. Biol., 215:403-410 (1990).
Altschul et al., Gapped Blast and PSI-Blast: a new generation of protein database search programs, Nucleic Acids Research, 25(17):3389-3402 (1997).
Bankar et al., "Environmental and industrial applications of Yarrowia lipolytica," Appl Microbiol Biotechnol. 84(5):847-65 (Oct. 2009).
Bateman et al., "Pfam 3.1: 1313 multiple alignments and profile HMMs match the majority of proteins," Nucl Acids Res. 27(1):260-2 (1999).
Bay et al., "Diversity and evolution of the small multidrug resistance protein family," BMC Evol. Biol. 9:140 (Jun. 2009).
Baykov et al., "A malachite green procedure for orthophosphate determination and its use in alkaline phosphatase-based enzyme immunoassay," Anal Biochem. 171(2):266-70 (Jun. 1988).
Beopoulos et al., "Yarrowia lipolytica: A model and a tool to understand the mechanisms implicated in lipid accumulation," Biochimie 91(6):692-6 (Jun. 2009).
Brachmann et al., "Designer deletion strains derived from Saccharomyces cerevisiae S288C: a useful set of strains and plasmids for PCR-mediated gene disruption and other applications," Yeast 14:115-32 (1998).
Brandle et al., "Leaf ESTs from Stevia rebaudiana: A Resource for Gene Discovery in Diterpene Synthesis," Plant Mol Biol. 50(4-5):613-22 (2002).
Brandle et al., "Steviol glycoside biosynthesis," Phytochemistry 68(14):1855-63 (2007).
Brochado et al. "Improved vanillin production in baker's yeast through in silico design," Microb Cell Fact. 9:84-98 (2010).
Budiman, Muhammad A. et al., "A deep-coverage tomato BAC library and prospects toward development of an STC framework for genome sequencing", Genome Research, Jan. 1, 2000, pp. 129-136, http://www.ncbi.nlm.nih.gov/pubmed/10645957.
Carretero-Paulet et al., "Expression and Molecular Analysis of the Arabidopsis DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).
Ceunen et al., "Steviol glycosides: chemical diversity, metabolism, and function," J. Nat. Prod. 76(6):1201-28 (Jun. 2013).
Chemler et al., "Biosynthesis of isoprenoids, polyunsaturated fatty acids and flavonoids in Saccharomyces cerevisiae," Microb Cell Fact. 5:20 (2006).
Chen et al., "Fusion protein linkers: Property, design, and functionality", Advanced Drug Delivery reviews, 65(0):1257-69 (2013).

Chen et al., "Progress in the Application of Affinity Tags for the Expression and Purification of Recombinant Proteins," China Biotechnology, vol. 32, No. 12, pp. 93-103, Dec. 15, 2012 (English Abstract).
Chen et al., "Sugar transporters for intercellular exchange and nutrition of pathogens," Nature 468(7323):527-32 (2010).
Chen et al., "Transferring a biosynthetic cycle into a productive Escherichia coli strain: large-scale synthesis of galactosides," J Am Chem Soc. 123(36):8866-7 (2001).
Chen et al., "MolProbity: all-atom structure validation for macromolecular crystallography," Acta Crystallogr D Biol Crystallogr 66(Pt 1):12-21 (Jan. 2010).
Chen, "Summary on Study of Stevioside," China Pharmacist, vol. 10, No. 6, p. 598-599 (2007).
Chenna et al., "Multiple sequence alignment with the Clustal series of programs," Nucleic Acids Res. 31(13):3497-500 (2003).
Chica et al., "Semi-rational approaches to engineering enzyme activity: combining the benefits of directed evolution and rational design," Curr Opin Biotechnol.16(4):378-84 (2005).
Chow et al., "Enzyme encapsulation in permeabilized Saccharomyces cerevisiae cells," Biotechnol Prog. 20(2):449-56 (2004).
Correa et al., "Genetic mapping of 1,3-beta-glucanase-encoding genes in Saccharomyces cerevisiae," Current Genet. 22(4):283-8 (1992).
Daran et al., "Genetic and biochemical characterization of the UGP1 gene encoding the UDP-glucose pyrophosphorylase from Saccharomyces cerevisiae," Eur J Biochem. 233(2):520-30 (1995).
Darise et al., "Enzymic Transglucosylation of Rubusoside and the Structure-Sweetness Relationship of Steviol-Bisglycosides," Agric. Biol. Chem. 48(10):2483-8 (Jan. 1984).
Davis et al., "MolProbity: all-atom contacts and structure validation for proteins and nucleic acids," Nucleic Acids Res. 35:W375-83 (Apr. 2007).
Del Sorbo et al., "Fungal transporters involved in efflux of natural toxic compounds and fungicides," Fungal. Genet. Biol. 30(1):1-15 (Jun. 2000).
Diener et al., "Arabidopsis ALF5, a multidrug efflux transporter gene family member, confers resistance to toxins," Plant Cell 13(7):1625-38 (Jul. 2001).
Dodhia et al., "Engineering human cytochrome P450 enzymes into catalytically self-sufficient chimeras using molecular Lego," J Biol Inorg Chem. 11(7):903-16 (Oct. 2006).
Dubey, et al., An overview of the non-mevalonate pathway for terpenoid biosynthesis in plants, J. Biosci. 28(5):637-46 (2003).
Dubois et al., "Diterpenoid sweeteners. Synthesis and sensory evaluation of stevioside analogues with improved organoleptic properties," J. Med. Chem. 28(1):93-8 (Jan. 1985).
EBI accession GSP BBR03844, Stevia rebaudiana UGT1 protein, seq 88, Data base accession BBR03844, Jan. 29, 2015.
EBI Accession No. AAY05902, "Jerusalem artichoke in-chain hydroxylase CYP81B1" (1 page), Jun. 15, 2009.
EBI Accession No. ABM86477, "Rice abiotic stress responsive polypeptide Seq ID No. 4723" (1 page), dated Jun. 2, 2005.
EBI accession Uniprot K4BW0, Glycosyltransferase, Feb. 4, 2015.
EBI accession Uniprot K4D509_02-2015, Glycosyltransferase, Apr. 2, 2015.
EBI accession Uniprot K4D509_07-2015, Glycosyltransferase, Jul. 22, 2015.
EFSA Panel on Food Additives and Nutrient Sources added to Food (ANS), "Scientific Opinion on the safety of steviol glycosides for the proposed uses as a food additive," EFSA Journal 8(4):1537 (2010).
Eisenreich et al., "Biosynthesis of isoprenoids via the non-mevalonate pathway," Cell Mol Life Sci. 61(12):1401-6 (2004).
EMBOSS Needle results for Alignment of Seq ID No. 5 of EP'432 and UGT91D1, dated Apr. 4, 2016 (2 pages).
Emmerstorfer et al., "Over-expression of ICE2 stabilizes cytochrome P450 reductase in Saccharomyces cerevisiae and Pichia pastoris," Biotechnol J. 10(4):623-35 (Apr. 2015).
Fernandez et al., "Activation of chitin synthetase in permeabilized cells of a Saccharomyces cerevisiae mutant lacking proteinase B," J Bacteriol. 152(3):1255-64 (1982).

(56) References Cited

OTHER PUBLICATIONS

Orihara et al., "Biotransformation of steviol by cultured cells of eucalyptus perriniana and Coffea Arabica," Phytochemistry 30(12):3989-92 (1991).
Osmani et al., "Catalytic key amino acids and UDP-sugar donor specificity of a plant glucuronosyltransferase, UGT94B1: molecular modeling substantiated by site-specific mutagenesis and biochemical analyses," Plant Phys. 148(3):1295-1308 (2008).
Osmani et al., "Substrate specificity of plant UDP-dependent glycosyltransferases predicted from crystal structures and homology modeling," Phytochemistry 70(3):325-47 (2009).
Paradise et al., "Redirection of flux through the FPP branch-point in Saccharomyces cerevisiae by down-regulating squalene synthase," Biotechnol Bioeng. 100(2):371-8 (2008).
Partow et al., "Characterization of different promoters for designing a new expression vector in Saccharomyces cerevisiae," Yeast 27:955-64 (2010).
Pearson et al., "Improved tools for biological sequence comparison," Proc Natl Acad Sci. 85(8):2444-8 (1998).
Piirainen et al., "Glycoengineering of yeasts from the perspective of glycosylation efficiency," N Biotechnol. 31(6):532-7 (Dec. 2014).
Pompon et al., "Yeast Expression of Animal and Plant P450s in Optimized Redox Environments," Methods Enzymol 272:51-64 (1996).
Prelich, Gregory, "Gene overexpression: uses, mechanisms, and interpretation," Genetics 190(3):841-54 (Mar. 2012).
Presecki et al., "Production of L-malic acid by permeabilized cells of commercial Saccharomyces sp. strains," Biotechnol Lett. 27(23-24):1835-9 (2005).
Prisic et al, "Synergistic substrate inhibition of ent-copalyl diphosphate synthase: a potential feed-forward inhibition mechanism limiting gibberellin metabolism," Plant Physiol. 144(1):445-54 (2007).
Rice et al., EMBOSS: The European Molecular Biology Open Software Suite, Resource Internet, 16(6):276-277 (2000).
Richman et al., "Functional genomics uncovers three glucosyltransferases involved in the synthesis of the major sweet glucosides of Stevia rebaudiana," Plant J. 41(1):56-67 (2005).
Riesmeier et al., "Isolation and characterization of a sucrose carrier cDNA from spinach by functional expression in yeast," EMBO J 11(13):4705-13 (1992).
Ro et al., "Production of the antimalarial drug precursor artemisinic acid in engineered yeast," Nature 440(7086):940-3 (2006).
Robinson et al., "A scaling normalization method for differential expression analysis of RNA-seq data," Genome Biol. 11(3):R25 (2010).
Rodriguez-Concepcion et al., "Elucidation of the methylerythritol phosphate pathway for isoprenoid biosynthesis in bacteria and plastids. A metabolic milestone achieved through genomics," Plant Physiol. 130(3):1079-89 (2002).
Rudinger et al., "Characteristics of the amino acids as components of a peptide hormone sequence," Peptide Hormones. Biol. Council. pp. 5-7 (1976).
Saenge et al., "Potential use of oleaginous red yeast Rhodotorula glutinis for the bioconversion of crude glycerol from biodiesel plant to lipids and carotenoids," Process Biochemistry 46(1):210-8 (Jan. 2011).
Saier et al., "The Transporter Classification Database: recent advances," Nucleic Acids Res. 37:D274-8 (Jan. 2009).
Saier Jr et al., "The major facilitator superfamily," J. Mol. Microbiol. Biotechnol. 1(2):257-79 (Nov. 1999).
Saier Jr. et al., "The transporter classification database," Nucl. Acids Res., 42(1):D251-258 (2014).
Saier, "Families of transmembrane sugar transport proteins," Mol Microbiol., 35(4):699-710 (2000).
Sauer et al., "The soluble and membrane-bound transhydrogenases UdhA and PntAB have divergent functions in NADPH metabolism of Escherichia coli," J Biol Chem. 279(8):6613-9 (2004).
Sawada et al., "UDP-glucuronic acid:anthocyanin glucuronosyltransferase from red daisy (Bellis perennis) flowers.
Enzymology and phylogenetics of a novel glucuronosyltransferase involved in flower pigment biosynthesis," J Biol Chem. 280(2):899-906 (2005).
Schwab et al., Poster, "Watchmaker®- Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol.143(3):212-23 (2007).
Senthilraja et al., "RNA secondary structure prediction: Analysis of Saccharomyces cerevisiae RNAs," Int. J. Pharm. Rev. Res. 25(2):287-91 (Mar.-Apr. 2014).
Shao et al., "Crystal structures of a multifunctional triterpene/flavonoid glycosyltransferase from Medicago truncatula," Plant Cell 17(11):3141-54 (2005).
Shao et al., "Enhanced production of alpha-galactosyl epitopes by metabolically engineered Pichia pastoris," Appl Environ Microbiol. 69(9):5238-42 (2003).
Shibata et al., "Glucosylation of Steviol and Steviol-Glucosides in Extracts from Stevia rebaudiana Bertoni" Plant Physiol. 95(1):152-56 (1991).
Singh et al., "Compendium of Transgenic Crop Plants: Transgenic Sugar, Tuber and Fiber," Ed. Kole & Hall, Blackwell Publishing Ltd. pp. 97-115 (2008).
Son et al., "Production of flavonoid o-glucoside using sucrose synthase and flavonoid o-glucosyltransferase fusion protein," J Microbiol Biotechnol. 19(7):709-12 (2009).
Song et al., "The Aspergillus fumigatus 1-29 damage resistance protein family coordinately regulates ergosterol biosynthesis and azole susceptibility," MBIO, 7:1-13 (2016).
Sonnhammer et al., "Pfam: a comprehensive database of protein domain families based on seed alignments," Proteins 28(3):405-420 (1997).
Sonnhammer et al., "Pfam: multiple sequence alignments and HMM-profiles of protein domains," Nucleic Acids Res. 26(1):320-2 (1998).
Starratt et al., "Rebaudioside F, a diterpene glycoside from Stevia redaudiana", Phytochemistry, 59(4):367-370. (Feb. 2002). Abstract.
Sun et al., "Regulation and Function of Escherichia coli Sugar Efflux Transporter A (SetA) during Glucose-Phosphate Stress" Journal of Bacteriology, 193(1):143-55 (Jan. 2011).
Tiwari et al., "Plant secondary metabolism linked glycosyltransferases: An update on expaning knowledge and scopes", Biotechnology Advances, 34:714-739 (May 2016).
U.S Food and Drug Administration Gras Notice Notice 329, "Notice to the U.S. Food and Drug Administration that the use of RebpureTM (Rebaudioside A) derived from Stevia rebaudiana, as a Food Ingredient is Generally Recognized as Safe (GRAS)," pp. 1-275 (Mar. 2010).
U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).
UniProt Accession No. B5MEX6, Nov. 4, 2008 (1 page).
UniProt Accession No. E4MVV7, Feb. 8, 2011 (1 page).
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
Unitprot Accession No. Q75183, dated Jul. 22, 2008 (pp. 1-2).
Unitprot Accession No. Q75183, dated Jul. 5, 2004 (pp. 1-4).
Unligil et al., "Glycosyltransferase structure and mechanism," Curr Opin Struct Biol. 10(5):510-7 (2000).
Vazquez De Aldana et al., "Nucleotide sequence of the exo-1,3-beta-glucanase-encoding gene, EXG1, of the yeast Saccharomyces cerevisiae," Gene 97(2):173-82 (1991).
"PREDICTED: Solanum lycopersicum beta-D-glucosyl crocetin beta-1,6-glucosyltransferase (LOC10126725), mRNA", NCIB, Aug. 8, 2018, pp. 1-2, XM_004238649.2.
Wang, Jun et al., "Glycosylation and Glycosyltransferase of Small Molecular Compounds of Plant", China Academic Journal Electronic Publishing House, Oct. 2008, pp. 997-1003, vol. 44, No. 5.

* cited by examiner

SEQUENCE LISTING

<160> NUMBER OF SEQ ID NOS: 84

<210> SEQ ID NO 1
<211> LENGTH: 473
<212> TYPE: PRT
<213> ORGANISM: Artificial sequence
<220> FEATURE:
<223> OTHER INFORMATION: UGT2_1b variant

<400> SEQUENCE: 1

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Gln
            20                  25                  30

Leu Ala Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Phe Val Lys Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                    85                  90                  95

Leu Ala Ser Asp Gly Leu Gln Glu Pro Leu Thr Arg Phe Leu Glu Ser
            100                 105                 110

Ser Ser Pro Asp Trp Ile Ile Tyr Asp Tyr Thr His Tyr Trp Leu Pro
        115                 120                 125

Glu Ile Ala Ala Ser Leu Gly Val Ala Arg Ala His Phe Ser Val Thr
    130                 135                 140

Thr Pro Trp Ala Leu Ala Phe Met Gly Pro Ser Ala Asp Ala Met Ile
145                 150                 155                 160

Asn Gly Ser Asp Gly Arg Thr Glu Val Glu Asp Phe Thr Val Pro Pro
                165                 170                 175

Lys Trp Ile Pro Phe Pro Thr Thr Val Ala Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Cys Asp Cys Leu Leu Ser Arg Thr Tyr
    210                 215                 220

His Glu Phe Gly Thr Gln Trp Leu Pro Leu Leu Glu Glu Leu His Gln
225                 230                 235                 240

Val Pro Val Val Pro Val Gly Leu Leu Pro Pro Ser Ile Pro Gly Asp
                245                 250                 255

Glu Lys Asp Glu Asn Trp Val Ser Ile Lys Asp Trp Leu Asp Lys Gln
            260                 265                 270

Glu Lys Gly Ser Val Val Tyr Val Ala Leu Gly Ser Glu Val Leu Leu
        275                 280                 285

Thr Glu Glu Glu Val Val Glu Leu Ala Leu Gly Leu Glu Leu Ser Gly
    290                 295                 300

Leu Pro Phe Phe Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Gly Gly Phe Val Thr His Cys Gly Ser Gly Ser Ile Val
```

```
                        355                 360                 365
Glu Gly Leu Met Phe Gly His Pro Leu Ile Met Leu Pro Ile Phe Gly
    370                 375                 380
Asp Gln Pro Leu Asn Ala Arg Leu Leu Glu Asp Lys Gln Val Gly Ile
385                 390                 395                 400
Glu Ile Pro Arg Asn Glu Asp Gly Cys Leu Thr Lys Glu Ser Val
                405                 410                 415
Ala Glu Ser Leu Arg Leu Val Val Glu Lys Glu Gly Glu Ile Tyr
            420                 425                 430
Arg Glu Lys Ala Arg Glu Met Ser Lys Val Tyr Ser Asp Thr Lys Arg
        435                 440                 445
Glu Lys Glu Tyr Val Asp Gln Phe Val Asp Tyr Leu Glu Lys Asn Ala
    450                 455                 460
Arg Ala Val Ala Ile Asp His Glu Ser
465                 470

<210> SEQ ID NO 2
<211> LENGTH: 1419
<212> TYPE: DNA
<213> ORGANISM: Artificial sequence
<220> FEATURE:
<223> OTHER INFORMATION: UGT2_1b CpO for S. cerevisiae

<400> SEQUENCE: 2
atggccactt ctgactccat cgttgatgac agaaagaagt tgcacatcgt tatgttccca      60
tggttagctt tcggtcacat tatcccatac ttgcaattgg ctaaattgat tgctgaaaag     120
ggtcacaaag tctctttctt gtccaccacc agaaacatcc aaagattatc ttctcacatt     180
tctccattga tcaacttcgt caagttgact ttaccaagag ttcaagaatt gccagaagat     240
gctgaagcta ccaccgatgt ccatccagaa gatatcccat acttgaagtt ggcttctgat     300
ggtttgcaag aaccattgac tagattcttg gaatcttctt ctccagactg gattatctac     360
gactacactc actactggtt accagaaatt gctgcctctt gggtgttgc tcgtgctcat     420 ttctccgtta ccactccatg ggctttggct ttcatgggtc catctgctga tgctatgatc     480
aacggttctg atggtagaac cgaagtcgaa gacttcaccg ttccaccaaa atggatccca     540
ttcccaacca ctgtcgcttg agaaagcac gatttggcca gattagttcc atacaaggcc     600
ccaggtatct ctgacggtta cagaatgggt ttagtcttga agggttgtga ctgtttgttg     660
tccagaactt accatgaatt cggtactcaa tggttacctt tgttggaaga attgcaccaa     720
gtcccagttg ttccagttgg tttgttgcct ccttctatcc caggtgacga aaaggacgaa     780
aactgggttt ccatcaagga ctggttagat aagcaagaaa agggttccgt tgtctacgtt     840
gctttgggtt ctgaagtctt gttgactgaa gaagaagttg ttgaattggc tttgggtttg     900
gaattgtccg gtctaccatt tttctgggct tacagaaagc caagggtcc agctaagtct     960 gactctgttg aattgccaga tggtttcgtc gaaagaacca gagacagagg tttggtctgg    1020
acttcctggg ctccacaatt gagaattttg tcccacgaat ctgttggtgg tttcgttacc    1080
cactgtggtt ctggttccat tgtcgaaggt tgatgttcg gtcacccatt gatcatgttg    1140
ccaatcttcg gtgaccaacc attgaacgct agattattgg aagacaagca agtcggtatt    1200
gaaatcccaa gaaacgaaga agacggttgt ttgaccaagg aatctgttgc cgaatctcta    1260
agattggttt tgtcgaaaaa ggaaggtgaa atctacagag aaaaggctag agaaatgtcc    1320
aaggtttact ctgataccaa gagagaaaag gaatatgtcg accaatttgt tgactacttg    1380
```
gaaaagaacg ctcgtgccgt tgccattgac cacgaaagc                    1419

<210> SEQ ID NO 3
<211> LENGTH: 473
<212> TYPE: PRT
<213> ORGANISM: Artificial sequence
<220> FEATURE:
<223> OTHER INFORMATION: UGT2_2b variant

<400> SEQUENCE: 3

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Gln
            20                  25                  30

Leu Ala Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Phe Val Lys Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Cys Asp Cys Leu Leu Ser Arg Thr Tyr
    210                 215                 220

His Glu Phe Gly Thr Gln Trp Leu Pro Leu Leu Glu Glu Leu His Gln
225                 230                 235                 240

Val Pro Val Val Pro Val Gly Leu Leu Pro Pro Ser Ile Pro Gly Asp
                245                 250                 255

Glu Lys Asp Glu Asn Trp Val Ser Ile Lys Asp Trp Leu Asp Lys Gln
            260                 265                 270

Glu Lys Gly Ser Val Val Tyr Val Ala Leu Gly Ser Glu Val Leu Leu
        275                 280                 285

Thr Glu Glu Glu Val Val Glu Leu Ala Leu Gly Leu Glu Leu Ser Gly
    290                 295                 300

Leu Pro Phe Phe Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Gly Gly Phe Val Thr His Cys Gly Ser Gly Ser Ile Val
```

```
                355             360             365
Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Gln Arg Asn Glu Glu Asp Gly Cys Leu Thr Lys Glu Ser Val
                405                 410                 415

Ala Glu Ser Leu Arg Leu Val Val Glu Lys Glu Gly Glu Ile Tyr
            420                 425                 430

Arg Glu Lys Ala Arg Glu Met Ser Lys Val Tyr Ser Asp Thr Lys Arg
        435                 440                 445

Glu Lys Glu Tyr Val Asp Gln Phe Val Asp Tyr Leu Glu Lys Asn Ala
    450                 455                 460

Arg Ala Val Ala Ile Asp His Glu Ser
465                 470

<210> SEQ ID NO 4
<211> LENGTH: 1419
<212> TYPE: DNA
<213> ORGANISM: Artificial sequence
<220> FEATURE:
<223> OTHER INFORMATION: UGT2_2b CpO for S. cerevisiae

<400> SEQUENCE: 4
atggccactt ctgactccat cgttgatgac agaaagaagt tgcacatcgt tatgttccca      60
tggttagctt tcggtcacat tatcccatac ttgcaattgg ctaaattgat tgctgaaaag     120
ggtcacaaag tctctttctt gtccaccacc agaaacatcc aaagattatc ttctcacatt     180
tctccattga tcaacttcgt caagttgact ttaccaagag ttcaagaatt gccagaagat     240
gctgaagcta ccaccgatgt ccatccagaa gatatcccat acttgaagaa ggcttctgat     300
ggtttgcaac cagaagtcac tgaattcttg aacaacactc tccagactga gattatctac     360
gactacactc actactggtt accatccatt gctactaagc acggtgtttc tcgtgctcat     420
ttctccgtta ccactccatg ggctattgct tacatgggtc aactgctga tgctatgatc      480 aacggttctg atggtagaac cactccagaa gacttcaccg ttccaccaaa atggttccca     540
ttcccaacca aggtctgttg agaaagcac gatttggcca gattagttcc atacaaggcc      600
ccaggtatct ctgacggtta cagaatgggt ttagtcttga agggttgtga ctgtttgttg     660
tccagaactt accatgaatt cggtactcaa tggttacctt tgttggaaga attgcaccaa     720
gtcccagttg ttccagttgg tttgttgcct ccttctatcc aggtgacga aaaggacgaa      780 aactgggttt ccatcaagga ctggttagat aagcaagaaa agggttccgt tgtctacgtt     840
gctttgggtt ctgaagtctt gttgactgaa gaagaagttg ttgaattggc tttgggtttg     900
gaattgtccg gtctaccatt tttctgggct tacagaaagc caagggtcc agctaagtct      960 gactctgttg aattgccaga tggtttcgtc gaaagaacca gagacagagg tttggtctgg    1020
acttcctggg ctccacaatt gagaattttg tcccacgaat ctgttggtgg tttcgttacc    1080
cactgtggtt ctggttccat tgtcgaaggt ttgatgttcg tcacccatt gatcatgttg     1140 ccaatcttcg gtgaccaacc attgaacgct agattattgg aagacaagca agtcggtatt    1200
gaaatccaaa gaaacgaaga agacggttgt ttgaccaagg aatctgttgc cgaatctcta    1260
agattggttt tgtcgaaaa ggaaggtgaa atctacagag aaaaggctag agaaatgtcc     1320
aaggtttact ctgataccaa gagagaaaag gaatatgtcg accaatttgt tgactacttg    1380
```

```
gaaaagaacg ctcgtgccgt tgccattgac cacgaaagc                          1419
```

<210> SEQ ID NO 5
<211> LENGTH: 1419
<212> TYPE: DNA
<213> ORGANISM: Artificial sequence
<220> FEATURE:
<223> OTHER INFORMATION: UGT2_2b CpO for Y. lipolitica

<400> SEQUENCE: 5

```
atggccacct ccgactccat tgtcgacgac cgaaagaagc tccacattgt catgttcccc     60
tggctcgcct ttggccacat cattccctac ctccagctcg ccaagctcat tgctgagaag    120
ggccacaagg tttctttcct ctccaccacc cgaaacatcc agcgactctc ttcccacatc    180
tctcccctca tcaactttgt caagctcacc ctcccccgag tccaggagct tcccgaggat    240
gctgaggcca ccactgatgt ccaccccgag gacatcccct acctcaagaa ggcttccgac    300
ggtctgcagc ccgaggtcac tgagtttctc gagcagcact ctcccgactg gatcatctac    360
gactacaccc actactggct ccctccatt gccaccaagc acgtgtctc tcgagcccac     420
ttctccgtca ccaccccctg gccattgct tacatgggtc ccactgccga tgccatgatc     480
aacggttccg acgccgaac cactcccgag gacttcactg tccctcccaa gtggttcccc    540
ttccccacca aggtctgctg gcgaaagcac gatctcgccc gactcgtccc ctacaaggcc    600
cccggtatct ccgacggtta cgaatgggt ctggtcctca agggctgtga ctgcctcctc     660
tctcgaacct accacgagtt cggcacccag tggctccccc ccttgagga gctgcaccag    720
gtccccgttg tccccgtcgg tctgctccct ccctccatcc ccggtgacga aggacgag     780
aactgggttt ccatcaagga ctggctcgac aagcaggaga agggctctgt tgtctacgtt    840
gctctcggct ccgaggttct gctcaccgag aagaggttg ttgagctggc tctcggtctg    900
gagctgtccg gcctccccct cttctggggcc taccgaaagc ccaagggccc cgccaagtcc    960
gactccgtcg agctgcccga cggtttcgtc gagcgaaccc gagatcgagg tctggtctgg   1020
acctcttggg ctccccagct ccgaatcctc tcccacgagt ccgttggtgg tttcgtcacc   1080
cactgcggtt ccggctccat cgtcgagggt ctgatgttcg ccacccctct catcatgctc   1140
cccatcttcg gtgaccagcc cctcaacgcc cgactgctcg aggataagca ggtcggtatc   1200
gagatccagc gaaacgaaga ggacggctgt ctgaccaagg agtccgtcgc cgagtctctc   1260
cgactcgttg ttgtcgagaa agaggggtgag atctaccgag agaaggcccg agagatgtcc   1320
aaggtctact ccgacaccaa gcgtgagaag gagtacgtcg accagttcgt cgactacctc   1380
gagaagaacg cccgagctgt tgccattgac cacgagtct                          1419
```

<210> SEQ ID NO 6
<211> LENGTH: 473
<212> TYPE: PRT
<213> ORGANISM: Artificial sequence
<220> FEATURE:
<223> OTHER INFORMATION: UGT2_3b variant

<400> SEQUENCE: 6

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Gln
            20                  25                  30

Leu Ala Lys Leu Ile Ala Glu Lys Gly His Lys Val Ser Phe Leu Ser
        35                  40                  45
```

```
Thr Thr Arg Asn Ile Gln Arg Leu Ser Ser His Ile Ser Pro Leu Ile
    50                  55                  60

Asn Phe Val Lys Leu Thr Leu Pro Arg Val Gln Glu Leu Pro Glu Asp
 65              70                  75                  80

Ala Glu Ala Thr Thr Asp Val His Pro Glu Asp Ile Pro Tyr Leu Lys
                 85                  90                  95

Lys Ala Ser Asp Gly Leu Gln Pro Glu Val Thr Glu Phe Leu Glu Gln
                100                 105                 110

His Ser Pro Asp Trp Ile Ile Tyr Asp Tyr Thr His Tyr Trp Leu Pro
                115                 120                 125

Ser Ile Ala Thr Lys His Gly Val Ser Arg Ala His Phe Ser Val Thr
130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
                180                 185                 190

Ala Arg Leu Val Pro Tyr Lys Ala Pro Gly Ile Ser Asp Gly Tyr Arg
                195                 200                 205

Met Gly Leu Val Leu Lys Gly Ser Asp Leu Leu Ser Arg Ser Tyr
                210                 215                 220

His Glu Phe Gly Thr Glu Trp Leu Arg Leu Leu Glu Thr Leu His Arg
225                 230                 235                 240

Val Pro Val Val Pro Val Gly Leu Leu Pro Pro Glu Ile Pro Gly Asp
                245                 250                 255

Gly Glu Asp Glu Ser Trp Val Ser Ile Lys Asp Trp Leu Asp Lys Lys
                260                 265                 270

Glu Lys Gly Ser Val Val Tyr Val Ala Leu Gly Ser Glu Val Leu Val
                275                 280                 285

Ser Gln Glu Glu Leu Asn Glu Leu Ala Leu Gly Leu Glu Leu Ser Gly
                290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Glu Glu Arg Thr Arg Gly Arg
                325                 330                 335

Gly Val Val Trp Thr Ser Trp Ala Pro Gln Leu Arg Ile Leu Ser His
                340                 345                 350

Glu Ser Val Ala Gly Phe Leu Thr His Cys Gly Ser Gly Ser Ile Val
                355                 360                 365

Glu Gly Leu Met Phe Gly His Pro Leu Ile Met Leu Pro Leu Phe Gly
                370                 375                 380

Asp Gln Pro Leu Asn Ala Arg Leu Leu Glu Asp Lys Gln Val Gly Ile
385                 390                 395                 400

Glu Ile Pro Arg Asp Glu Glu Asp Gly Cys Leu Thr Lys Glu Ser Val
                405                 410                 415

Ala Arg Ser Leu Arg Leu Val Met Val Glu Lys Glu Gly Glu Ile Tyr
                420                 425                 430

Arg Glu Lys Ala Arg Glu Met Ser Lys Ile Tyr Asn Asn Thr Glu Val
                435                 440                 445

Glu Asp Gln Tyr Val Ser Gln Phe Val Glu Tyr Leu Glu Lys Asn Ala
450                 455                 460

Arg Ala Val Ala Ile Asp His Glu Ser
```

<210> SEQ ID NO 7
<211> LENGTH: 1419
<212> TYPE: DNA
<213> ORGANISM: Artificial sequence
<220> FEATURE:
<223> OTHER INFORMATION: UGT2_3b CpO for S. cerevisiae

<400> SEQUENCE: 7

| | | | | | | |
|---|---|---|---|---|---|---|
| atggccactt | ctgactccat | cgttgatgac | agaaagaagt | tgcacatcgt | tatgttccca | 60 |
| tggttagctt | tcggtcacat | tatcccatac | ttgcaattgg | ctaaattgat | tgctgaaaag | 120 |
| ggtcacaaag | tctctttctt | gtccaccacc | agaaacatcc | aaagattatc | ttctcacatt | 180 |
| tctccattga | tcaacttcgt | caagttgact | ttaccaagag | ttcaagaatt | gccagaagat | 240 |
| gctgaagcta | ccaccgatgt | ccatccagaa | gatatcccat | acttgaagaa | ggcttctgat | 300 |
| ggtttgcaac | cagaagtcac | tgaattcttg | gaacaacact | ctccagactg | gattatctac | 360 |
| gactacactc | actactggtt | accatccatt | gctactaagc | acggtgtttc | tcgtgctcat | 420 |
| ttctccgtta | ccactccatg | ggctattgct | tacatgggtc | caactgctga | tgctatgatc | 480 |
| aacggttctg | atggtagaac | cactccagaa | gacttcaccg | ttccaccaaa | atggttccca | 540 |
| ttcccaacca | aggtctgttg | gagaaagcac | gatttggcca | gattagttcc | atacaaggcc | 600 |
| ccaggtatct | tgacggtta | cagaatgggt | ttagtcttga | agggtctga | cttgttgttg | 660 |
| tccagatctt | accatgaatt | cggtactgaa | tggttaagat | tgttggaaac | tttgcacaga | 720 |
| gtcccagttg | ttccagttgg | tttgttgcct | cctgaaatcc | aggtgacgg | tgaagacgaa | 780 |
| tctttgggttt | ccatcaagga | ctggttagat | aagaaggaaa | agggttccgt | tgtctacgtt | 840 |
| gctttggttt | ctgaagtctt | ggtttctcaa | gaagaattga | acgaattggc | tttgggtttg | 900 |
| gaattgtccg | gtctaccatt | tgtctgggct | tacagaaagc | caaagggtcc | agctaagtct | 960 |
| gactctgttg | aattgccaga | tggtttcgaa | gaaagaacca | gaggtagagg | tgttgtctgg | 1020 |
| acttcctggg | ctccacaatt | gagaattttg | tcccacgaat | ctgttgctgg | tttcttgacc | 1080 |
| cactgtggtt | ctggttccat | tgtcgaaggt | ttgatgttcg | gtcacccatt | gatcatgttg | 1140 |
| ccattgttcg | gtgaccaacc | attgaacgct | agattattgg | aagacaagca | agtcggtatt | 1200 |
| gaaatcccaa | gagatgaaga | agacggttgt | ttgaccaagg | aatctgttgc | cgttctcta | 1260 |
| agattggtta | tggtcgaaaa | ggaaggtgaa | atctacagag | aaaaggctag | agaaatgtcc | 1320 |
| aagatctaca | caacaccga | agtcgaagac | caatatgtct | cccaatttgt | tgaatacttg | 1380 |
| gaaaagaacg | ctcgtgccgt | tgccattgac | cacgaaagc | | | 1419 |

<210> SEQ ID NO 8
<211> LENGTH: 1419
<212> TYPE: DNA
<213> ORGANISM: Artificial sequence
<220> FEATURE:
<223> OTHER INFORMATION: UGT2_3b CpO for Y. lipolitica

<400> SEQUENCE: 8

| | | | | | | |
|---|---|---|---|---|---|---|
| atggccacct | ccgactccat | tgtcgacgac | cgaaagaagc | tccacattgt | catgttcccc | 60 |
| tggctcgcct | ttggccacat | catcccttac | ctccagctcg | ccaagctcat | tgctgagaag | 120 |
| ggccacaagg | tttccttcct | ctccaccacc | cgaaacatcc | agcgactctc | ctcccacatc | 180 |
| tctcctctca | tcaactttgt | caagctcacc | ctccccgag | tccaggagct | gcccgaggat | 240 |
| gctgaggcca | ccaccgatgt | ccaccccgag | gacatcccct | acctcaagaa | ggcctccgat | 300 |

```
ggcctccagc ccgaggtcac cgagttcctc gagcagcact ctcccgactg gatcatctac      360
gactacaccc actactggct cccctccatt gccaccaagc acggtgtctc tcgagcccac      420
ttctccgtca ccaccccctg ggccattgcc tacatgggtc ccactgctga cgccatgatc      480
aacggttccg acgccgaac cactcccgag gacttcactg tccctcccaa gtggttcccc       540
ttccccacca aggtctgctg gcgaaagcac gacctcgccc gactcgtccc ctacaaggct      600
cccggtatct ccgacggcta ccgaatgggt ctggtcctca agggctctga tctcctcctc      660
tctcgatctt accacgagtt cggcaccgag tggctccgac tgctcgagac tctccaccga      720
gtccccgttg tcccgtcgg tctgctccct cccgagatcc ccgtgacgg tgaggacgag        780
tcttgggttt ccatcaagga ctggctcgac aagaaggaga agggctccgt tgtctacgtt      840
gctctcggtt ccgaggttct tgtctcccaa gaggagctta acgagctggc tctcggtctg      900
gagctgtccg gtctgccctt tgtctgggcc taccgaaagc ccaagggccc cgccaagtcc      960
gactccgtcg agcttcccga cggtttcgag gagcgaaccc gaggccgagg tgttgtctgg     1020
acctcttggg ctccccagct ccgaatcctc tcccacgagt ccgtcgccgg tttcctcacc     1080
cactgcggtt ccggctccat tgttgagggt ctgatgttcg ccaccccct catcatgctc      1140
cccctcttcg gtgaccagcc cctcaacgcc cgacttctcg aggacaagca ggtcggtatt     1200
gagatccccc gagatgaaga ggacggctgt ctgaccaagg agtctgttgc ccgatctctg     1260
cgactcgtca tggtcgagaa ggaaggtgag atctaccgag agaaggcccg agagatgtcc     1320
aagatctaca acaaccacga ggtcgaggac cagtacgttt cccagttcgt cgagtacctt     1380
gagaagaacg cccgagctgt tgccattgac cacgaatca                            1419
```

<210> SEQ ID NO 9
<211> LENGTH: 473
<212> TYPE: PRT
<213> ORGANISM: Artificial sequence
<220> FEATURE:
<223> OTHER INFORMATION: UGT2_4b variant

<400> SEQUENCE: 9

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Leu Ala Ser Asp Gly Leu Gln Glu Pro Leu Thr Arg Phe Leu Glu Ser
            100                 105                 110

Ser Ser Pro Asp Trp Ile Ile Tyr Asp Tyr Thr His Tyr Trp Leu Pro
        115                 120                 125

Glu Ile Ala Ala Ser Leu Gly Val Ala Arg Ala His Phe Ser Val Thr
    130                 135                 140

Thr Pro Trp Ala Leu Ala Phe Met Gly Pro Ser Ala Asp Ala Met Ile
145                 150                 155                 160
```

| | | | | | | | | | | | |
|---|---|---|---|---|---|---|---|---|---|---|---|
|Asn|Gly|Ser|Asp|Gly|Arg|Thr|Glu|Val|Glu|Asp|Phe|Thr|Val|Pro|Pro|
| | |165| | | |170| | | |175| |

Lys Trp Ile Pro Phe Pro Thr Thr Val Ala Trp Arg Lys His Asp Leu
          180                 185                 190

Ala Arg Leu Val Pro Tyr Lys Ala Pro Gly Ile Ser Asp Gly Tyr Arg
          195                 200                 205

Met Gly Leu Val Leu Lys Gly Cys Asp Cys Leu Leu Ser Arg Thr Tyr
          210                 215                 220

His Glu Phe Gly Thr Gln Trp Leu Pro Leu Leu Glu Glu Leu His Gln
225                 230                 235                 240

Val Pro Val Val Pro Val Gly Leu Leu Pro Pro Ser Ile Pro Gly Asp
                    245                 250                 255

Glu Lys Asp Glu Asn Trp Val Ser Ile Lys Asp Trp Leu Asp Lys Gln
          260                 265                 270

Glu Lys Gly Ser Val Val Tyr Val Ala Leu Gly Ser Glu Val Leu Leu
          275                 280                 285

Thr Glu Glu Val Val Glu Leu Ala Leu Gly Leu Glu Leu Ser Gly
          290                 295                 300

Leu Pro Phe Phe Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                    325                 330                 335

Gly Leu Val Trp Thr Ser Trp Ala Pro Gln Leu Arg Ile Leu Ser His
                    340                 345                 350

Glu Ser Val Ala Gly Phe Leu Thr His Cys Gly Ser Gly Ser Ile Val
          355                 360                 365

Glu Gly Leu Met Phe Gly His Pro Leu Ile Met Leu Pro Leu Phe Gly
          370                 375                 380

Asp Gln Pro Leu Asn Ala Arg Leu Leu Glu Asp Lys Gln Val Gly Ile
385                 390                 395                 400

Glu Ile Pro Arg Asp Glu Asp Gly Cys Leu Thr Lys Glu Ser Val
          405                 410                 415

Ala Arg Ser Leu Arg Leu Val Met Val Glu Lys Glu Gly Glu Ile Tyr
          420                 425                 430

Arg Glu Lys Ala Arg Glu Met Ser Lys Ile Tyr Asn Asn Thr Glu Val
          435                 440                 445

Glu Asp Gln Tyr Val Ser Gln Phe Val Glu Tyr Leu Glu Lys Asn Ala
          450                 455                 460

Arg Ala Val Ala Ile Asp His Glu Ser
465                 470

<210> SEQ ID NO 10
<211> LENGTH: 1419
<212> TYPE: DNA
<213> ORGANISM: Artificial sequence
<220> FEATURE:
<223> OTHER INFORMATION: UGT2_4b CpO for S. cerevisiae

<400> SEQUENCE: 10
atggccactt ctgactccat cgttgatgac agaaagaagt tgcacatcgt tatgttccca    60
tggttagctt tcggtcacat tatcccatac ttggaattgt ccaaattgat tgctcaaaag   120
ggtcacaaag tctctttctt gtccaccacc aagaacatcg acagattatc ttctcacatt   180
tctccattga tcaacgttgt ccaattgact ttaccaagag ttcaagaatt gccagaagat   240
gctgaagcta ccaccgatgt ccatccagaa gatatcccat acttgaagtt ggcttctgat   300

```
ggtttgcaag aaccattgac tagattcttg gaatcttctt ctccagactg gattatctac    360
gactacactc actactggtt accagaaatt gctgcctctt ggtgtgttgc tcgtgctcat    420
ttctccgtta ccactccatg ggctttggct tcatgggtc catctgctga tgctatgatc     480
aacggttctg atggtagaac cgaagtcgaa gacttcaccg ttccaccaaa atggatccca    540
ttcccaacca ctgtcgcttg gagaaagcac gatttggcca gattagttcc atacaaggcc    600
ccaggtatct ctgacggtta cagaatgggt ttagtcttga aggggtgtga ctgtttgttg    660
tccagaactt accatgaatt cggtactcaa tggttacctt tgttggaaga attgcaccaa    720
gtcccagttg ttccagttgg tttgttgcct ccttctatcc caggtgacga aaaggacgaa    780
aactgggttt ccatcaagga ctggttagat aagcaagaaa agggttccgt tgtctacgtt    840
gctttgggtt ctgaagtctt gttgactgaa gaagaagttg ttgaattggc tttgggtttg    900
gaattgtccg gtctaccatt tttctgggct tacagaaagc caagggtcc agctaagtct     960 gactctgttg aattgccaga tggtttcgtc gaaagaacca gagacagagg tttggtctgg   1020
acttcctggg ctccacaatt gagaattttg tcccacgaat ctgttgctgg tttcttgacc   1080
cactgtggtt ctggttccat tgtcgaaggt ttgatgttcg gtcacccatt gatcatgttg   1140
ccattgttcg gtgaccaacc attgaacgct agattattgg aagacaagca gtcggtatt    1200 gaaatcccaa gagatgaaga agacggttgt ttgaccaagg aatctgttgc ccgttctcta   1260
agattggtta tggtcgaaaa ggaaggtgaa atctacagag aaaaggctag agaaatgtcc   1320
aagatctaca acaacaccga agtcgaagac caatatgtct cccaatttgt tgaatacttg   1380
gaaaagaacg ctcgtgccgt tgccattgac cacgaaagc                          1419
```

<210> SEQ ID NO 11
<211> LENGTH: 473
<212> TYPE: PRT
<213> ORGANISM: Artificial sequence
<220> FEATURE:
<223> OTHER INFORMATION: UGT2_5b variant

<400> SEQUENCE: 11

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
            85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160
```

-continued

```
Asn Gly Ser Asp Gly Arg Thr Thr Pro Glu Asp Phe Thr Val Pro Pro
            165                 170                 175
Lys Trp Phe Pro Phe Pro Thr Lys Val Cys Trp Arg Lys His Asp Leu
        180                 185                 190
Ala Arg Leu Val Pro Tyr Lys Ala Pro Gly Ile Ser Asp Gly Tyr Arg
    195                 200                 205
Met Gly Leu Val Leu Lys Gly Ser Asp Leu Leu Ser Arg Ser Tyr
210                 215                 220
His Glu Phe Gly Thr Glu Trp Leu Arg Leu Leu Glu Thr Leu His Arg
225                 230                 235                 240
Val Pro Val Val Pro Val Gly Leu Leu Pro Pro Glu Ile Pro Gly Asp
                245                 250                 255
Gly Glu Asp Glu Ser Trp Val Ser Ile Lys Asp Trp Leu Asp Lys Lys
            260                 265                 270
Glu Lys Gly Ser Val Val Tyr Val Ala Leu Gly Ser Glu Val Leu Val
        275                 280                 285
Ser Gln Glu Glu Leu Asn Glu Leu Ala Leu Gly Leu Glu Leu Ser Gly
    290                 295                 300
Leu Pro Phe Val Trp Ala Tyr Arg Lys Pro Lys Gly Pro Ala Lys Ser
305                 310                 315                 320
Asp Ser Val Glu Leu Pro Asp Gly Phe Glu Glu Arg Thr Arg Gly Arg
                325                 330                 335
Gly Val Val Trp Thr Ser Trp Ala Pro Gln Leu Arg Ile Leu Ser His
            340                 345                 350
Glu Ser Val Gly Gly Phe Val Thr His Cys Gly Ser Gly Ser Ile Val
        355                 360                 365
Glu Gly Leu Met Phe Gly His Pro Leu Ile Met Leu Pro Ile Phe Gly
    370                 375                 380
Asp Gln Pro Leu Asn Ala Arg Leu Leu Glu Asp Lys Gln Val Gly Ile
385                 390                 395                 400
Glu Ile Pro Arg Asn Glu Glu Asp Gly Cys Leu Thr Lys Glu Ser Val
                405                 410                 415
Ala Glu Ser Leu Arg Leu Val Val Glu Lys Glu Gly Glu Ile Tyr
            420                 425                 430
Arg Glu Lys Ala Arg Glu Met Ser Lys Val Tyr Ser Asp Thr Lys Arg
        435                 440                 445
Glu Lys Glu Tyr Val Asp Gln Phe Val Asp Tyr Leu Glu Lys Asn Ala
    450                 455                 460
Arg Ala Val Ala Ile Asp His Glu Ser
465                 470
```

<210> SEQ ID NO 12
<211> LENGTH: 1419
<212> TYPE: DNA
<213> ORGANISM: Artificial sequence
<220> FEATURE:
<223> OTHER INFORMATION: UGT2_5b CpO for S. cerevisiae

<400> SEQUENCE: 12

```
atggccactt ctgactccat cgttgatgac agaaagaagt tgcacatcgt tatgttccca      60
tggttagctt tcggtcacat tatcccatac ttggaattgt ccaaattgat tgctcaaaag     120
ggtcacaaag tctctttctt gtccaccacc aagaacatcg acagattatc ttctcacatt     180
tctccattga tcaacgttgt ccaattgact ttaccaagag ttcaagaatt gccagaagat     240
gctgaagcta ccaccgatgt ccatccagaa gatatcccat acttgaagaa ggcttctgat     300
```

```
ggtttgcaac cagaagtcac tgaattcttg gaacaacact ctccagactg gattatctac    360
gactacactc actactggtt accatccatt gctactaagc acggtgtttc tcgtgctcat    420
ttctccgtta ccactccatg ggctattgct tacatgggtc caactgctga tgctatgatc    480
aacggttctg atggtagaac cactccagaa gacttcaccg ttccaccaaa atggttccca    540
ttcccaacca aggtctgttg agaaagcac gatttggcca gattagttcc atacaaggcc     600
ccaggtatct ctgacggtta cagaatgggt ttagtcttga agggtctga cttgttgttg     660 tccagatctt accatgaatt cggtactgaa tggttaagat tgttggaaac tttgcacaga    720
gtcccagttg ttccagttgg tttgttgcct cctgaaatcc caggtgacgg tgaagacgaa    780
tcttgggttt ccatcaagga ctggttagat aagaaggaaa agggttccgt tgtctacgtt    840
gctttgggtt ctgaagtctt ggtttctcaa gaagaattga cgaattggc tttgggtttg     900 gaattgtccg gtctaccatt tgtctgggct tacagaaagc caagggtcc agctaagtct     960 gactctgttg aattgccaga tggtttcgaa gaaagaacca gaggtagagg tgttgtctgg   1020
acttcctggg ctccacaatt gagaattttg tcccacgaat ctgttggtgg tttcgttacc   1080
cactgtggtt ctggttccat tgtcgaaggt ttgatgttcg gtcacccatt gatcatgttg   1140
ccaatcttcg gtgaccaacc attgaacgct agattattgg aagacaagca agtcggtatt   1200
gaaatcccaa gaaacgaaga gacggttgt tgaccaagg aatctgttgc cgaatctcta     1260
agattggttg ttgtcgaaaa ggaaggtgaa atctacagag aaaaggctag agaaatgtcc   1320
aaggtttact ctgataccaa gagagaaaag gaatatgtcg accaatttgt tgactacttg   1380
gaaaagaacg ctcgtgccgt tgccattgac cacgaaagc                          1419

<210> SEQ ID NO 13
<211> LENGTH: 1419
<212> TYPE: DNA
<213> ORGANISM: Artificial sequence
<220> FEATURE:
<223> OTHER INFORMATION: UGT2_5b CpO for Y. lipolitica

<400> SEQUENCE: 13
atggccacct ccgactccat tgtcgacgac cgaaagaagc tccacattgt catgttcccc     60
tggctcgcct tcggccacat catcccttac ctggagctgt ccaagctcat gcccagaag    120 ggccacaagg tttcttttcct ctccaccacc aagaacattg accgactctc ctcccacatc    180
tctcctctca tcaacgttgt ccagctcacc ctccccgag tccaggagct tcccgaggat      240
gctgaggcca ccaccgacgt ccaccccgag gacatcccct acctcaagaa ggcctccgat    300
ggcctccagc ccgaggtcac cgagttcctc gagcagcact ccccgactg gatcatctac     360 gactacaccc actactggct cccctccatt gccaccaagc acggtgtctc tcgagcccac    420
ttctccgtca ccaccccctg ggccattgcc tacatgggtc ccactgccga cgccatgatc    480
aacggttccg acggccgaac caccccgag gatttcactg tccctcccaa gtggttcccc     540
ttccccacca aggtctgctg gcgaaagcac gacctcgctc gactcgtccc ctacaaggcc    600
cccggtatct ccgacggtta ccgaatgggt ctggttctca gggctccga tctcctcctc    660 tctcgatctt accgcgagtt tggtactgag tggctccgac tgctcgagac ctccaccga    720 gtccccgttg tccccgtcgg cctcctccct cccgagatcc ccggtgatgg tgaggacgag    780
tcttgggttt ccatcaagga ctggctcgac aagaaggaga agggctctgt tgtctacgtt    840
gctctcggtt ccgaggtcct tgtctctcaa gaggagctta cgagcttgc tctgggcctc    900
```

```
gagctgtccg gcctcccctt cgtctgggcc taccgaaagc ccaagggtcc cgccaagtcc    960
gactccgtcg agctgcccga cggtttcgag gagcgaaccc gaggccgagg tgttgtctgg   1020
acctcttggg ctccccagct ccgaatcctc tcccacgagt ccgtcggtgg ctttgtcacc   1080
cactgcggtt ccggctccat cgtcgagggt ctgatgtttg ccaccccct catcatgctc    1140 cccatcttcg gtgaccagcc cctcaacgcc cgactccttg aggacaagca ggtcggtatt   1200
gagatccccc gaaacgagga agatggttgt ctgaccaagg agtctgttgc tgagtctctg   1260
cgactcgttg ttgtcgagaa agagggtgag atctaccggg agaaggcccg agagatgtcc   1320
aaggtctact ccgacaccaa gcgagagaag gagtacgtcg accagttcgt cgactacctc   1380
gagaagaacg cccgagctgt tgccattgac cacgaatcc                           1419
```

<210> SEQ ID NO 14
<211> LENGTH: 473
<212> TYPE: PRT
<213> ORGANISM: Artificial sequence
<220> FEATURE:
<223> OTHER INFORMATION: UGT2_6b variant

<400> SEQUENCE: 14

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Ile Lys Gly Cys Asp Cys Leu Leu Ser Lys Thr Tyr
    210                 215                 220

His Glu Phe Gly Thr Gln Trp Leu Arg Leu Leu Glu Thr Leu His Arg
225                 230                 235                 240

Lys Pro Val Ile Pro Val Gly Leu Leu Pro Pro Ser Ile Pro Gly Ser
                245                 250                 255

Asp Lys Asp Asp Ser Trp Val Ser Ile Lys Glu Trp Leu Asp Gly Gln
            260                 265                 270
```

```
Glu Lys Gly Ser Val Val Tyr Val Ala Leu Gly Ser Glu Val Leu Val
            275                 280                 285
Thr Gln Asp Glu Val Val Glu Leu Ala His Gly Leu Glu Leu Ser Gly
        290                 295                 300
Leu Pro Phe Val Trp Ala Tyr Arg Asn Pro Lys Gly Pro Ala Lys Ser
305                 310                 315                 320
Asp Ser Val Glu Leu Pro Asp Gly Phe Val Glu Arg Val Arg Asp Arg
                325                 330                 335
Gly Leu Val Trp Thr Ser Trp Ala Pro Gln Leu Arg Ile Leu Ser His
            340                 345                 350
Glu Ser Val Cys Gly Phe Leu Thr His Cys Gly Ser Gly Ser Ile Val
        355                 360                 365
Glu Gly Leu Met Phe Gly His Pro Leu Ile Met Leu Pro Ile Phe Gly
    370                 375                 380
Asp Gln Pro Leu Asn Ala Arg Leu Leu Glu Asp Lys Gln Val Gly Ile
385                 390                 395                 400
Glu Ile Pro Arg Asn Glu Glu Asp Gly Ser Phe Thr Arg Asp Ser Val
                405                 410                 415
Ala Glu Ser Leu Arg Leu Val Met Val Glu Glu Gly Lys Ile Tyr
            420                 425                 430
Arg Glu Lys Ala Lys Glu Met Ser Lys Leu Phe Gly Asp Lys Asp Leu
        435                 440                 445
Gln Asp Gln Tyr Val Asp Asp Phe Val Glu Tyr Leu Gln Lys His Arg
    450                 455                 460
Arg Ala Val Ala Ile Asp His Glu Ser
465                 470

<210> SEQ ID NO 15
<211> LENGTH: 1419
<212> TYPE: DNA
<213> ORGANISM: Artificial sequence
<220> FEATURE:
<223> OTHER INFORMATION: UGT2_6b CpO for S. cerevisiae

<400> SEQUENCE: 15
atggccactt ctgactccat cgttgatgac agaaagaagt tgcacatcgt tatgttccca      60
tggttagctt tcggtcacat tatcccatac ttggaattgt ccaaattgat tgctcaaaag     120
ggtcacaaag tctctttctt gtccaccacc aagaacatcg acagattatc ttctcacatt     180
tctccattga tcaacgttgt ccaattgact ttaccaagag ttcaagaatt gccagaagat     240
gctgaagcta ccaccgatgt ccatccagaa gatatcccat acttgaagaa ggcttctgat     300
ggtttgcaac cagaagtcac tgaattcttg aacaacact ctccagactg gattatctac     360
gactacactc actactggtt accatccatt gctactaagc acgtgtttc tcgtgctcat     420 ttctccgtta ccactccatg ggctattgct acatgggtc caactgctga tgctatgatc     480
aacggttctg atggtagaac cactccagaa gacttcaccg ttccaccaaa atggttccca     540
ttcccaacca aggtctgttg agaaagcac gatttggcca gattagttcc atacaaggcc     600
ccaggtatct ctgacggtta cagaatgggt ttagtcatca agggttgtga ctgtttgttg     660
tccaagactt accatgaatt cggtactcaa tggttaagat gttggaaac tttgcacaga     720 aagccagtta tcccagttgg tttgttgcct ccttctatcc aggttctga caaggacgac     780 tcttgggttt ccatcaagga atggttagat ggtcaagaaa agggttccgt tgtctacgtt     840
gctttgggtt ctgaagtctt ggttactcaa gacgaagttg ttgaattggc tcacggtttg     900
```

```
gaattgtccg gtctaccatt tgtctgggct tacagaaacc caaagggtcc agctaagtct    960
gactctgttg aattgccaga tggtttcgtc gaaagagtta gagacagagg tttggtctgg    1020
acttcctggg ctccacaatt gagaattttg tcccacgaat ctgtttgtgg tttcttgact    1080
cactgtggtt ctggttctat cgtcgaaggt ttgatgttcg gtcatccttt gatcatgttg    1140
cctatctttg gtgaccaacc attgaacgct agattgttgg aagacaagca agttggtatt    1200
gaaattccaa gaaacgaaga gatggttct ttcaccagag actctgttgc tgaatctttg     1260
agattagtca tggttgaaga agaaggtaag atctacagag aaaaggccaa ggaaatgtcc    1320
aagttgtttg gtgacaaaga tttgcaagac caatacgtcg atgacttcgt cgaatacttg    1380
caaaagcacc gtcgtgccgt tgccattgac cacgaatca                           1419

<210> SEQ ID NO 16
<211> LENGTH: 1419
<212> TYPE: DNA
<213> ORGANISM: Artificial sequence
<220> FEATURE:
<223> OTHER INFORMATION: UGT2_6b CpO for Y. lipolitica

<400> SEQUENCE: 16
atggctactt ccgactccat tgtcgacgac cgaaagaagc tccacattgt catgttcccc     60
tggctcgcct ttggccacat cattccctac ctcgagcttt ccaagctcat tgcccagaag    120
ggccacaagg tttctttcct ctccaccacc aagaacattg accgactctc ctcccacatc    180
tctcctctca tcaacgttgt ccagctcacc ctcccccgag tccaggagct gcccgaggac    240
gccgaggcca ccaccgatgt ccaccccgag gatatcccct acctcaagaa ggcctccgac    300
ggtctgcagc ccgaggtcac cgagttcctc gagcagcact ctcccgactg gatcatctac    360
gactacaccc actactggct ccccctccat tgccaccaag acggtgtctc tcgagcccac    420
ttctccgtca ccaccccctg ggccattgcc tacatgggcc ccactgctga cgccatgatc    480
aacggttccg atggccgaac caccccccgag gacttcactg tccctcccaa gtggttcccc    540
ttccccacca aggtctgctg gcgaaagcac gatctggccc gactcgttcc ctacaaggcc    600
cccggtatct ccgacggcta ccgaatgggt ctggtcatca gggctgcga ctgtctgctc     660 tccaagacct accacgagtt tggcacccag tggctccgac tcctcgagac tctccaccga    720
aagcccgtca tccccgtcgg tctgctccct cctccatcc ccggctccga caaggacgac    780
tcttgggttt ccatcaagga gtggctcgac ggccaggaga agggctctgt tgtctacgtt    840
gctctcggtt ccgaggttct cgtcacccag gacgaggttg ttgagctggc cacgggtctg    900
gagctgtccg gcctcccctt cgtctgggct taccgaaacc ccaagggtcc cgccaagtcc    960
gactccgtcg agcttcccga tggtttcgtc gagcgagtcc gagatcgagg tctggtctgg    1020
acctcttggg ctccccagct ccgaatcctc tcccacgagt ccgtctgtgg tttcctcacc    1080
cactgcggtt ccggctccat cgtcgagggt ctgatgttcg gccaccccct catcatgctc    1140
cccatcttcg gtgaccagcc cctcaacgcc cgactccttg aggacaagca ggtcggtatc    1200
gagatccccc gaaacgaaga ggacggttcc ttcccgag actctgttgc tgagtctctc     1260
cgactcgtca tggtcgagga gagggtaag atctaccgag agaaggccaa ggagatgtcc    1320
aagctgttcg gtgacaagga tctccaggac cagtacgtcg acgactttgt cgagtacctc    1380
cagaagcacc gacgagctgt tgccattgac cacgagtct                          1419

<210> SEQ ID NO 17
<211> LENGTH: 473
```

<212> TYPE: PRT
<213> ORGANISM: Artificial sequence
<220> FEATURE:
<223> OTHER INFORMATION: UGT2_7b variant

<400> SEQUENCE: 17

Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Glu Ile Ala Lys Ser Leu Gly Val Ser Arg Ala His Phe Ser Val Thr
    130                 135                 140

Thr Pro Trp Ala Ile Ala Tyr Ile Gly Pro Thr Ala Asp Ala Met Ile
145                 150                 155                 160

Asn Gly Ser Asp Tyr Arg Thr Glu Leu Glu Asp Phe Thr Val Pro Pro
                165                 170                 175

Lys Trp Phe Pro Phe Pro Thr Thr Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Ile Lys Gly Cys Asp Cys Leu Leu Ser Lys Thr Tyr
    210                 215                 220

His Glu Phe Gly Thr Gln Trp Leu Arg Leu Leu Glu Thr Leu His Arg
225                 230                 235                 240

Lys Pro Val Ile Pro Val Gly Leu Leu Pro Pro Ser Ile Pro Gly Ser
                245                 250                 255

Asp Lys Asp Asp Ser Trp Val Ser Ile Lys Glu Trp Leu Asp Gly Gln
            260                 265                 270

Glu Lys Gly Ser Val Val Tyr Val Ala Leu Gly Ser Glu Val Leu Val
        275                 280                 285

Thr Gln Asp Glu Val Val Glu Leu Ala His Gly Leu Glu Leu Ser Gly
    290                 295                 300

Leu Pro Phe Val Trp Ala Tyr Arg Asn Pro Lys Gly Pro Ala Lys Ser
305                 310                 315                 320

Asp Ser Val Glu Leu Pro Asp Gly Phe Val Glu Arg Val Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

```
Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Phe Thr Arg Asp Ser Val
            405                 410                 415

Ala Glu Ser Leu Arg Leu Val Met Val Glu Glu Gly Lys Ile Tyr
        420                 425                 430

Arg Glu Lys Ala Lys Glu Met Ser Lys Leu Phe Gly Asp Lys Asp Leu
        435                 440                 445

Gln Asp Gln Tyr Val Asp Asp Phe Val Glu Tyr Leu Gln Lys His Arg
        450                 455                 460

Arg Ala Val Ala Ile Asp His Glu Ser
465                 470
```

<210> SEQ ID NO 18
<211> LENGTH: 1419
<212> TYPE: DNA
<213> ORGANISM: Artificial sequence
<220> FEATURE:
<223> OTHER INFORMATION: UGT2_7b CpO for S. cerevisiae

<400> SEQUENCE: 18

```
atggccactt ctgactccat cgttgatgac agaaagaagt tgcacatcgt tatgttccca      60
tggttagctt tcggtcacat tatcccatac ttggaattgt ccaaattgat tgctcaaaag     120
ggtcacaaag tctctttctt gtccaccacc aagaacatcg acagattatc ttctcacatt     180
tctccattga tcaacgttgt ccaattgact ttaccaagag ttcaagaatt gccagaagat     240
gctgaagcta ccaccgatgt ccatccagaa gatatcccat acttgaagaa ggcttctgat     300
ggtttgcaac agaagtcac tgaattcttg aacaacact ctccagactg gattatctac      360
gactacactc actactggtt accagaaatt gctaagtctt gggtgtttc tcgtgctcat      420
ttctccgtta ccactccatg ggctattgct acattggtc caactgctga tgctatgatc     480
aacggttctg attacagaac cgaattggaa gacttcaccg ttccaccaaa atggttccca     540
ttcccaacca ctgtctgttg agaaagcac gatttggcca gattagttcc atacaaggcc      600
ccaggtatct ctgacggtta cagaatgggt ttagtcatca agggtgtga ctgtttgttg      660
tccaagactt accatgaatt cggtactcaa tggttaagat tgttggaaac tttgcacaga     720
aagccagtta tcccagttgg tttgttgcct ccttctatcc aggttctga caaggacgac      780
tcttgggttt ccatcaagga tggttagat ggtcaagaaa agggttccgt tgtctacgtt      840
gctttgggtt ctgaagtctt ggttactcaa gacgaagttg ttgaattggc tcacggtttg     900
gaattgtccg gtctaccatt tgtctgggct acagaaaacc caagggtcc agctaagtct      960
gactctgttg aattgccaga tggtttcgtc gaaagagtta gagacagagg tttggtctgg    1020
acttcctggg ctccacaatt gagaattttg tcccacgaat ctgtttgtgg tttcttgact    1080
cactgtggtt ctggttctat cgtcgaaggt ttgatgttcg gtcatccttt gatcatgttg    1140
cctatctttg gtgaccaacc attgaacgct agattgttgg aagacaagca agttggtatt    1200
gaaattccaa gaaacgaaga agatggttct ttcaccagag actctgttgc tgaatctttg    1260
agattagtca tggttgaaga agaaggtaag atctacagag aaaaggccaa ggaaatgtcc    1320
aagttgtttg gtgacaaaga tttgcaagac caatacgtcg atgacttcgt cgaatacttg    1380
caaaagcacc gtcgtgccgt tgccattgac cacgaatca                           1419
```

<210> SEQ ID NO 19
<211> LENGTH: 1419

```
<212> TYPE: DNA
<213> ORGANISM: Artificial sequence
<220> FEATURE:
<223> OTHER INFORMATION: UGT2_7b CpO for Y. lipolitica

<400> SEQUENCE: 19
atggccacct ccgactccat tgttgacgac cgaaagaagc tccacattgt catgttcccc     60
tggctcgcct tcggccacat cattccctac ctcgagcttt ccaagctcat tgcccagaag    120
ggccacaagg tttctttcct ctccaccacc aagaacattg accgactctc ctcccacatc    180
tctcctctca tcaacgttgt ccagctcacc ctcccccgag tccaggagct gcccgaggat    240
gctgaggcca ccaccgacgt ccaccccgag gatatcccct acctcaagaa ggcctccgat    300
ggtctgcagc ccgaggtcac cgagttcctc gagcagcact ctcccgactg gatcatctac    360
gactacaccc actactggct ccccgagatt gccaagtctc tcggtgtctc tcgagcccac    420
ttctccgtca ccaccccctg ggccattgct acatcggtc ccactgctga cgccatgatc    480
aacggctccg actaccgaac tgaactcgag gacttcactg ttcctcccaa gtggttcccc    540
ttccccacca ccgtctgctg cgaaagcac gatctcgccc gactggtccc ctacaaggct    600
cccggtatct ccgacggcta ccgaatgggt ctggtcatca agggttgcga ctgtctgctc    660
tccaagacct accacgagtt tggcacccag tggctgcgac tcctcgagac tctccaccga    720
aagcccgtca tccccgtcgg tctgctgccc ccttccatcc ccggttccga caaggacgac    780
tcttgggttt ccatcaagga gtggctcgac ggccaggaga agggctctgt tgtctacgtt    840
gctctcggct ccgaggttct cgtcacccag gacgaggttg tcgagctggc cacggtctg     900
gagctgtccg gtctgccctt cgtctgggcc taccgaaacc ccaagggccc cgccaagtcc    960
gactccgtcg agcttcccga tggtttcgtc gagcgagtcc gagatcgagg tctggtctgg   1020
acctcttggg ctccccagct ccgaatcctc tcccacgagt ccgtctgcgg tttcctcacc   1080
cactgtggtt ccggctccat tgtcgagggt ctgatgttcg ccaccccct catcatgctc   1140
cccatcttcg gtgaccagcc cctcaacgcc cgactccttg aggacaagca ggtcggtatc   1200
gagatccccc gaaacgaaga ggacggctct ttcacccgag actccgttgc cgagtctctc   1260
cgactcgtca tggtcgagga gagggtaag atctaccgag agaaggccaa ggagatgtcc   1320
aagctctttg gtgacaagga tctccaggac cagtacgtcg acgactttgt cgagtacctc   1380
cagaagcacc gacgagctgt tgccatcgac cacgagtcg                          1419

<210> SEQ ID NO 20
<211> LENGTH: 473
<212> TYPE: PRT
<213> ORGANISM: Artificial sequence
<220> FEATURE:
<223> OTHER INFORMATION: UGT2_8b

<400> SEQUENCE: 20

Met Ala Thr Ser Asp Ser Ile Val Asp Asp Arg Lys Gln Leu His Ile
1               5                  10                  15

Val Met Phe Pro Trp Leu Ala Phe Gly His Ile Ile Pro Tyr Leu Glu
                20                  25                  30

Leu Ser Lys Leu Ile Ala Glu Lys Gly His Lys Val Ser Phe Leu Ser
            35                  40                  45

Thr Pro Lys Asn Ile Gln Arg Leu Ser Ser His Leu Ser Pro Leu Ile
        50                  55                  60

Asn Val Val Gln Leu Pro Leu Pro Arg Val Gln Glu Leu Pro Glu Asp
65                  70                  75                  80
```

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Ile Lys Gly Cys Asp Cys Leu Leu Ser Lys Thr Tyr
    210                 215                 220

His Glu Phe Gly Thr Gln Trp Leu Arg Leu Leu Glu Thr Leu His Arg
225                 230                 235                 240

Lys Pro Val Ile Pro Val Gly Leu Leu Pro Pro Ser Ile Pro Gly Ser
                245                 250                 255

Asp Lys Asp Asp Ser Trp Val Ser Ile Lys Glu Trp Leu Asp Gly Gln
            260                 265                 270

Glu Lys Gly Ser Val Val Tyr Val Ala Leu Gly Ser Glu Val Leu Val
        275                 280                 285

Thr Gln Asp Glu Val Val Glu Leu Ala His Gly Leu Glu Leu Ser Gly
    290                 295                 300

Leu Pro Phe Val Trp Ala Tyr Arg Asn Pro Lys Gly Pro Ala Lys Ser
305                 310                 315                 320

Asp Ser Val Glu Leu Pro Asp Gly Phe Val Glu Arg Val Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Phe Thr Arg Asp Ser Val
                405                 410                 415

Ala Glu Ser Leu Arg Leu Val Met Val Glu Glu Gly Lys Ile Tyr
            420                 425                 430

Arg Glu Lys Ala Lys Glu Met Ser Lys Leu Phe Gly Asp Lys Asp Leu
        435                 440                 445

Gln Asp Gln Tyr Val Asp Asp Phe Val Glu Tyr Leu Gln Lys His Arg
    450                 455                 460

Arg Ala Val Ala Ile Asp His Glu Ser
465                 470

<210> SEQ ID NO 21
<211> LENGTH: 1419

<212> TYPE: DNA
<213> ORGANISM: Artificial sequence
<220> FEATURE:
<223> OTHER INFORMATION: UGT_8b CpO for S. cerevisiae

<400> SEQUENCE: 21

```
atggccactt ctgactccat cgttgatgac agaaagcaat gcacatcgt tatgttccca        60
tggttagctt tcggtcacat tatcccatac ttggaattgt ccaaattgat gctgaaaag       120
ggtcacaaag tctctttctt gtccaccca  aagaacatcc aaagattatc ttctcacttg      180
tctccattga tcaacgttgt ccaattgcca ttaccaagag ttcaagaatt gccagaagat      240
gctgaagcta ccaccgatgt ccatccagaa gatatcccat acttgaagaa ggcttctgat      300
ggtttgcaac agaagtcac  tgaattcttg aacaacact  ctccagactg gattatctac      360
gactacactc actactggtt accatccatt gctactaagc acggtgtttc tcgtgctcat      420
ttctccgtta ccactccatg ggctattgct tacatgggtc aactgctga  tgctatgatc      480
aacggttctg atggtagaac cactccagaa gacttcaccg ttccaccaaa atggttccca      540
ttcccaacca aggtctgttg agaaagcac  gatttggcca gattagttcc atacaaggcc      600
ccaggtatct ctgacggtta cagaatgggt ttagtcatca agggtgtga  ctgtttgttg      660
tccaagactt accatgaatt cggtactcaa tggttaagat tgttggaaac tttgcacaga      720
aagccagtta tcccagttgg tttgttgcct ccttctatcc aggttctga  caaggacgac      780
tcttgggttt ccatcaagga atggttagat ggtcaagaaa agggttccgt tgtctacgtt      840
gctttgggtt ctgaagtctt ggttactcaa gacgaagttg ttgaattggc tcacggtttg      900
gaattgtccg gtctaccatt tgtctgggct acagaaaacc caagggtcc  agctaagtct      960
gactctgttg aattgccaga tggtttcgtc gaaagagtta gagacagagg tttggtctgg     1020
acttcctggg ctccacaatt gagaattttg tcccacgaat ctgtttgtgg tttcttgact     1080
cactgtggtt ctggttctat cgtcgaaggt ttgatgttcg gtcatccttt gatcatgttg     1140
cctatctttg gtgaccaacc attgaacgct agattgttgg aagacaagca agttggtatt     1200
gaaattccaa gaaacgaaga agatggttct ttcaccagag actctgttgc tgaatctttg     1260
agattagtca tggttgaaga agaaggtaag atctacagag aaaaggccaa ggaaatgtcc     1320
aagttgtttg gtgacaaaga tttgcaagac caatacgtcg atgacttcgt cgaatacttg     1380
caaaagcacc gtcgtgccgt tgccattgac acgaatca                              1419
```

<210> SEQ ID NO 22
<211> LENGTH: 473
<212> TYPE: PRT
<213> ORGANISM: Artificial sequence
<220> FEATURE:
<223> OTHER INFORMATION: UGT2_9b variant

<400> SEQUENCE: 22

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Gln
            20                  25                  30

Leu Ser Lys Leu Leu Ala Gln Lys Gly His Lys Val Ser Phe Ile Ser
        35                  40                  45

Thr Pro Arg Asn Ile Gln Arg Leu Ser Ser His Ile Ser Pro Leu Ile
    50                  55                  60

Asn Leu Val Gln Leu Pro Leu Pro Arg Val Asp Asn Leu Pro Glu Asp
65                  70                  75                  80
```

```
Ala Glu Ala Thr Thr Asp Val His Pro Glu Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
            115                 120                 125

Glu Ile Ala Lys Ser Leu Gly Val Ser Arg Ala His Phe Ser Val Thr
            130                 135                 140

Thr Pro Trp Ala Ile Ala Tyr Met Gly Pro Thr Ala Asp Ala Met Ile
145                 150                 155                 160

Asn Gly Ser Asp Tyr Arg Thr Glu Leu Glu Asp Phe Thr Val Pro Pro
                165                 170                 175

Lys Trp Phe Pro Phe Pro Thr Thr Val Cys Trp Arg Lys His Asp Leu
            180                 185                 190

Ala Arg Leu Val Pro Tyr Lys Ala Pro Gly Ile Ser Asp Gly Tyr Arg
            195                 200                 205

Met Gly Leu Val Leu Lys Gly Ser Asp Leu Leu Ser Arg Ser Tyr
            210                 215                 220

His Glu Phe Gly Thr Glu Trp Leu Arg Leu Leu Glu Thr Leu His Arg
225                 230                 235                 240

Val Pro Val Val Pro Val Gly Leu Leu Pro Pro Glu Ile Pro Gly Asp
                245                 250                 255

Gly Glu Asp Glu Ser Trp Val Ser Ile Lys Asp Trp Leu Asp Lys Lys
            260                 265                 270

Glu Lys Gly Ser Val Val Tyr Val Ala Leu Gly Ser Glu Val Leu Val
            275                 280                 285

Ser Gln Glu Glu Leu Asn Glu Leu Ala Leu Gly Leu Glu Leu Ser Gly
            290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Glu Glu Arg Thr Arg Gly Arg
                325                 330                 335

Gly Val Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
            355                 360                 365

Glu Gly Leu Met Phe Gly His Pro Leu Ile Met Leu Pro Ile Phe Gly
370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Leu Thr Lys Glu Ser Val
                405                 410                 415

Ala Arg Ser Leu Arg Ser Val Val Glu Glu Glu Gly Lys Ile Tyr
            420                 425                 430

Arg Glu Lys Ala Lys Glu Met Ser Lys Leu Phe Gly Asp Lys Asp Leu
            435                 440                 445

Gln Asp Gln Tyr Val Asp Asp Phe Val Glu Tyr Leu Gln Lys His Arg
450                 455                 460

Arg Ala Val Ala Ile Asp His Glu Ser
465                 470

<210> SEQ ID NO 23
<211> LENGTH: 1419
```

```
<212> TYPE: DNA
<213> ORGANISM: Artificial sequence
<220> FEATURE:
<223> OTHER INFORMATION: UGT2_9b CpO for S.cerevisiae

<400> SEQUENCE: 23
atggccactt ctgactccat cgttgatgac agaaagaagt tgcacatcgt tatgttccca    60
tggttagctt ccggtcacat tatcccatac ttgcaattgt ccaaattgtt ggctcaaaag   120
ggtcacaaag tctctttcat ctccacccca gaaacatcc aaagattatc ttctcacatt   180
tctccattga tcaacttggt ccaattgcca ttaccaagag ttgacaactt gccagaagat   240
gctgaagcta ccaccgatgt ccatccagaa gatatcccat acttgaagaa ggcttctgat   300
ggtttgcaac cagaagtcac tgaattcttg aacaacact ctccagactg gattatctac   360
gactacactc actactggtt accagaaatt gctaagtctt gggtgtttc tcgtgctcat   420
ttctccgtta ccactccatg gctattgct tacatgggtc caactgctga tgctatgatc   480
aacggttctg attacagaac cgaattggaa gacttcaccg ttccaccaaa atggttccca   540
ttcccaacca ctgtctgttg agaaagcac gatttggcca gattagttcc atacaaggcc   600
ccaggtatct ctgacggtta cagaatgggt ttagtcttga agggtctga cttgttgttg   660
tccagatctt accatgaatt cggtactgaa tggttaagat tgttggaaac tttgcacaga   720
gtcccagttg ttccagttgg tttgttgcct cctgaaatcc caggtgacgg tgaagacgaa   780
tcttgggttt ccatcaagga ctggttagat aagaaggaaa agggttccgt tgtctacgtt   840
gctttgggtt ctgaagtctt ggtttctcaa gaagaattga cgaattggc tttgggtttg   900
gaattgtccg gtctaccatt tgtctgggct tacagaaagc caagggtcc agctaagtct   960
gactctgttg aattgccaga tggtttcgaa gaaagaacca gaggtagagg tgttgtctgg  1020
acttcctggg ctccacaatt gagaattttg tcccacgaat ctgtttgtgg tttcttgact  1080
cactgtggtt ctggttccat tgtcgaaggt ttgatgttcg gtcatccatt gatcatgttg  1140
ccaatctttg gtgaccaacc tttgaacgcc agattattgg aagacaagca agttggtatt  1200
gaaattccaa gaaacgaaga agacggttct ttgaccaagg aatctgttgc cagatctttg  1260
agatctgttg ttgtcgaaga agaaggtaag atctacagag aaaaggccaa ggaaatgtcc  1320
aaattgtttg gtgacaagga tttgcaagat caatatgtcg atgacttcgt cgaatactta  1380
caaaagcacc gtcgtgctgt tgccattgac catgaaagc                         1419

<210> SEQ ID NO 24
<211> LENGTH: 1419
<212> TYPE: DNA
<213> ORGANISM: Artificial sequence
<220> FEATURE:
<223> OTHER INFORMATION: UGT2_9b CpO for Y. lipolitica

<400> SEQUENCE: 24
atggccacct ccgactccat tgtcgacgac cgaaagaagc tccacattgt catgttcccc    60
tggctcgcct ttggccacat cattccctac ctccagctct ccaagctcct cgcccagaag   120
ggccacaagg tttctttcat ctccactccc cgaaacatcc agcgactctc ctcccacatc   180
tctcctctca tcaacctcgt ccagctcccc ctccccgag tcgacaacct ccccgaggat   240
gctgaggcca ccaccgatgt ccaccccgag gacatcccct acctcaagaa ggcctccgac   300
ggcctccagc ccgaggtcac cgagttcctc gagcagcact ccccgactg gatcatctac   360
gactacaccc actactggct ccccgagatt gccaagtctc tcggtgtctc tcgagcccac   420
```

```
ttctccgtca ccaccccctg ggccattgct tacatgggtc ccactgccga tgccatgatc    480
aacggctccg actaccgaac cgagcttgag gacttcaccg tccctcccaa gtggttcccc    540
ttccccacca ccgtctgctg gcgaaagcac gatctcgccc gactcgtccc ctacaaggct    600
cccggtatct ccgacggtta ccgaatgggc ctcgttctca agggttccga tctgctgctc    660
tcccgatctt accacgagtt tggtactgag tggctgcgac tcctcgagac tctgcaccga    720
gtccccgttg tccccgtcgg tctgctccct cccgagatcc ccggtgacgg tgaggacgag    780
tcttgggttt ccatcaagga ctggctcgac aagaaggaga agggctccgt cgtctacgtt    840
gccctcggct ccgaggttct cgtttcccaa gaggagctta acgagcttgc tctcggcctc    900
gagctgtccg gtctgcccct tgtctgggcc taccgaaagc ccaagggccc cgccaagtcc    960
gactccgtcg agctgcccga cggcttcgag gagcgaaccc gaggtcgagg tgttgtctgg   1020
acctcttggg ctccccagct ccgaatcctc tcccacgagt ccgtctgtgg tttcctgacc   1080
cactgcggtt ccggctctat cgtcgagggt ctgatgttcg ccaccccct catcatgctc    1140 cccatcttcg gtgaccagcc cctcaacgcc cgacttctcg aggacaagca ggtcggtatt   1200
gagatccccc gaaacgaaga ggacggctct ctcaccaagg agtctgttgc tcgatctctg   1260
cgatccgtcg ttgtcgagga gagggtaag atctaccgag agaaggccaa ggagatgtcc    1320
aagctgttcg gtgacaagga tctgcaggac cagtacgtcg acgacttcgt cgagtacctc   1380
cagaagcacc gacgagctgt tgccattgac cacgaatcc                            1419
```

<210> SEQ ID NO 25  
<211> LENGTH: 473  
<212> TYPE: PRT  
<213> ORGANISM: Artificial sequence  
<220> FEATURE:  
<223> OTHER INFORMATION: UGT2_10b variant

<400> SEQUENCE: 25

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Phe Val Lys Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Glu Ile Ala Lys Ser Leu Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Tyr Arg Thr Glu Leu Glu Asp Phe Thr Val Pro Pro
                165                 170                 175

Lys Trp Phe Pro Phe Pro Thr Thr Val Cys Trp Arg Lys His Asp Leu
            180                 185                 190
```

Ala Arg Leu Val Pro Tyr Lys Ala Pro Gly Ile Ser Asp Gly Tyr Arg
            195                 200                 205

Met Gly Leu Val Ile Lys Gly Cys Asp Cys Leu Leu Ser Lys Thr Tyr
            210                 215                 220

His Glu Phe Gly Thr Gln Trp Leu Arg Leu Leu Glu Glu Leu His Arg
225                 230                 235                 240

Val Pro Val Ile Pro Val Gly Leu Leu Pro Pro Ser Ile Pro Gly Ser
                245                 250                 255

Asp Lys Asp Asp Ser Trp Val Ser Ile Lys Glu Trp Leu Asp Gly Gln
            260                 265                 270

Glu Lys Gly Ser Val Val Tyr Val Ala Leu Gly Ser Glu Val Leu Val
            275                 280                 285

Thr Gln Glu Glu Val Val Glu Leu Ala His Gly Leu Glu Leu Ser Gly
            290                 295                 300

Leu Pro Phe Phe Trp Ala Tyr Arg Lys Pro Lys Gly Pro Ala Lys Ser
305                 310                 315                 320

Asp Ser Val Glu Leu Pro Asp Gly Phe Val Glu Arg Val Arg Asp Arg
                325                 330                 335

Gly Leu Val Trp Thr Ser Trp Ala Pro Gln Leu Arg Ile Leu Ser His
            340                 345                 350

Glu Ser Val Ala Gly Phe Leu Thr His Cys Gly Ser Gly Ser Ile Val
            355                 360                 365

Glu Gly Leu Met Phe Gly His Pro Leu Ile Met Leu Pro Ile Phe Gly
            370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Phe Thr Arg Asp Ser Val
                405                 410                 415

Ala Glu Ser Leu Arg Leu Val Met Val Glu Glu Gly Lys Ile Tyr
            420                 425                 430

Arg Glu Lys Ala Lys Glu Met Ser Lys Leu Phe Gly Asp Lys Asp Leu
            435                 440                 445

Gln Asp Gln Tyr Val Asp Asp Phe Val Glu Tyr Leu Gly Lys His Arg
            450                 455                 460

Arg Ala Val Ala Ile Asp His Glu Ser
465                 470

<210> SEQ ID NO 26
<211> LENGTH: 1419
<212> TYPE: DNA
<213> ORGANISM: Artificial sequence
<220> FEATURE:
<223> OTHER INFORMATION: UGT2_10b CpO for Y. lipolitica

<400> SEQUENCE: 26
atggccacct ccgactccat tgttgacgac cgaaagaagc tccacattgt catgttcccc      60
tggctcgcct ttggccacat catccccctat ctcgagcttt ccaagctcat tgcccagaag     120
ggccacaagg tttccttcct ctccaccacc aagaacattg accgactctc ctcccacatc     180
tctcccctca tcaactttgt caagctcacc ctcccccgag tccaggagct gcccgaggac     240
gccgaggcca ccactgatgt ccaccccgag gatatcccct acctcaagaa ggcctccgac     300
ggcctccagc ccgaggtcac tgagttcctc gagcagcact ctcccgactg gatcatctac     360
gactacaccc actactggct ccccgagatt gccaagtctc tcggtgtctc tcgagcccac     420

```
ttctccgtca ccaccccctg ggccattgct tacatgggtc ccactgccga tgccatgatc    480
aacggttccg actaccgaac cgagcttgag gacttcaccg tccctcccaa gtggttcccc    540
ttccccacca ccgtctgctg gcgaaagcac gatctggccc gactcgtccc ctacaaggct    600
cccggtatct ccgacggtta ccgaatgggc ctcgtcatca agggctgcga ctgtctgctc    660
tccaagacct accacgagtt cggtactcag tggctccgac ttctcgagga gctgcaccga    720
gtccccgtca tccccgttgg tctgctccct ccctccatcc ccggctctga caaggacgac    780
tcttgggttt ccatcaagga gtggctcgac ggccaggaga agggctccgt tgtctacgtt    840
gctctcggtt ccgaggttct cgtcacccag gaagaggttg tcgagcttgc tcacggtctg    900
gagctgtccg gtctgccctt cttctgggcc taccgaaagc ccaagggtcc cgccaagtcc    960
gactccgtcg agcttcccga tggtttcgtc gagcgagtcc gagatcgagg tctggtctgg   1020
acctcttggg ctccccagct ccgaatcctc tcccacgagt ccgttgctgg tttcctcacc   1080
cactgcggtt ccggctccat tgtcgagggc ctcatgttcg ccaccctct catcatgctc   1140
cccatcttcg gtgaccagcc cctcaacgcc cgactccttg aggacaagca ggtcggtatc   1200
gagatccccc gaaacgagga agatggttct ttcacccgag actctgttgc cgagtctctg   1260
cgactcgtca tggtcgagga gagggtaag atctaccgag agaaggccaa ggagatgtcc   1320
aagctctttg gcgacaagga cctccaggac cagtacgtcg acgactttgt cgagtacctc   1380
cagaagcacc gacgagctgt tgccattgac cacgaaagc                          1419
```

<210> SEQ ID NO 27
<211> LENGTH: 473
<212> TYPE: PRT
<213> ORGANISM: Stevia rebaudiana

<400> SEQUENCE: 27

```
Met Ala Thr Ser Asp Ser Ile Val Asp Asp Arg Lys Gln Leu His Val
1               5                   10                  15
Ala Thr Phe Pro Trp Leu Ala Phe Gly His Ile Leu Pro Tyr Leu Gln
            20                  25                  30
Leu Ser Lys Leu Ile Ala Glu Lys Gly His Lys Val Ser Phe Leu Ser
        35                  40                  45
Thr Thr Arg Asn Ile Gln Arg Leu Ser Ser His Ile Ser Pro Leu Ile
    50                  55                  60
Asn Val Val Gln Leu Thr Leu Pro Arg Val Gln Glu Leu Pro Glu Asp
65                  70                  75                  80
Ala Glu Ala Thr Thr Asp Val His Pro Glu Asp Ile Pro Tyr Leu Lys
                85                  90                  95
Lys Ala Ser Asp Gly Leu Gln Pro Glu Val Thr Arg Phe Leu Glu Gln
            100                 105                 110
His Ser Pro Asp Trp Ile Ile Tyr Asp Tyr Thr His Tyr Trp Leu Pro
        115                 120                 125
Ser Ile Ala Ala Ser Leu Gly Ile Ser Arg Ala His Phe Ser Val Thr
    130                 135                 140
Thr Pro Trp Ala Ile Ala Tyr Met Gly Pro Ser Ala Asp Ala Met Ile
145                 150                 155                 160
Asn Gly Ser Asp Gly Arg Thr Thr Val Glu Asp Leu Thr Pro Pro
                165                 170                 175
Lys Trp Phe Pro Phe Pro Thr Lys Val Cys Trp Arg Lys His Asp Leu
            180                 185                 190
Ala Arg Leu Val Pro Tyr Lys Ala Pro Gly Ile Ser Asp Gly Tyr Arg
```

```
            195                 200                 205
Met Gly Leu Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
                260                 265                 270

Gln Lys Gly Ser Val Val Tyr Val Ala Leu Gly Ser Glu Val Leu Val
            275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
                340                 345                 350

Glu Ser Val Cys Gly Phe Leu Thr His Cys Gly Ser Gly Ser Ile Val
            355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Glu Lys Glu Gly Glu Ile Tyr
                420                 425                 430

Lys Ala Asn Ala Arg Glu Leu Ser Lys Ile Tyr Asn Asp Thr Lys Val
            435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470

<210> SEQ ID NO 28
<211> LENGTH: 1422
<212> TYPE: DNA
<213> ORGANISM: Artificial sequence
<220> FEATURE:
<223> OTHER INFORMATION: UGT2_1a CpO for S. cerevisiae

<400> SEQUENCE: 28
atggctacat ctgattctat tgttgatgac aggaagcagt tgcatgtggc tactttccct      60
tggcttgctt tcggtcatat actgccttac ctacaactat caaaactgat agctgaaaaa     120
ggacataaag tgtcattcct ttcaacaact agaaacattc aaagattatc ttcccacata     180
tcaccattga ttaacgtcgt tcaattgaca cttccaagag tacaggaatt accagaaagat    240 gctgaagcta caacagatgt gcatcctgaa gatatccctt acttgaaaaa ggcatccgat     300
ggattacagc tgaggtcac tagattcctt gagcaacaca gtccagattg gatcatatac      360
gactacactc actattggtt gccttcaatt gcagcatcac taggcatttc tagggcacat     420
ttcagtgtaa ccacaccttg ggccattgct tacatgggtc catccgctga tgctatgatt     480
```

| | |
|---|---|
| aacggcagtg atggtagaac taccgttgaa gatttgacaa ccccaccaaa gtggtttcca | 540 |
| tttccaacta aagtctgttg gagaaaacac gacttagcaa gactggttcc atacaaggca | 600 |
| ccaggaatct cagacggcta tagaatgggt ttagtcctta aagggtctga ctgcctattg | 660 |
| tctaagtgtt accatgagtt tgggacacaa tggctaccac ttttggaaac attacaccaa | 720 |
| gttcctgtcg taccagttgg tctattacct ccagaaatcc ctggtgatga aaggacgag | 780 |
| acttgggttt caatcaaaaa gtggttagac gggaagcaaa aaggctcagt ggtatatgtg | 840 |
| gcactgggtt ccgaagtttt agtatctcaa acagaagttg tggaacttgc cttaggtttg | 900 |
| gaactatctg gattgccatt tgtctgggcc tacagaaaac caaaaggccc tgcaaagtcc | 960 |
| gattcagttg aattgccaga cggctttgtc gagagaacta gagatagagg ttggtatgg | 1020 |
| acttcatggg ctccacaatt gagaatcctg agtcacgaat ctgtgtgcgg tttcctaaca | 1080 |
| cattgtggtt ctggttctat agttgaagga ctgatgtttg gtcatccact tatcatgttg | 1140 |
| ccaatctttg gtgaccagcc tttgaatgca cgtctgttag aagataaaca agttggaatt | 1200 |
| gaaatcccac gtaatgagga gatggatgt ttaaccaagg agtctgtggc cagatcatta | 1260 |
| cgttccgttg tcgttgaaaa ggaaggcgaa atctacaagg ccaatgcccg tgaactttca | 1320 |
| aagatctaca atgacacaaa agtagagaag gaatatgttt ctcaatttgt agattaccta | 1380 |
| gagaaaaacg ctagagccgt agctattgat catgaatcct aa | 1422 |

<210> SEQ ID NO 29
<211> LENGTH: 1422
<212> TYPE: DNA
<213> ORGANISM: Artificial sequence
<220> FEATURE:
<223> OTHER INFORMATION: UGT2_1a CpO for Y. lipolitica

<400> SEQUENCE: 29

| | |
|---|---|
| atggccacct ccgactccat tgtcgacgac cgaaagcagc tgcacgttgc caccttcccc | 60 |
| tggctcgcct ttggccacat tctgccctac ctccagctct ccaagctcat tgctgagaag | 120 |
| ggccacaagg tttctttcct gtccaccacc cgaaacatcc agcgactctc ctcccacatc | 180 |
| tctcctctca tcaacgttgt ccagctcacc ctcccccgag tccaggagct ccccgaggat | 240 |
| gccgaggcca ccactgatgt ccaccccgag gacatcccct acctcaagaa ggcctccgac | 300 |
| ggtctgcagc ccgaggtcac ccgattcctc gagcagcact ctcccgactg gatcatctac | 360 |
| gactacaccc actactggct cccctccatt gctgcttctc tcggtatctc tcgagcccac | 420 |
| ttctccgtca ccacccctg gccattgct tacatgggcc cctctgctga cgccatgatc | 480 |
| aacggttccg acggccgaac caccgtcgag gatctcacca cccctcccaa gtggttcccc | 540 |
| ttccccacca aggtctgctg gcgaaagcac gatctcgccc gactcgtccc ctacaaggcc | 600 |
| cccggtatct ccgacggtta ccgaatgggt ctggttctca agggctccga ctgtctgctc | 660 |
| tccaagtgct accacgagtt tggtaccag tggctccccc tgctcgagac tctgcaccag | 720 |
| gtccccgttg tccccgtcgg tctgctccct cccgagatcc ccgtgacga aaggacgag | 780 |
| acttgggttt ccatcaagaa gtggctcgac ggcaagcaga agggctccgt cgtctacgtt | 840 |
| gctctcggct ccgaggttct tgtctcccag actgaggtcg tcgagctcgc cctcggtctg | 900 |
| gagctctccg gtctgcccct cgtctgggcc taccgaaagc ccaagggtcc cgccaagtcc | 960 |
| gactccgtcg agctccccga cggtttcgtc gagcgaactc gagatcgagg tctggtctgg | 1020 |
| acctcttggg ctccccagct ccgaatcctc tcccacgagt ccgtctgcgg tttcctgacc | 1080 |
| cactgtggtt ccggctccat tgtcgagggc ctcatgttcg gccaccccct catcatgctg | 1140 |

```
cccatcttcg gtgaccagcc cctcaacgcc cgactcctcg aggacaagca ggtcggtatc    1200
gagatccccc gaaacgaaga ggacggctgc ctcaccaagg agtctgttgc ccgatctctg    1260
cgatctgttg ttgtcgagaa agagggtgag atctacaagg ccaacgcccg agagctctcc    1320
aagatctaca cgacaccaa ggtcgagaag gagtacgttt cccagtttgt cgactacctc    1380
gagaagaacg cccgagctgt cgccattgac cacgagagtt aa    1422
```

<210> SEQ ID NO 30
<211> LENGTH: 600
<212> TYPE: DNA
<213> ORGANISM: Artificial sequence
<220> FEATURE:
<223> OTHER INFORMATION: ScEno2 promoter

<400> SEQUENCE: 30

```
gtgtcgacgc tgcgggtata gaaagggttc tttactctat agtacctcct cgctcagcat    60
ctgcttcttc ccaaagatga acgcggcgtt atgtcactaa cgacgtgcac caacttgcgg   120
aaagtggaat cccgttccaa aactggcatc cactaattga tacatctaca caccgcacgc   180
cttttttctg aagcccactt tcgtggactt tgccatatgc aaaattcatg aagtgtgata   240
ccaagtcagc atacacctca ctagggtagt ttctttggtt gtattgatca tttggttcat   300
cgtggttcat taatttttt tctccattgc tttctggctt tgatcttact atcatttgga   360
tttttgtcga aggttgtaga attgtatgtg acaagtggca ccaagcatat ataaaaaaaa   420
aaagcattat cttcctacca gagttgattg ttaaaaacgt atttatagca aacgcaattg   480
taattaattc ttattttgta tcttttcttc ccttgtctca atctttatt tttatttat    540 ttttctttttc ttagtttctt tcataacacc aagcaactaa tactataaca tacaataata   600
```

<210> SEQ ID NO 31
<211> LENGTH: 1056
<212> TYPE: DNA
<213> ORGANISM: Saccharomyces cerevisiae

<400> SEQUENCE: 31

```
atggcttctg aaaaggaaat cagaagagaa cgtttcttga atgttttccc aaaattggtt    60
gaagaattga acgcttctct attagcttac ggtatgccaa aggaagcttg tgactggtac   120
gctcactctt tgaactacaa caccccaggt ggtaagttga acagaggtct atccgttgtt   180
gacacctacg ccattttgtc caacaagacc gtcgaacaat taggtcaaga agaatacgaa   240
aaggttgcca tcttaggttg gtgtatcgaa ttgttgcaag cttacttctt ggttgctgat   300
gacatgatgg acaaatctat caccagaaga ggtcaaccat gttggtacaa ggttccagaa   360
gtcggtgaaa ttgccatcaa cgatgctttc atgttggaag ctgccatcta caagttgttg   420
aagtctcact tcagaaacga aaagtactac attgacatca ctgaattatt ccacgaagtt   480
actttccaaa ccgaattggg tcaattgatg gacttgatta ccgctccaga agataaggtc   540
gatttgtcca aattttcctt gaagaaacac tctttcattg tcactttcaa gactgcttac   600
tactcctttt acttgcctgt tgctttggcc atgtatgtcg ctggtatcac cgatgaaaag   660
gacttgaagc aagctcgtga tgtcttgatt ccattaggtg aatacttcca aatccaagat   720
gactacttgg actgtttcgg tactccagaa caaatcggta agattggtac tgatatccaa   780
gacaacaagt gttcctgggt tatcaacaag gctttggaat tggcttctgc tgaacaagag   840
aagactttgg acgaaaacta cggtaagaag gactctgttg ctgaagctaa gtgtaagaag   900
```

| | |
|---|---:|
| atcttcaacg atttgaaaat tgaacaatta taccatgaat acgaagaatc tattgccaag | 960 |
| gacttgaaag ccaagatctc tcaagtcgac gaatccagag gtttcaaggc tgatgtcttg | 1020 |
| actgctttct tgaacaaggt ctacaagaga tcaaaa | 1056 |

<210> SEQ ID NO 32
<211> LENGTH: 301
<212> TYPE: DNA
<213> ORGANISM: Artificial sequence
<220> FEATURE:
<223> OTHER INFORMATION: Adh1 terminator

<400> SEQUENCE: 32

| | |
|---|---:|
| agcgaatttc ttatgattta tgattttat tattaaataa gttataaaaa aaataagtgt | 60 |
| atacaaattt taaagtgact cttaggtttt aaaacgaaaa ttcttattct tgagtaactc | 120 |
| tttcctgtag gtcaggttgc tttctcaggt atagcatgag gtcgctctta ttgaccacac | 180 |
| ctctaccggc atgccgagca aatgcctgca aatcgctccc catttcaccc aattgtagat | 240 |
| atgctaactc cagcaatgag ttgatgaatc tcggtgtgta ttttatgtcc tcagaggaca | 300 |
| a | 301 |

<210> SEQ ID NO 33
<211> LENGTH: 600
<212> TYPE: DNA
<213> ORGANISM: Artificial sequence
<220> FEATURE:
<223> OTHER INFORMATION: Sc Fba1 promoter

<400> SEQUENCE: 33

| | |
|---|---:|
| ctacttggct tcacatacgt tgcatacgtc gatatagata ataatgataa tgacagcagg | 60 |
| attatcgtaa tacgtaatag ttgaaaatct caaaaatgtg tgggtcatta cgtaaataat | 120 |
| gataggaatg ggattcttct atttttcctt tttccattct agcagccgtc gggaaaacgt | 180 |
| ggcatcctct ctttcgggct caattggagt cacgctgccg tgagcatcct ctctttccat | 240 |
| atctaacaac tgagcacgta accaatggaa aagcatgagc ttagcgttgc tccaaaaaag | 300 |
| tattggatgg ttaataccat ttgtctgttc tcttctgact tgactcctc aaaaaaaaaa | 360 |
| aatctacaat caacagatcg cttcaattac gccctcacaa aaactttttt ccttcttctt | 420 |
| cgcccacgtt aaattttatc cctcatgttg tctaacggat ttctgcactt gatttattat | 480 |
| aaaaagacaa agacataata cttctctatc aatttcagtt attgttcttc cttgcgttat | 540 |
| tcttctgttc ttcttttct tttgtcatat ataaccataa ccaagtaata catattcaaa | 600 |

<210> SEQ ID NO 34
<211> LENGTH: 1575
<212> TYPE: DNA
<213> ORGANISM: Saccharomyces cerevisiae

<400> SEQUENCE: 34

| | |
|---|---:|
| atggaccaat tggtcaagac tgaagtcacc aagaaatctt tcactgctcc agtccaaaag | 60 |
| gcttccactc cagttttgac caacaagacc gtcatctccg gttccaaggt taaatctttg | 120 |
| tcctctgctc aatcttcctc ctctggtcca tcttcttctt ctgaagaaga tgattccaga | 180 |
| gatatcgaat ctttggacaa gaaaatcaga ccattggaag aattggaagc tctattgtcc | 240 |
| tctggtaaca ctaagcaatt aaagaacaag gaagttgctg ctttggttat ccacggtaaa | 300 |
| ttgccattgt acgctttgga aaagaaatta ggtgacacca ccagagctgt tgctgtcaga | 360 |
| agaaaggctt tgtccatttt ggctgaagct ccagtcttgg cttccgacag attaccatac | 420 |

```
aagaactacg actacgaccg tgtctttggt gcttgttgtg aaaatgtcat tggttacatg        480
ccattaccag ttggtgtcat tggtccattg gttatcgacg gtacttctta ccacatccca        540
atggctacca ctgaaggttg tttggttgct tctgccatga gaggttgtaa ggccatcaac        600
gctggtggtg gtgctaccac cgttttgact aaggatggta tgaccagagg tcctgttgtc        660
agattcccaa ctttgaagag atctggtgct tgtaagatct ggttggattc tgaagaaggt        720
caaaacgcca tcaagaaggc tttcaactcc acttccagat cgctagatt gcaacacatt         780 caaacttgtt tagctggtga cttgttgttc atgagattca gaaccaccac tggtgacgct        840
atgggtatga acatgatctc caagggtgtt gaatactctt tgaagcaaat ggttgaagaa        900
tacggttggg aagatatgga agttgtctct gtttctggta actactgtac cgacaagaag        960
ccagctgcca tcaactggat cgaaggtcgt ggtaagtccg ttgttgctga agctaccatt       1020
ccaggtgacg ttgtcagaaa ggttttgaaa tctgatgttt ctgctttagt cgaattgaac       1080
attgccaaga acttggtcgg ttctgccatg gctggttccg tcggtggttt caacgctcat       1140
gccgctaact tggtcactgc tgtttttcttg gctttaggtc aagatccagc tcaaaatgtc      1200
gaatcctcta actgtatcac tttgatgaag gaagttgacg tgatttgag aatttctgtt        1260 tccatgccat ccattgaagt cggtactatc ggtggtggta ctgtcttgga accacaaggt       1320
gccatgttgg acttgttggg tgttcgtggt ccacacgcta ccgctccagg tactaacgcc       1380
agacaattgg ccagaattgt tgcctgtgcc gtcttggctg gtgaattgtc tctatgtgcc       1440
gctttggctg ctggtcactt ggttcaatct cacatgaccc acaacagaaa gcctgctgaa       1500
ccaaccaaac caaacaactt ggatgctact gacattaaca gattaaagga cggttctgtc       1560
acctgtatca agtct                                                        1575

<210> SEQ ID NO 35
<211> LENGTH: 301
<212> TYPE: DNA
<213> ORGANISM: Artificial sequence
<220> FEATURE:
<223> OTHER INFORMATION: Adh2 terminator

<400> SEQUENCE: 35
agcggatctc ttatgtcttt acgatttata gttttcatta tcaagtatgc ctatattagt         60
atatagcatc tttagatgac agtgttcgaa gtttcacgaa taaagataa tattctactt         120 tttgctccca ccgcgtttgc tagcacgagt gaacaccatc cctcgcctgt gagttgtacc        180
cattcctcta aactgtagac atggtagctt cagcagtgtt cgttatgtac ggcatcctcc        240
aacaaacagt cggttatagt ttgtcctgct cctctgaatc gtgtccctcg atatttctca        300
t                                                                         301

<210> SEQ ID NO 36
<211> LENGTH: 600
<212> TYPE: DNA
<213> ORGANISM: Artificial sequence
<220> FEATURE:
<223> OTHER INFORMATION: Sc Tef1 promoter

<400> SEQUENCE: 36
ttggctgata atagcgtata aacaatgcat actttgtacg ttcaaaatac aatgcagtag         60
atatatttat gcatattaca tataatacat atcacatagg aagcaacagg cgcgttggac        120
ttttaatttt cgaggaccgc gaatccttac atcacaccca atcccccaca agtgatcccc        180
```

```
cacacaccat agcttcaaaa tgtttctact ccttttttac tcttccagat tttctcggac    240
tccgcgcatc gccgtaccac ttcaaaacac ccaagcacag catactaaat ttcccctctt    300
tcttcctcta gggtgtcgtt aattaccgt actaaaggtt tggaaaagaa aaaagacacc    360
gcctcgtttc ttttcttcg tcgaaaaagg caataaaaat ttttatcacg tttcttttc    420 ttgaaaattt tttttttga ttttttctc tttcgatgac ctcccattga tatttaagtt    480
aataaacggt cttcaatttc tcaagtttca gtttcatttt tcttgttcta ttacaacttt    540
ttttacttct tgctcattag aaagaaagca tagcaatcta atctaagttt taattacaaa    600
```

<210> SEQ ID NO 37
<211> LENGTH: 1005
<212> TYPE: DNA
<213> ORGANISM: Saccharomyces cerevisiae

<400> SEQUENCE: 37

```
atggaagcta agattgacga attgatcaac aacgaccctg tctggtcctc tcaaaacgaa     60
tctttgatct ccaagccata caaccacatc ttgttgaagc aggtaagaa cttcagatta    120 aacttgattg ttcaaatcaa cagagttatg aacttgccaa aggaccaatt ggccattgtt    180
tcccaaattg tcgaattgtt gcacaactcc tctctattga tcgatgacat tgaagataat    240
gctccattaa gaagaggtca aaccacttct catttgattt tcggtgtccc atccaccatc    300
aacactgcta actacatgta cttcagagcc atgcaattgg tttctcaatt gaccaccaag    360
gaaccattat accacaactt gatcactatc tttaacgaag aattgattaa cttgcaccgt    420
ggtcaaggtt tggacatcta ctggagagat tccttgccag aaattattcc aactcaagaa    480
atgtacttga acatggtcat gaacaagact ggtggtttat tcagattgac tttacgtttg    540
atggaagctt tgtctccatc ttcccaccac ggtcactctt tggttccatt catcaatcta    600
ttaggtatca tctaccaaat cagagatgat tacttgaact tgaaggactt ccaaatgtcc    660
tctgaaaagg gttcgctga agatatcact gaaggtaaat tgtcttcc aattgtccac    720 gccttgaact ttaccaagac caagggtcaa actgaacaac acaacgaaat tttgagaatc    780
ttattgttga aacttctga caggacatc aagttgaaat tgatccaaat cttggaattc    840
gataccaact ctttggctta caccaagaac ttcatcaacc aattggttaa catgatcaag    900
aatgacaacg aaaacaaata cttgccagac ttggcttccc actccgatac cgctaccaac    960
ttgcacgacg aattgttgta cattattgac catttgtctg agtta                   1005
```

<210> SEQ ID NO 38
<211> LENGTH: 301
<212> TYPE: DNA
<213> ORGANISM: Artificial sequence
<220> FEATURE:
<223> OTHER INFORMATION: Sc Gmp1 terminator

<400> SEQUENCE: 38

```
agtctgaaga atgaatgatt tgatgatttc ttttccctc catttttctt actgaatata     60
tcaatgatat agacttgtat agtttattat ttcaaattaa gtagctatat atagtcaaga    120
taacgtttgt ttgacacgat tacattattc gtcgacatct tttttcagcc tgtcgtggta    180
gcaatttgag gagtattatt aattgaatag gttcattttg cgctcgcata aacagttttc    240
gtcagggaca gtatgttgga atgagtggta attaatggtg acatgacatg ttatagcaat    300
a                                                                    301
```

<210> SEQ ID NO 39
<211> LENGTH: 600
<212> TYPE: DNA
<213> ORGANISM: Artificial sequence
<220> FEATURE:
<223> OTHER INFORMATION: Sc Pgk1 promoter

<400> SEQUENCE: 39

```
gggccagaaa aaggaagtgt ttccctcctt cttgaattga tgttaccctc ataaagcacg      60
tggcctctta tcgagaaaga aattaccgtc gctcgtgatt tgtttgcaaa agaacaaaa     120
ctgaaaaaac ccagacacgc tcgacttcct gtcttcctat tgattgcagc ttccaatttc    180
gtcacacaac aaggtcctag cgacggctca caggttttgt aacaagcaat cgaaggttct    240
ggaatggcgg gaaagggttt agtaccacat gctatgatgc ccactgtgat ctccagagca    300
aagttcgttc gatcgtactg ttactctctc tctttcaaac agaattgtcc gaatcgtgtg    360
acaacaacag cctgttctca cacactcttt tcttctaacc aaggggggtgg tttagtttag    420
tagaacctcg tgaaacttac atttacatat atataaactt gcataaattg gtcaatgcaa    480
gaaatacata tttggtcttt tctaattcgt agttttcaa gttcttagat gctttctttt     540
tctctttttt acagatcatc aaggaagtaa ttatctactt tttacaacaa atataaaaca    600
```

<210> SEQ ID NO 40
<211> LENGTH: 1001
<212> TYPE: DNA
<213> ORGANISM: Artificial sequence
<220> FEATURE:
<223> OTHER INFORMATION: Kl prom 12 promoter

<400> SEQUENCE: 40

```
cgtaaaaact aaaacgagcc cccaccaaag aacaaaaaag aaggtgctgg gcccccactt      60
tcttcccttg cacgtgatag gaagatggct acagaaacaa gaagatggaa atcgaaggaa    120
agagggagac tggaagctgt aaaaactgaa atgaaaaaa aaaaaaaaa aaaaaaacaa     180
gaagctgaaa atggaagact gaaatttgaa aaatggtaaa aaaaaaaaag aaacacgaag    240
ctaaaaacct ggattccatt ttgagaagaa gcaagaaagg taagtatggt aacgaccgta    300
caggcaagcg cgaaggcaaa tggaaaagct ggagtccgga agataatcat ttcatcttct    360
tttgttagaa cagaacagtg gatgtccctc atctcggtaa cgtattgtcc atgccctaga    420
actctctgtc cctaaaaaga ggacaaaaac ccaatggttt ccccagcttc cagtggagcc    480
accgatccca ctggaaacca ctggacagga agagaaaatc acggacttcc tctattgaag    540
gataattcaa cactttcacc agatcccaaa tgtcccgccc ctattcccgt gttccatcac    600
gtaccataac ttaccatttc atcacgttct ctatggcaca ctggtactgc ttcgactgct    660
ttgcttcatc ttctctatgg gccaatgagc taatgagcac aatgtgctgc gaaataaagg    720
gatatctaat ttatattatt acattataat atgtactagt gtggttattg gtaattgtac    780
ttaattttga tatataaagg gtggatcttt ttcattttga atcagaattg gaattgcaac    840
ttgtctcttg tcactattac ttaatagtaa ttatatttct tattaacctt ttttttaagt    900
caaaacacca aggacaagaa ctactcttca aaggtatttc aagttatcat acgtgtcaca    960
cacgcttcac agtttcaagt aaaaaaaaag aatattacac a                       1001
```

<210> SEQ ID NO 41
<211> LENGTH: 2229
<212> TYPE: DNA
<213> ORGANISM: Stevia rebaudiana

```
<400> SEQUENCE: 41
atgtgtaaag ctgtttccaa ggaatactct gacttgttgc aaaaggatga agcctccttc      60
accaaatggg atgatgacaa agttaaggac catttagaca ctaacaagaa cttgtaccca     120
aacgatgaaa tcaaggaatt cgtcgaatct gtcaaagcta tgttcggttc catgaatgat     180
ggtgaaatca acgtttccgc ttacgacacc gcttgggttg ctttggttca agacgttgat     240
ggttccggtt ctccacaatt cccatcttct ttggaatgga ttgccaacaa ccaattgtct     300
gatggttctt ggggtgacca tttgttattc tctgctcacg acagaattat taacacttta     360
gcttgtgtca ttgctttgac ttcctggaat gtccatccat ccaagtgtga aaagggtttg     420
aacttcttga gagaaaacat ctgtaagttg gaagatgaaa atgctgaaca catgccaatt     480
ggtttcgaag ttaccttccc atctttgatt gatatcgcca agaagttgaa catcgaagtc     540
ccagaagaca ccccagcttt gaaggaaatc tacgccagaa gagatatcaa gttgaccaaa     600
atcccaatgg aagttttgca caaggttcca accaccttgt tgcactcttt ggaaggtatg     660
ccagacttgg aatgggaaaa gttgttaaag ttgcaatgta aggacggttc tttcttgttc     720
tctccatctt ctaccgcctt tgctttgatg caaactaagg acgaaaagtg tctacaatac     780
ttaactaata tcgttaccaa attcaacggt ggtgtcccaa acgtttaccc tgttgacttg     840
tttgaacaca tctgggttgt tgacagattg caacgtttgg gtattgctcg ttatttcaag     900
tctgaaatca aggactgtgt tgaatacatc aacaagtact ggactaagaa cggtatctgt     960
tgggctcgta cacccacgt tcaagatatc gacgacactg ctatgggttt cagagtcttg    1020
agagctcatg gttacgatgt caccccagat gtcttcagac aattcgaaaa ggatggtaag    1080
ttcgtttgtt ttgccggtca atccactcaa gccgtcactg gtatgttcaa cgtctacaga    1140
gcttctcaaa tgttgttccc aggtgaaaga atcctagaag acgctaagaa gttctcctac    1200
aactacttga agaaaagca atctactaac gaattgttgg acaaatggat cattgccaaa    1260
gacttaccag gtgaagtcgg ttacgctttg atattccat ggtacgcttc tctaccaaga    1320
ttagaaacca gatactactt ggaacaatac ggtggtgaag acgatgtctg gatcggtaag    1380
accttgtaca gaatgggtta cgtttccaac aacacttact tggaaatggc caaattggac    1440
tacaacaact acgtcgccgt cttacaattg gaatggtaca ccattcaaca atggtacgtt    1500
gacattggta ttgaaaagtt tgaatccgac aacatcaagt ccgtcttggt ttcctactac    1560
ttggctgctg cttccatctt tgaaccagaa agatccaagg aaagaattgc ttgggctaag    1620
accaccatct tggttgacaa gatcacttct attttcgact cttcccaatc ttccaaggaa    1680
gatatcaccg ctttcattga caaattcaga aacaagtctt cttccaagaa gcactccatt    1740
aacggtgaac catggcacga agttatggtt gctttgaaga gactttgca cggttttgct    1800
ttggatgctt tgatgactca ctctcaagat attcaccctc aattcacca agcttgggaa    1860
atgtggttaa ccaagttgca agatggtgtc gatgtcactg ctgaattgat ggttcaaatg    1920
atcaacatga ctgccggtag atgggtttct aaggaattgt tgactcaccc tcaataccaa    1980
cgtttgtcca ccgtcaccaa ctctgtctgt cacgacatca ctaagttgca caacttcaaa    2040
gaaaactcca ctactgtcga ttctaaggtt caagaattgg ttcaattagt tttctctgac    2100
accccagatg acttggacca agacatgaag caaactttct tgactgtcat gaagaccttc    2160
tactacaagg cttggtgtga cccaaacacc atcaacgacc atatttctaa ggtcttcgaa    2220
attgttatc                                                            2229
```

<210> SEQ ID NO 42
<211> LENGTH: 2271
<212> TYPE: DNA
<213> ORGANISM: Stevia rebaudiana

<400> SEQUENCE: 42

| | | | | | |
|---|---|---|---|---|---|
| atgacttctc | acggtggtca | aaccaaccca | accaacttga | ttattgacac | caccaaggaa | 60 |
| agaatccaaa | agcaattcaa | gaatgttgaa | atctccgttt | cctcctacga | cactgcttgg | 120 |
| gttgccatgg | ttccatctcc | aaactcccca | aagtctccat | gtttcccaga | atgtttgaac | 180 |
| tggttaatca | acaaccaatt | gaacgatggt | tcctggggtt | tagtcaatca | cacccacaac | 240 |
| cacaatcacc | cattgttgaa | ggactctcta | tcctccactt | tggcttgtat | cgttgctttg | 300 |
| aagagatgga | acgttggtga | agaccaaatc | aacaagggtt | tgtcctttat | tgaatccaac | 360 |
| ttggcttctg | ctactgaaaa | gtcccaacca | tctcctatcg | gttttgacat | cattttccca | 420 |
| ggtttattgg | aatacgctaa | gaacttggac | atcaacttat | tatctaagca | aaccgatttc | 480 |
| tccttgatgt | tgcacaagag | agaattgaa | caaaagagat | gtcactccaa | cgaaatggac | 540 |
| ggttacttgg | cttacatttc | tgaaggtttg | ggtaacttgt | acgactggaa | catggtcaag | 600 |
| aaataccaaa | tgaagaacgg | ttccgttttc | aactctccat | ctgctaccgc | tgctgctttc | 660 |
| atcaaccatc | aaaacccagg | ttgtttgaac | tacttgaact | ctttgttgga | caaattcggt | 720 |
| aacgctgttc | caactgtcta | cccacacgat | ttgtttatca | gattatccat | ggttgacacc | 780 |
| attgaacgtt | tgggtatttc | tcatcacttc | agagtcgaaa | tcaagaacgt | tttggatgaa | 840 |
| acttacagat | gttgggttga | agagatgaa | caaatcttca | tggatgtcgt | cacttgtgcc | 900 |
| ttggccttca | gattattgag | aattaacggt | tacgaagttt | ctccagaccc | attggctgaa | 960 |
| atcactaacg | aattggcttt | gaaggacgaa | tacgccgctt | tggaaactta | ccatgcctct | 1020 |
| cacatcttat | accaagaaga | cttgtcctct | ggtaagcaaa | tcttgaagtc | tgctgacttc | 1080 |
| ttgaaggaaa | ttatctctac | tgattctaac | agattgtcca | gttgattca | caggaagtt | 1140 |
| gaaaacgcct | tgaaattccc | aatcaacact | ggtttggaaa | gaattaacac | cagaagaaac | 1200 |
| atccaattat | acaacgttga | caacactaga | atcttgaaga | ctacttatca | ctcttccaac | 1260 |
| atctccaaca | ctgactactt | gagattggct | gtcgaagatt | tctacacctg | tcaatctatt | 1320 |
| tacagagaag | aattgaaggg | tttggaaaga | tgggttgtcg | aaaacaaatt | ggaccaattg | 1380 |
| aaatttgcta | gacaaaagac | cgcctactgt | tacttctccg | ttgctgccac | tttgtcctct | 1440 |
| ccagaattat | ctgacgccag | aatctcctgg | gctaagaatg | gtatcttgac | accgttgtc | 1500 |
| gatgacttct | tcgatattgg | tggtaccatt | gacgaattga | ccaacttgat | tcaatgtgtt | 1560 |
| gaaaagtgga | acgtcgatgt | cgataaggac | tgttgttctg | aacacgtcag | aatcttattc | 1620 |
| ttggctttga | agatgctat | ctgttggatc | ggtgacgaag | ctttcaaatg | gcaagctcgt | 1680 |
| gacgttacct | ctcacgtcat | ccaaacctgg | ttggaattga | tgaactctat | gttgagagaa | 1740 |
| gccatctgga | cccgtgatgc | ttacgtccca | actttgaacg | aatacatgga | aaatgcttac | 1800 |
| gtttctttcg | ctttgggtcc | aattgtcaag | cctgctattt | acttcgttgg | tccaaagttg | 1860 |
| tccgaagaaa | ttgttgaatc | ttctgaatac | cacaacttgt | tcaaattgat | gtctactcaa | 1920 |
| ggtcgtttgt | tgaacgatat | ccactctttc | aagcgtgaat | tcaaggaagg | taagttgaat | 1980 |
| gctgttgctt | tgcatttgtc | taacggtgaa | tctggtaagg | tcgaagaaga | agttgtcgaa | 2040 |
| gaaatgatga | tgatgatcaa | gaacaagaga | aaggaattga | tgaagttgat | cttgaagaa | 2100 |
| aacggttcta | ttgtcccaag | agcttgtaag | gatgctttct | ggaacatgtg | tcacgtcttg | 2160 |

```
aacttcttct acgctaacga tgacggtttc actggtaaca ccatcttaga caccgtcaag    2220
gacatcattt acaacccatt agtcttggtt aacgaaaacg aagaacaaag a             2271
```

<210> SEQ ID NO 43
<211> LENGTH: 301
<212> TYPE: DNA
<213> ORGANISM: Artificial sequence
<220> FEATURE:
<223> OTHER INFORMATION: Sc Tal1 terminator

<400> SEQUENCE: 43

```
aggaagtatc tcggaaatat taatttaggc catgtcctta tgcacgtttc ttttgatact      60
tacgggtaca tgtacacaag tatatctata tatataaatt aatgaaaatc ccctatttat     120
atatatgact ttaacgagac agaacagttt tttattttt atcctatttg atgaatgata     180
cagtttctta ttcacgtgtt atacccacac caaatccaat agcaataccg gccatcacaa    240
tcactgtttc ggcagcccct aagatcagac aaaacatccg gaaccaccct aaatcaacgt    300
c                                                                     301
```

<210> SEQ ID NO 44
<211> LENGTH: 1575
<212> TYPE: DNA
<213> ORGANISM: Gibberella fujikuroi

<400> SEQUENCE: 44

```
atgtccaagt ctaactccat gaactccact tctcacgaaa ctttattcca acaattggtt      60
ttgggtttgg acagaatgcc attgatggat gtccactggt tgatctacgt tgctttcggt    120
gcttggttat gttcctacgt cattcacgtt ttgtcctctt cttctaccgt caaggttcca    180
gttgtcggtt acagatccgt tttcgaacca acctggttat tgagattaag atttgtctgg    240
gaaggtggtt ccattattgg tcaaggttac aacaaattca aggactctat cttccaagtc    300
agaaagttgg gtactgacat tgttatcatc ccaccaaaact acatcgatga agtcagaaag    360
ttgtcccaag acaagaccag atctgttgaa ccattcatca acgatttcgc tggtcaatac    420
accagaggta tggtctttct acaatctgat ttgcaaaaacc gtgtcatcca acaaagattg    480
actccaaagt tggtttcttt gactaaggtc atgaaggaag aattggacta cgctttgacc    540
aaggaaatgc cagacatgaa gaacgacgaa tgggttgaag ttgacatttc ttccatcatg    600
gtcagattga tctccagaat ctctgcccgt gttttcttgg gtccagaaca ctgtcgtaac    660
caagaatggt tgaccaccac tgctgaatac tctgaatctt tattcatcac tggtttcatc    720
ttgagagttg tcccacacat cttaagacca ttcattgctc cattgttgcc ttcttacaga    780
actttgttga gaaatgtctc ttctggtaga gagttatcg gtgatatcat cagatctcaa    840
caaggtgatg gtaacgaaga tatcttgtcc tggatgagag atgctgctac cggtgaagaa    900
aagcaaattg acaacattgc tcaaagaatg ttgatcttgt cttttggcttc cattcacacc    960 accgccatga ccatgaccca tgccatgtac gacttgtgtg cctgtccaga atacattgaa    1020
ccattacgtg acgaagtcaa atccgttgtt ggtgcttctg gttgggacaa gactgctttg    1080
aacagattcc acaagttgga ctcttttcttg aaggaatctc aaagattcaa cccagttttc    1140
ttgttgactt tcaacagaat ctaccatcaa tccatgactt tgtccgatgg taccaacatt    1200
ccatctggta ccagaattgc tgttccatct cacgctatgt tgcaagattc tgctcacgtt    1260
ccaggtccaa ctcctccaac tgaatttgac ggtttcagat actccaagat cagatctgac    1320
tctaactatg ctcaaaagta cttgttctcc atgaccgatt cttccaacat ggctttcggt    1380
```

```
tacggtaagt acgcttgtcc aggtcgtttc tacgcctcca acgaaatgaa attgactttg   1440
gccattttgt tgttgcaatt tgaattcaaa ttgccagatg gtaagggtag accaagaaac   1500
atcactatcg actctgacat gattccagac ccaagagcta gattatgtgt cagaaagaga   1560
tctctacgtg acgaa                                                    1575

<210> SEQ ID NO 45
<211> LENGTH: 301
<212> TYPE: DNA
<213> ORGANISM: Artificial sequence
<220> FEATURE:
<223> OTHER INFORMATION: Sc Tpi1 terminator

<400> SEQUENCE: 45
agattaatat aattatataa aaatattatc ttcttttctt tatatctagt gttatgtaaa     60
ataaattgat gactacggaa agcttttta tattgtttct ttttcattct gagccactta    120
aatttcgtga atgttcttgt aagggacggt agatttacaa gtgatacaac aaaaagcaag   180 gcgcttttc taataaaaag aagaaaagca tttaacaatt gaacacctct atatcaacga    240
agaatattac tttgtctcta aatccttgta aaatgtgtac gatctctata tgggttactc   300
a                                                                   301

<210> SEQ ID NO 46
<211> LENGTH: 403
<212> TYPE: DNA
<213> ORGANISM: Artificial sequence
<220> FEATURE:
<223> OTHER INFORMATION: Ag lox_TEF1 promoter

<400> SEQUENCE: 46
taccgttcgt ataatgtatg ctatacgaag ttatgtcccc gccgggtcac ccggccagcg    60
acatggaggc ccagaatacc ctccttgaca gtcttgacgt gcgcagctca ggggcatgat   120
gtgactgtcg cccgtacatt tagcccatac atccccatgt ataatcattt gcatccatac   180
attttgatgg ccgcacggcg cgaagcaaaa attacggctc ctcgctgcag acctgcgagc   240
agggaaacgc tccccctcaca gacgcgttga attgtcccca cgccgcgccc ctgtagagaa   300
atataaaagg ttaggatttg ccactgaggt tcttctttca tatacttcct tttaaaatct   360
tgctaggata cagttctcac atcacatccg aacataaaca aca                     403

<210> SEQ ID NO 47
<211> LENGTH: 810
<212> TYPE: DNA
<213> ORGANISM: Artificial sequence
<220> FEATURE:
<223> OTHER INFORMATION: KANMX

<400> SEQUENCE: 47
atgggtaagg aaaagactca cgtttcgagg ccgcgattaa attccaacat ggatgctgat    60
ttatatgggt ataaatgggc tcgcgataat gtcgggcaat caggtgcgac aatctatcga   120
ttgtatggga agcccgatgc gccagagttg tttctgaaac atggcaaagg tagcgttgcc   180
aatgatgtta cagatgagat ggtcagacta aactggctga cggaatttat gcctcttccg   240
accatcaagc attttatccg tactcctgat gatgcatggt tactcaccac tgcgatcccc   300
ggcaaaacag cattccaggt attagaagaa tatcctgatt caggtgaaaa tattgttgat   360
gcgctggcag tgttcctgcg ccggttgcat tcgattcctg tttgtaattg tccttttaac   420
```

```
agcgatcgcg tatttcgttt ggctcaggcg caatcacgaa tgaataacgg tttggttgat    480
gcgagtgatt ttgatgacga gcgtaatggc tggcctgttg aacaagtctg gaaagaaatg    540
cataagcttt tgccattctc accggattca gtcgtcactc atggtgattt ctcacttgat    600 aaccttatt ttgacgaggg gaaattaata ggttgtattg atgttggacg agtcggaatc    660
gcagaccgat accaggatct tgccatccta tggaactgcc tcggtgagtt ttctccttca    720
ttacagaaac ggcttttttca aaaatatggt attgataatc ctgatatgaa taaattgcag    780
tttcatttga tgctcgatga gttttttctaa                                    810
```

<210> SEQ ID NO 48
<211> LENGTH: 285
<212> TYPE: DNA
<213> ORGANISM: Artificial sequence
<220> FEATURE:
<223> OTHER INFORMATION: Ag Tef1_lox terminator

<400> SEQUENCE: 48

```
atcagtactg acaataaaaa gattcttgtt ttcaagaact tgtcatttgt atagtttttt     60
tatattgtag ttgttctatt ttaatcaaat gttagcgtga tttatatttt ttttcgcctc    120
gacatcatct gcccagatgc gaagttaagt gcgcagaaag taatatcatg cgtcaatcgt    180
atgtgaatgc tggtcgctat actgctgtcg attcgatact aacgccgcca tccagtgtcg    240
aaaacgagct cataacttcg tataatgtat gctatacgaa cggta                    285
```

<210> SEQ ID NO 49
<211> LENGTH: 1575
<212> TYPE: DNA
<213> ORGANISM: Arabidopsis thaliana

<400> SEQUENCE: 49

```
atggaatctt tagtcgttca caccgtcaat gccatctggt gtattgtcat tgttggtatt     60
ttctctgttg gttaccacgt ttacggtcgt gccgttgttg aacaatggag aatgagaaga    120
tctttgaaat tgcaaggtgt caagggtcca ccaccatcca ttttcaacgg taatgtctct    180
gaaatgcaaa gaatccaatc tgaagctaag cactgttccg gtgacaacat catttctcac    240
gattactcct cctctttgtt ccctcacttt gaccactgga gaaagcaata cggtagaatc    300
tacacctact ccactggttt gaaacaacat ttgtacatca accatccaga atggtcaag    360 gaattatctc aaaccaacac tttgaactta ggtcgtatca ctcacatcac caagagattg    420
aacccaatct taggtaacgg tatcatcact ccaacggtc cacactgggc tcatcaaaga    480
agaattattg cttacgaatt cacccacgac aaaatcaagg gtatggtcgg tttgatggtc    540
gaatctgcca tgccaatgtt gaacaaatgg aagaaatgg ttaagagagg tggtgaaatg    600
ggttgtgaca tccgtgttga cgaagatttg aaggatgttt ctgctgatgt cattgctaag    660
gcttgtttcg gttcctcttt ctccaagggt aaggctatct tctccatgat cagagacttg    720
ttgactgcca tcactaagag atctgttttg ttcagattca acggtttcac cgacatggtt    780
ttcggttcca agaagcatgg tgatgtcgat atcgatgctt ggaaatgga attggaatct    840 tctatctggg aaaccgttaa ggaaagagaa attgaatgta aggacactca caagaaggat    900
ttgatgcaat taatcttgga aggtgccatg agatcttgtg acggtaactt gtgggacaag    960
tctgcttaca gaaagatttgt tgtcgacaac tgtaaatcca tctactttgc cggtcacgac   1020
tctactgctg tctccgtttc ctggtgtttg atgttgctag ctttgaaccc atcctggcaa   1080
gtcaagatca gagatgaaat cttatcttct tgtaagaacg gtattccaga tgctgaatcc   1140
```

```
attccaaact tgaagaccgt taccatggtc attcaagaaa ctatgagatt gtacccacca    1200
gctccaattg tcggtagaga agcttccaag gacatcagat taggtgactt ggttgttcca    1260
aagggtgttt gtatctggac tttgattcca gctttgcacc gtgacccaga aatctggggt    1320
ccagatgcta acgacttcaa gccagaaaga ttctctgaag gtatttccaa ggcttgtaaa    1380
tacccacaat cttacatccc attcggtttg ggtccaagaa cctgtgtcgg taagaacttc    1440
ggtatgatgg aagtcaaagt tttggtttct ttgattgttt ccaagttctc tttcaccttg    1500
tctccaactt accaacactc tccatctcac aagttgttgg ttgaacctca acacggtgtt    1560
gtcattagag tcgtt                                                    1575

<210> SEQ ID NO 50
<211> LENGTH: 1000
<212> TYPE: DNA
<213> ORGANISM: Artificial sequence
<220> FEATURE:
<223> OTHER INFORMATION: Kl prom 6 promoter

<400> SEQUENCE: 50 caaaggggg gcagggacag ggatacgaca agggctgggg aaaaaaaaaa agatagatac      60
gattggccgg gtaagcctgg ggaaatgtag caagtgcggg taagttaaaa ggtaaccacg    120
tgactccgga agagtcacgt ggttacggac ttttttctct agatctcagc ttttatcgg    180 tcttaccctg ccctcctgcc ccctgcccct tcccttcgcc ccaaaaagaa aggaaatctg    240
ttggatttcg ctcaggccat ccctttcgtt aatatcggtt atcgctttac acactgcaca    300
tccttctgtc caaaggaat ccagaagttt agcttttcct tcctttccca cagacattag     360
cctaggccct ctctcatcat ttgcatgcct cagccaatgt accaagaata acgcaacgag    420
gttgggaaat tttaacccaa caatcgatgc agatgtgaca agagattaga cacgttccag    480
ataccagatt acacagcttg tgctagcaga gtgacatatg gtggtgttgt gtctcgttta    540
gtacctgtaa tcgagagtgt tcaaatcagt cgatttgaac accctactg ccactgaata     600 ttgattgaat accgtttatt gaaggtttta tgagtgatct tctttcggtc caggacaatt    660
tgttgagctt tttctatgta gagttccgtc ccttttttt tttttttgc tttctcgcac      720 ttactagcac tatttttttt tcacacacta aaacacttta ttttaatcta tatatatata   780
tatatatata tgtaggaatg gaatcacaga catttgatac tcatcctcat ccttattaat    840
tcttgtttta atttgtttga cttagccaaa ccaccaatct caacccatcg tatttcaggt    900
attgtgtgtc tagtgtgtct ctggtatacg gaaataagtg ccagaagtaa ggaagaaaca    960
aagaacaagt gtctgaatac tactagcctc tcttttcata                         1000

<210> SEQ ID NO 51
<211> LENGTH: 2133
<212> TYPE: DNA
<213> ORGANISM: Arabidopsis thaliana

<400> SEQUENCE: 51
atgtcctctt cttcttcttc ttctacttcc atgattgatt tgatggctgc catcatcaag     60
ggtgaaccag tcattgtctc tgacccagcc aacgcttctg cttacgaatc cgttgctgct    120
gaattgtcct ccatgttgat tgaaaacaga caattcgcta tgattgtcac tacttccatt    180
gctgtcttga ttggttgtat cgtcatgttg gtctggagaa gatccggttc cggtaactcc    240
aagagagttg aaccattgaa gccattagtc atcaagccaa gagaagaaga aattgatgac    300
```

```
ggtagaaaga aggtcaccat cttctttggt actcaaaccg gtactgctga aggttttgct    360
aaggctttgg gtgaagaagc caaagctaga tacgaaaaga ccagattcaa gatcgttgac    420
ttggacgact acgctgctga tgacgacgaa tacgaagaaa agttgaagaa ggaagatgtt    480
gccttcttct tcttggctac ttacggtgat ggtgaaccaa ctgacaatgc tgccagattc    540
tacaaatggt tcaccgaagg taacgacaga ggtgaatggt taaagaactt gaaatacggt    600
gttttcggtc taggtaacag acaatacgaa cacttcaaca aggttgccaa ggttgtcgat    660
gacatcttgg ttgaacaagg tgctcaaaga ttagtccaag tcggtttggg tgatgatgac    720
caatgtatcg aagatgactt cactgcttgg agagaagctt gtggccaga attggacacc    780
atcttaagag aagaaggtga taccgctgtt gccacccat acactgctgc tgttttggaa    840
tacagagttt ctatccacga ctctgaagat gccaagttca cgacatcaa catggctaac    900
ggtaacggtt acactgtttt cgacgctcaa cacccataca aggccaatgt tgctgtcaag    960
agagaattgc acactccaga atctgatcgt tcttgtatcc acttggaatt tgacattgct   1020
ggttctggtt tgacctacga aaccggtgac cacgtcggtg tcttatgtga caacttgtct   1080
gaaactgtcg atgaagcttt gagattattg gacatgtctc cagacactta tttctccttg   1140
catgctgaaa aggaagatgg tactccaatt tcttcttcct tgcctcctcc attcccacca   1200
tgtaacttga gaaccgcttt aaccagatac gcttgtttgc tatcctctcc aaagaagtcc   1260
gctttggttg ctttggctgc tcacgcttct gacccaactg aagctgaaag attgaaacat   1320
ttggcttccc cagctggtaa ggatgaatac tccaaatggg ttgttgaatc tcaaagatct   1380
ttgttggaag tcatggctga attcccatct gccaagccac cattgggtgt tttcttcgcc   1440
ggtgttgctc caagattgca accaagattt tactccatct cttcttctcc aaagattgct   1500
gaaaccagaa ttcacgttac ctgtgccttg gtctacgaaa agatgccaac cggtagaatt   1560
cacaagggtg tttgttccac ctggatgaag aacgctgttc catacgaaaa gtctgaaaac   1620
tgttcttctg ctccaatctt cgtccgtcaa tccaacttca agttgccatc tgactccaag   1680
gtcccaatca tcatgatcgg tccaggtact ggtttagctc cattcagagg tttcttgcaa   1740
gaaagattgg ccttagttga atctggtgtc gaattgggtc cttctgtttt gttcttcggt   1800
tgtagaaacc gtcgtatgga cttcatctac gaagaagaat tgcaaagatt tgtcgaatct   1860
ggtgctttgg ctgaattgtc cgttgctttc tctcgtgaag gtccaaccaa gaatacgtt    1920
caacacaaga tgatggacaa agcctccgac atctggaaca tgatctccca aggtgcttac   1980
ttgtacgttt gtggtgatgc taaaggtatg gccagagatg tccacagatc tttacatacc   2040
attgcccaag aacaaggttc catggactcc accaaggctg aaggtttcgt taagaacttg   2100
caaacttctg gtcgttactt gagagatgtt tgg                                2133

<210> SEQ ID NO 52
<211> LENGTH: 301
<212> TYPE: DNA
<213> ORGANISM: Artificial sequence
<220> FEATURE:
<223> OTHER INFORMATION: Sc Pdc1 terminator

<400> SEQUENCE: 52
agcgatttaa tctctaatta ttagttaaag ttttataagc attttatgt aacgaaaaat    60
aaattggttc atattattac tgcactgtca cttaccatgg aaagaccaga caagaagttg   120
ccgacagtct gttgaattgg cctggttagg cttaagtctg ggtccgcttc tttcaaaatt   180
tggagaattt ctcttaaacg atatgtatat tcttttcgtt ggaaaagatg tcttccaaaa   240
```

```
aaaaaaccga tgaattagtg gaaccaagga aaaaaaaaga ggtatccttg attaaggaac    300
a                                                                   301
```

<210> SEQ ID NO 53
<211> LENGTH: 1000
<212> TYPE: DNA
<213> ORGANISM: Artificial sequence
<220> FEATURE:
<223> OTHER INFORMATION: Kl prom 3 promoter

<400> SEQUENCE: 53

```
gagcctgtcc aagcaaatgc cttctcataa atggtgccaa agacccgcaa gcccaaagca     60
attacccccc aaaagaaat gatatagtgc aagatacgta tatgaccatg acttgactag    120
gtgaaacagt gcagaaacag ccgcacaaaa gcagccctaa ccctcagagt cgattttact    180
cttcaggta ataaagcctc gacatcaatt ttagacagaa gccaggctgg cctcgagatt     240
atagccatag gcaagcaaga ggagagaagg ggaggccccc catgggggc ctccccccg      300
ctgtcaaggt ttggcagaac ctagcttcat taggccacta gcccagccta aaacgtcaac    360
gggcaggagg aacactccca caagacggcg tagtattctc gattcataac cattttctca    420
atcgaattac acagaacaca ccgtacaaac ctctctatca taactactta atagtcacac    480
acgtactcgt ctaaatacac atcatcgtcc tacaagttca tcaaagtgtt ggacagacaa    540
ctataccagc atggatctct tgtatcggtt ctttctccc gctctctcgc aataacaatg     600
aacactgggt caatcatagc ctacacaggt gaacagagta gcgtttatac agggtttata    660
cggtgattcc tacggcaaaa atttttcatt tctaaaaaaa aaagaaaaa ttttctttc      720
caacgctaga aggaaaagaa aaatctaatt aaattgattt ggtgattttc tgagagttcc    780
cttttttcata tatcgaattt tgaatataaa aggagatcga aaaattttt ctattcaatc    840
tgttttctgg ttttatttga tagtttttttt gtgtattatt attatggatt agtactggtt    900
tatatgggtt tttctgtata acttcttttt attttagttt gtttaatctt atttttgagtt    960
acattatagt tccctaactg caagagaagt aacattaaaa                          1000
```

<210> SEQ ID NO 54
<211> LENGTH: 1443
<212> TYPE: DNA
<213> ORGANISM: Stevia rebaudiana

<400> SEQUENCE: 54

```
atggacgcta tggccaccac tgaaaagaag cctcacgtta tctttattcc attcccagct     60
caatctcata tcaaggctat gttgaaattg gctcaattat tgcaccacaa gggtttgcaa    120
atcacttttg tcaacaccga cttcattcac aaccaattct tggaatcttc tggtcctcac    180
tgtttggacg gtgctccagg tttcagattc gaaaccattc cagatggtgt tcccactct     240
ccagaagcct ccatcccaat cagagaatcc ttgttgagat ctattgaaac caacttcttg    300
gaccgtttca tcgatttggt taccaaattg ccagacccac caacctgtat catttctgac    360
ggtttcttgt ccgttttcac catcgatgct gccaagaaat tgggtattcc agtcatgatg    420
tactggactt tggctgcttg tggtttcatg ggtttctacc atattcactc tttgattgaa    480
aagggttcg ctccattaaa ggatgcttct tacttgacca cggttactt ggacaccgtc     540
attgactggg ttccaggtat ggaaggtatc agattgaaag attcccatt ggactggtct    600
actgacttga atgacaaggt cttgatgttc actactgaag ctccacaaag atctcataag    660
```

```
gtttctcacc acatcttcca cactttcgat gaattagaac catctatcat caagactcta    720
tccttgagat acaaccatat ctacaccatt ggtccattac aattgttgtt ggaccaaatc    780
ccagaagaaa agaagcaaac cggtatcact tctttgcacg gttactcttt agtcaaggaa    840
gaaccagaat gtttccaatg gttacaatcc aaggaaccaa actctgttgt ctacgttaac    900
tttggttcca ccactgttat gtccttggaa gatatgactg aatttggttg gggtttggct    960
aactctaacc actacttctt atggatcatc agatctaact ggtcattggg tgaaaacgcc   1020
gttttgcctc cagaattgga agaacacatc aagaagagag gtttcattgc ttcctggtgt   1080
tctcaagaaa aggtcttgaa gcacccatct gttggtggtt tcttgaccca ctgtggttgg   1140
ggttccacca ttgaatccct atctgctggt gttccaatga tctgttggcc atactcctgg   1200
gaccaattga ctaactgtcg ttacatctgt aaggaatggg aagttggttt ggaaatgggt   1260
actaaggtca agagagatga agtcaagaga ttagtccaag aattgatggg tgaaggtggt   1320
cacaagatga gaaacaaagc caaggactgg aaggaaaagg ccagaattgc tattgctcca   1380
aacggttctt cctccttgaa catcgataaa atggttaagg aaatcactgt cttggctcga   1440
aac                                                                  1443

<210> SEQ ID NO 55
<211> LENGTH: 301
<212> TYPE: DNA
<213> ORGANISM: Artificial sequence
<220> FEATURE:
<223> OTHER INFORMATION: Sc TDH1 terminator

<400> SEQUENCE: 55
aataaagcaa tcttgatgag gataatgatt tttttttgaa tatacataaa tactaccgtt     60
tttctgctag attttgtgaa gacgtaaata agtacatatt acttttttaag ccaagacaag    120 attaagcatt aactttaccc ttttctcttc taagtttcaa tactagttat cactgtttaa    180
aagttatggc gagaacgtcg gcggttaaaa tatattaccc tgaacgtggt gaattgaagt    240
tctaggatgg tttaaagatt tttccttttt gggaaataag taaacaatat attgctgcct    300
t                                                                    301

<210> SEQ ID NO 56
<211> LENGTH: 1000
<212> TYPE: DNA
<213> ORGANISM: Artificial sequence
<220> FEATURE:
<223> OTHER INFORMATION: Kl prom 2 promoter

<400> SEQUENCE: 56
gagcctgtcc aagcaaatgc cttctcataa atggtgccaa agaccgcaa gcccaaagca      60 attacccccc aaaaagaaat gatatagtgc aagatacgta tatgaccatg acttgactag    120
gtgaaacagt gcagaaacag ccgcacaaaa gcagccctaa ccctcagagt cgatttact    180 cttcaggta ataaagcctc gacatcaatt ttagacagaa gccaggctgg cctcgagatt    240
atagccatag gcaagcaaga ggagagaagg ggaggccccc catggggggc ctccccccg    300 ctgtcaaggt ttggcagaac ctagcttcat taggccacta gcccagccta aaacgtcaac    360
gggcaggagg aacactccca caagacggcg tagtattctc gattcataac catttttctca   420 atcgaattac acagaacaca ccgtacaaac ctctctatca taactactta atagtcacac    480
acgtactcgt ctaaatacac atcatcgtcc tacaagttca tcaaagtgtt ggacagacaa    540
ctataccagc atggatctct tgtatcggtt cttttctccc gctctctcgc aataacaatg    600
```

```
aacactgggt caatcatagc ctacacaggt gaacagagta gcgtttatac agggtttata      660
cggtgattcc tacggcaaaa attttcatt tctaaaaaaa aaagaaaaa tttttctttc        720 caacgctaga aggaaaagaa aaatctaatt aaattgattt ggtgattttc tgagagttcc     780 cttttttcata tatcgaattt tgaatataaa aggagatcga aaaattttt ctattcaatc     840 tgttttctgg ttttatttga tagttttttt gtgtattatt attatggatt agtactggtt    900
tatatgggtt tttctgtata acttcttttt attttagttt gtttaatctt attttgagtt    960
acattatagt tccctaactg caagagaagt aacattaaaa                           1000
```

<210> SEQ ID NO 57
<211> LENGTH: 1380
<212> TYPE: DNA
<213> ORGANISM: Stevia rebaudiana

<400> SEQUENCE: 57

```
atggctgaac aacaaaagat caagaaatct ccacacgtct tgttgattcc attcccattg     60
caaggtcaca tcaacccatt catccaattc ggtaagagat tgatttccaa gggtgtcaag   120
accactttag tcaccactat tcacacttta aactccactt taaaccactc taacactact   180
accacctcta ttgaaatcca agccatttct gacggttgtg acgaaggtgg tttcatgtct  240
gctggtgaat cttacttgga aactttcaag caagtcggtt ccaagtcttt ggctgatttg  300
atcaagaaat tgcaatccga aggtactacc atcgatgcta tcatctacga ctccatgact  360
gaatgggttt tggatgttgc cattgaattt ggtattgacg tggttctttt cttcacccaa  420
gcctgtgttg ttaactcttt gtactaccac gtccacaagg gtttgatctc tctaccatta  480
ggtgaaaccg tttccgtccc aggtttccca gtcttgcaaa gatgggaaac tccattgatc  540
ttacaaaacc atgaacaaat ccaatctcca tggtcccaaa tgttgtttgg tcaattcgct  600
aacattgacc aagctagatg ggttttcacc aactctttct acaagttgga agaagaagtc  660
attgaatgga ccagaaagat ctggaacttg aaggttatcg gtccaactct accatccatg  720
tacttggaca agagattgga tgacgacaag gacaacggtt tcaacttgta caaggctaac  780
catcacgaat gtatgaactg gttggatgac aagccaaagg aatctgttgt ttacgttgct  840
ttcggttctt tggtcaagca tggtccagaa caagttgaag aaatcaccag agctttgatt  900
gactccgatg ttaacttctt atgggttatc aagcacaagg aagaaggtaa attgccagaa  960
aacttgtctg aagttatcaa gaccggtaag ggtttgattg ttgcttggtg taagcaattg  1020 gatgtttgg ctcacgaatc cgtcggttgt ttcgtcactc actgtggttt caactctact  1080
ttggaagcta tctccttggg tgttccagtt gttgccatgc ctcaattctc tgaccaaacc  1140
accaacgcca aattgttgga tgaaatcttg ggtgtcggtg tccgtgtcaa ggctgatgaa  1200
aacggtattg ttagaagagg taacttagct tcctgtatca agatgatcat ggaagaagaa  1260
cgtggtgtca ttatcagaaa gaatgctgtc aaatggaagg acttggctaa ggttgctgtc  1320
cacgaaggtg gttcctctga caatgacatt gttgaatttg tctctgaatt gatcaaagcg  1380
```

<210> SEQ ID NO 58
<211> LENGTH: 1374
<212> TYPE: DNA
<213> ORGANISM: Stevia rebaudiana

<400> SEQUENCE: 58

```
atggaaaaca agactgaaac cactgttaga agaagaagaa gaatcatctt attcccagtt     60
```

```
ccattccaag gtcacattaa cccaatcttg caattggcta acgtcttata ctccaagggt      120
ttctccatca ccatcttcca caccaacttc aacaaaccta aaacttccaa ctacccacac      180
ttcaccttca gatttatctt ggacaacgac ccacaagatg aaagaatttc taacttgcca      240
acccatggtc cattggccgg tatgagaatt ccaatcatca acgaacacgg tgctgacgaa      300
ttgagaagag aattggaatt gttgatgttg gcttctgaag aagatgaaga agtctcttgt      360
ttgatcactg atgctttatg gtactttgct caatctgttg ctgactcttt gaacttgaga      420
agattagtct tgatgacctc ttctttgttc aacttccacg ctcacgtttc tctaccacaa      480
tttgatgaat tgggttactt ggacccagat gacaagacca gattggaaga acaagcctcc      540
ggtttcccaa tgttgaaggt caaggatatc aagtctgcct actccaactg gcaaatcttg      600
aaggaaattt tgggtaagat gatcaagcaa accaaggctt cttctggtgt catctggaac      660
tccttcaagg aattggaaga atctgaattg gaaaccgtca tcagagaaat tccagctcca      720
tctttcttga ttccattacc aaagcatttg actgcttcct cctcttctct attggaccac      780
gacagaactg ttttccaatg gttggaccaa caaccaccat cttccgtctt atacgtttcc      840
tttggttcca cttctgaagt tgacgaaaag gacttcttgg aaattgctcg tggtttggtt      900
gactccaagc aatctttctt atgggttgtc agaccaggtt cgtcaaggg ttccacctgg      960 gttgaacctt tgccagacgg tttcttgggt gaaagaggta gaattgtcaa atgggttcca     1020
caacaagaag ttttggctca cggtgccatt ggtgctttct ggactcactc tggttggaac     1080
tctactttgg aatccgtttg tgaaggtgtt ccaatgattt tctctgactt cggtttggac     1140
caaccattga atgctcgtta catgtccgat gttttgaagg ttggtgtcta cttggaaaac     1200
ggttgggaac gtggtgaaat tgctaacgcc atcagaagag tcatggtcga tgaagaaggt     1260
gaatacatca gacaaaatgc tcgtgtcttg aaacaaaagg ctgatgtttc tttgatgaag     1320
ggtggttctt cttacgaatc tttggaatct ttggtttcct acatctccag tctc            1374

<210> SEQ ID NO 59
<211> LENGTH: 602
<212> TYPE: DNA
<213> ORGANISM: Artificial sequence
<220> FEATURE:
<223> OTHER INFORMATION: Sc Eno1 terminator

<400> SEQUENCE: 59
aagcttttga ttaagccttc tagtccaaaa aacacgtttt tttgtcattt atttcatttt       60
cttagaatag tttagtttat tcattttata gtcacgaatg ttttatgatt ctatataggg      120
ttgcaaacaa gcattttttca ttttatgtta aaacaatttc aggtttacct tttattctgc     180
ttgtggtgac gcgtgtatcc gcccgctctt tggtcaccc atgtatttaa ttgcataaat      240
aattcttaaa agtggagcta gtctatttct atttacatac ctctcatttc tcatttcctc     300
caagcttttg attaagcctt ctagtccaaa aacacgtttt tttgtcatt tatttcattt      360 tcttagaata gtttagttta ttcattttat agtcacgaat gttttatgat tctatatagg     420 ttgcaaaca agcattttc attttatgtt aaaacaattt caggtttacc ttttattctg      480
cttgtggtga cgcgtgtatc cgcccgctct tttggtcacc catgtattta attgcataaa     540
taattcttaa aagtggagct agtctatttc tatttacata cctctcattt ctcatttcct     600
cc                                                                    602

<210> SEQ ID NO 60
<211> LENGTH: 600
```

```
<212> TYPE: DNA
<213> ORGANISM: Saccharomyces cerevisiae

<400> SEQUENCE: 60
ccgcggaacc gccagatatt cattacttga cgcaaaagcg tttgaaataa tgacgaaaaa        60
gaaggaagaa aaaaaagaa aaataccgct tctaggcggg ttatctactg atccgagctt       120
ccactaggat agcacccaaa cacctgcata tttggacgac ctttacttac accaccaaaa       180
accactttcg cctctcccgc ccctgataac gtccactaat tgagcgatta cctgagcggt       240
cctcttttgt ttgcagcatg agacttgcat actgcaaatc gtaagtagca acgtgtcaag       300
gtcaaaactg tatggaaacc ttgtcacctc acttaattct agctagccta ccctgcaagt       360
caagaggtgt ccgtgattcc tagccacctc aaggtatgcc tctccccgga aactgtggcc       420
ttttctggca cacatgatct ccacgatttc aacatataaa tagcttttga taatggcaat       480
attaatcaaa tttattttac ttctttcttg taacatctct cttgtaatcc cttattcctt       540
ctagctattt ttcataaaaa accaagcaac tgcttatcaa cacacaaaca ctaaatcaaa       600

<210> SEQ ID NO 61
<211> LENGTH: 301
<212> TYPE: DNA
<213> ORGANISM: Kluyveromyces lactis

<400> SEQUENCE: 61
aattactctt ttaagttaac gaacgctttt gatgagacta acgatatttc aagtgattcc        60
attttttact tctaagtttt tatcacctttt atcttaacca ttctatgcca gtctttgctt       120 tatggactttt gattcaaatt atgaagggaa gttttttacgc caaataaaaa ctactacaac       180
aaattattaa aaaaaatgac gaataatatg aagtgtctaa cgactgccaa aattattcat       240
tcctttttta tacacataac catttcactt catttactgg tttgagtggt ttattacgtc       300
g                                                                       301

<210> SEQ ID NO 62
<211> LENGTH: 803
<212> TYPE: DNA
<213> ORGANISM: Yarrowia lipolytica

<400> SEQUENCE: 62
taccaaccac agattacgac ccattcgcag tcacagttca ctagggtttg ggttgcatcc        60
gttgagagtg gtttgttttt aaccttctcc atgtgctcac tcaggttttg ggttcagatc       120
aaatcaaggc gtgaaccact gtttgaggac aaatgtgaca caaccaacca gtgtcagggg       180
caagtccgtg acaaagggga agatacaatg caattactga cagttacgga ctgcctcgat       240
gccctaacct tgccccaaaa taagacaact gtcctcgttt aagcgcaacc ctattcagcg       300
tcacgtcata atagcgtttg gatagcacta gtctatgagg agcgttttat gttgcggtga       360
gggcgattgg tgctcatatg ggttcaattg aggtggtgga acgagcttag tcttcaattg       420
aggtgcgagc gacacaattg ggtgtcacgt ggcctaattg acctcggatc gtggagtccc       480
cagttataca gcaaccacga ggtgcatgag taggagacgt caccagacaa tagggttttt       540
ttggactgga gagggtaggg caaaagcgct caacgggctg tttggggagc tatggggag       600 gaattggcga tatttgtgag gttgacggct ccgatttgcg tgttttgtcg cttctgcatc       660
tccccatacc catatcttcc ctccccacct ctttccacga taattttacg gatcagcaat       720
aaggttcctt ctcctagttt ccacgtccat atatatctat gctgcgtcgt ccttttcgtg       780
```
acatcaccaa aacacataca aaa 803

<210> SEQ ID NO 63
<211> LENGTH: 995
<212> TYPE: DNA
<213> ORGANISM: Yarrowia lipolytica

<400> SEQUENCE: 63

| | |
|---|---|
| ctgtacctgc tgtggaccac gcacggcgga acgtaccgta caaatatttt cttgctcaca | 60 |
| tgactctctc tcggccgcgc acgccggtgg caaattgctc ttgcattggc tctgtctcta | 120 |
| gacgtccaaa ccgtccaaag tggcagggtg acgtgatgcg acgcacgaag gagatggccc | 180 |
| ggtggcgagg aaccggacac ggcgagccgg cgggaaaaaa ggcggaaaac gaaaagcgaa | 240 |
| gggcacaatc tgacggtgcg gctgccacca acccaaggag gctattttgg gtcgctttcc | 300 |
| atttcacatt cgccctcaat ggccactttg cggtggtgaa catggtttct gaaacaaccc | 360 |
| cccagaatta gagtatattg atgtgtttaa gattgggttg ctatttggcc attgtggggg | 420 |
| agggtagcga cgtggaggac attccagggc gaattgagcc tagaaagtgg taccattcca | 480 |
| accgtctcag tcgtccgaat tgatcgctat aactatcacc tctctcacat gtctacttcc | 540 |
| ccaaccaaca tccccaacct cccccacact aaagttcacg ccaataatgt aggcactctt | 600 |
| tctgggtgtg ggacagcaga gcaatacgga ggggagatta cacaacgagc cacaattggg | 660 |
| gagatggtag ccatctcact cgacccgtcg acttttggca acgctcaatt acccaccaaa | 720 |
| tttgggctgg agttgagggg accgtgttcc agcgctgtag gaccagcaac acacacggta | 780 |
| tcaacagcaa ccaacgcccc cgctaatgca cccagtactg cgcaggtgtg ggccaggtgc | 840 |
| gttccagatg cgagttggcg aaccctaagc cgacagtgta ctttttggga cgggcagtag | 900 |
| caatcgtggg cggagacccc ggtgtatata aaggggtgga gaggacggat tattagcacc | 960 |
| aacacacaca cttatactac atgctagcca caaaa | 995 |

<210> SEQ ID NO 64
<211> LENGTH: 1004
<212> TYPE: DNA
<213> ORGANISM: Yarrowia lipolytica

<400> SEQUENCE: 64

| | |
|---|---|
| gtcagaaggg gcagctctaa acgaagaact gcggtcaggt gacacaactt tttccatctc | 60 |
| agggtgtgtc gcgtgtgctt catccaaact ttagttgggg ttcgggttcg cgcgagatga | 120 |
| tcacgtgccc tgatttggtg tcgtcccccg tcgcgctgcg cacgtgattt atttatttcc | 180 |
| ggtggctgct gtctacgcgg ggccttctct gcccttctgt ttcaaccttc gggcggttct | 240 |
| cgtaaccagc agtagcaatc catttcgaaa ctcaaagagc taaaaacgtt aaacctcagc | 300 |
| agtcgctcga cgaatgggct gcggttggga agcccacgag gcctatagcc agagcctcga | 360 |
| gttgacagga gcccagacgc cttttccaac ggcaacttt atataaaatg gcaatgtatt | 420 |
| catgcaattg cggccgtgtc aggttggaga cactggacca cactctccat tgcttcctga | 480 |
| ggagatggat cattgctagt gcatctacgc gcagcaatcc cgcaagctcg acaaccgtag | 540 |
| atgggctttg gtgggccaat caattacgca acccgcacgt taaattgtat gaggaaggaa | 600 |
| ggccacggta caaagtgggt ggtcttcacc cagtggttgt tggtggcgtc atgcagacca | 660 |
| tgcattgggg atagcacagg gttggggtgt cttgtggact caatgggtga aggagatgg | 720 |
| aaaagggcgg tgaaaagtgg tagaatcgaa atccctgacg tcaatttata aagtaaaatg | 780 |
| cgtttctgcc attttgctcc cctccttctt tcgcaatcgc ctccccaaaa gttgtcgtgg | 840 |

```
cagtacacat gcttgcatac aatgaagcta atccggcttg ctcagtagtt gctatatcca    900
ggcatggtgt gaaaccccctc aaagtatata taggagcggg gagccccagt ctggggtctt    960
ttctctccat ctcaaaacta ctttctcaca tgctagccac aaaa                    1004
```

<210> SEQ ID NO 65
<211> LENGTH: 1422
<212> TYPE: DNA
<213> ORGANISM: Yarrowia lipolytica

<400> SEQUENCE: 65

```
atttcttgtg tgtgcggcaa acgtagcaat tgcaactgca taaacgatga ttgtaaaagt     60
atcacacttt gctcagacag gttagattca cctggtacga gggcagtgtc ttaaaggttc    120
catctacctc ggcccttgtt tcttgaagag tggtcaatat gtgttttata cagctgaaat    180
ttcccctgta tgttgagatc gtgtatattg gtcataatct gggctcttta gtcgatccca    240
gttttctcgg gcaagttttt ttctccacaa agtaccgctg gaaaactcta tgtgacttgt    300
tgacagatta cttgggttat ctgcgggata tgtcttggat aggcaaccgg gcatatatca    360
ccgggcggac tgttggttct gtacgtacat acagcacttt gagctcatgt ctcacacgca    420
accatggtgc gtggaggctt tggcatcctt tctacttgta gtggctatag tacttgcagt    480
ccaagcaaac atgagtatgt gcttgtatgt actgaaaccc gtctacggta atatttaga    540 gtgtggaact atgggatgag tgctcattcg atactatgtt gtcacccgat ttgccgtttg    600
cgaggtaaga cacattcggt ggttcaggcg gctacttgta tgtagcatcc acgttcatgt    660
tttgtggatc agattaatgg tatggatatg cacggggcgt ttccccggta acgtgtaggc    720
agtccagtgc aacccagaca gctgagctct ctatagccgt gcgtgtgcgg tcatatcacg    780
ctacacttag ctacagaata aagctcggta gcgccaacag cgttgacaaa tagctcaagg    840
gcgtggagca cagggtttag gaggttttaa tgggcgagaa ggcgcgtaga tgtagtcttc    900
ctcggtccca tcggtaatca cgtgtgtgcc gatttgcaag acgaaaagcc acgagaataa    960
accgggagag gggatggaag tccccgaaca gcaaccagcc cttgccctcg tggacataac   1020 cttcacttg ccagaactct aagcgtcacc acggtataca agcgcacgta gaagattgtg   1080
gaagtcgtgt tggagactgt tgatttgggc ggtggagggg ggtatttgag agcaagtttg   1140
agatttgtgc cattgagggg gaggttattg tggccatgca gtcggatttg ccgtcacggg   1200
accgcaacat gcttttcatt gcagtccttc aactatccat ctcacctccc ccaatggctt   1260
ttaactttcg aatgacgaaa gcaccccccct ttgtacagat gactatttgg gaccaatcca   1320
atagcgcaat tgggtttgca tcatgtataa aaggagcaat cccccactag ttataaagtc   1380
acaagtatct cagtataccc gtctaaccac acatttatca cc                     1422
```

<210> SEQ ID NO 66
<211> LENGTH: 865
<212> TYPE: DNA
<213> ORGANISM: Yarrowia lipolytica

<400> SEQUENCE: 66

```
atgctcactt tgttgtcct gatgatctcc cgttatttcg ccgctcctct ggaaaccatc     60
cgcccgcaaa tcccctctgc ccatcttgac aatgcacaat gcatcattct cagcctgcat    120
gaatgcgaaa gatggcaata ttggtggagg aggcgacggc ggtaaacaat ggagatagag    180
accacaaaag agacctggag acccaaaatg gactcacgac aactccccca ctccccccact    240
```

```
ccccatctcc ccctgggcat cagttgccca tcggtatctc aactgtcgca ctagttagcg    300
caaccatcac atactttaga cgccaaacaa tgggacaact catcgcgccg aactatgggc    360
agattttaac tcgcacaaca ttaccccaac tctaaaaggt aacctcgacc ggaaaacggg    420
aagacaggat cagcaaccgt gatcgacaga atcttcaggg cactacagtt gatagacata    480
ggttatgttg gtaggtctag acgggcctcg gggaattgac cccaccagtt gcaagtcacg    540
tgcccctgat acagctagtt tagcacatct gcccactacg tctggacgca ccatggtggt    600
gccagtcgcg tgaactcaaa cacccactag cctcgggaag gattcagtta aatccgcacc    660
ttatttccaa cacaaagaag cggttggcgg acaaagaaca tgtcctttct ggggcactgt    720
acattccagg actctgttca aggtcaaata tacaaaacac agatagagaa acatagacag    780
ctgcggcctt ataaatacct gggcgcactt ctctcttttt ccctcctcat cacacattcg    840
ttcaccacta agtcactcgt tcaaa                                          865

<210> SEQ ID NO 67
<211> LENGTH: 880
<212> TYPE: DNA
<213> ORGANISM: Yarrowia lipolytica

<400> SEQUENCE: 67
aaacaaaaga gctgaaatca tatccttcag tagtagtata gtcctgttat cacagcatca     60 attaccccccg tccaagtaag ttgattggga tttttgttta cagatacagt aatatacttg    120
actatttctt tacaggtgac tcagaaagtg catgttggaa atgagccaca gaccaagaca    180
agatatgaca aaattgcact attcgatgca gaattcgacg tgtttccat ggtgttatg     240 acattcatct gcattcatac aaaaaagtct tggtagtggt actttgcgt tattacctcc    300 gatatctacg cacccccccaa ccccctgct acagtaaaga gtgtgagtct actgtacatg    360
cttactaaac cacctactgt acagcgaaac ccctcagcaa aatcacacaa tcagctcatt    420
acaacacacc caatgacctc accacaaatt ctatacgcct tttgacgcca ttattacagt    480
agcttgcaac gccgttgtct taggttccat ttttagtgct ctattacctc acttaacccg    540
tataggcaga tcaggccatg gcactaagtg tagagctaga ggttgatatc gccacgagtg    600
ctccatcagg gctagggtgg ggttagaaat acagtccgtg cgcactcaaa aggcgtccgg    660
gttagggcat ccgataatat cgcctggact cggcgccata ttctcgactt ctgggcgcgt    720
tgtattcatc tcctccgctt cccaacactt ccaccgttt ctccatccca accaatagaa    780
tagggtaacc ttattcggga cactttcgtc atacatagtc agatatacaa gcaatgtcac    840
tctccttcgt actcgtacat acaacacaac tacattcaaa                         880

<210> SEQ ID NO 68
<211> LENGTH: 1000
<212> TYPE: DNA
<213> ORGANISM: Yarrowia lipolytica

<400> SEQUENCE: 68
caattcatgt atcgtgtcaa ttcatgtatc gtgtcaattc atgtatcgtg tcaatactta     60
tatctcaagt ggttgcatcg caaacagcca tcgcatactc cactctactc tcactgagtt    120
cactcttacc cggctccacc ttctagaagc caccaccgat ccaccgacga tgatcagtcc    180
accacttgct ctgaatgtgc gttggagctg caccatgatt gatgacgtca ccgccattca    240
gatagggcaa aagacgagcg ccaatcgcaa caatgggcga gtgtcgacga ctccccccgct    300 ctctgcggtt tcagcgactc caaccgtcgc caaaagaccg tcattttcgt ctaaagcgca    360
```

```
gcccagccca tctcttctaa aagattccag aaagataggg ttcaccaact acgcaccaat      420
atgtacagta tcgtagctac tccggcttgg ctgatctgag agatagagat ggctccgaaa      480
cgcggaaaac ggcggggtcg gaccgatcac gtgacacgta ctcatccgtc gcgccccgag      540
cgccatttca acaccaaata ctcccggtca cgtgccaccc cgcccgctct acccacgaga      600
tgtttctaca ctatacactg ccacgccgtc atacctgcag ctaggttaac attcgattaa      660
ttagtggagt caccagtgta caggactatg gcggaaaccg ggttacacaa accggcccgg      720
aatagcagca ttataccgct ggacgagatc accgtcaata aattgcgtcg ttactcggga      780
caaccattgc tcctccggct acacctgctc aaaggacttg ttccacactc ttccccagct      840
ctcccacgca aacaaagaga gcaaccttaa gtggacagct catgagcact cccctcgttt      900
gctgcccacg ctcgattata taagaccagc cggatcccct tctatttgga cttgcatcaa      960
ccaaccacaa cccacaccaa gcacacaaag cacaagaaca                          1000

<210> SEQ ID NO 69
<211> LENGTH: 127
<212> TYPE: DNA
<213> ORGANISM: Yarrowia lipolytica

<400> SEQUENCE: 69
aattaacaga tagtttgccg gtgataattc tcttaacctc ccacactcct ttgacataac       60
gatttatgta acgaaactga aatttgacca gatattgttg taaatagaaa atctggcttg      120
taggtgg                                                                127

<210> SEQ ID NO 70
<211> LENGTH: 200
<212> TYPE: DNA
<213> ORGANISM: Yarrowia lipolytica

<400> SEQUENCE: 70 gtttttttgat caatgatcca atggctttca catacccccc cacgcctata attaaaacac       60
agagaaatat aatctaactt aataaatatt acggagaatc tttcgagtgt tcagcagaaa      120
tatagccatt gtaacaaaag ccggctatcg accgctttat cgaagaatat ttcccgcccc      180
ccagtggcca aacgatatcg                                                  200

<210> SEQ ID NO 71
<211> LENGTH: 200
<212> TYPE: DNA
<213> ORGANISM: Yarrowia lipolytica

<400> SEQUENCE: 71
ctatccgaag atcaagagcg aagcaagttg taagtccagg acatgtttcc cgcccacgcg       60
agtgatttat aacacctctc tttttgaca cccgctcgcc ttgaaattca tgtcacataa      120
attatagtca acgacgtttg aataacttgt cttgtagttc gatgatgatc atatgattac      180
attaatagta attactgtat                                                  200

<210> SEQ ID NO 72
<211> LENGTH: 200
<212> TYPE: DNA
<213> ORGANISM: Yarrowia lipolytica

<400> SEQUENCE: 72
acttcgagct aatccagtag cttacgttac ccaggggcag gtcaactggc tagccacgag       60
```

```
tctgtcccag gtcgcaattt agtgtaataa acaatatata tattgagtct aaagggaatt    120
gtagctattg tgattgtgtg attttcgtct tgctggttct tattgtgtcc cattcgtttc    180
atcctgatga ggacccctgg                                                200

<210> SEQ ID NO 73
<211> LENGTH: 200
<212> TYPE: DNA
<213> ORGANISM: Yarrowia lipolytica

<400> SEQUENCE: 73
gctatttaca gcatgtgtaa tgaggaatat aacgttgatt gaattgtttg tgaaaaatgt     60
agaaaatttc agtgaagttg tgttttctat atagtaagca cttttggtac aagtatctgc    120
acatccctgc atgttacaag cctgatcatg cagggcaata ttctgactat aaatatacct    180
cgatatttta gcaagctata                                                200

<210> SEQ ID NO 74
<211> LENGTH: 300
<212> TYPE: DNA
<213> ORGANISM: Yarrowia lipolytica

<400> SEQUENCE: 74
atgtggtgat tgctgttgtg caagcctttg ctcgttttct gctgtatgta atttaaagaa     60
cgattgtatg aatcgaagtc aaggtgagtg tagtttgaga agtgtaaccc cagtgtcata    120
gctgtgtact ccattcattg aagggtgtag tcgtgtttta ttgcatgagc gcctattact    180
cgtataagta actgttttgt aacacttcat gaacggagat ggtatgaaca gaagtaataa    240
tatcctggaa gtcagctgtg cccagaggtg tgtgtgggtg tggcatactt tgggacaaca    300

<210> SEQ ID NO 75
<211> LENGTH: 1503
<212> TYPE: DNA
<213> ORGANISM: Artificial sequence
<220> FEATURE:
<223> OTHER INFORMATION: tHMG CpO for Yarrowia lipolitica

<400> SEQUENCE: 75
atgacccagt ctgtgaaggt ggttgagaag cacgttccta tcgtcattga gaagcccagc     60
gagaaggagg aggacacctc ttctgaagac tccattgagc tgactgtcgg aaagcagccc    120
aagcccgtga ccgagacccg ttctctggac gacttggagg ctatcatgaa ggcaggtaag    180
accaagctcc tggaggacca cgaggttgtc aagctctctc tcgaaggcaa gctcccttty    240
tatgctcttg agaagcagct tggtgacaac acccgagctg ttggcatccg acgatctatc    300
atctcccagc agtctaatac caagactctt gagacctcaa agctcccctta cctgcactac    360 gactacgacc gtgttttgg agcctgttgc gagaacgtta ttggttacat gcctctcccc    420
gttggtgttg ctggccccat gaacattgat ggcaagaact accacattcc tatgccacc     480 actgagggtt gtcttgttgc ctcaaccatg cgaggttgca aggccatcaa cgccggtggc    540
ggtgttacca ctgtgcttac tcaggacggt atgacacgag gtccttgtgt tccttccccc    600
tctctcaagc gggctggagc cgctaagatc tggcttgatt ccgaggaggg tctcaagtcc    660
atgcgaaagg ccttcaactc cacctctcga tttgctcgtc tccagtctct tcactctacc    720
cttgctggta acctgctgtt tattcgattc cgaaccacca ctggtgatgc catgggcatg    780
aacatgatct ccaagggcgt cgaacactct ctggccgtca tggtcaagga gtacggcttc    840
cctgatatgg acattgtgtc tgtctcgggt aactactgca ctgacaagaa gcccgcagcg    900
```

| | |
|---|---|
| atcaactgga tcgaaggccg aggcaagagt gttgttgccg aagccaccat ccctgctcac | 960 |
| attgtcaagt ctgttctcaa aagtgaggtt gacgctcttg ttgagctcaa catcagcaag | 1020 |
| aatctgatcg gtagtgccat ggctggctct gtgggaggtt tcaatgcaca cgccgcaaac | 1080 |
| ctggtgaccg ccatctacct tgccactggc caggatcctg ctcagaatgt cgagtcttcc | 1140 |
| aactgcatca cgctgatgag caacgtcgac ggtaacctgc tcatctccgt ttccatgcct | 1200 |
| tctatcgagg tcggtaccat tggtggaggt actattttgg agccccaggg tgctatgctg | 1260 |
| gagatgcttg gcgtgcgagg tcctcacatc gagaccccg gtgccaacgc ccaacagctt | 1320 |
| gctcgcatca ttgcttctgg agttcttgca gcggagcttt cgctgtgttc tgctcttgct | 1380 |
| gccggccatc ttgtgcaaag tcatatgacc cacaaccgtt cccaggctcc tactccggcc | 1440 |
| aagcagtctc aggccgatct gcagcgtctc caaaacggtt cgaatatctg cattcggtca | 1500 |
| tag | 1503 |

<210> SEQ ID NO 76
<211> LENGTH: 984
<212> TYPE: DNA
<213> ORGANISM: Artificial sequence
<220> FEATURE:
<223> OTHER INFORMATION: GGS CpO for Yarrowia lipolitica

<400> SEQUENCE: 76

| | |
|---|---|
| atggattata acagcgcgga tttcaaggag atctggggca aggccgccga caccgcgctg | 60 |
| ctgggaccgt acaactacct cgccaacaac cggggccaca acatcagaga acacttgatc | 120 |
| gcagcgttcg gagcggttat caaggtggac aagagcgatc tcgaaaccat ttcgcacatc | 180 |
| accaagattt tgcataactc gtcgctgctt gttgatgacg tggaagacaa ctcgatgctc | 240 |
| cgacgaggcc tgccggcagc ccattgtctg tttggagtcc cccaaaccat caactccgcc | 300 |
| aactacatgt actttgtggc tctgcaggag gtgctcaagc tcaagtctta tgatgccgtc | 360 |
| tccattttca ccgaggaaat gatcaacttg catagaggtc agggtatgga tctctactgg | 420 |
| agagaaacac tcacttgccc ctcggaagac gagtatctgg agatggtggt gcacaagacc | 480 |
| ggaggactgt ttcggctggc tctgagactt atgctgtcgg tggcatcgaa acaggaggac | 540 |
| catgaaaaga tcaactttga tctcacacac cttaccgaca cactgggagt catttaccag | 600 |
| attctggatg attacctcaa cctgcagtcc acggaattga ccgagaacaa gggattctgc | 660 |
| gaagatatca gcgaaggaaa gttttcgttt ccgctgattc acagcatccg gaccaacccg | 720 |
| gataaccacg agattctcaa cattctcaaa cagcgaacaa gcgacgcttc actcaaaaag | 780 |
| tacgccgtgg actacatgag aacagaaacc aagagtttcg actactgcct caagagaatc | 840 |
| caggccatgt cactcaaggc aagttcgtac attgatgatc tcgcagcagc cggccacgat | 900 |
| gtctccaagt tgcgagccat tttgcattat tttgtgtcca cctctgactg tgaggagaga | 960 |
| aagtactttg aggatgcgca gtga | 984 |

<210> SEQ ID NO 77
<211> LENGTH: 1446
<212> TYPE: DNA
<213> ORGANISM: Artificial sequence
<220> FEATURE:
<223> OTHER INFORMATION: UGT1 CpO for Yarrowia lipolitica

<400> SEQUENCE: 77

| | |
|---|---|
| atggacgcca tggccaccac cgagaagaag ccccacgtca tcttcatccc cttccccgcc | 60 |

```
cagtcccaca tcaaggccat gctcaagctc gcccagctcc tccaccacaa gggcctccag      120
atcacctttg tcaacaccga cttcatccac aaccagttcc tcgagtcctc cggcccccac      180
tgtctggacg gtgctcccgg tttccgattt gagactatcc ccgatggtgt ctcccactcc      240
cccgaggcct ccatccccat ccgagagtct ctgctccgat ccattgagac taacttcctc      300
gaccgattca ttgatctcgt caccaagctc cccgatcctc ccacctgtat catctccgac      360
ggtttcctgt ccgttttcac cattgatgct gccaagaagc tcggtatccc cgtcatgatg      420
tactggactc tggctgcctg tggtttcatg ggtttctacc acatccactc tctgatcgag      480
aagggctttg ctcctctcaa ggacgcctcc tacctcacca acggttacct cgacaccgtc      540
attgactggg tccccggtat ggagggtatc cgactcaagg acttccccct cgactggtcc      600
accgacctca cgacaaggt tctcatgttc accaccgagg ctccccagcg atcccacaag      660
gtttcccacc acatcttcca caccttcgac gagctcgagc cctccatcat caagactctg      720
tctctgcgat acaaccacat ctacaccatt ggccccctcc agctcctcct cgaccagatc      780
cccgaggaga agaagcagac cggtatcacc tctctgcacg gctactctct cgtcaaggaa      840
gagcccgagt gcttccagtg gctccagtcc aaggagccca actccgttgt ctacgtcaac      900
tttggctcca ccaccgtcat gtctctcgag gacatgaccg agtttggctg gggtctggcc      960
aactccaacc actacttcct gtggatcatc cgatccaacc tcgtcattgg cgagaacgcc     1020
gttctgcctc ccgagctcga ggagcacatc aagaagcgag gcttcattgc ctcttggtgc     1080
tcccaggaga aggttctcaa gcaccccctcc gtcggtggtt tcctgaccca ctgcggctgg     1140
ggctccacca ttgagtctct gtccgctggt gtccccatga tctgctggcc ctactcctgg     1200
gaccagctca ccaactgccg atacatctgc aaggagtggg aggttggtct ggagatgggt     1260
accaaggtca agcgagatga ggtcaagcga ctcgtccagg agctcatggg cgagggtggt     1320
cacaagatgc gaaacaaggc caaggactgg aaggagaagg cccgaattgc cattgccccc     1380
aacggctctt cttctctcaa cattgacaag atggtcaagg agatcactgt tctcgctcga     1440
aactaa                                                                1446
```

<210> SEQ ID NO 78
<211> LENGTH: 1383
<212> TYPE: DNA
<213> ORGANISM: Artificial sequence
<220> FEATURE:
<223> OTHER INFORMATION: UGT3 CpO for Yarrowia lipolitica

<400> SEQUENCE: 78

```
atggccgagc agcagaagat caagaagtct ccccacgttc tgctcatccc cttccctctg       60
cagggccaca tcaacccctt catccagttc ggcaagcgac tcatctccaa gggtgtcaag      120
accactctgg tcaccaccat ccacaccctc aactccactc tcaaccactc caacaccacc      180
accacctcca tcgagatcca ggccatctcc gacggctgtg acgagggtgg tttcatgtct      240
gctggtgagt cttacctcga cttttcaag caggtcggtt ccagtctctc tggctgacctc      300 atcaagaagc tccagtccga gggtaccacc attgacgcca tcatctacga ctccatgacc      360
gagtgggttc tcgatgtcgc catcgagttt ggtattgacg gtggctcctt cttcacccag      420
gcctgtgtcg tcaactctct ctactaccac gtccacaagg gtctgatctc tctgcccctc      480
ggcgagactg tctccgtccc cggttttccc gttctgcagc gatgggagac tcctctcatt      540
ctccagaacc acgagcagat ccagtccccc tggtcccaga tgctcttcgg ccagttcgcc      600
aacattgacc aggcccgatg ggttttcacc aactccttct acaagctcga ggaagaggtc     660
```

```
attgagtgga cccgaaagat ctggaacctc aaggtcattg gccccaccct ccctccatg     720 tacctcgaca agcgactcga tgacgacaag gacaacggtt tcaacctcta caaggccaac    780
caccacgagt gcatgaactg gctcgacgac aagcccaagg agtccgttgt ctacgttgcc    840
tttggctctc tggtcaagca cggccccgag caggttgagg agatcacccg agctctgatt    900
gactccgatg tcaacttcct gtgggtcatc aagcacaagg aagagggtaa gctccccgag    960
aacctgtccg aggtcatcaa gaccggcaag ggcctcattg ttgcctggtg caagcagctc   1020
gacgttctcg cccacgagtc cgtcggctgc tttgtcaccc actgcggttt caactccacc   1080
ctcgaggcta tctctctcgg tgtccccgtt gttgccatgc cccagttctc cgaccagacc   1140
accaacgcca agctcctcga tgagattctc ggtgtcggtg tccgagtcaa ggctgacgag   1200
aacggtattg tccgacgagg taacctggct tcttgtatca agatgatcat ggaggaagag   1260
cgaggtgtca tcatccgaaa gaacgccgtc aagtggaagg atctggccaa ggttgctgtc   1320
cacgagggtg gctcttccga caacgacatt gtcgagtttg tctccgagct catcaaggcc   1380
taa                                                                  1383

<210> SEQ ID NO 79
<211> LENGTH: 1377
<212> TYPE: DNA
<213> ORGANISM: Artificial sequence
<220> FEATURE:
<223> OTHER INFORMATION: UGT4 CpO for Yarrowia lipolitica

<400> SEQUENCE: 79
atggagaaca agaccgagac taccgtccga cgacgacgac gaatcattct cttcccccgtc     60 cccttccagg gccacatcaa ccccattctg cagctcgcca acgttctgta ctccaagggc    120
ttctccatca ccatcttcca caccaacttc aacaagccca gacctccaa ctaccccccac    180 ttcacttttcc gattcatcct cgacaacgac ccccaggacg agcgaatctc caacctgccc    240
acccacggtc ctctggctgg tatgcgaatc cccatcatca acgagcacgg tgctgacgag    300
ctccgacgag agctcgagct gctcatgctc gcctccgaag aggacgagga agtctcctgt    360
ctgatcaccg atgctctgtg gtactttgcc cagtccgtcg ccgactctct caacctgcga    420
cgactcgttc tcatgaccctc ctctctgttc aacttccacg cccacgtttc tctgccccag    480
tttgacgagc tcggttacct cgaccccgat gacaagaccc gactgaggga gcaggcttcc    540 ggttttcccca tgctcaaggt caaggacatc aagtccgcct actccaactg gcagattctc    600
aaggagattc tcggcaagat gatcaagcag accaaggcct cctccggtgt catctggaac    660
tccttcaagg agctcgagga gtccgagctc gagactgtca tccgagagat ccccgctccc    720
tctttcctca tccccctgcc caagcacctc accgcttcct cctcttctct gctcgaccac    780
gaccgaaccg tctttcagtg gctcgaccag cagcccccctt cctccgtcct ctacgtttcc    840
ttcggctcca cctccgaggt cgacgagaag gacttcctcg agattgctcg aggcctcgtt    900
gactccaagc agtccttcct gtgggttgtc cgacccggct tgtcaagggg ctccacctgg    960
gttgagcccc tgcccgatgg tttcctcggt gagcgaggcc gaattgtcaa gtgggtcccc   1020
cagcaggaag ttctggccca cggtgccatt ggtgccttct ggacccactc cggctggaac   1080
tccactctcg agtccgtctg cgagggtgtc cccatgatct tctccgactt ggcctcgac    1140 cagccctca acgccgata catgtccgat gttctcaagg tcggtgtcta cctcgagaac    1200
ggctgggagc gaggtgagat tgccaacgcc atccgacgag tcatggtcga cgaggaaggt   1260
```

| | |
|---|---|
| gagtacatcc gacagaacgc ccgagtcctc aagcagaagg ccgatgtctc tctcatgaag | 1320 |
| ggtggttctt cttacgagtc tctcgagtct ctcgtttcct acatctcttc tttgtaa | 1377 |

<210> SEQ ID NO 80
<211> LENGTH: 2232
<212> TYPE: DNA
<213> ORGANISM: Artificial sequence
<220> FEATURE:
<223> OTHER INFORMATION: tCPS_SR CpO for Yarrowia lipolitica

<400> SEQUENCE: 80

| | |
|---|---|
| atgtgcaagg ctgtttccaa ggagtactcc gatctgctcc agaaggacga ggcctctttc | 60 |
| accaagtggg acgacgacaa ggtcaaggac cacctcgaca ccaacaagaa cctctacccc | 120 |
| aacgacgaga tcaaggagtt tgtcgagtcc gtcaaggcca tgttcggctc catgaacgac | 180 |
| ggcgagatta atgtctctgc ttacgacacc gcctgggttg ctctggtcca ggatgtcgac | 240 |
| ggttccggct ctcctcagtt cccttcctct ctcgagtgga tcgccaacaa ccagctgtcc | 300 |
| gacggttctt ggggtgacca cctgctcttc tctgctcacg accgaatcat caacaccctg | 360 |
| gcctgtgtca ttgctctgac ctcttggaac gtccacccct ccaagtgcga aagggtctg | 420 |
| aacttcctcc gagagaacat ctgcaagctc gaggacgaga acgccgagca catgcccatt | 480 |
| ggcttcgagg tcaccttccc ctctctgatt gacattgcca agaagctcaa cattgaggtc | 540 |
| cccgaggaca ccccgctct caaggagatc tacgctcgac gagacatcaa gctcaccaag | 600 |
| atccccatgg aggttctcca aggtccccc accactctcc tccactctct cgagggtatg | 660 |
| cccgatctcg agtgggagaa gctgctcaag ctgcagtgca aggacggctc tttcctcttc | 720 |
| tcccctctt ccactgcctt cgccctcatg cagaccaagg acgagaagtg tctccagtac | 780 |
| ctcaccaaca ttgtcaccaa gttcaacggt ggtgtcccca acgtctaccc cgttgacctc | 840 |
| tttgagcaca tctgggttgt tgaccgactc cagcgactcg gtatcgcccg atacttcaag | 900 |
| tccgagatca aggactgtgt cgagtacatc aacaagtact ggaccaagaa cggtatctgc | 960 |
| tgggcccgaa cacccacgt ccaggacatt gacgacaccg ccatgggctt ccgagttctg | 1020 |
| cgagcccacg gctacgatgt caccccccgat gtctttcgac agtttgagaa ggacggcaag | 1080 |
| tttgtctgtt tcgccggtca gtccaccag gccgtcaccg gtatgttcaa cgtctaccga | 1140 |
| gcttctcaga tgctcttccc cggtgagcga atcctgagg acgccaagaa gttctcctac | 1200 |
| aactacctca aggagaagca gtccaccaac gagctgctcg acaagtggat cattgccaag | 1260 |
| gatctgcccg gtgaggttgg ctacgccctc gacatcccct ggtacgcctc tctgccccga | 1320 |
| ctggagactc gatactacct cgagcagtac ggtggtgagg acgatgtctg gatcggtaag | 1380 |
| accctgtacc gaatgggcta cgtttccaac aacacctacc tcgagatggc caagctcgac | 1440 |
| tacaacaact acgttgccgt cctccagctc gagtggtaca ccatccagca gtggtacgtc | 1500 |
| gacattggta tcgagaagtt cgagtccgac aacatcaagt ccgtccttgt ctcctactac | 1560 |
| ctcgctgctg cctccatctt cgagcccgag cgatccaagg agcgaattgc ctgggccaag | 1620 |
| accaccatcc tcgtcgacaa gatcacctcc atcttcgact cctcccagtc ctccaaggaa | 1680 |
| gatatcaccg ccttcattga caagttccga aacaagtcct cctccaagaa gcactccatc | 1740 |
| aacggcgagc cctggcacga ggtcatggtt gctctcaaga aaactctcca cggcttttgcc | 1800 |
| ctcgacgctc tgatgaccca ctctcaggac atccacccc agctccacca ggcctgggag | 1860 |
| atgtggctca ccaagctcca ggacggtgtt gatgtcactg ctgagctcat ggtccagatg | 1920 |
| atcaacatga ccgccggccg atgggtttcc aaggagctcc tcacccaccc ccagtaccag | 1980 |

```
cgactctcca ctgtcaccaa ctctgtctgc cacgacatca ccaagctcca caacttcaag      2040
gagaactcca ccaccgtcga ctccaaggtc caggagctgg tccagctcgt tttctccgac      2100 accccccgatg atctcgacca ggacatgaag cagaccttcc tgactgtcat gaaaactttc    2160
tactacaagg cctggtgcga ccccaacacc atcaacgacc acatctccaa ggtctttgag      2220
attgtgattt aa                                                          2232

<210> SEQ ID NO 81
<211> LENGTH: 2274
<212> TYPE: DNA
<213> ORGANISM: Artificial sequence
<220> FEATURE:
<223> OTHER INFORMATION: tKS-SR CpO for Yarrowia lipolitica

<400> SEQUENCE: 81
atgacctccc acggcggcca gaccaacccc accaacctca tcattgacac caccaaggag      60
cgaatccaga agcagttcaa gaacgtcgag atctccgttt cctcctacga caccgcctgg     120
gtcgccatgg tccctctcc caactccccc aagtctccct gcttccccga gtgtctcaac      180
tggctcatca caaccagct caacgacggc tcttggggtc tggtcaacca cacccacaac      240
cacaaccacc cctcctcaa ggactctctc tcttccactc tcgcctgcat tgttgctctc      300
aagcgatgga acgttggcga ggaccagatc aacaagggtc tgtctttcat tgagtccaac     360
ctcgcctccg ccaccgagaa gtcccagccc tcccccattg gctttgatat catcttcccc    420
ggtctgctcg agtacgccaa gaacctcgat atcaacctgc tctccaagca gaccgacttc     480
tctctcatgc tgcacaagcg agagctcgag cagaagcgat gccactccaa cgagatggac      540
ggctacctgg cctacatttc cgagggtctg ggtaacctct acgactggaa catggtcaag     600
aagtaccaga tgaagaacgg ttccgttttc aactccccct ctgccaccgc tgctgccttc      660
atcaaccacc agaaccccgg ctgtctcaac tacctcaact ctctgctcga caagtttggt    720
aacgccgtcc ccactgtcta ccccacgat ctcttcatcc gactctccat ggtcgacacc      780
attgagcgac tcggtatttc ccaccacttc cgagtcgaga tcaagaacgt tctcgatgag     840
acttaccgat gctgggttga gcgagatgag cagatcttca tggacgttgt cacctgtgct     900
ctggccttcc gactcctccg aatcaacggt tacgaggttt ccccgaccc cctcgccgag     960 atcaccaacg agctggctct caaggacgag tacgccgccc tcgagactta ccacgcttct    1020
cacattctgt accaagagga tctgtcctcc ggcaagcaga ttctcaagtc cgccgacttc    1080
ctcaaggaga tcatctccac tgactccaac cgactctcca agctcatcca aggaagtc      1140 gagaacgctc tcaagttccc catcaacacc ggtctggagc gaatcaacac ccgacgaaac    1200
atccagctct acaacgtcga caacacccga attctcaaga ccacctacca ctcttccaac    1260
atctccaaca ccgactacct gcgactcgcc gtcgaggact tctacacctg ccagtccatc    1320
taccgagagc agctcaaggg tctggagcga tgggttgtcg agaacaagct cgaccagctc    1380
aagtttgccc gacaaagac tgcctactgc tacttctccg ttgctgccac cctctcttct    1440
cccgagctct ccgacgcccg aatctcttgg gccaagaacg gtatcctgac cactgttgtc    1500
gacgacttct ttgacattgg tggcaccatt gacgagctga ccaacctcat ccagtgcgtc    1560
gagaagtgga acgtcgacgt tgacaaggac tgttgttccg agcacgtccg aatcctcttc    1620
ctggctctca aggacgccat ctgctggatc ggtgacgagg ccttcaagtg gcaggctcga    1680
gatgtcactt cccacgtcat ccagacctgg ctcgagctca tgaactccat gctgcgagag    1740
```

```
gccatctgga cccgagatgc ctacgtcccc accctcaacg agtacatgga gaacgcctac    1800
gtcagctttg ctctcggtcc cattgtcaag cccgccatct actttgtcgg tcccaagctg    1860
tccgaggaga ttgtcgagtc ctccgagtac cacaacctct tcaagctcat gtccacccag    1920
ggccgactcc tcaacgatat ccactccttc aagcgagagt tcaaggaagg taagctcaac    1980
gccgttgctc tgcacctgtc caacggtgag tccggcaagg tcgaggaaga ggtcgtcgag    2040
gagatgatga tgatgatcaa gaacaagcga aaggagctca tgaagctcat cttcgaggag    2100
aacggctcca ttgtcccccg agcctgcaag gacgccttct ggaacatgtg ccacgtcctc    2160
aacttcttct acgccaacga cgacggtttc accggcaaca ccattctcga caccgtcaag    2220
gacatcatct acaaccctct ggttctggtc aacgagaacg aggagcagag gtaa          2274
```

<210> SEQ ID NO 82
<211> LENGTH: 1578
<212> TYPE: DNA
<213> ORGANISM: Artificial sequence
<220> FEATURE:
<223> OTHER INFORMATION: KAH_4 CpO for Yarrowia lipolitica

<400> SEQUENCE: 82

```
atggagtctc tggttgtcca caccgtcaac gccatctggt gcattgtcat tgtcggtatc      60
ttctccgtcg gctaccacgt ctacggccga gctgttgtcg agcagtggcg aatgcgacga     120
tctctcaagc tccagggtgt caagggtcct cctcccctcca tcttcaacgg taacgttttcc   180 gagatgcagc gaatccagtc cgaggccaag cactgctccg gtgacaacat catctcccac     240
gactactctt cttctctgtt cccccacttt gaccactggc gaaagcagta cggccgaatc     300
tacacctact ccactggcct caagcagcac ctctacatca ccacccccga gatggtcaag     360
gagctctccc agaccaacac cctcaacctc ggccgaatca cccacatcac caagcgactc     420
aaccccattc tcggtaacgg tatcatcacc tccaacggcc cccactgggc ccaccagcga     480
cgaatcattg cctacgagtt cacccacgac aagatcaagg gtatggtcgg tctgatggtc     540
gagtccgcca tgcccatgct caacaagtgg gaggagatgg tcaagcgagg tggtgagatg     600
ggctgtgaca tccgagtcga cgaggacctc aaggatgtct ccgctgacgt cattgccaag     660 gcctgttcg ctcttccttc tccaagggc aaggccatct tctccatgat ccgagatctg       720
ctcaccgcca tcaccaagcg atccgtcctc ttccgattca acggtttcac cgacatggtt     780
ttcggctcca agaagcacgg tgacgttgac attgacgctc tcgagatgga gctcgagtcc     840
tccatctggg agactgtcaa ggagcgagag attgagtgca aggacacca caagaaggac      900 ctcatgcagc tcattctcga gggtgccatg cgatcttgtg acggtaacct gtgggacaag     960
tctgcttacc gacgattcgt tgtcgacaac tgcaagtcca tctactttgc cggccacgac    1020
tccaccgccg tttccgtttc ttggtgcctc atgctgctcg ctctcaaccc ctcttggcag    1080
gtcaagatcc gagatgagat tctgtcctcc tgcaagaacg gtatcccga cgccgagtcc     1140 atccccaacc tcaagaccgt caccatggtc atccaggaga ctatgcgact ctaccctccc    1200
gctcccattg tcggccgaga ggcctccaag gacattcgac tcggtgatct ggttgtcccc    1260
aagggtgtct gtatctggac cctcatcccc gctctgcacc gagatcccga gatctggggt    1320
cccgacgcca acgacttcaa gcccgagcga ttctccgagg gtatctccaa ggcctgcaag    1380 taccccagt cctacatccc ctttggcctc ggccccgaa cctgtgtcgg caagaacttt     1440
ggtatgatgg aggtcaaggt cctcgttct ctgattgtct ccaagttctc cttcactctg    1500
tctcccacct accagcactc tccctcccac aagctgctcg tcgagcccca gcacggtgtt    1560
```
gtcatccgag ttgtataa                                              1578

<210> SEQ ID NO 83
<211> LENGTH: 1578
<212> TYPE: DNA
<213> ORGANISM: Artificial sequence
<220> FEATURE:
<223> OTHER INFORMATION: KO_Gib CpO for Yarrowia lipolitica

<400> SEQUENCE: 83

```
atgtccaagt ccaactccat gaactccacc tcccacgaga ctctcttcca gcagctcgtt      60
ctcggcctcg accgaatgcc cctcatggac gtccactggc tcatctacgt tgcctttggt     120
gcctggctct gctcctacgt catccacgtt ctgtcctctt cctccactgt caaggtcccc     180
gtcgtcggtt accgatccgt tttcgagccc acctggctcc tccgactgcg attcgtctgg     240
gagggtggtt ccatcattgg ccagggctac aacaagttca aggactccat cttccaggtc     300
cgaaagctcg gtaccgacat tgtcatcatc cctcccaact acattgacga ggtccgaaag     360
ctctcccagg acaagacccg atccgtcgag cccttcatca acgactttgc cggccagtac     420
acccgaggta tggtctttct gcagtccgat ctccagaacc gagtcatcca gcagcgactc     480
acccccaagc ttgtctctct caccaaggtc atgaaggaag agctcgacta cgctctgacc     540
aaggagatgc ccgacatgaa gaacgacgag tgggttgagg tcgacatctc ttccatcatg     600
gtccgactca tctctcgaat ctccgcccga gttttcctcg gccccgagca ctgccgaaac     660
caggagtggc tcaccaccac cgccgagtac tccgagtctc tcttcatcac cggcttcatc     720
ctccgagttg tcccccacat tctccgaccc ttcattgctc ctctgctgcc ctcttaccga     780
accctgctgc gaaacgtttc ttccggccga cgagtcattg gtgatatcat ccgatcccag     840
cagggtgacg gtaacgagga catcctctct tggatgcgag atgctgccac tggtgaggag     900
aagcagatcg acaacattgc ccagcgaatg ctcattctgt ctctcgcctc catccacacc     960
accgccatga ccatgaccca cgccatgtac gatctgtgtg cctgccccga gtacattgag    1020
cccctccgag atgaggtcaa gtccgtcgtt ggtgcttctg gctgggacaa gaccgctctc    1080
aaccgattcc acaagctcga ctctttcctc aaggagtccc agcgattcaa cccgttttc    1140
ctgctcacct tcaaccgaat ctaccaccag tccatgaccc tctccgatgg taccaacatc    1200
ccctccggta cccgaattgc tgtccctct cacgccatgc tccaggactc cgcccacgtc    1260
cccggtccca ctcctcccac tgagttcgac ggtttccgat actccaagat ccgatccgac    1320
tccaactacg cccagaagta cctcttctcc atgaccgact cttccaacat ggcctttggc    1380
tacggtaagt acgcctgccc cggccgattc tacgcctcca acgagatgaa gctgactctg    1440
gccattctgc tcctccagtt tgagttcaag ctccccgacg gtaagggccg accccgaaac    1500
atcaccatcg actccgacat gatccccgac ccccgagctc gactctgtgt ccgaaagcga    1560
tctctgcgtg acgagtaa                                                 1578
```

<210> SEQ ID NO 84
<211> LENGTH: 2133
<212> TYPE: DNA
<213> ORGANISM: Artificial sequence
<220> FEATURE:
<223> OTHER INFORMATION: CPR_3 CpO for Yarrowia lipolitica

<400> SEQUENCE: 84

```
atgtcctcct cttcttcttc ttccacctcc atgattgatc tcatggctgc catcatcaag      60
```

```
ggtgagcccg tcattgtctc cgaccccgcc aacgcctccg cctacgagtc cgttgctgcc      120
gagctgtcct ccatgctcat cgagaaccga cagtttgcca tgatcgtcac cacctccatt      180
gctgttctca ttggctgcat tgtcatgctc gtctggcgac gatctggctc cggtaactcc      240
aagcgagtcg agcccctcaa gcccctggtc atcaagcccc gagaagagga gatcgacgac      300
ggccgaaaga aggtcaccat cttctttggc acccagaccg gtactgctga gggcttcgcc      360
aaggctctcg gtgaggaagc caaggctcga tacgaaaaga cccgattcaa gattgtcgac      420
ctcgatgatt acgctgccga tgacgacgag tacgaggaga agctcaagaa agaggacgtt      480
gccttcttct tcctcgccac ctacggtgac ggtgagccca ccgacaacgc tgcccgattc      540
tacaagtggt tcaccgaggg taacgaccga ggcgagtggc tcaagaacct caagtacggt      600
gttttcggtc tgggcaaccg acagtacgag cacttcaaca aggttgccaa ggttgtcgac      660
gacatcctcg tcgagcaggg tgcccagcga ctcgtccagg tcggcctcgg tgatgatgac      720
cagtgcatcg aggacgactt cactgcctgg cgagaggctc tgtggcccga gctcgacacc      780
attctgcgag aggaaggtga caccgccgtt gccacccct acaccgccgc cgtcctcgag      840
taccgagtct ccatccacga ctccgaggat gccaagttca cgacatcaa catggccaac      900 ggtaacggct acaccgtctt tgacgcccag caccctaca aggccaacgt cgccgtcaag      960
cgagagctcc acacccccga gtccgaccga tcttgtatcc acctcgagtt tgacattgct     1020
ggttccggtc tgacctacga gactggtgac acgttggtg tcctctgtga caacctgtcc     1080
gagactgtcg acgaggctct gcgactcctc gacatgtccc ccgacactta cttctctctg     1140
cacgccgaga aagaggacgg tactcccatc tcttcttctc tgcccctcc cttcctccc     1200 tgcaacctgc gaaccgctct gacccgatac gcctgcctcc tctcttctcc caagaagtct     1260
gctctcgttg ctctggccgc ccacgcctcc gaccccaccg aggctgagcg actcaagcac     1320
ctcgcctctc ccgctggcaa ggacgagtac tccaagtggg ttgtcgagtc ccagcgatct     1380
ctgctcgagg tcatggccga gttcccctcc gccaagcccc ctctcggtgt tttcttcgcc     1440
ggtgttgctc cccgactcca gccccgattc tactccatct cctcttcccc caagatcgcc     1500
gagactcgaa tccacgttac ctgtgctctg gtctacgaga agatgccac cggccgaatc     1560 cacaagggtg tctgctccac ctggatgaag aacgccgttc cctacgagaa gtccgagaac     1620
tgttcctctg ctcccatctt tgtccgacag tccaacttca agctcccctc cgactccaag     1680
gtccccatca tcatgattgg ccccggtacc ggcctcgccc ccttccgagg cttcctgcag     1740
gagcgactcg ccctcgtcga gtccggtgtc gagctcggcc cctccgtcct cttctttggc     1800
tgccgaaacc gacgaatgga cttcatctac gaagaggagc tccagcgatt cgtcgagtcc     1860
ggtgctctcg ccgagctctc cgttgccttc tcccgagagg gtcccaccaa ggagtacgtc     1920
cagcacaaga tgatggacaa ggcctccgac atctggaaca tgatctccca gggcgcctac     1980
ctctacgtct gcggtgacgc caagggtatg gcccgagatg tccaccgatc tctgcacacc     2040
attgcccagg agcagggctc catggactcc accaaggccg agggtttcgt caagaacctc     2100
cagacctccg gccgatacct ccgagatgtc tgg                                  2133
```

UDP-GLYCOSYLTRANSFERASES

CROSS-REFERENCE TO RELATED APPLICATIONS

This application is a divisional of U.S. application Ser. No. 15/558,133, filed Sep. 13, 2017, which is a National Stage entry of International Application No. PCT/EP2016/055734, filed Mar. 16, 2016, which claims priority to U.S. Provisional Application No. 62/133,606, filed Mar. 16, 2015. The disclosure of the priority applications are incorporated in their entirety herein by reference.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-460001_ST25.txt" created on 26 Jan. 2020, and 159,448 bytes in size) is submitted concurrently with the instant application, and the entire contents of the Sequence Listing are incorporated herein by reference.

BACKGROUND OF THE INVENTION

Field of the Invention

The present invention relates to a recombinant host comprising a recombinant nucleic acid sequence encoding a variant UDP-glycosyltransferase (UGT) polypeptide. The invention also relates to a process for the preparation of a glycosylated diterpene using such a recombinant host and to a fermentation broth which may be the result of such a process. The invention further relates to a glycosylated diterpene obtained by such a process or obtainable from such a fermentation broth and to a composition comprising two or more such glycosylated diterpenes. In addition the invention relates to a foodstuff, feed or beverage which comprises such a glycosylated diterpene or a such composition. The invention also relates to a method for converting a first glycosylated diterpene into a second glycosylated diterpene using the above-mentioned recombinant host. Furthermore, the invention relates to variant UGT polypeptides, to nucleic acid sequences encoding such polypeptides, to a nucleic acid construct comprising such a polynucleotide sequence and to a method for producing the variant UGT polypeptides using the above-mentioned recombinant host.

Description of Related Art

The leaves of the perennial herb, Stevis rebaudiana Bert., accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in Stevia leaves where they may comprise from 10 to 20% of the leaf dry weight. Stevioside and rebaudioside A are both heat and pH stable and suitable for use in carbonated beverages and many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in Stevia leaves. It may be about 200 times sweeter than sucrose. Rebaudioside M is a further high-potency diterpene glycoside sweetener. It is present in trace amounts in certain stevia variety leaves, but has been suggested to have a superior taste profile.

Steviol glycosides have traditionally been extracted from the *Stevia* plant. In *Stevia*, (−)-kaurenoic acid, an intermediate in gibberellic acid (GA) biosynthesis, is converted into the tetracyclic dipterepene steviol, which then proceeds through a multi-step glycosylation pathway to form the various steviol glycosides. However, yields may be variable and affected by agriculture and environmental conditions. Also, Stevia cultivation requires substantial land area, a long time prior to harvest, intensive labour and additional costs for the extraction and purification of the glycosides.

SUMMARY

More recently, interest has grown in producing steviol glycosides using fermentative processes. WO2013/110673 and WO2015/007748 describe microorganisms that may be used to produce at least the steviol glycosides rebaudioside A and rebaudioside D.

Further improvement of such microoganisms is desirable in order that higher amounts of steviol glycosides may be produced and/or additional or new steviol glycosides and/or higher amounts of specific steviol glycosides and/or mixtures of steviol glycosides having desired ratios of different steviol glycosides.

In *Stevia rebaudiana*, steviol is synthesized from GGPP, which is formed by the deoxyxylulose 5-phosphate pathway. The activity of two diterpene cyclases (−)-copalyl diphosphate synthase (CPS) and (−)-kaurene synthase (KS) results in the formation of (−)-Kaurene which is then oxidized in a three step reaction by (−)-kaurene oxidase (KO) to form (−)-kaurenoic acid.

In *Stevia rebaudiana* leaves, (−)-kaurenoic acid is then hydroxylated, by ent-kaurenoic acid 13-hydroxylase (KAH) to form steviol. Steviol is then glycosylated by a series of UDP-glycosyltransferases (UGTs) leading to the formation of a number of steviol glycosides. Specifically, these molecules can be viewed as a steviol molecule, with its carboxyl hydrogen atom replaced by a glucose molecule to form an ester, and an hydroxyl hydrogen with combinations of glucose and rhamnose to form an acetal.

These pathways may be reconstructed in recombinant hosts, for example yeasts such as *Saccharomyces* and *Yarrowia*.

The invention relates to the identification of new variant UDP-glycosyltransferase (UGT) polypeptides, typically having improved properties in comparison to those that are currently known. These polypeptides may be used to generate recombinant hosts that produce higher amounts of steviol glycosides and/or additional or new steviol glycosides and/or higher amounts of specific steviol glycosides and/or mixtures of steviol glycosides having desired ratios of different steviol glycosides.

Thus, the invention also relates to a recombinant host capable of producing a a glycosylated diterpene (i.e. a diterpene glycoside such as a steviol glycoside), such as steviolmonoside, steviolbioside, stevioside, rebaudioside A, rebaudioside B, rebaudioside C, rebaudioside D, rebaudioside E, rebaudioside F, rebaudiosideM, rubusoside, dulcoside A, steviol-13-monoside, steviol-19-monoside or 13-[(β-D-Glucopyranosyl)oxy)kaur-16-en-18-oic acid 2-O-β-D-glucopyranosyl-β-D-glucopyranosyl ester steviol-19-diside, Accordingly, the invention relates to a recombinant host comprising a recombinant nucleic acid sequence, typically having UDP-glycosyltransferase (UGT) activity such as UGT2 activity, encoding a polypeptide having at least about:
 a. 85% identity to the amino acid sequence set forth in SEQ ID NO: 1;
 b. 85% identity to the amino acid sequence set forth in SEQ ID NO: 3;
 c. 85% identity to the amino acid sequence set forth in SEQ ID NO: 6;
 d. 85% identity to the amino acid sequence set forth in SEQ ID NO: 9;
 e. 85% identity to the amino acid sequence set forth in SEQ ID NO: 11;
 f. 85% identity to the amino acid sequence set forth in SEQ ID NO: 14;
 g. 85% identity to the amino acid sequence set forth in SEQ ID NO: 17;
 h. 85% identity to the amino acid sequence set forth in SEQ ID NO: 20;
 i. 85% identity to the amino acid sequence set forth in SEQ ID NO: 22; or
 j. 85% identity to the amino acid sequence set forth in SEQ ID NO: 25.

The invention also relates to:
a process for the preparation of a glycosylated diterpene which comprises fermenting a recombinant host of the invention in a suitable fermentation medium, and optionally recovering the glycosylated diterpene;
a fermentation broth comprising a glycosylated diterpene obtainable by the process of the invention;
a glycosylated diterpene obtained by such a process or obtainable from such a fermentation broth;
a composition comprising two or more such diterpenes;
a foodstuff, feed or beverage which comprises such a glycosylated diterpene;
a method for converting a first glycosylated diterpene into a second glycosylated diterpene, which method comprises:
 contacting said first glycosylated diterpene with a recombinant host of the invention, a cell free extract derived from such a recombinant host or an enzyme preparation derived from either thereof;
 thereby to convert the first glycosylated diterpene into the second glycosylated diterpene.
a polypeptide having UGT2 activity, wherein said polypeptide is selected from the group consisting of:
 (a) a polypeptide comprising an amino acid sequence as set out in any one of SEQ ID NOs: 1, 3, 6, 9, 11, 14, 17, 20, 22 or 25; or
 (b) a polypeptide comprising an amino acid sequence having at least about 85% sequence identity with the amino acid sequence of any one of SEQ ID NOs: 1, 3, 6, 9, 11, 14, 17, 20, 22 or 25; or
 (c) a polypeptide encoded by a polynucleotide comprising the polynucleotide sequence as set out in any one SEQ ID NOs: 2, 4, 5, 7, 8, 10, 12, 13, 15, 16, 18, 19, 21, 23, 24 or 26; or
 (d) a polypeptide encoded by a polynucleotide comprising a polynucleotide sequence having at least 50% sequence identity to the polypeptide coding sequence in any one SEQ ID NOs: 2, 4, 5, 7, 8, 10, 12, 13, 15, 16, 18, 19, 21, 23, 24 or 26; or
 (e) a polypeptide encoded by a polynucleotide which hybridises, preferably under at least low stringency conditions, with the complementary strand of any one SEQ ID NOs: 2, 4, 5, 7, 8, 10, 12, 13, 15, 16, 18, 19, 21, 23, 24 or 26; or
 (f) a polypeptide encoded by a polynucleotide which hybridises, preferably under at least low stringency conditions, with the complementary strand of a polynucleotide having at least 50% sequence identity to any one SEQ ID NOs: 2, 4, 5, 7, 8, 10, 12, 13, 15, 16, 18, 19, 21, 23, 24 or 26; or
 (g) a fragment of a polypeptide as defined in (a), (b), (c), (d), (e) or (f).
a polynucleotide sequence coding for such a polypeptide;
a nucleic acid construct comprising such a polynucleotide sequence; and
a method of producing the polypeptide of the invention, comprising:
 (a) cultivating a recombinant host of the invention under conditions conducive to the production of the polypeptide by the host cell, and optionally,
 (b) recovering the polypeptide.

BRIEF DESCRIPTION OF THE DRAWINGS

FIG. 12 sets out the production of rebaudiosideM in *Saccharomyces* strains expressing different variants of UGT2, as a percentage of the rebaudioside M production in a *Saccharomyces* strain expressing UGT2_1a.

FIG. 13 sets out the map of plasmid MB6969, carrying genes tHMG and UGT2_1a

FIG. 29 sets out the production of rebaudioside M in *Yarrowia* strains expressing different variants of UGT2, as a percentage of the rebaudioside M production in a *Yarrowia* strain expressing UGT2_1a.

DESCRIPTION OF THE SEQUENCE LISTING

Figure 1:
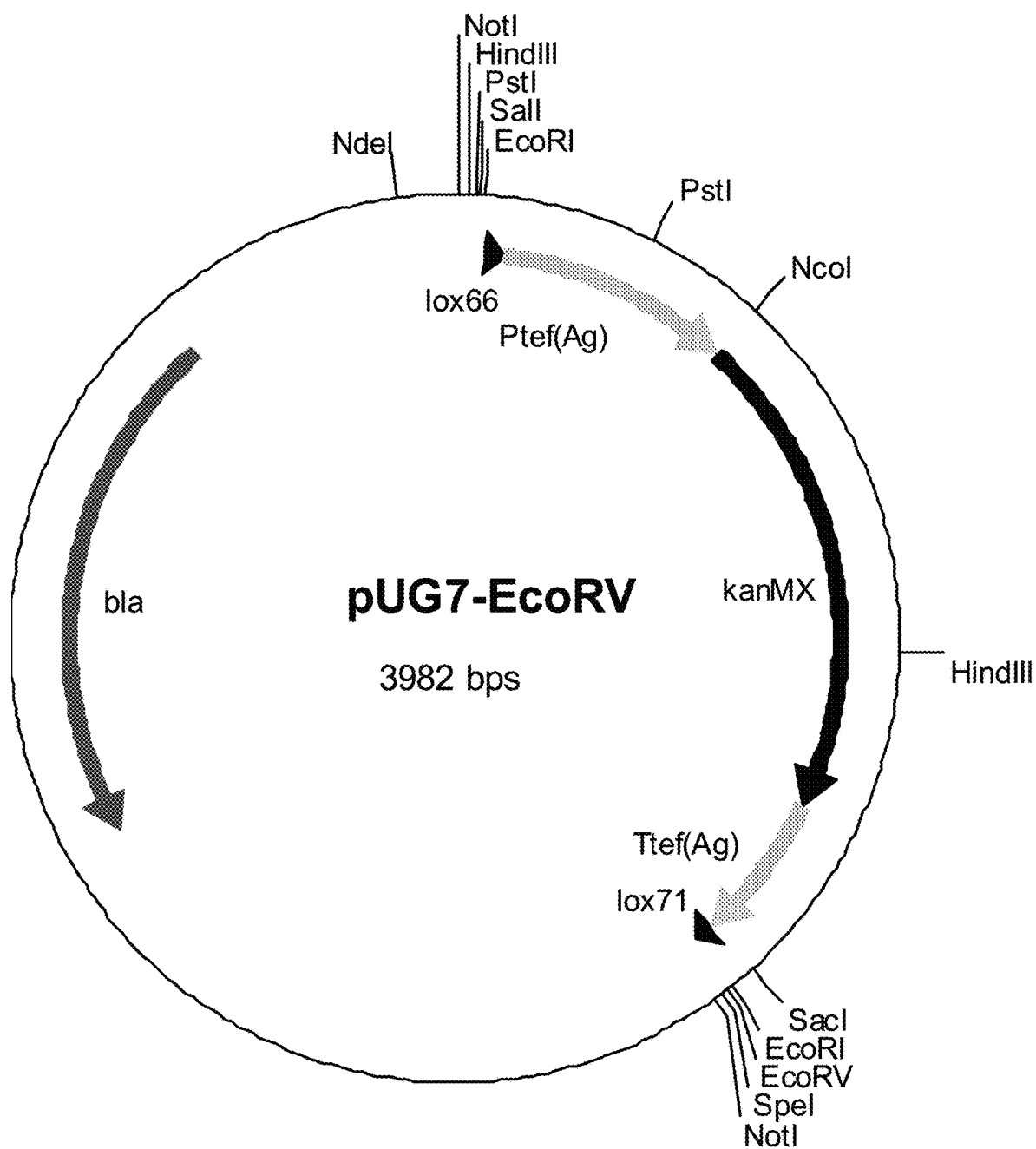
FIG. 1 sets out a schematic representation of the plasmid pUG7-EcoRV.

A description of the sequences is set out in Table 13. Sequences described herein may be defined with reference to the sequence listing or with reference to any database accession numbers set out herein, for example in Table 13.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or more than one (i.e. to one or at least one) of the grammatical object of the article. By way of example, "an element" may mean one element or more than one element.

Herein, "rebaudioside" may be shortened to ""reb". That is rebaudioside A and rebA, for example, are intended to indicate the same molecule.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. The term "recombinant" is synonymous with "genetically modified".

The invention relates to new variant polypeptides having UDP-glycosyltransferase (UGT) activity. For the purposes of this invention, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose). A polypeptide of the invention typically has UGT activity and a polynucleotide sequence of the invention typically encodes such a polypeptide. Typically, the polypeptides of the invention are variant polypeptides having UGT2-type activity.

According to the invention, there is thus provided a polypeptide, typically one having UGT activity, wherein said polypeptide is selected from the group consisting of:
  (a) a polypeptide comprising an amino acid sequence as set out in any one of SEQ ID NOs: 1, 3, 6, 9, 11, 14, 17, 20, 22 or 25; or
  (b) a polypeptide comprising an amino acid sequence having at least about 85% sequence identity with the amino acid sequence of any one of SEQ ID NOs: 1, 3, 6, 9, 11, 14, 17, 20, 22 or 25; or
  (c) a polypeptide encoded by a polynucleotide comprising the polynucleotide sequence as set out in any one SEQ ID NOs: 2, 4, 5, 7, 8, 10, 12, 13, 15, 16, 18, 19, 21, 23, 24 or 26; or
  (d) a polypeptide encoded by a polynucleotide comprising a polynucleotide sequence having at least 50% sequence identity to the polypeptide coding sequence in any one SEQ ID NOs: 2, 4, 5, 7, 8, 10, 12, 13, 15, 16, 18, 19, 21, 23, 24 or 26; or
  (e) a polypeptide encoded by a polynucleotide which hybridizes, preferably under at least low stringency conditions, with the complementary strand of any one SEQ ID NOs: 2, 4, 5, 7, 8, 10, 12, 13, 15, 16, 18, 19, 21, 23, 24 or 26; or
  (f) a polypeptide encoded by a polynucleotide which hybridizes, preferably under at least low stringency conditions, with the complementary strand of a polynucleotide having at least 50% sequence identity to any one SEQ ID NOs: 2, 4, 5, 7, 8, 10, 12, 13, 15, 16, 18, 19, 21, 23, 24 or 26; or
  (g) a fragment of a polypeptide as defined in (a), (b), (c), (d), (e) or (f).

Such a polypeptide may comprise an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to any one of SEQ ID NOs: 1, 3, 6, 9, 11, 14, 17, 20, 22 or 25.

Thus, the invention relates to:

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 1;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO 3;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 6;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 9;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 11;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 14;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 17;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 20;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 22; and a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 25.

As used herein, the term "polypeptide" refers to a molecule comprising amino acid residues linked by peptide bonds and containing more than five amino acid residues. The amino acids are identified by either the single-letter or three-letter designations. The term "protein" as used herein is synonymous with the term "polypeptide" and may also refer to two or more polypeptides. Thus, the terms "protein", "peptide" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity may be referred to as enzymes. It will be understood that, as a result of the degeneracy of the genetic code, a multitude of nucleotide sequences encoding a given polypeptide may be produced.

A polypeptide of the invention may comprise a signal peptide and/or a propeptide sequence. In the event that a polypeptide of the invention comprises a signal peptide and/or a propeptide, sequence identity may be calculated over the mature polypeptide sequence.

Figure 31:
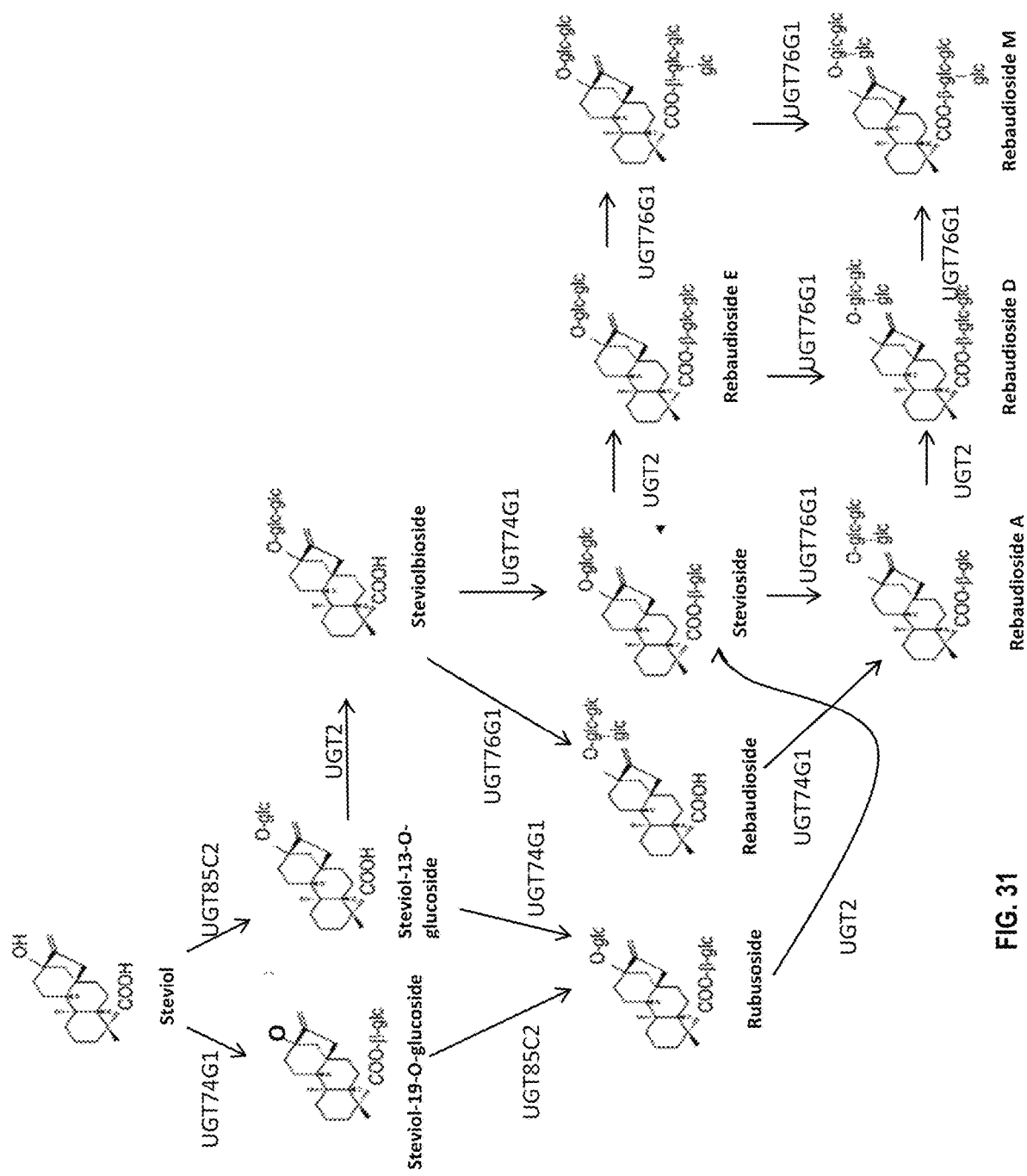
FIG. 31 sets out sets out a schematic diagram of the potential pathways leading to biosynthesis of steviol glycosides.
Figure 32:
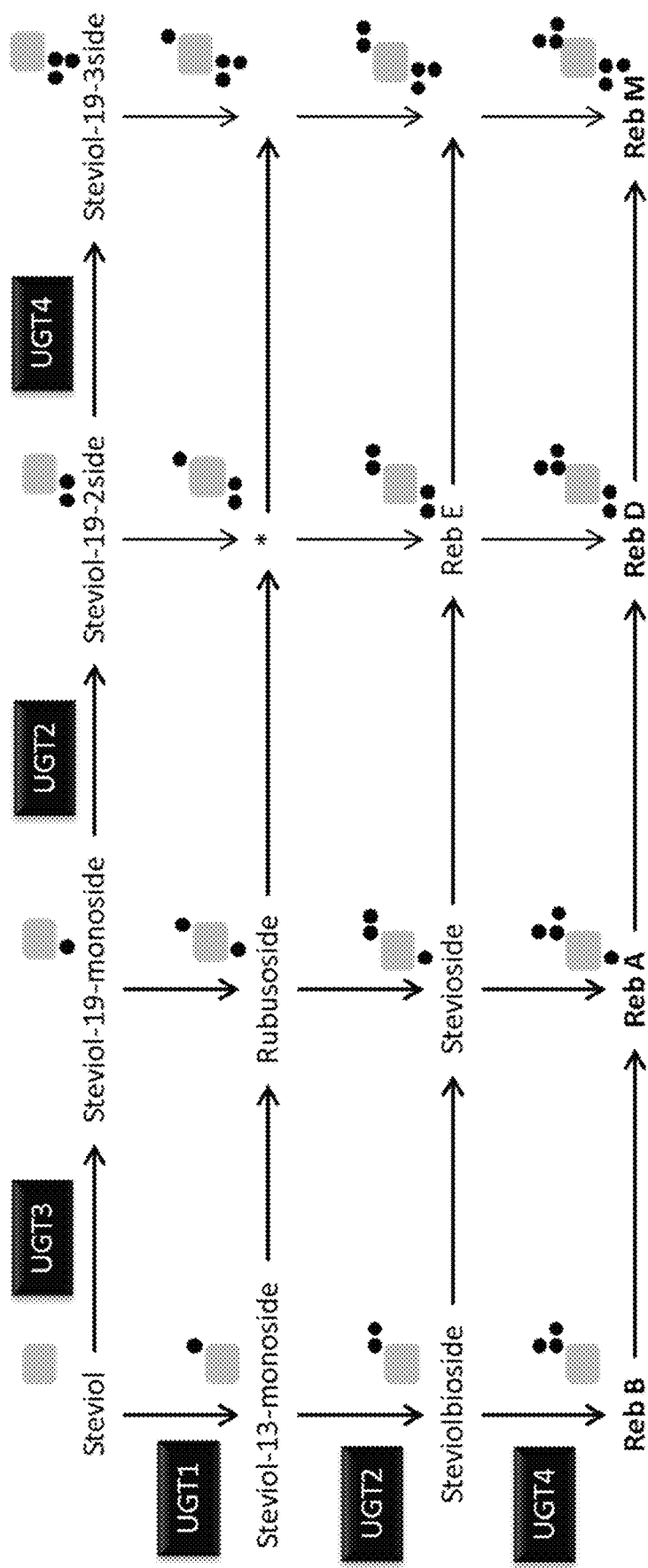
FIG. 32 sets out sets out a schematic diagram of the potential pathways leading to biosynthesis of steviol glycosides. The compound shown with an asterisk is 13-[(β-D-Glucopyranosyl)oxy)kaur-16-en-18-oic acid 2-O-β-D-glucopyranosyl-β-D-glucopyranosyl ester

A polypeptide of the invention typically has UGT activity and more preferably has UGT2 activity. FIGS. 31 and 32 illustrate a non-exhaustive list of reactions that may be catalyzed by a polypeptide having UGT2.

A polypeptide having UGT2 activity is one which functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-0-glucoside and rubusoside, e.g., a functional UGT2 polypeptide may utilize stevioside as a substrate, transferring a glucose moiety to the C-2' of the 19-O-glucose residue to produce rebaudioside E. A functional UGT2 polypeptide may also utilize rebaudioside A as a substrate, transferring a glucose moiety to the C-2' of the 19-O-glucose residue to produce rebaudioside D.

A polypeptide having UGT2 activity may also catalyze reactions that utilize steviol-19-glucoside or rubusoside as a substrate, e.g., a functional UGT2 polypeptide may utilize steviol-19-glucoside or rubusoside as a substrate, transferring a glucose moiety to the 19 position to produce steviol- 19-2side or 13-[(β-D-Glucopyranosyl)oxy)kaur-16-en-18-oic acid 2-O-β-D-glucopyranosyl-β-D-glucopyranosyl ester respectively.

However, a functional UGT2 polypeptide typically does not transfer a glucose moiety to steviol compounds having a 1,3-bound glucose at the C-13 position, i.e., transfer of a glucose moiety to steviol 1,3-bioside and 1,3-stevioside typically does not occur.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl: steviol-13-0-glucoside transferase, transferring a rhamnose moiety to the C-2' of the 13-O-glucose of the acceptor molecule, steviol.

One or more of the above-described activities may be used to define a polypeptide having UGT2 activity. A polypeptide of the invention may have improved UGT2 activity in respect of one or more of the above-described activities in comparison with the UGT2_1a polypeptide (SEQ ID NO: 27).

A polypeptide of the invention may be used to steer production of steviol glycosides in a recombinant cell to a desired steviol glycoside, such as rebaudioside A, rebaudioside D or rebaudioside M. For example, a UGT2 polypeptide which preferentially catalyzes conversion of steviol-13-monoside to steviolbioside and/or conversion of rubusoside to stevioside may help to steer production towards rebaudiosideA, whereas a UGT2 polypeptide which preferentially catalyzes conversion of stevioside to rebE or rubusoside to a compound with an additional sugar at the 19 position may help to steer production towards rebaudioside M. That is to say preference for addition of a sugar moiety at the 13 position may help steer production towards rebaudioside A, whereas preference for addition of a sugar moiety at the 19 position may help steer production towards rebaudioside M.

The invention further provides a polynucleotide sequence coding for a polypeptide as described herein.

Such a polynucleotide sequence may be selected from the group consisting of:
(a) a polynucleotide sequence comprising any one of SEQ ID NOs: 2, 4, 5, 7, 8, 10, 12, 13, 15, 16, 18, 19, 21, 23, 24 or 26 or comprising a polynucleotide sequence having at least 30% sequence identity with the polynucleotide sequence of any one of SEQ ID NOs: 2, 4, 5, 7, 8, 10, 12, 13, 15, 16, 18, 19, 21, 23, 24 or 26; or
(b) a polynucleotide sequence which hybridizes, preferably under at least low stringency conditions, with the complementary strand of any one SEQ ID NOs: 2, 4, 5, 7, 8, 10, 12, 13, 15, 16, 18, 19, 21, 23, 24 or 26; or
(c) a polynucleotide sequence which hybridizes, preferably under at least low stringency conditions with the complementary strand of a polynucleotide having at least 30% sequence identity to any one of any one SEQ ID NOs: 2, 4, 5, 7, 8, 10, 12, 13, 15, 16, 18, 19, 21, 23, 24 or 26;
(d) a polynucleotide sequence which is degenerate as a result of the degeneracy of the genetic code to a polynucleotide sequence as defined in any one of (a), (b) or (c); or
(e) a polynucleotide sequence which is the complement of a nucleotide sequence as defined in (a), (b), (c) or (d).

A polynucleotide sequence of the invention may have a sequence identity of at least 40%, at least 50%, at least 60%, preferably at least 70%, more preferably at least 80%, most preferably at-least 90%, most preferably at least 93%, most preferably at least about 95%, most preferably at least about 96%, most preferably at least about 97%, even most preferably at least about 98%, and even more preferred at least 99% to any one of any one SEQ ID NOs: 2, 4, 5, 7, 8, 10, 12, 13, 15, 16, 18, 19, 21, 23, 24 or 26.

The term "nucleic acid" as used in the present invention refers to a nucleotide polymer including at least 5 nucleotide units. A nucleic acid refers to a ribonucleotide polymer (RNA), deoxynucleotide polymer (DNA) or a modified form of either type of nucleic acid or synthetic form thereof or mixed polymers of any of the above. Nucleic acids may include either or both naturally-occurring and modified nucleic acids linked together by naturally-occurring and/or non-naturally occurring nucleic acid linkages. The nucleic acid molecules may be modified chemically or biochemically or may contain non-natural or derivatized nucleic acid bases, as will be readily appreciated by those of skill in the art. Such modifications include, for example, labels, methylation, substitution of one or more of the naturally occurring nucleic acids with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) The term nucleic acid is also intended to include any topological conformation, including single-stranded (sense strand and antisense strand), double-stranded, partially duplexed, triplex, hairpinned, circular and padlocked conformations. Also included are synthetic molecules that mimic nucleic acids in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers. The term "nucleic acid", "polynucleotide" and "polynucleotide sequence" can be used interchangeably herein.

As used herein, the term "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleotide bases (nucleotides) of the strands of oligomeric compounds. For example, adenine and thymine are complementary nucleic acids which pair through the formation of hydrogen bonds. Hybridization can occur under varying circumstances. "Stringency hybridization" or "hybridizes under low stringency, medium stringency, high stringency, or very high stringency conditions" is used herein to describe conditions for hybridization and washing, more specifically conditions under which an oligomeric compound will hybridize to its target sequence, but to a minimal number of other sequences. So, the oligomeric compound will hybridize to the target sequence to a detectably greater degree than to other sequences. Guidance for performing hybridization reactions can be found in Current Protocols in Molecular Biology, John Wiley & Sons, N.Y. (1989), 6.3.1-6:3.6. Aqueous and non-aqueous methods are described in that reference and either can be used. Stringency conditions are sequence-dependent and will be different in different circumstances. Generally, stringency conditions are selected to be about 5° C. lower than the thermal melting point ($T_m$) for the oligomeric compound at a defined ionic strength and pH. The $T_m$ is the temperature (under defined ionic strength and pH) at which 50% of an oligomeric compound hybridizes to a perfectly matched probe. Stringency conditions may also be achieved with the addition of destabilizing agents such as formamide.

Examples of specific hybridization conditions are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C.

In general, high stringency conditions, such as high hybridization temperature and optionally low salt concentrations, permit only hybridization between sequences that are highly similar, whereas low stringency conditions, such as low hybridization temperature and optionally high salt concentrations, allow hybridization when the sequences are less similar.

The invention also provides a nucleic acid construct comprising the polynucleotide sequence of the invention.

The term "nucleic acid construct" refers to as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

A nucleic acid of the invention may be an expression vector, wherein a polynucleotide sequence of the invention is operably linked to at least one control sequence for the expression of the polynucleotide sequence in a host cell.

The term "operably linked" as used herein refers to two or more nucleic acid sequence elements that are physically linked and are in a functional relationship with each other. For instance, a promoter is operably linked to a coding sequence if the promoter is able to initiate or regulate the transcription or expression of a coding sequence, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

An expression vector comprises a polynucleotide coding for a polypeptide of the invention, operably linked to the appropriate control sequences (such as a promoter, and transcriptional and translational stop signals) for expression and/or translation in vitro, or in the host cell of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e., a vector, which exists as an extra-chromosomal entity, the replication of which is independent of chromosomal replication, e.g., a plasmid, an extra-chromosomal element, a mini-chromosome, or an artificial chromosome.

Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. A vector of the invention may comprise one or more selectable markers, which permit easy selection of transformed cells.

The invention also provides a recombinant host which comprises a recombinant nucleic acid sequence encoding a polypeptide of the invention.

That is to say, a recombinant host of the invention may comprise, for example, a recombinant nucleic acid sequence encoding a polypeptide having at least about:
 a. 85% identity to the amino acid sequence set forth in SEQ ID NO: 1;
 b. 85% identity to the amino acid sequence set forth in SEQ ID NO: 3;
 c. 85% identity to the amino acid sequence set forth in SEQ ID NO: 6;
 d. 85% identity to the amino acid sequence set forth in SEQ ID NO: 9;
 e. 85% identity to the amino acid sequence set forth in SEQ ID NO: 11;
 f. 85% identity to the amino acid sequence set forth in SEQ ID NO: 14;
 g. 85% identity to the amino acid sequence set forth in SEQ ID NO: 17;
 h. 85% identity to the amino acid sequence set forth in SEQ ID NO: 20;
 i. 85% identity to the amino acid sequence set forth in SEQ ID NO: 22; or
 j. 85% identity to the amino acid sequence set forth in SEQ ID NO: 25.

A recombinant host of the invention may comprise any polynucleotide encoding a polypeptide of the invention as described herein. A recombinant host of the invention is typically capable of expressing a polypeptide of the invention.

Typically, a recombinant host of the invention is capable of producing a glycosylated diterpene, such as a steviol glycoside. For example, a recombinant host of the invention may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebE, rebD or rebM.

A recombinant host according to the invention may comprise one or more recombinant nucleotide sequence(s) encoding one of more of:
 a polypeptide having ent-copalyl pyrophosphate synthase activity;

a polypeptide having ent-Kaurene synthase activity;
a polypeptide having ent-Kaurene oxidase activity; and
a polypeptide having kaurenoic acid 13-hydroxylase activity.

For the purposes of this invention, a polypeptide having ent-copalyl pyrophosphate synthase (EC 5.5.1.13) is capable of catalyzing the chemical reation:

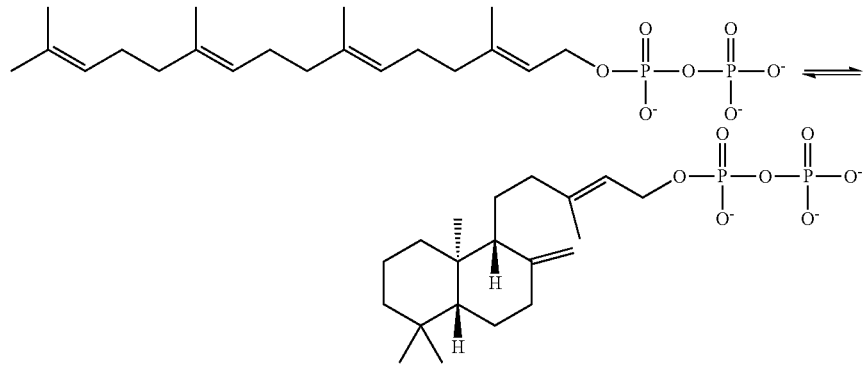

This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this invention, a polypeptide having ent-kaurene synthase activity (EC 4.2.3.19) is a polypeptide that is capable of catalyzing the chemical reaction:

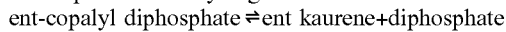

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleotide sequence used in the invention may encode a polypeptide having ent-copalyl pyrophosphate synthase activity and ent-kaurene synthase activity. Alternatively, the two activities may be encoded two distinct, separate nucleotide sequences.

For the purposes of this invention, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

For the purposes of the invention, a polypeptide having kaurenoic acid 13-hydroxylase activity (EC 1.14.13) is one which is capable of catalyzing the formation of steviol (ent-kaur-16-en-13-ol-19-oic acid) using NADPH and $O_2$. Such activity may also be referred to as ent-ka 13-hydroxylase activity.

Suitable nucleic acid sequences encoding a kaurenoic acid 13-hydroxylase may for instance comprise a sequence as set out in SEQ ID. NO: 27, 29, 31, 33, 69, 89, 91, 93, 95, 97, 146, 164, 165, 166, 167 or 185 of WO2015/007748.

A recombinant host of the invention may comprise a recombinant nucleic acid sequence encoding a polypeptide having NADPH-cytochrome p450 reductase activity. That is to say, a recombinant host of the invention may be capable of expressing a nucleotide sequence encoding a polypeptide having NADPH-cytochrome p450 reductase activity. For the purposes of the invention, a polypeptide having NADPH-Cytochrome P450 reductase activity (EC 1.6.2.4; also known as NADPH:ferrihemoprotein oxidoreductase, NADPH:hemoprotein oxidoreductase, NADPH:P450 oxidoreductase, P450 reductase, POR, CPR, CYPOR) is typically one which is a membrane-bound enzyme allowing electron transfer to cytochrome P450 in the microsome of the eukaryotic cell from a FAD- and FMN-containing enzyme NADPH:cytochrome P450 reductase (POR; EC 1.6.2.4).

A recombinant host according to any one of the preceding claims which comprises a one or more recombinant nucleic acid sequences encoding one or more of:
(i) a polypeptide having UGT74G1 activity (UGT3 activity);
(ii) a polypeptide having UGT85C2 activity (UGT1 activity); and
(iii) a polypeptide having UGT76G1 activity (UGT4 activity).

FIGS. 31 and 32 set out schematic diagram of the potential pathways leading to biosynthesis of steviol glycosides.

A recombinant host of the invention will typically comprise at least one recombinant nucleic acid encoding a polypeptide having UGT1 activity, at least one recombinant nucleic acid encoding a polypeptide having UGT2 activity, at least one recombinant nucleic acid encoding a polypeptide having UGT3 activity and at least one recombinant nucleic acid encoding a polypeptide having UGT4 activity. One nucleic acid may encode two or more of such polypeptides.

A nucleic acid encoding a polypeptide of the invention may be used to steer production of steviol glycosides in a recombinant cell to a desired steviol glycoside, such as rebaudioside A, rebaudioside D or rebaudioside M. For example, a recombinant nucleic acid which encodes a UGT2 polypeptide which preferentially catalyzes conversion of steviol-13-monoside to steviolbioside and/or conversion of rubusoside to stevioside may help to steer production towards rebaudiosideA, whereas a recombinant nucleic acid which encodes a UGT2 polypeptide which preferentially catalyzes conversion of stevioside to rebE or rubusoside to a compound with an additional sugar at the 19 position may help to steer production towards rebaudioside M. That is to say preference for addition of a sugar moiety at the 13 position may help steer production towards rebaudioside A, whereas preference for addition of a sugar moiety at the 19 position may help steer production towards rebaudioside M.

A recombinant host of the invention may comprises a nucleotide sequence encoding a polypeptide capable of catalyzing the addition of a C-13-glucose to steviol. That is to say, a recombinant host of the invention may comprise a UGT which is capable of catalyzing a reaction in which steviol is converted to steviolmonoside.

Such a recombinant host of the invention may comprise a nucleotide sequence encoding a polypeptide having the activity shown by UDP-glycosyltransferase (UGT) UGT85C2, whereby the nucleotide sequence upon transformation of the host confers on that host the ability to convert steviol to steviolmonoside.

UGT85C2 activity is transfer of a glucose unit to the 13-OH of steviol. Thus, a suitable UGT85C2 may function as a uridine 5'-diphospho glucosyl: steviol 13-OH transferase, and a uridine 5'-diphospho glucosyl: steviol-19-0-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein.

A recombinant host of the invention may comprise a nucleotide sequence encoding a polypeptide having UGT activity may comprise a nucleotide sequence encoding a polypeptide capable of catalyzing the addition of a C-13-glucose to steviol or steviolmonoside. That is to say, a recombinant of the invention may comprise a UGT which is capable of catalyzing a reaction in which steviolmonoside is converted to steviolbioside. Accordingly, such a recombinant host may be capable of converting steviolmonoside to steviolbioside. Expression of such a nucleotide sequence may confer on the host the ability to produce at least steviolbioside.

A recombinant microorganism of the invention also comprises a nucleotide sequence encoding a polypeptide having UGT activity may comprise a nucleotide sequence encoding a polypeptide capable of catalyzing the addition of a C-19-glucose to steviolbioside. That is to say, a microorganism of the invention may comprise a UGT which is capable of catalyzing a reaction in which steviolbioside is converted to stevioside. Accordingly, such a microorganism may be capable of converting steviolbioside to stevioside. Expression of such a nucleotide sequence may confer on the microorganism the ability to produce at least stevioside.

A microorganism of the invention may thus also comprise a nucleotide sequence encoding a polypeptide having the activity shown by UDP-glycosyltransferase (UGT) UGT74G1, whereby the nucleotide sequence upon transformation of the microorganism confers on the cell the ability to convert steviolbioside to stevioside.

Suitable UGT74G1 polypeptides may be capable of transferring a glucose unit to the 13-OH or the 19-COOH, respectively, of steviol. A suitable UGT74G1 polypeptide may function as a uridine 5'-diphospho glucosyl: steviol 19-COOH transferase and a uridine 5'-diphospho glucosyl: steviol-13-O-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences.

A recombinant host of the invention may comprise a nucleotide sequence encoding a polypeptide capable of catalyzing glucosylation of the C-3' of the glucose at the C-13 position of stevioside. That is to say, a recombinant host of the invention may comprise a UGT which is capable of catalyzing a reaction in which stevioside to rebaudioside A. Accordingly, such a recombinant host may be capable of converting stevioside to rebaudioside A. Expression of such a nucleotide sequence may confer on the host the ability to produce at least rebaudioside A.

A recombinant microorganism of the invention may thus also comprise a nucleotide sequence encoding a polypeptide having the activity shown by UDP-glycosyltransferase (UGT) UGT76G1, whereby the nucleotide sequence upon transformation of the microorganism confers on the cell the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-0-1,2 glucoside C-3' glucosyl transferase and a uridine 5'-diphospho glucosyl: steviol-19-0-glucose, 13-0-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences.

A recombinant host of the invention typically comprises nucleotide sequences encoding polypeptides having all four UGT activities described above. A given nucleic acid may encode a polypeptide having one or more of the above activities. For example, a nucleic acid encode for a polypeptide which has two, three or four of the activities set out above. Preferably, a recombinant host of the invention comprises UGT1, UGT2 and UGT3 and UGT4 activity. Suitable UGT1, UGT3 and UGT4 sequences are described in in Table 1 of WO2015/007748.

A recombinant host of the invention may comprise a recombinant nucleic acid sequence encoding an additional polypeptide having UGT2 activity. That is to say, a recombinant host of the invention may comprise a nucleic acid sequence encoding a variant UGT2 of the invention and one or more additional, different, variant of the invention or any another, different, UGT2.

Use of a nucleic acid sequence encoding a UGT2_1b, UGT2_2b, UGT2_3b, UGT2_4b, UGT2_5b, UGT2_6b, UGT2_7b, UGT2_8b, UGT2_9b or UGT2_10b polypeptide (or related polypeptide as described herein) may be useful in improving rebA production.

Use of a nucleic acid sequence encoding a UGT2_7b polypeptide (or related polypeptide as described herein) may be useful in improving rebM production.

In a recombinant host of the invention, the ability of the host to produce geranylgeranyl diphosphate (GGPP) may be upregulated. Upregulated in the context of this invention implies that the recombinant host produces more GGPP than an equivalent non-recombinant host.

Accordingly, a recombinant host of the invention may comprise one or more nucleotide sequence(s) encoding hydroxymethyglutaryl-CoA reductase, farnesyl-pyrophosphate synthetase and geranylgeranyl diphosphate synthase, whereby the nucleotide sequence(s) upon transformation of the microorganism confer(s) on the microorganism the ability to produce elevated levels of GGPP. Thus, a recombinant host according to the invention may comprise one or more recombinant nucleic acid sequence(s) encoding one or more of hydroxymethylglutaryl-CoA reductase, farnesyl-pyrophosphate synthetase and geranylgeranyl diphosphate synthase.

Accordingly, a recombinant host of the invention may comprise nucleic acid sequences encoding one or more of:

a polypeptide having hydroxymethylglutaryl-CoA reductase activity;

a polypeptide having farnesyl-pyrophosphate synthetase activity;

a polypeptide having geranylgeranyl diphosphate synthase activity.

A host or host cell as defined herein is an organism suitable for genetic manipulation and one which may be cultured at cell densities useful for industrial production of a target product. A suitable host may be a microorganism, for example one which may be maintained in a fermentation device. A host cell may be a host cell found in nature or a host cell derived from a parent host cell after genetic manipulation or classical mutagenesis.

As used herein, a recombinant host is one which is genetically modified or transformed/transfected with one or more of the nucleotide sequences as defined herein. The presence of the one or more such nucleotide sequences alters the ability of the microorganism to produce diterpene glycosides, in particular one or more steviol glycosides. A non-recombinant host, i.e. one that is not transformed/transfected or genetically modified, typically does not comprise one or more of the nucleotide sequences enabling the cell to produce a diterpene glycoside. Hence, a non-recombinant host is typically a host that does not naturally produce a diterpene glycoside, although a host which naturally produces a diterpene or diterpene glycoside and which has been modified according to the invention (and which thus has an altered ability to produce a diterpene glycoside) is considered a recombinant host according to the invention.

In particular, it may be possible that the enzymes selected from the group consisting of ent-copalyl pyrophosphate synthase, ent-Kaurene synthase, ent-Kaurene oxidase, and kaurenoic acid 13-hydroxylase, UGTs, hydroxymethylglutaryl-CoA reductase, farnesyl-pyrophosphate synthetase, geranylgeranyl diphosphate synthase and NADPH-cytochrome p450 reductase are native to the host and that transformation with one or more of the nucleotide sequences encoding these enzymes may not be required to confer the host cell the ability to produce a diterpene glycoside. A preferred host according to the present invention may be a recombinant host which is naturally capable of producing GGPP (i.e. in its non-recombinant form).

Further improvement of diterpene glycoside production by the host microorganism may be obtained by classical strain improvement.

A host cell may be a prokaryotic, archaebacterial or eukaryotic host cell.

A prokaryotic host cell may, but is not limited to, a bacterial host cell. An eukaryotic host cell may be, but is not limited to, a yeast, a fungus, an amoeba, an algae, an animal, an insect host cell.

An eukaryotic host cell may be a fungal host cell. "Fungi" include all species of the subdivision Eumycotina (Alexopoulos, C. J., 1962, In: Introductory Mycology, John Wiley & Sons, Inc., New York). The term fungus thus includes among others filamentous fungi and yeast.

"Filamentous fungi" are herein defined as eukaryotic microorganisms that include all filamentous forms of the subdivision Eumycotina and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Sordaria, Talaromyces, Rasmsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*. Reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

An eukaryotic host cell may be a yeast cell. Preferred yeast host cells may be selected from the genera: *Saccharomyces* (e.g., *S. cerevisiae, S. bayanus, S. pastorianus, S. carlsbergensis*), *Brettanomyces, Kluyveromyces, Candida* (e.g., *C. krusei, C. revkaufi, C. pulcherrima, C. tropicalis, C. utilis*), *Issatchenkia* (eg. *I. orientalis*) *Pichia* (e.g., *P. pastoris*), *Schizosaccharomyces, Hansenula, Kloeckera, Pachysolen, Schwanniomyces, Trichosporon, Yarrowia* (e.g., *Y. lipolytica* (formerly classified as *Candida lipolytica*)), *Yamadazyma*.

Prokaryotic host cells may be bacterial host cells. Bacterial host cell may be Gram negative or Gram positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus*), *Acinetobacter, Nocardia, Xanthobacter, Escherichia* (e.g., *E. coli* (e.g., strains DH 1 OB, Stbl2, DH5-alpha, DB3, DB3.1), DB4, DB5, JDP682 and ccdA-over (e.g., U.S. application Ser. No. 09/518, 188))), *Streptomyces, Erwinia, Klebsiella, Serratia* (e.g., *S. marcessans*), *Pseudomonas* (e.g., *P. aeruginosa*), *Salmonella* (e.g., *S. typhimurium, S. typhi*). Bacteria also include, but are not limited to, photosynthetic bacteria (e.g., green non-sulfur bacteria (e.g., *Choroflexus* bacteria (e.g., *C. aurantiacus*), *Chloronema* (e.g., *C. gigateum*)), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okenii*)), and purple non-sulfur bacteria (e.g., *Rhodospirillum* (e.g., *R. rubrum*), Rhodobacter (e.g. *R. sphaeroides, R. capsulatus*), and Rhodomicrobium bacteria (e.g., *R. vanellii*)).

Host cells may be host cells from non-microbial organisms. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis cells*); reptilian cells; and mammalian cells (e.g., NIH3T3, 293, CHO, COS, VERO, C127, BHK, Per-C6, Bowes melanoma and HeLa cells).

The invention further provides a method for producing a polypeptide of the invention comprising:
 (a) cultivating a recombinant host cell of the invention under conditions conducive to the production of the polypeptide by the host cell, and optionally,
 (b) recovering the polypeptide.

A recombinant host according to the present invention may be able to grow on any suitable carbon source known in the art and convert it to a glycosylated diterpene, e.g. a steviol glycoside. The recombinant host may be able to convert directly plant biomass, celluloses, hemicelluloses, pectines, rhamnose, galactose, fucose, maltose, maltodextrines, ribose, ribulose, or starch, starch derivatives, sucrose, lactose and glycerol. Hence, a preferred host expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the host is able to convert a carbon source selected from the group consisting of glucose, xylose, arabinose, sucrose, lactose and glycerol. The host cell may for instance be a eukaryotic host cell as described in WO03/062430, WO06/009434, EP1499708B1, WO2006096130 or WO04/099381.

Thus, in a further aspect, the invention also provides a process for the preparation of a glycosylated diterpene, such as a steviol glycoside, which comprises fermenting a recombinant host of the invention which is capable of producing at least one glycosylated diterpene in a suitable fermentation medium, and optionally recovering the glycosylated diterpene.

The glycosylated terpene, for example a steviol glycoside, may be stevio-19-monoside, steviol-19-diside, steviol-19-3side, steviol-13-monoside, rubusoside, 13-[(β-D-Glucopyranosyl)oxy)kaur-16-en-18-oic acid 2-O-β-D-glucopyranosyl-β-D-glucopyranosyl ester, steviolbioside, stevioside, rebaudioside E, rebaudioside B, rebaudioside A, rebaudioside D or rebaudioside M. Thus, the invention provides a process for the production of one or more such steviol glycosides.

The fermentation medium used in the process for the production of a glycosylated diterpene may be any suitable fermentation medium which allows growth of a particular eukaryotic host cell. The essential elements of the fermentation medium are known to the person skilled in the art and may be adapted to the host cell selected.

Preferably, the fermentation medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, sucrose, lactose, fatty acids, triglycerides and glycerol. Preferably, the fermentation medium also comprises a nitrogen source such as urea, or an ammonium salt such as ammonium sulphate, ammonium chloride, ammonium nitrate or ammonium phosphate.

The fermentation process according to the present invention may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. A SSF process may be particularly attractive if starch, cellulose, hemicelluose or pectin is used as a carbon source in the fermentation process, where it may be necessary to add hydrolytic enzymes, such as cellulases, hemicellulases or pectinases to hydrolyse the substrate.

The recombinant host used in the process for the preparation of a glycosylated diterpene may be any suitable recombinant host as defined herein above. It may be advantageous to use a recombinant eukaryotic recombinant host according to the invention in the process since most eukaryotic cells do not require sterile conditions for propagation and are insensitive to bacteriophage infections. In addition, eukaryotic host cells may be grown at low pH to prevent bacterial contamination.

The recombinant host according to the present invention may be a facultative anaerobic microorganism. A facultative anaerobic recombinant host can be propagated aerobically to a high cell concentration. This anaerobic phase can then be carried out at high cell density which reduces the fermentation volume required substantially, and may minimize the risk of contamination with aerobic microorganisms.

The fermentation process for the production of a glycosylated diterpene according to the present invention may be an aerobic or an anaerobic fermentation process.

An anaerobic fermentation process may be herein defined as a fermentation process run in the absence of oxygen or in which substantially no oxygen is consumed, preferably less than 5, 2.5 or 1 mmol/Uh, and wherein organic molecules serve as both electron donor and electron acceptors. The fermentation process according to the present invention may also first be run under aerobic conditions and subsequently under anaerobic conditions.

The fermentation process may also be run under oxygen-limited, or micro-aerobical, conditions. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used.

The production of a glycosylated diterpene in the process according to the present invention may occur during the growth phase of the host cell, during the stationary (steady state) phase or during both phases. It may be possible to run the fermentation process at different temperatures.

The process for the production of a glycosylated diterpene may be run at a temperature which is optimal for the recombinant host. The optimum growth temperature may differ for each transformed recombinant host and is known to the person skilled in the art. The optimum temperature might be higher than optimal for wild type organisms to grow the organism efficiently under non-sterile conditions under minimal infection sensitivity and lowest cooling cost. Alternatively, the process may be carried out at a temperature which is not optimal for growth of the recombinant host.

The process for the production of a glycosylated diterpene according to the present invention may be carried out at any suitable pH value. If the recombinant host is a yeast, the pH in the fermentation medium preferably has a value of below 6, preferably below 5.5, preferably below 5, preferably below 4.5, preferably below 4, preferably below pH 3.5 or below pH 3.0, or below pH 2.5, preferably above pH 2. An advantage of carrying out the fermentation at these low pH values is that growth of contaminant bacteria in the fermentation medium may be prevented.

Such a process may be carried out on an industrial scale. The product of such a process is one or more glycosylated diterpenes, such as one or more steviol glycosides, for example one or more of 13-[(β-D-Glucopyranosyl)oxy)kaur-16-en-18-oic acid 2-O-βD-glucopyranosyl-β-D-glucopyranosyl ester, steviolbioside, stevioside, rebaudioside E, rebaudioside B, rebaudioside A, rebaudioside D or rebaudioside M.

Recovery of glycosylated diterpene(s) from the fermentation medium may be performed by known methods in the art, for instance by distillation, vacuum extraction, solvent extraction, or evaporation.

In the process for the production of a glycosylated diterpene according to the invention, it may be possible to achieve a concentration of above 5 mg/l fermentation broth, preferably above 10 mg/l, preferably above 20 mg/l, preferably above 30 mg/l fermentation broth, preferably above 40 mg/l, more preferably above 50 mg/l, preferably above 60 mg/l, preferably above 70, preferably above 80 mg/l, preferably above 100 mg/l, preferably above 1 g/l, preferably above 5 g/l, preferably above 10 g/l, for example above 20 g/l, but usually up to a concentration of about 200 g/l, such as up to about 150 g/l, such as up to about 100 g/l, for example up to about 70 g/l. Such concentrations may be concentration of the total broth or of the supernatant.

The invention further provides a fermentation broth comprising a glycosylated diterpene obtainable by the process of the invention for the preparation of a glycosylated diterpene.

In the event that one or more glycosylated diterpenes is expressed within the microorganism, such cells may need to be treated so as to release them. Preferentially, at least one glycosylated diterpene, such as a steviol glycoside, for example rebA or rebM, is produced extracellularly.

The invention also provides a glycosylated diterpene obtained by a process according to the invention for the preparation of a glycosylated diterpene or obtainable from a fermentation broth of the invention. Such a glycosylated diterpene may be a non-naturally occurring glycosylated diterpene, that is to say one which is not produced in plants.

Also provided is a composition comprising two or more glycosylated diterpenes obtainable by a process of the invention for the preparation of a glycosylated diterpene or obtainable from a fermentation broth of the invention. In such a composition, one or more of the glycosylated diterpenes may be a non-naturally occurring glycosylated diterpene, that is to say one which is not produced in plants.

Furthermore, the invention provides a method for converting a first glycosylated diterpene into a second glycosylated diterpene, which method comprises:
contacting said first glycosylated diterpene with a recombinant host of the invention, a cell free extract derived from such a recombinant host or an enzyme preparation derived from either thereof;
thereby to convert the first glycosylated diterpene into the second glycosylated diterpene.

In such a method, the second glycosylated diterpene may be steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

In such a method, the first glycosylated diterpene may be steviol-13-monoside, steviol-19-monoside, rubusoside, stevioside, rebaudioside A or 13-[(β-D-Glucopyranosyl)oxy)kaur-16-en-18-oic acid 2-O-β-D-glucopyranosyl-β-D-glucopyranosyl ester and the second glycosylated diterpene is steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

These are the first and second steviol glycosides in relation to a reaction catalysed by a polypeptide of the invention having UGT2 activity.

That is to say, the invention relates to a method of bioconversion or biotransformation.

A steviol glycoside or composition produced by the fermentation process according to the present invention may be used in any application known for such compounds. In particular, they may for instance be used as a sweetener, for example in a food or a beverage. According to the invention therefore, there is provided a foodstuff, feed or beverage which comprises a glycosylated diterpene such as a steviol glycoside or a composition of the invention.

For example a glycosylated diterpene or a composition of the invention may be formulated in soft drinks, as a tabletop sweetener, chewing gum, dairy product such as yoghurt (eg. plain yoghurt), cake, cereal or cereal-based food, nutraceutical, pharmaceutical, edible gel, confectionery product, cosmetic, toothpastes or other oral cavity composition, etc. In addition, a glycosylated diterpene or a composition of the invention can be used as a sweetener not only for drinks, foodstuffs, and other products dedicated for human consumption, but also in animal feed and fodder with improved characteristics.

Accordingly, the invention provides, inter alia, a foodstuff, feed or beverage which comprises a diterpene or glycosylated prepared according to a process of the invention.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

The glycosylated diterpene, for example a steviol glycoside, or a composition of the invention can be used in dry or liquid forms. It can be added before or after heat treatment of food products. The amount of the sweetener depends on the purpose of usage. It can be added alone or in the combination with other compounds.

Compounds produced according to the method of the invention may be blended with one or more further non-calorific or calorific sweeteners. Such blending may be used to improve flavour or temporal profile or stability. A wide range of both non-calorific and calorific sweeteners may be suitable for blending with a glycosylated diterpene or a composition of the invention. For example, non-calorific sweeteners such as mogroside, monatin, aspartame, acesulfame salts, cyclamate, sucralose, saccharin salts or erythritol. Calorific sweeteners suitable for blending with a glycosylated diterpene or a composition of the invention include sugar alcohols and carbohydrates such as sucrose, glucose, fructose and HFCS. Sweet tasting amino acids such as glycine, alanine or serine may also be used.

A glycosylated diterpene or a composition of the invention can be used in the combination with a sweetener suppressor, such as a natural sweetener suppressor. It may be combined with an umami taste enhancer, such as an amino acid or a salt thereof.

A glycosylated diterpene or a composition of the invention can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/thiols, amino acids, a protein, a vitamin, a mineral, and/or a substance classified based on a health benefits, such as cardiovascular, cholesterol-reducing or anti-inflammatory.

A composition with a glycosylated diterpene or a composition of the invention may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A glycosylated diterpene or a composition of the invention may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a glycosylated diterpene or a composition of the invention may be used as a sweetener not only for drinks, foodstuffs, and other products dedicated for human consumption, but also in animal feed and fodder with improved characteristics.

The examples of products where a glycosylated diterpene or a composition of the invention can be used as a sweetening compound can be as alcoholic beverages such as vodka, wine, beer, liquor, sake, etc; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principal it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

A glycosylated diterpene or a composition of the invention can be used in dry or liquid forms. It can be added before or after heat treatment of food products. The amount of the sweetener depends on the purpose of usage. It can be added alone or in the combination with other compounds.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions of the present invention can be made by any method known to those skilled in the art that provide homogenous even or homogeneous mixtures of the ingredients. These methods include dry blending, spray drying, agglomeration, wet granulation, compaction, co-crystallization and the like.

In solid form a glycosylated diterpene or a composition of the invention can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

The composition may include various bulking agents, functional ingredients, colorants, flavors.

The terms "sequence homology" or "sequence identity" are used interchangeably herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at ncbi.nlm.nih.gov.

EMBODIMENTS OF THE INVENTION

1. A recombinant host comprising a recombinant nucleic acid sequence encoding a polypeptide having at least about:
   a. 85% identity to the amino acid sequence set forth in SEQ ID NO: 1;
   b. 85% identity to the amino acid sequence set forth in SEQ ID NO: 3;
   c. 85% identity to the amino acid sequence set forth in SEQ ID NO: 6;
   d. 85% identity to the amino acid sequence set forth in SEQ ID NO: 9;
   e. 85% identity to the amino acid sequence set forth in SEQ ID NO: 11;
   f. 85% identity to the amino acid sequence set forth in SEQ ID NO: 14;
   g. 85% identity to the amino acid sequence set forth in SEQ ID NO: 17;
   h. 85% identity to the amino acid sequence set forth in SEQ ID NO: 20;
   i. 85% identity to the amino acid sequence set forth in SEQ ID NO: 22; or
   j. 85% identity to the amino acid sequence set forth in SEQ ID NO: 25.

2. A recombinant host according to embodiment 1 which is capable of producing a glycosylated diterpene, such as a steviol glycoside.

3. A recombinant host according to embodiment 1 or 2 which comprises one or more recombinant nucleotide sequence(s) encoding:
   a polypeptide having ent-copalyl pyrophosphate synthase activity;
   a polypeptide having ent-Kaurene synthase activity;
   a polypeptide having ent-Kaurene oxidase activity; and
   a polypeptide having kaurenoic acid 13-hydroxylase activity.

4. A recombinant host according to any one of the preceding embodiments, which comprises a recombinant nucleic acid sequence encoding a polypeptide having NADPH-cytochrome p450 reductase activity.

5. A recombinant host according to any one of the preceding embodiments which comprises a recombinant nucleic acid sequence encoding one or more of:
   (i) a polypeptide having UGT74G1 (UGT3) activity;
   (ii) a polypeptide having UGT85C2 (UGT1) activity; and
   (iii) a polypeptide having UGT76G1 (UGT4) activity.

6. A recombinant host according to any one of the preceding embodiments which comprises a recombinant nucleic acid sequence encoding an additional polypeptide having UGT2 activity.

7. A recombinant host according to any one of the preceding embodiments, wherein the host belongs to one of the genera *Saccharomyces*, *Aspergillus*, *Pichia*, *Kluyveromyces*, *Candida*, *Hansenula*, *Humicola*, *Issatchenkia*, *Trichosporon*, *Brettanomyces*, *Pachysolen*, *Yarrowia*, *Yamadazyma* or *Escherichia*.

8. A recombinant host according to embodiment 7, wherein the recombinant host is a *Saccharomyces cerevisiae* cell, a *Yarrowia lipolytica* cell, a *Candida krusei* cell, an *Issatchenkia orientalis* or an *Escherichia coli* cell.

9. A recombinant host according to any one of the preceding embodiments, wherein the ability of the host to produce geranylgeranyl diphosphate (GGPP) is upregulated.

10. A recombinant host according to any one of the preceding embodiments, comprising one or more recombinant nucleic acid sequence(s) encoding hydroxymethylglutaryl-CoA reductase, farnesyl-pyrophosphate synthetase and geranylgeranyl diphosphate synthase.

11. A recombinant host according to any one of the preceding embodiments which comprises a nucleic acid sequence encoding one or more of:
   a polypeptide having hydroxymethylglutaryl-CoA reductase activity;
   a polypeptide having farnesyl-pyrophosphate synthetase activity;
   a polypeptide having geranylgeranyl diphosphate synthase activity.

12. A process for the preparation of a glycosylated diterpene which comprises fermenting a recombinant host according to any one of embodiments 2 to 11 in a suitable fermentation medium, and optionally recovering the glycosylated diterpene.

13. A process according to any one of embodiment 12 for the preparation of a glycosylated diterpene, wherein the process is carried out on an industrial scale.

14. A fermentation broth comprising a glycosylated diterpene obtainable by the process according to embodiment 12 or 13.

15. A glycosylated diterpene obtained by a process according to embodiment 12 or 13 or obtainable from a fermentation broth according to embodiment 14.

16. A composition comprising two or more glycosylated diterpenes obtained by a process according to embodiment 12 or 13 or obtainable from a fermentation broth according to embodiment 14.

17. A foodstuff, feed or beverage which comprises a glycosylated diterpene according to embodiment 15 or a composition according to embodiment 16.

18. A method for converting a first glycosylated diterpene into a second glycosylated diterpene, which method comprises:
   contacting said first glycosylated diterpene with a recombinant host according to any one of embodiments 1 to 11, a cell free extract derived from such a recombinant host or an enzyme preparation derived from either thereof;
   thereby to convert the first glycosylated diterpene into the second glycosylated diterpene.

19. A method according to embodiment 18, wherein the second glycosylated diterpene is steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

20. A method according to claim 19, wherein the first glycosylated diterpene is steviol-13-monoside, steviol-19-monoside, rubusoside, stevioside, rebaudioside A or 13-[(β-D-Glucopyranosyl)oxy)kaur-16-en-18-oic acid 2-O-β-D-glucopyranosyl-β-D-glucopyranosyl ester and the second glycosylated diterpene is steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

21. A polypeptide having UGT2 activity, wherein said polypeptide is selected from the group consisting of:
   (a) a polypeptide comprising an amino acid sequence as set out in any one of SEQ
       ID NOs: 1, 3, 6, 9, 11, 14, 17, 20, 22 or 25; or
   (b) a polypeptide comprising an amino acid sequence having at least about 85% sequence identity with the amino acid sequence of any one of SEQ ID NOs: 1, 3, 6, 9, 11, 14, 17, 20, 22 or 25; or
   (c) a polypeptide encoded by a polynucleotide comprising the polynucleotide sequence as set out in any one SEQ ID NOs: 2, 4, 5, 7, 8, 10, 12, 13, 15, 16, 18, 19, 21, 23, 24 or 26; or
   (d) a polypeptide encoded by a polynucleotide comprising a polynucleotide sequence having at least 30% sequence identity to the polypeptide coding sequence in any one SEQ ID NOs: 2, 4, 5, 7, 8, 10, 12, 13, 15, 16, 18, 19, 21, 23, 24 or 26; or
   (e) a polypeptide encoded by a polynucleotide which hybridises, preferably under at least low stringency conditions, with the complementary strand of any one SEQ ID NOs: 2, 4, 5, 7, 8, 10, 12, 13, 15, 16, 18, 19, 21, 23, 24 or 26; or
   (f) a polypeptide encoded by a polynucleotide which hybridises, preferably under at least low stringency conditions, with the complementary strand of a polynucleotide having at least 30% sequence identity to any one SEQ ID NOs: 2, 4, 5, 7, 8, 10, 12, 13, 15, 16, 18, 19, 21, 23, 24 or 26; or
   (g) a fragment of a polypeptide as defined in (a), (b), (c), (d), (e) or (f).

22. A polypeptide according to embodiment 21, comprising a polypeptide having an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to any one of SEQ ID NOs: 1, 3, 6, 9, 11, 14, 17, 20, 22 or 25.

23. A polynucleotide sequence coding for a polypeptide according to embodiment 21 or 22.

24. A polynucleotide sequence according to embodiment 23, wherein the polynucleotide sequence is selected from the group consisting of:
   (a) a polynucleotide sequence comprising any one of SEQ ID NOs: 2, 4, 5, 7, 8, 10, 12, 13, 15, 16, 18, 19, 21, 23, 24 or 26 or comprising a polynucleotide sequence having at least 30% sequence identity with the polynucleotide sequence of any one of SEQ ID NOs: 2, 4, 5, 7, 8, 10, 12, 13, 15, 16, 18, 19, 21, 23, 24 or 26; or
   (b) a polynucleotide sequence which hybridises, preferably under at least low stringency conditions, with the complementary strand of any one SEQ ID NOs: 2, 4, 5, 7, 8, 10, 12, 13, 15, 16, 18, 19, 21, 23, 24 or 26; or
   (c) a polynucleotide sequence which hybridises, preferably under at least low stringency conditions with the complementary strand of a polynucleotide having at least 30% sequence identity to any one of any one SEQ ID NOs: 2, 4, 5, 7, 8, 10, 12, 13, 15, 16, 18, 19, 21, 23, 24 or 26;
   (d) a polynucleotide sequence which is degenerate as a result of the degeneracy of the genetic code to a polynucleotide sequence as defined in any one of (a), (b) or (c); or
   (e) a polynucleotide sequence which is the complement of a nucleotide sequence as defined in (a), (b), (c) or (d).

25. A polynucleotide sequence according to embodiment 5, having a sequence identity of at least 60%, preferably at least 70%, more preferably at least 80%, most preferably at-least 90%, most preferably at least 93%, most preferably at least about 95%, most preferably at least about 96%, most preferably at least about 97%, even most preferably at least about 98%, and even more preferred at least 99% to any one of any one SEQ ID NOs: 2, 4, 5, 7, 8, 10, 12, 13, 15, 16, 18, 19, 21, 23, 24 or 26.

26. A nucleic acid construct comprising the polynucleotide sequence of any one of embodiments 23 to 25.

27. A nucleic acid construct according to embodiment 26 which is an expression vector, wherein the polynucleotide sequence according to any one of embodiments 23 to 25 is operably linked to at least one control sequence for the expression of the polynucleotide sequence in a host cell.

28. A method of producing the polypeptide of embodiment 21 or 22, comprising:

(a) cultivating a host cell according to embodiment 1 under conditions conducive to the production of the polypeptide by the host cell, and optionally, (b) recovering the polypeptide.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

Example 1: Over-expression of ERG20, BTS1 and tHMG in *S. cerevisiae*

For over-expression of ERG20, BTS1 tHMG1, expression cassettes were designed to be integrated in one locus using technology described in WO2013/076280. To amplify the 5' and 3' integration flanks for the integration locus, suitable primers and genomic DNA from a CEN.PK yeast strain (van Dijken et al. Enzyme and Microbial Technology 26 (2000) 706-714) was used. The different genes were ordered as cassettes (containing homologous sequence, promoter, gene, terminator, homologous sequence) at DNA2.0. The genes in these cassettes were flanked by constitutive promoters and terminators. See Table 1. Plasmid DNA from DNA2.0 containing the ERG20, tHMG1 and BTS1 cassettes were dissolved to a concentration of 100 ng/μl. In a 50 μl PCR mix 20 ng template was used together with 20 pmol of the primers. The material was dissolved to a concentration of 0.5 μg/μl.

TABLE 1

Composition of the over-expression constructs

| Promoter | ORF | Terminator |
| --- | --- | --- |
| Eno2 (SEQ ID NO: 30) | ERG20 (SEQ ID NO: 31) | Adh1 (SEQ ID NO: 32) |
| Fba1 (SEQ ID NO: 33) | tHMG1 (SEQ ID NO: 34) | Adh2 (SEQ ID NO: 35) |
| Tef1 (SEQ ID NO: 36) | BTS1 (SEQ ID NO: 37) | Gmp1 (SEQ ID NO: 38) |

For amplification of the selection marker, the pUG7-EcoRV construct (FIG. 1) and suitable primers were used. The KanMX fragment was purified from gel using the Zymoclean Gel DNA Recovery kit (ZymoResearch). Yeast strain Cen.PK113-3C was transformed with the fragments listed in Table 2.

TABLE 2

DNA fragments used for transformation of ERG20, tHMG1 and BTS1 Fragment

5'YPRcTau3
ERG20 cassette
tHMG1 cassette
KanMX cassette
BTS1 cassette
3'YPRcTau3

Figure 2:
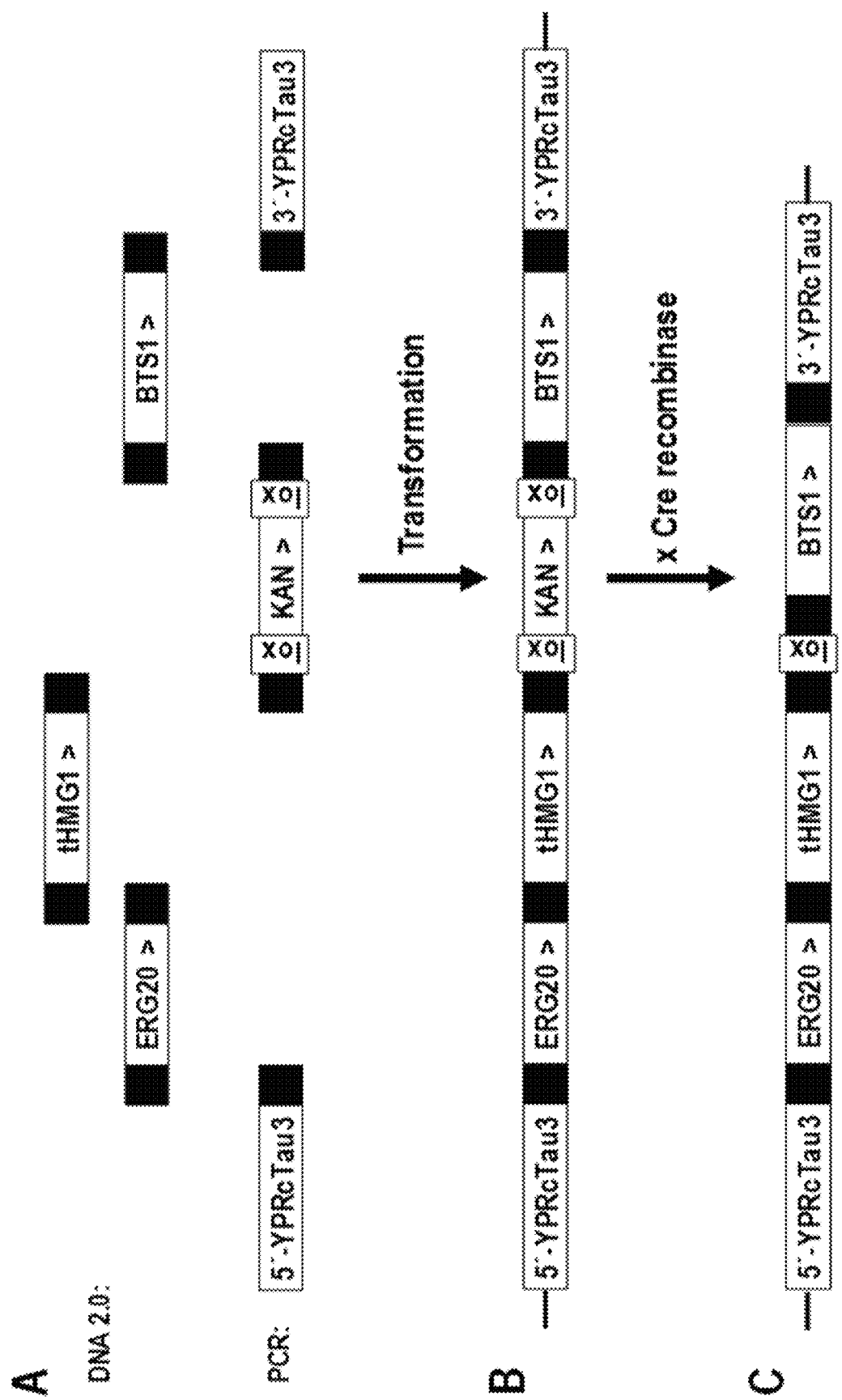
FIG. 2 sets out a schematic representation of the method by which the ERG20, tHMG1 and BTS1 over-expression cassettes are designed (A) and integrated (B) into the yeast genome. (C) shows the final situation after removal of the KANMX marker by the Cre recombinase.

After transformation and recovery for 2.5 hours in YEPhD (yeast extract phytone peptone glucose; BBL Phytone Peptone from BD) at 30° C. the cells were plated on YEPhD agar with 200 μg/ml G418 (Sigma). The plates were incubated at 30° C. for 4 days. Correct integration was established with diagnostic PCR and sequencing. Over-expression was confirmed with LC/MS on the proteins. The schematic of the assembly of ERG20, tHMG1 and BTS1 is illustrated in FIG. 2. This strain is named STV002.

Expression of CRE-recombinase in this strain led to out-recombination of the KanMX marker. Correct out-recombination, and presence of ERG20, tHMG and BTS1 was established with diagnostic PCR.

Example 2. Knock Down of Erg9

For reducing the expression of Erg9, an Erg9 knock down construct was designed and used that contains a modified 3' end, that continues into the TRP1 promoter driving TRP1 expression.

Figure 3:
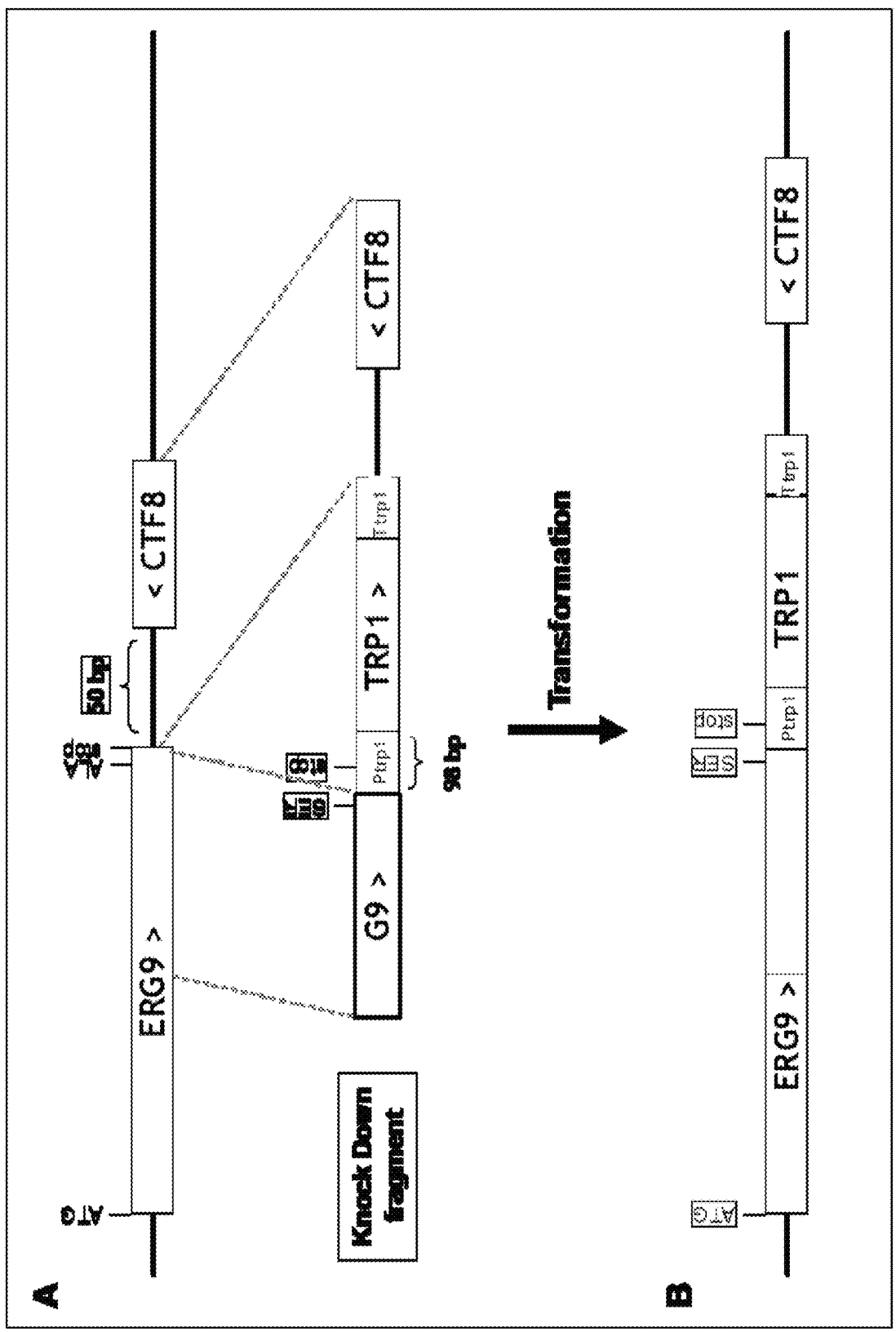
FIG. 3 sets out a schematic representation of the ERG9 knock down construct. This consists of a 500 bp long 3' part of ERG9, 98 bp of the TRP1 promoter, the TRP1 open reading frame and terminator, followed by a 400 bp long downstream sequence of ERG9. Due to introduction of a XbaI site at the end of the ERG9 open reading frame the last amino acid changes into Ser and the stop codon into Arg. A new stop codon is located in the TPR1 promoter, resulting in an extension of 18 amino acids.

The construct containing the Erg9-KD fragment was transformed to *E. coli* TOP10 cells. Transformants were grown in 2PY(2 times Phytone peptone Yeast extract), sAMP medium. Plasmid DNA was isolated with the QIAprep Spin Miniprep kit (Qiagen) and digested with SalI-HF (New England Biolabs). To concentrate, the DNA was precipitated with ethanol. The fragment was transformed to *S. cerevisiae*, and colonies were plated on mineral medium (Verduyn et al, 1992. Yeast 8:501-517) agar plates without tryptophan. Correct integration of the Erg9-KD construct was confirmed with diagnostic PCR and sequencing. The schematic of performed transformation of the Erg9-KD construct is illustrated in FIG. 3. The strain was named STV003.

Example 3. Over-Expression of UGT2_1a

For over-expression of UGT2_1a, technology was used as described in patent application nos. WO2013/076280 and WO2013/144257. The UGT2_1a was ordered as a cassette (containing homologous sequence, promoter, gene, terminator, homologous sequence) at DNA2.0. For details, see Table 3. To obtain the fragments containing the marker and Crerecombinase, technology was used as described in patent application no. WO2013/135728. The NAT marker, conferring resistance to nourseothricin was used for selection.

TABLE 3

Composition of the over-expression construct

| Promoter | ORF | Terminator |
| --- | --- | --- |
| Pgk1 (SEQ ID NO: 39) | UGT2_1a (SEQ ID NO: 28) | Adh2 (SEQ ID NO: 35) |

Suitable primers were used for amplification. To amplify the 5' and 3' integration flanks for the integration locus, suitable primers and genomic DNA from a CEN.PK yeast strain was used.

S. cerevisiae yeast strain STV003 was transformed with the fragments listed in Table 4, and the transformation mix was plated on YEPhD agar plates containing 50 µg/ml nourseothricin (Lexy NTC from Jena Bioscience).

TABLE 4

DNA fragments used for transformation of UGT2 1a
Fragment

5'Chr09.01
UGT2_1a cassette
NAT-CR
RE
3'Chr09.01

Figure 4:
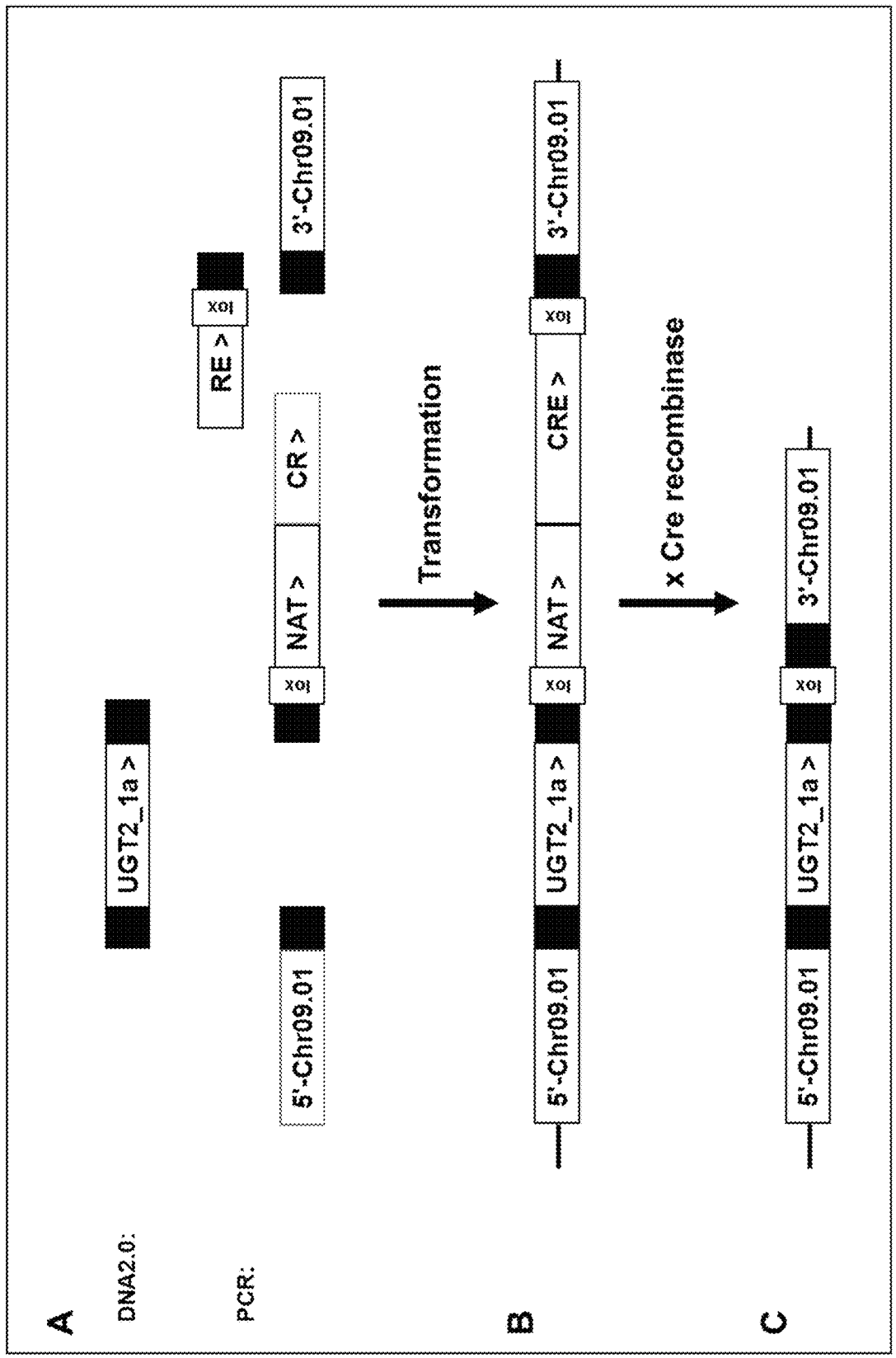
FIG. 4 sets out a schematic representation of how UGT2 is integrated into the genome. A. different fragments used in transformation; B. situation after integration; C. situation after expression of Cre recombinase).

Expression of the CRE recombinase is activated by the presence of galactose. To induce the expression of the CRE recombinase, transformants were restreaked on YEPh Galactose medium. This resulted in out-recombination of the marker(s) located between lox sites. Correct integration of the UGT2_1a and out-recombination of the NAT marker was confirmed with diagnostic PCR. The resulting strain was named STV004. The schematic of the performed transformation of the UGT2_1a construct is illustrated in FIG. 4.

Example 4. Over-Expression of Production Pathway to RebA: CPS, KS, KO, KAH, CPR, UGT1, UGT3 and UGT4

All pathway genes leading to the production of RebA were designed to be integrated in one locus using technology described in patent application nos. WO2013/076280 and WO2013/144257. To amplify the 5' and 3' integration flanks for the integration locus, suitable primers and genomic DNA from a CEN.PK yeast strain was used. The different genes were ordered as cassettes (containing homologous sequence, promoter, gene, terminator, homologous sequence) at DNA2.0 (see Table 5 for overview). The DNA from DNA2.0 was dissolved to 100 ng/µl. This stock solution was further diluted to 5 ng/µl, of which 1 µl was used in a 50 µl-PCR mixture. The reaction contained 25 pmol of each primer. After amplification, DNA was purified with the NucleoSpin 96 PCR Clean-up kit (Macherey-Nagel) or alternatively concentrated using ethanol precipitation.

TABLE 5

Sequences used for production pathway to RebA

| Promoter | ORF | SEQ ID | Terminator |
|---|---|---|---|
| KI prom 12.pro (SEQ ID NO: 40) | trCPS_SR | 41 | Sc ADH2.ter (SEQ ID NO: 35) |
| Sc PGK1.pro (SEQ ID NO: 39) | trKS_SR | 42 | Sc TAL1.ter (SEQ ID NO: 43) |
| Sc ENO2.pro (SEQ ID NO: 30) | KO_Gibfu | 44 | Sc TPI1.ter (SEQ ID NO: 45) |
| Ag lox_TEF1.pro (SEQ ID NO: 46) | KANMX | 47 | Ag TEF1_lox.ter (SEQ ID NO: 48) |
| Sc TEF1.pro (SEQ ID NO: 36) | KAH_4 | 49 | ScGPM1.ter (SEQ ID NO: 38) |
| KI prom 6.pro (SEQ ID NO: 50) | CPR_3 | 51 | Sc PDC1.ter (SEQ ID NO: 52) |
| KI prom 3.pro (SEQ ID NO: 53) | UGT1_SR | 54 | Sc TDH1.ter (SEQ ID NO: 55) |

TABLE 5-continued

Sequences used for production pathway to RebA

| Promoter | ORF | SEQ ID | Terminator |
|---|---|---|---|
| KI prom 2.pro (SEQ ID NO: 56) | UGT3_SR | 57 | Sc ADH1.ter (SEQ ID NO: 32) |
| Sc FBA1.pro (SEQ ID NO: 33) | UGT4_SR | 58 | Sc ENO1.ter (SEQ ID NO: 59) |

All fragments for the pathway to RebA, the marker and the flanks (see overview in Table 6) were transformed to S. cerevisiae yeast strain STV004. After overnight recovery in YEPhD at 20° C. the transformation mixes were plated on YEPhD agar containing 200 µg/ml G418. These were incubated 3 days at 25° C. and one night at RT.

TABLE 6

DNA fragments used for transformation of CPS, KS, KO, KanMX, KAH, CPR, UGT1, UGT3 and UGT4
Fragment 5'INT1
CPS cassette
KS cassette
KO cassette
KanMX cassette
KAH cassette
CPR cassette
UGT1 cassette
UGT3 cassette
UGT4 cassette
3'INT1

Figure 5:
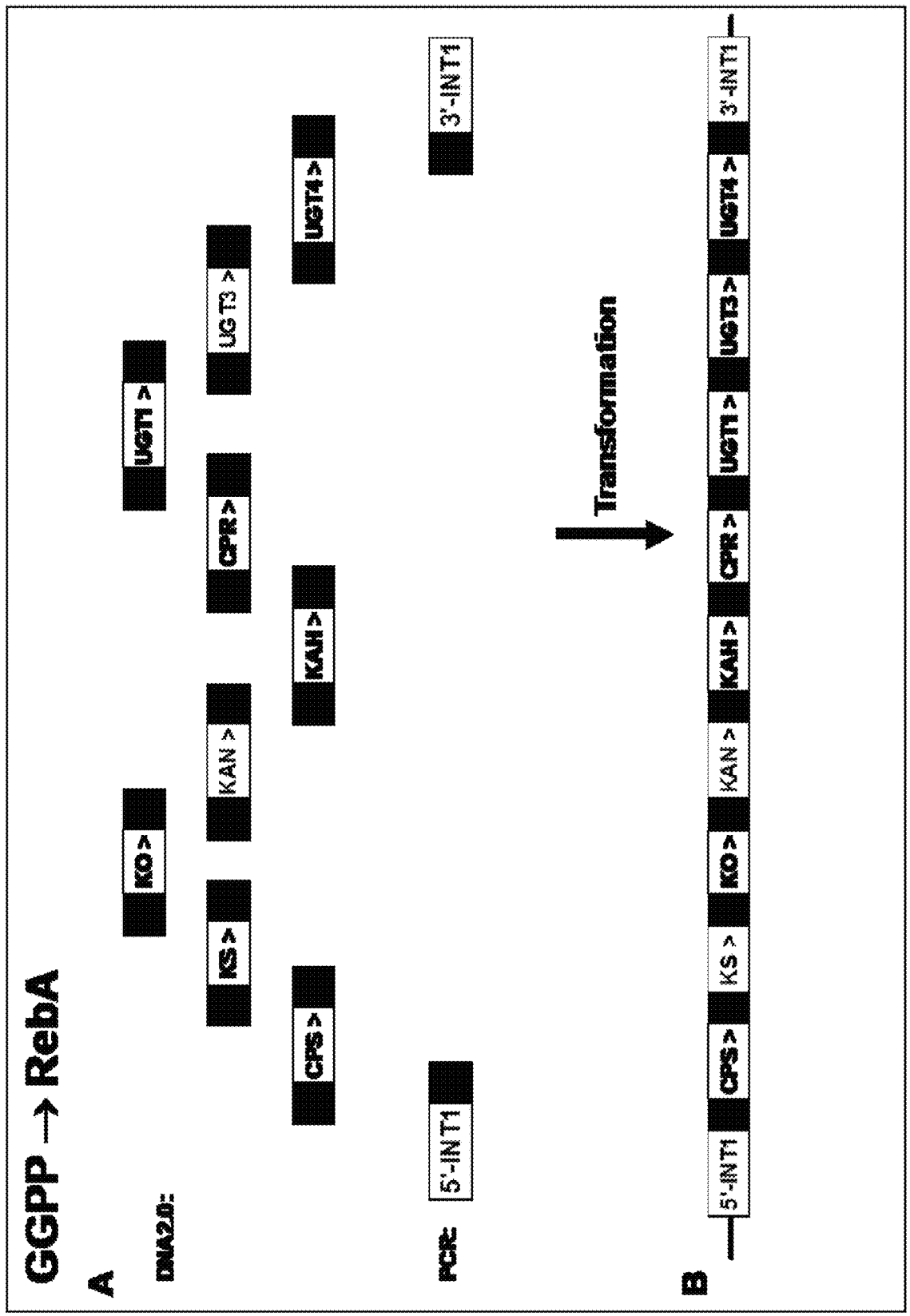
FIG. 5 sets out a schematic representation of how the pathway from GGPP to Steviol is integrated into the genome. A. different fragments used in transformation; B. situation after integration.

Correct integration was confirmed with diagnostic PCR and sequence analysis (3500 Genetic Analyzer, Applied Biosystems). The sequence reactions were done with the BigDye Terminator v3.1 Cycle Sequencing kit (Life Technologies). Each reaction (10 µl) contained 50 ng template and 3.2 pmol primer. The products were purified by ethanol/EDTA precipitation, dissolved in 10 µl HiDi formamide and applied onto the apparatus. The strain was named STV006. The schematic of how the pathway from GGPP to RebA is integrated into the genome is illustrated in FIG. 5. Table 7 sets out the strains used in Examples 1 to 5.

TABLE 7

Table of strains

| Strain | Background | Genotype |
|---|---|---|
| Cen.PK113-3C | — | MATa URA3 HIS3 LEU2 trp1-289 MAL2-8C SUC2 |
| STV002 | Cen.PK113-3C | MATa URA3 HIS3 LEU2 trp1-289 MAL2-8C SUC2 YPRcTau3::ERG20, tHMG1, KanMX, BTS1 |
| STV003 | STV002 | MATa URA3 HIS3 LEU2 trp1-289 MAL2-8C SUC2 YPRcTau3::ERG20, tHMG1, KanMX, BTS1 ERG9::ERG9-KD TRP1 |
| STV004 | STV003 | MATa URA3 HIS3 LEU2 trp1-289 MAL2-8C SUC2 YPRcTau3::ERG20, tHMG1, BTS1 ERG9::ERG9-KD TRP1 Chr09.01::UGT2_1a |
| STV006 | STV004 | MATa URA3 HIS3 LEU2 trp1-289 MAL2-8C SUC2 YPRcTau3::ERG20, tHMG1, BTS1 ERG9::ERG9-KD TRP1 Chr09.01::UGT2_1a INT1::CPS, KS, KO, KanMX, KAH, CPR, UGT1, UGT3, UGT4 |

Example 5. Removal of the KanMX Selection Marker of STV006

Figure 6:
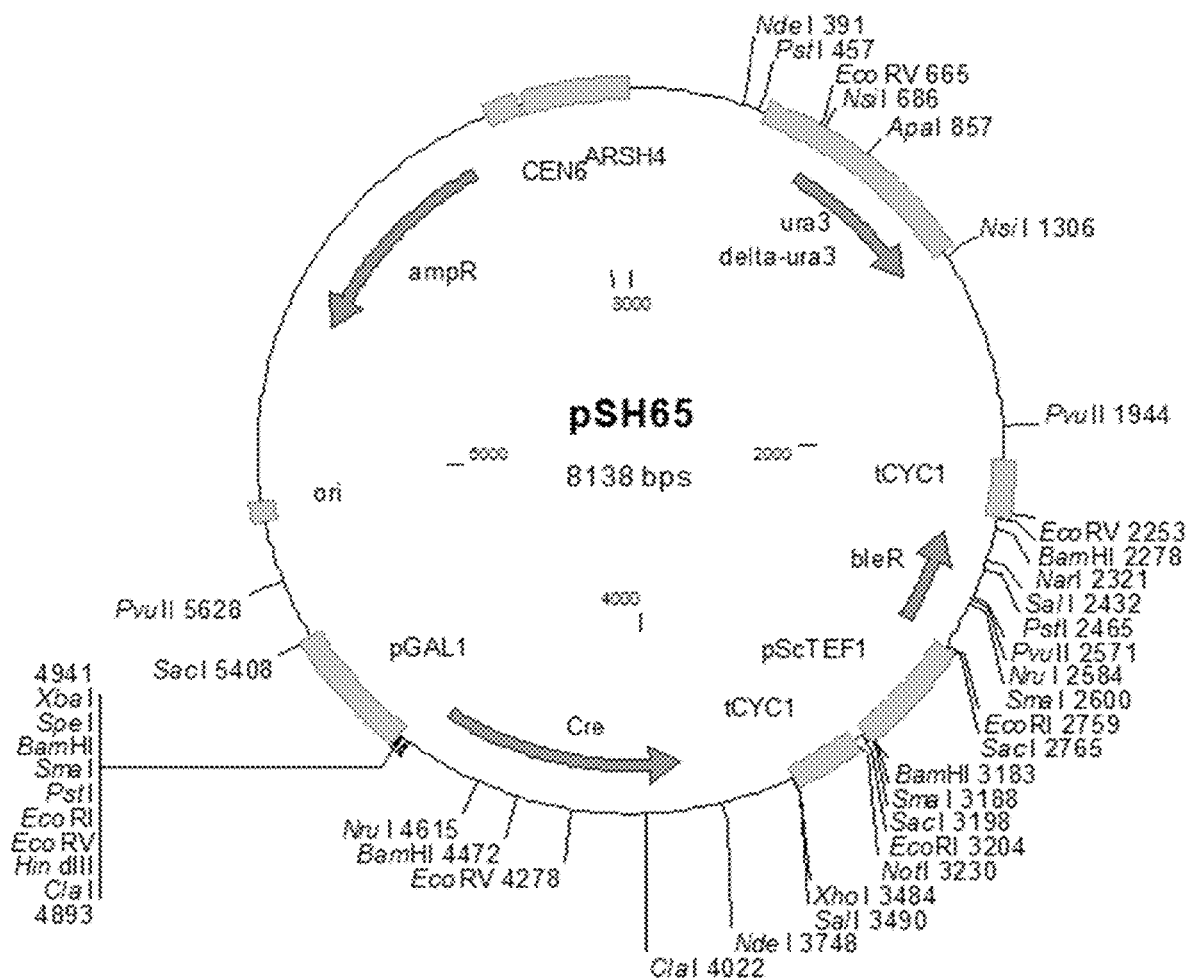
FIG. 6 sets out the pSH65 plasmid, carrying the CRE gene, which is used for removal of the antibiotic marker.

To remove the KanMX marker present in the strain, the plasmid pSH65, containing CRE recombinase (FIG. 6), was transformed to STV006. Transformants were first selected on YEPD containing 20 µg/ml Phleomycin (Invitrogen) and then restreaked on YEP Galactose medium to induce CRE recombinase expression. Correct out-recombination of the marker was established by diagnostic PCR. RebA production of this marker-free strain was confirmed in a production experiment. The marker free version of STV006 was called STV008.

Example 6. Removal of UGT2_1a in STV008 by the NAT Selection Marker

Figure 7:
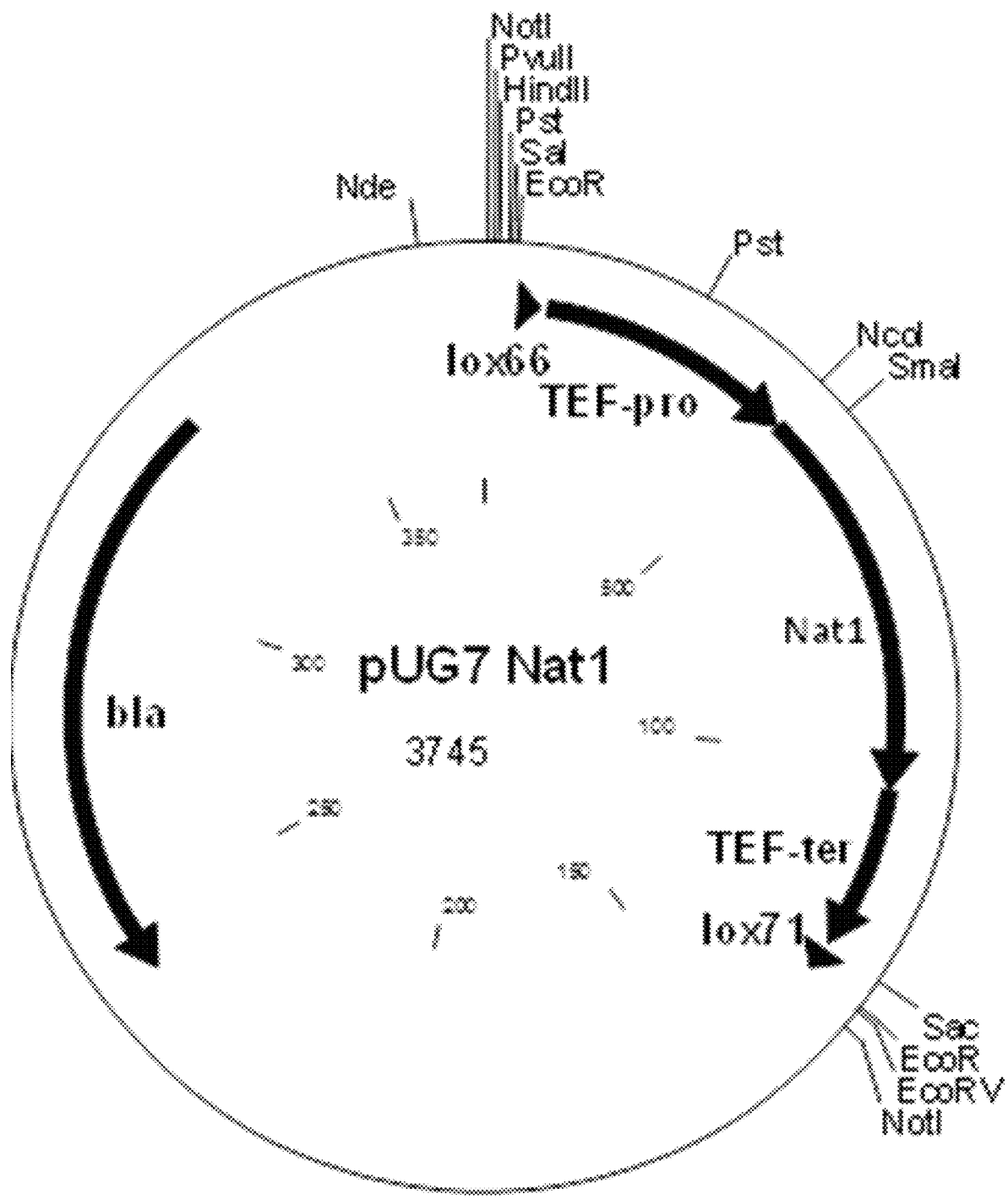
FIG. 7 sets out the map of plasmid pUG7-NAT.
Figure 8:
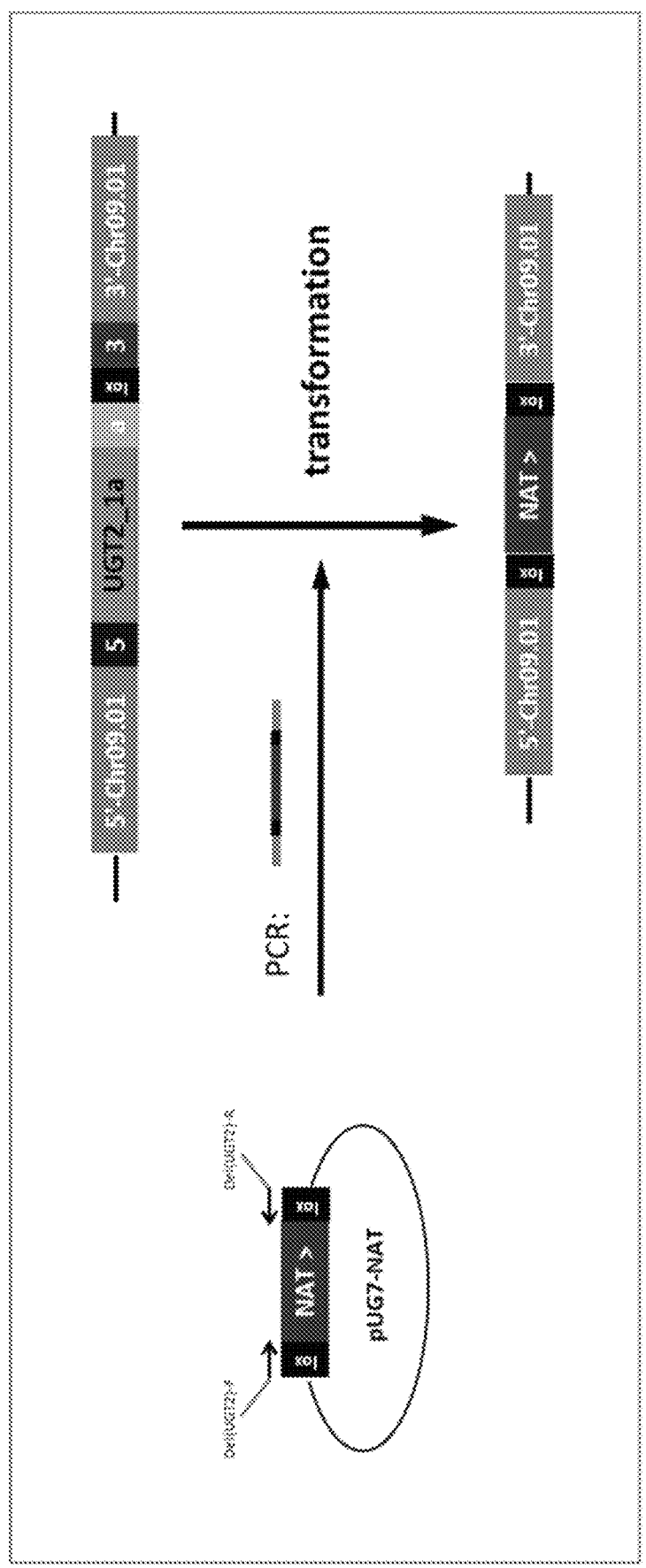
FIG. 8 sets out the replacement of UGT2_1a from STV008 with the Nat selection marker.

To remove the UGT2_1a, located at the Chr09.01 locus of STV008, the nourseothricin selection (NAT) marker and surrounding lox sites were amplified from the plasmid pUG7-NAT (FIG. 7) with primers containing additional 50 nt sequences homologous to the Chr09.01 integration flanks (FIG. 8). The PCR product was purified with the NucleoSpin Gel and PCR Clean-up kit (Macherey-Nagel) and transformed to STV008. Transformants were selected on YEPD containing 50 µg/ml nourseothricin (Lexy NTC from Jena Bioscience). Correct integration of the NAT marker and absence of UGT2_1a was confirmed by diagnostic PCR. This new strain was named STV009.

Example 7. Removal of the Nat Selection Marker of STV009

Figure 9:
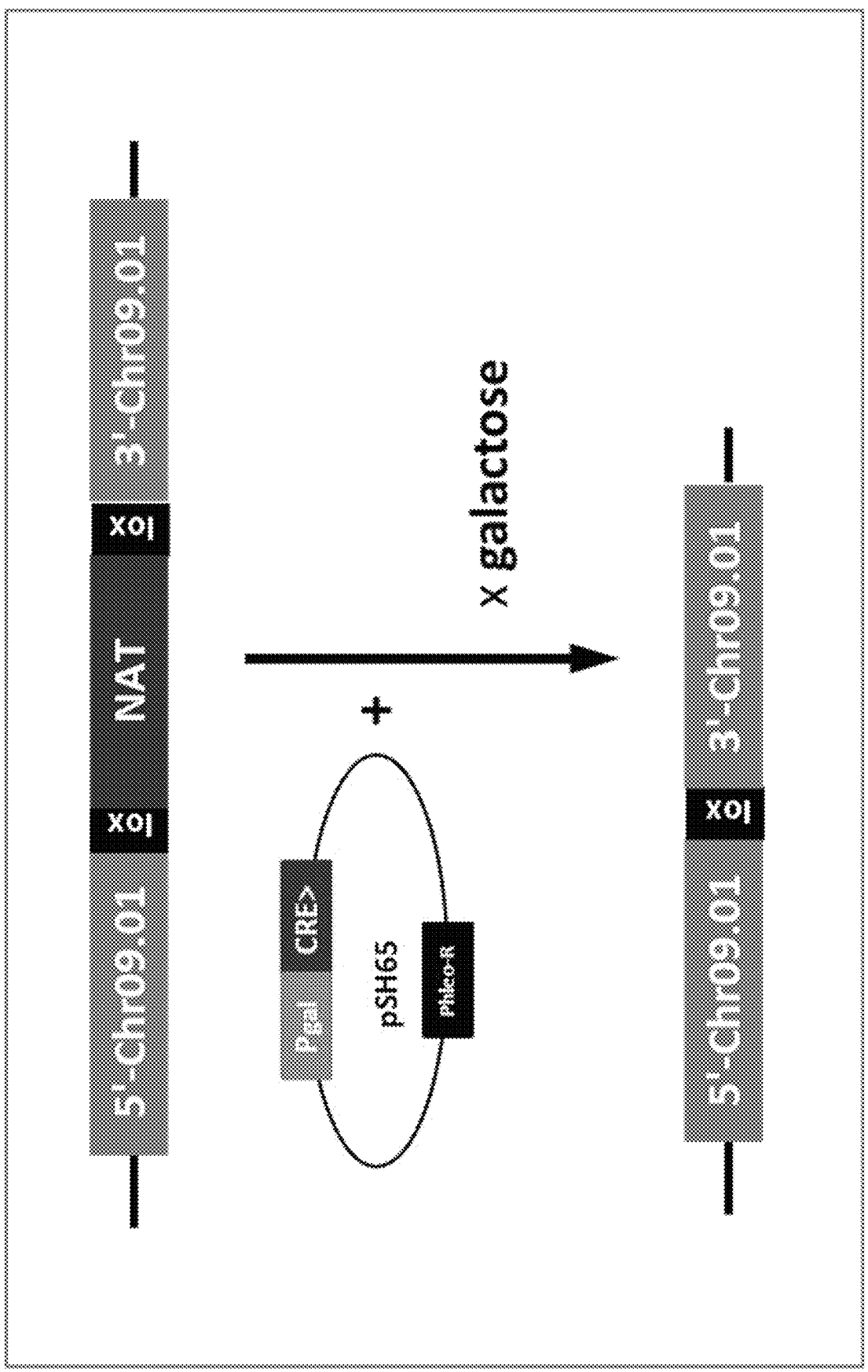
FIG. 9 sets out the removal of the NAT marker from STV008.

To be able to use the same integration locus for testing the UGT2 variants the NAT marker had to be removed from strain STV009 (FIG. 9). Therefore the CRE recombinase, located on the plasmid pSH65, was transformed to STV009 and transformants selected on YEPD containing 20 µg/ml Phleomycin. Colonies were restreaked on YEP Galactose agar plates. The plates were incubated at 30° C. Removal of the NAT marker by CRE recombinase was demonstrated by diagnostic PCR. In a production experiment it was shown that the STV009ΔNAT strain accumulates the same amount of rubusoside as its parent, STV009. The new strain was called STV053.

Example 8. Integration of UGT2 Gene Variants at the Chr09.01 Locus

Figure 10:
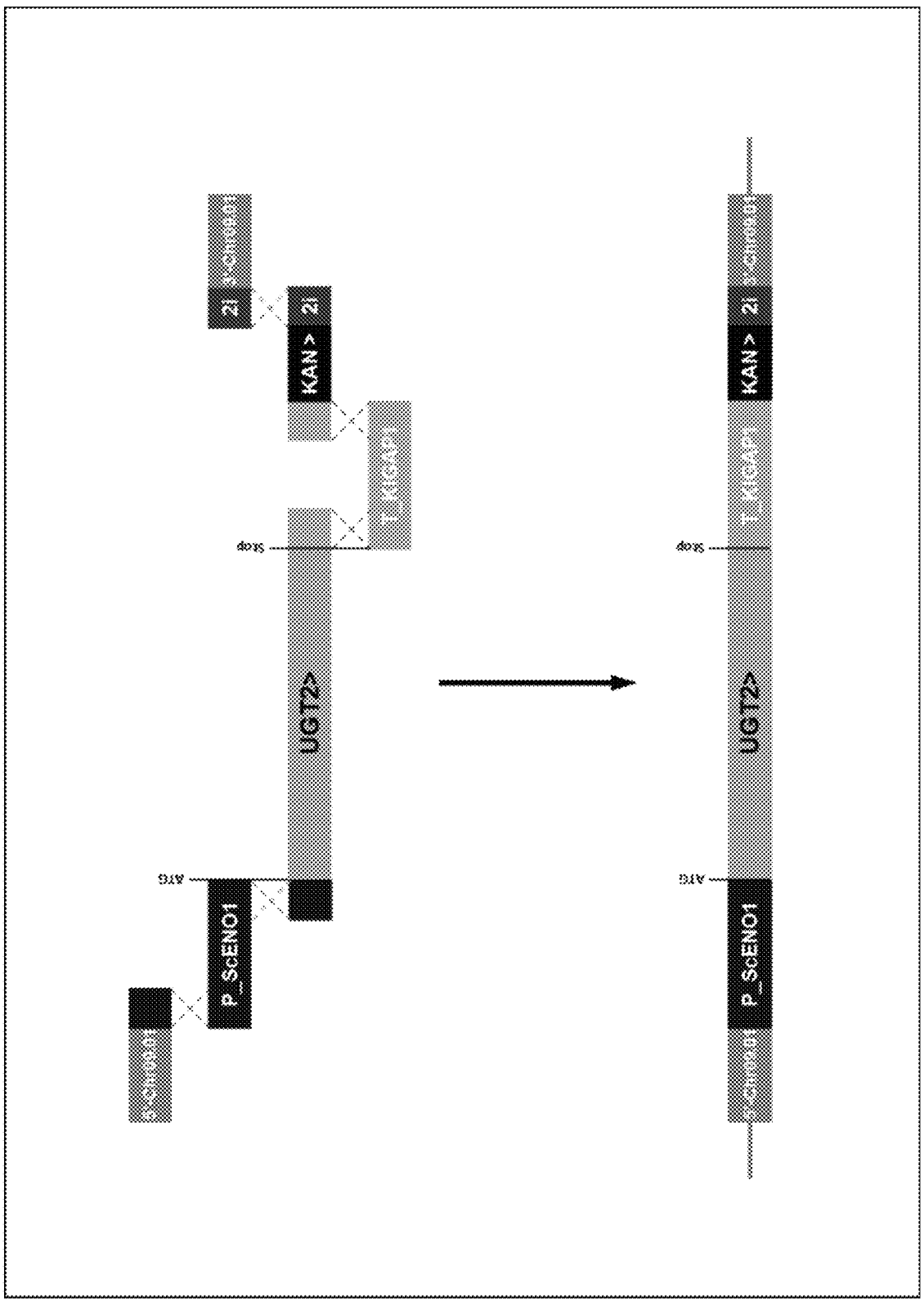
FIG. 10 sets out the integration of UGT2 genes at the Chr09.01 locus.

Different gene variants encoding UGT2 activity (SEQ ID NOs: 4, 7, 10, 12, 15, 18, 21, 23 and 28) were each separately integrated into the Chr09.01 locus by using several separate DNA fragments, containing 50 bp flanking homology segments for recombination (FIG. 10).

The 5'- and 3'-Chr09.01 integration flanks were amplified with suitable primers from genomic DNA from a CEN.PK yeast strain (van Dijken et al. Enzyme and Microbial Technology 26 (2000) 706-714). For the 5'-flank the reverse primer contained an extended 50 bp sequence homologous to promoter sequence to be used, namely the ScENO1 promoter (SEQ ID NO: 60). The forward primer for the 3'-flank contained a 50 bp linker extension.

The KanMX selection marker was amplified from the pUG7-EcoRV construct. The forward primer contained an additional 50 bp sequence homologous to the KIGAP1 (SEQ ID NO: 61) terminator. The reverse primer also possessed a 50 bp linker extension.

The different UGT2 gene variants were ordered at SGI-DNA. Their open reading frame was upstream flanked by 50 bp of the pScENO1 promoter (SEQ ID NO: 60) and downstream by 50 bp of the Klgap1T terminator (SEQ ID NO: 61). The genes were amplified from the SGI-DNA constructs by using primers annealing to these promoter and terminator sequences.

The PCR products were purified using the NucleoSpin 96 PCR Clean-up kit (Macherey-Nagel). Equimolar amounts of 5'-Chr09.01 flank, ENO1 promoter, UGT2 gene, KlGAP1 terminator, KanMX selection marker and 3'-Chr09.01 flank were combined for each UGT2 variant to be tested. One additional mixture was made containing the UGT2_1a. These mixtures were transformed to STV053 and plated on YEPD containing 200 µg/ml G418.

For each UGT2 variant, several replicate transformants were tested in a production experiment.

Example 9. Production of Rebaudioside A with *S. cerevisiae*

A pre-culture was inoculated with colony material from YEPD agar. The pre-culture was grown in 200 µl mineral medium with glucose as carbon source. The pre-culture was incubated 72 hours in an Infors incubator at 27° C., 750 rpm and 80% humidity. 40 µl of pre-culture was used to inoculate 2.5 ml mineral medium with glucose as carbon source. The main cultures were incubated 120 hours in an Infors incubator at 27° C., 550 rpm, 80% humidity. The cultures were well homogenized by pipetting up and down and 1 ml of culture was transferred to a 96-well plate. The 96-well plate was incubated for 15 minutes at 95° C. in a waterbath and cooled down to room temperature. To each well 0.5 ml of acetonitril was added and homogenized by pipetting up and down. The cell debris was pelleted by centrifugation at 3000 xg for 10 minutes. The supernatant was diluted 200 times in 33% acetonitril.

Figure 11:
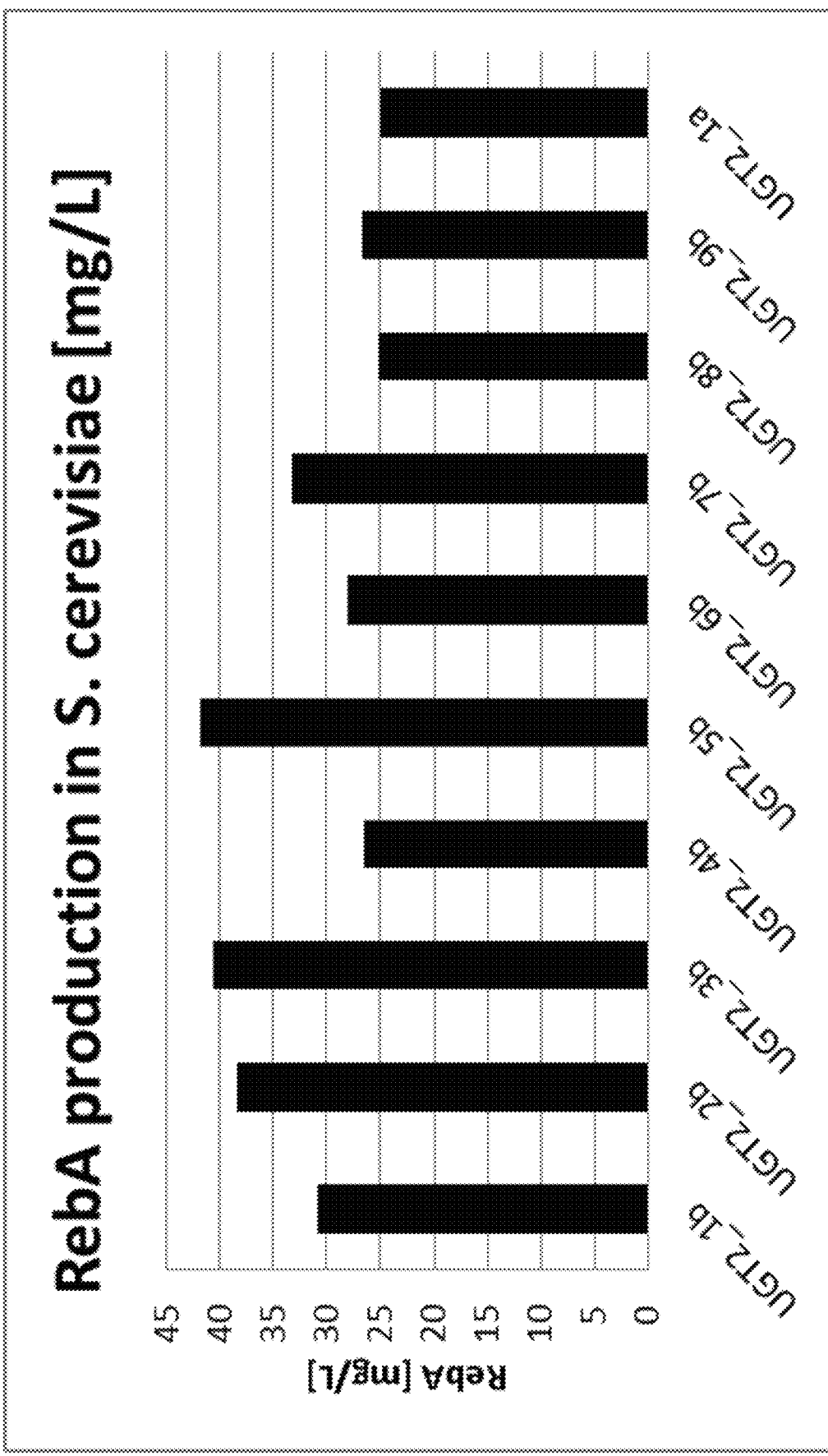
FIG. 11 sets out the production of rebaudioside A in *Saccharomyces* strains carrying different variants of UGT2

Samples were analyzed for RebA using LC/MS. RebA (RV0141-94, DAE Pyung Co. Ltd) was used as standard. We found that the strains that had the particular UGT2 gene variants as described, produced higher titers of RebA compared to the strain containing the UGT2_1a as set out in Table 8 and FIG. 11.

TABLE 8

Rebaudioside A production in *Saccharomyces* strains expressing UGT2 variant enzymes

| UGT2 variant | RebA (mg/L) |
| --- | --- |
| UGT2_1b | 30.8 |
| UGT2_2b | 38.4 |
| UGT2_3b | 40.6 |
| UGT2_4b | 26.5 |
| UGT2_5b | 41.8 |
| UGT2_6b | 28.1 |
| UGT2_7b | 33.3 |
| UGT2_8b | 25.2 |
| UGT2_9b | 26.7 |
| UGT2_1a | 25.0 |

Example 10: Production of Rebaudioside M with *S. cerevisiae*

A pre-culture was inoculated with colony material from YEPD agar. The pre-culture was grown in 200 µl mineral medium with glucose as carbon source. The pre-culture was incubated 72 hours in an Infors incubator at 27° C., 750 rpm and 80% humidity.

40 µl of pre-culture was used to inoculate 2.5 ml mineral medium with glucose as carbon source. The main cultures were incubated 120 hours in an Infors incubator at 27° C., 550 rpm, 80% humidity. The cultures were well homogenized by pipetting up and down and 1 ml of culture was transferred to a 96-well plate. The 96-well plate was incubated for 15 minutes at 95° C. in a waterbath and cooled down to room temperature. To each well 0.5 ml of acetonitril was added and homogenized by pipetting up and down. The cell debris was pelleted by centrifugation at 3000 xg for 10 minutes. The supernatant was diluted 200 times in 33% acetonitril.

The presence of RebM was confirmed by LC and MS analyzed with a LTQ orbitrap (Thermo), equipped with a Acella LC and a Waters Acquity UPLC BEH amide 1.7 µm 2.1"150 mm column. Eluentia used for the separation were A: 10 mM Ammonium acetate in MilliQ water, B: Acetonitrile, and the gradient started at 65% A and was kept here for 1.5 minutes, then increased to 95% B in 0.5 minutes and kept here for 0.5 minutes before regeneration for 1.5 min at 65% A. The flow-rate was 0.6 ml/min and the column temperature was kept at 50 C. Mass spectral analysis was performed in electrospray negative ionization mode, scanning from m/z 100-1800 at a resolution of 7500. Reb M elutes at tr=0.72 min, just after reb D at tr=0.63. Reb M is characterized by a deprotonated molecule of m/z 1289.5286. The elemental composition could be estimated using accurate mass analysis.

Figure 12:
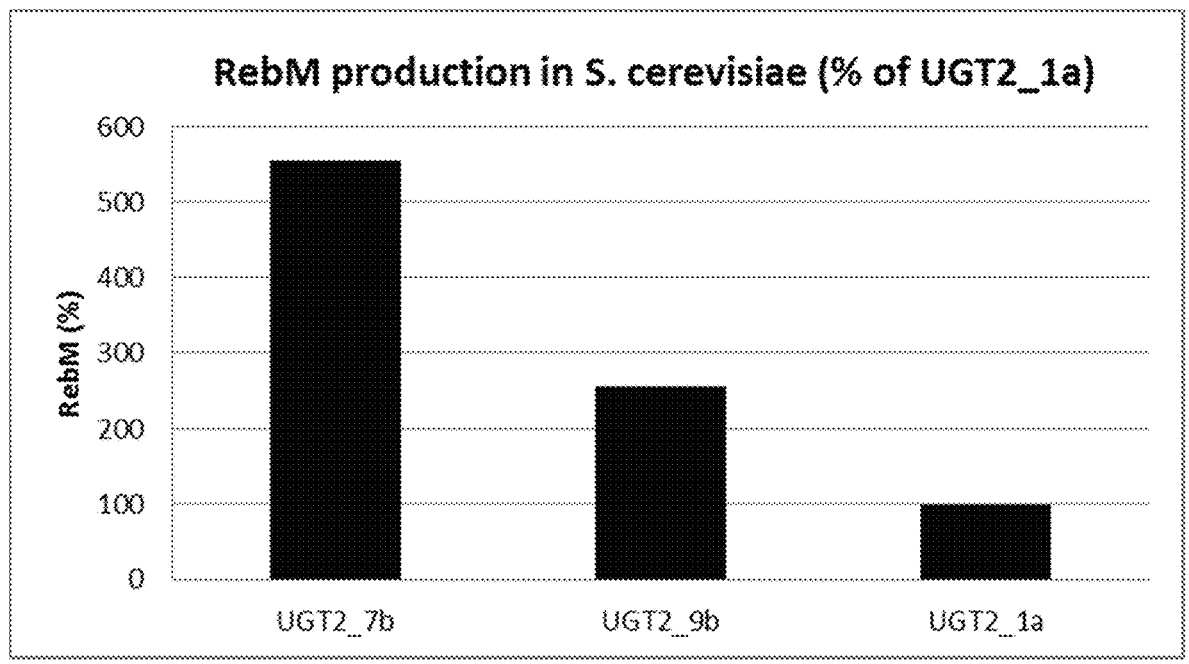

We found that the strains that had the particular UGT2 gene variants as described, produced higher titers of RebM compared to the strain containing the UGT2_1a as set out in FIG. 12 and Table 9.

TABLE 9

Rebaudioside M production in Saccharomyces strains expressing UGT2 variant enzymes, compared in percentages to UGT2 1a.

| UGT2 variant | RebM (relative to UGT2_1a) |
|---|---|
| UGT2_7b | 555 |
| UGT2_9b | 256 |
| UGT2_1a | 100 |

Example 11: Description of Steviol Alvcoside Production Strain ML14094 (MAT-A Lineage)

Two *Yarrowia lipolytica* strains of mating types MATA and MATB were engineered for steviol glycoside production. These strains were mated, the diploid sporulated, and spores with steviol glycoside production were selected. One of these spores was further developed for the production of steviol glycosides, including the production of rebaudioside A.

Figure 13:
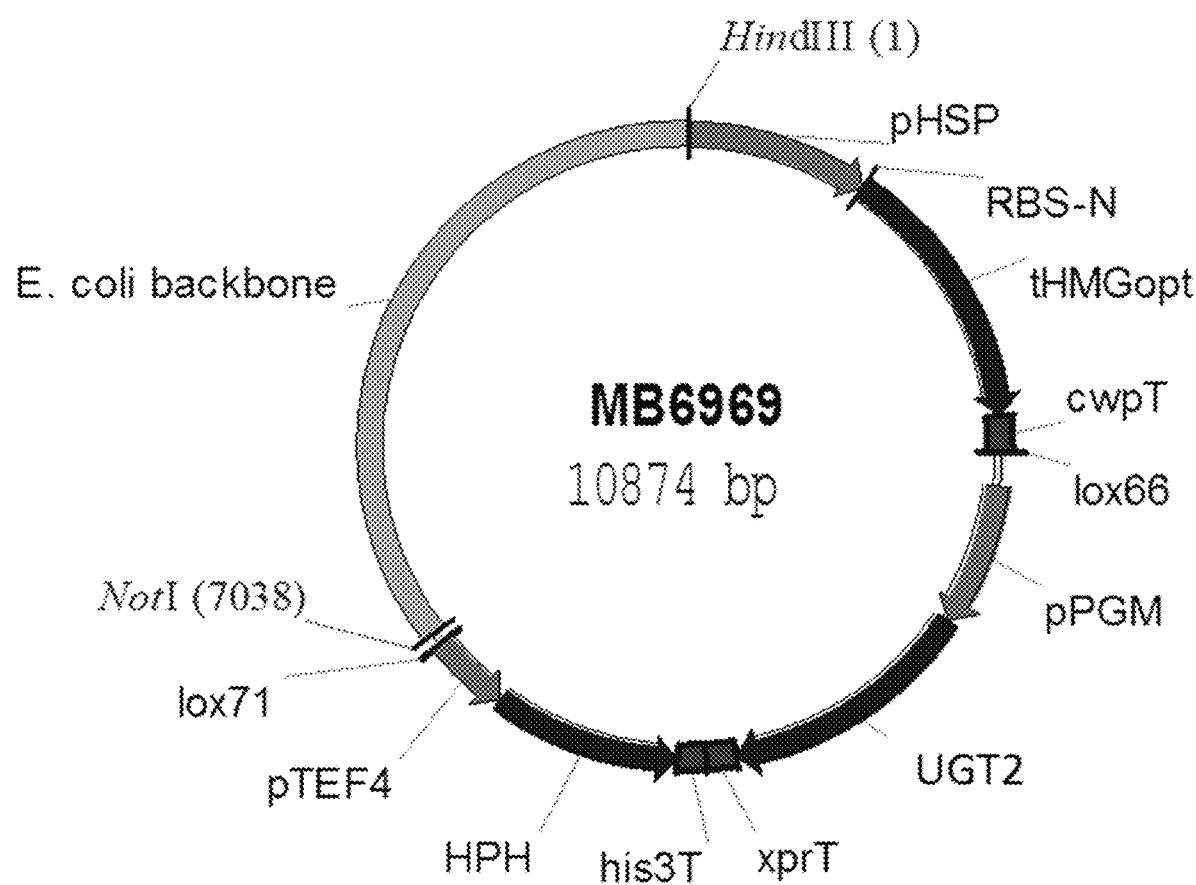

Step 1: Strain ML10371 (MAT-A, lys1-, ura3-, leu2-) was transformed with 5 defined DNA fragments. All transformations were carried out via a lithium acetate/PEG fungal transformation protocol method and transformants were selected on minimal medium, YPD+100 ug/ml nourseothricin or YPD+100 ug/ml hygromycin, as appropriate. 1) a 7.0 kb DNA fragment isolated by gel purification following HindIII/NotI digestion of plasmid MB6969 (FIG. 13). This construct encodes a synthetic construct for the overexpression of UGT2_1a (SEQ ID NO: 29) linked to the pPGM promoter (SEQ ID NO: 62) and xprT terminator (SEQ ID NO: 69) and the HPH hygromycin resistance gene, together flanked by lox sites (Güldener et al, 1996, Lambert et al, 2007), and a synthetic construct for the overexpression of the codon optimized *Y. lipolytica* hydroxymethylglutaryl-coenzyme A reductase open reading frame lacking the 5' membrane anchor sequence (tHMGopt: SEQ ID NO: 75) linked to the pHSP promoter (SEQ ID NO: 63) and cwpT terminator (SEQ ID NO: 70).

Figure 14:
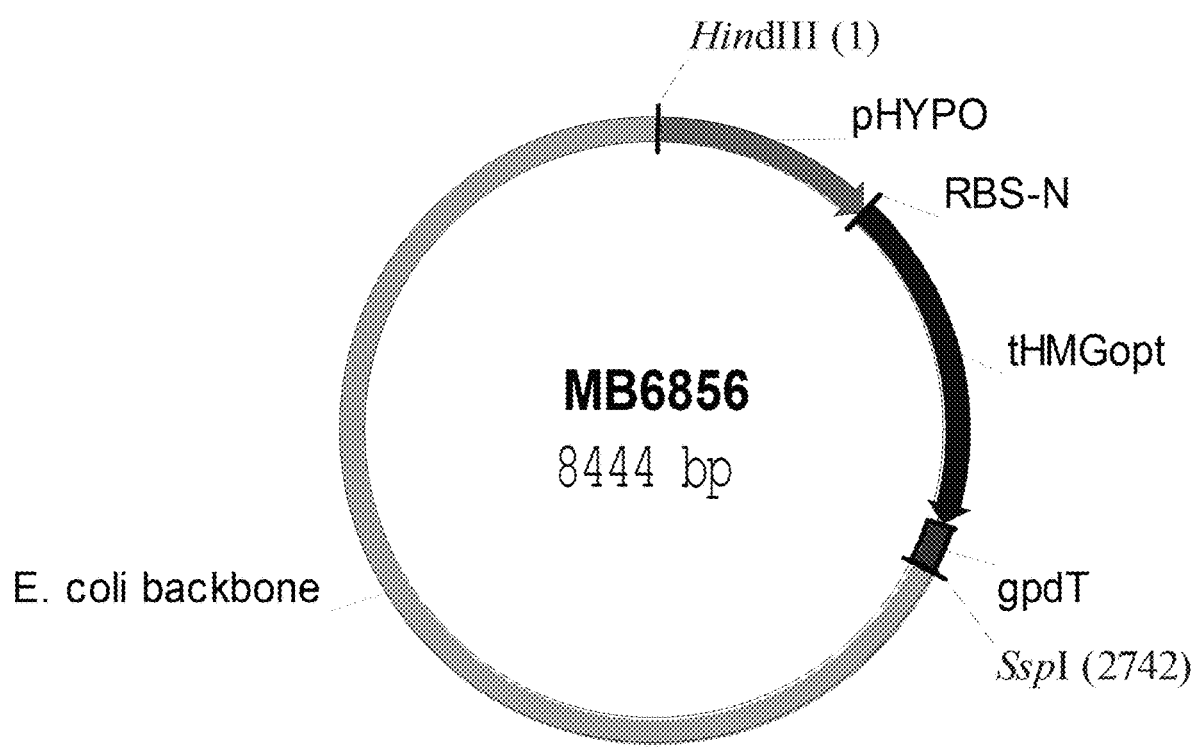
FIG. 14 sets out the map of plasmid MB6856, carrying gene tHMG

2) a 2.7 kb DNA fragment isolated by gel purification following HindIII/SspI digestion of MB6856 (FIG. 14). This construct encodes tHMGopt (SEQ ID NO: 75) linked to the pHYPO promoter (SEQ ID NO: 64) and gpdT terminator (SEQ ID NO: 71).

Figure 15:
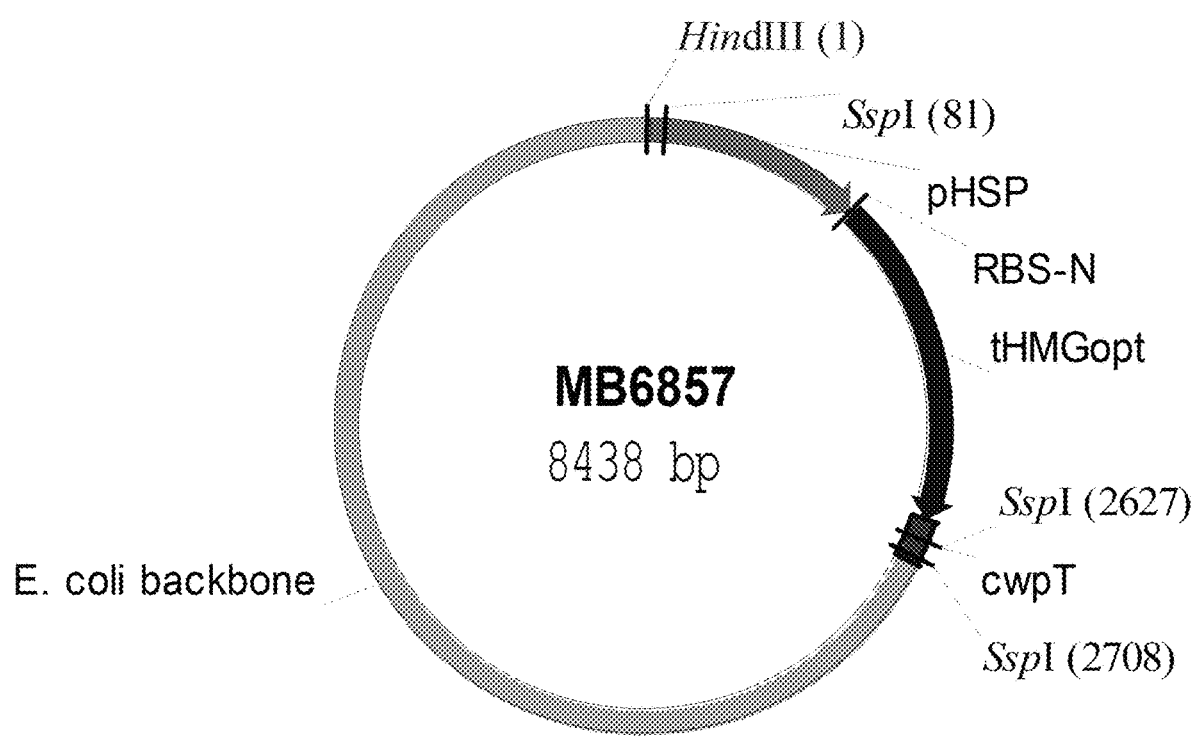
FIG. 15 sets out the map of plasmid MB6857, carrying gene tHMG

3) a 2.5 kb DNA fragment isolated by gel purification following SspI digestion of MB6857 (FIG. 15). This construct encodes tHMGopt (SEQ ID NO: 75) linked to the pHSP promoter (SEQ ID NO: 63) and cwpT terminator (SEQ ID NO: 70).

Figure 16:
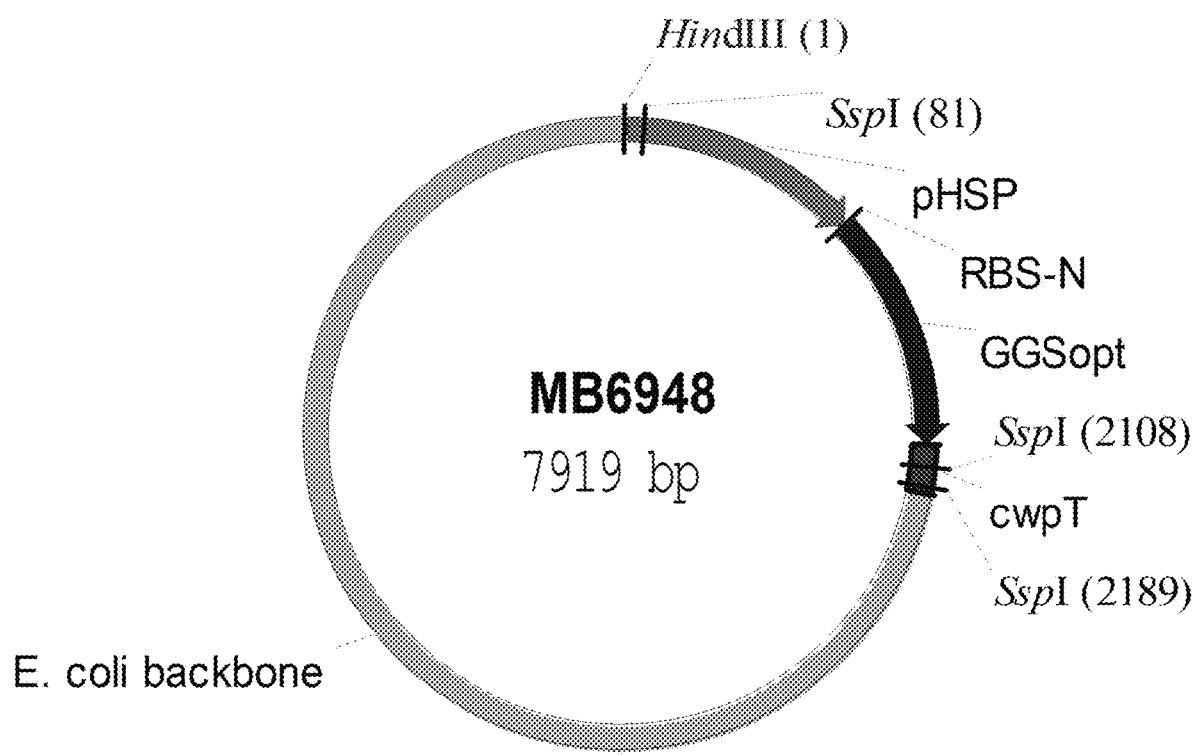
FIG. 16 sets out the map of plasmid MB6948, carrying gene GGS

4) a 2.0 kb DNA fragment isolated by gel purification following SspI digestion of MB6948 (FIG. 16). This construct encodes a synthetic construct for the overexpression of the codon optimized *Y. lipolytica* geranyl-geranyl-pyrophosphate synthetase (GGSopt: SEQ ID NO: 76) linked to the pHSP promoter (SEQ ID NO: 63) and cwpT terminator (SEQ ID NO: 70).

Figure 17:
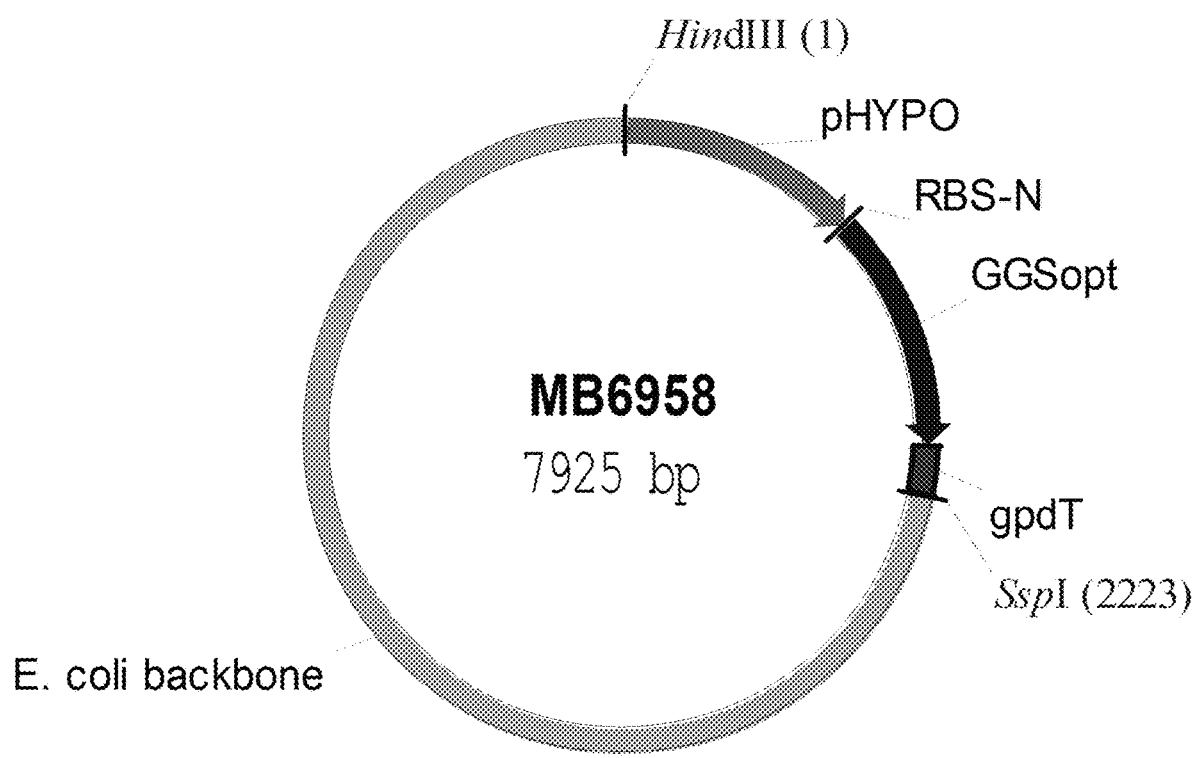
FIG. 17 sets out the map of plasmid MB6958, carrying gene GGS

5) a 2.2 kb DNA fragment isolated by gel purification following HindIII/SspI digestion of MB6958 (FIG. 17). This construct encodes GGSopt (SEQ ID NO: 76) linked to the pHYPO promoter (SEQ ID NO: 64) and gpdT terminator (SEQ ID NO: 71). The resulting strain was denoted ML13462.

Figure 18:
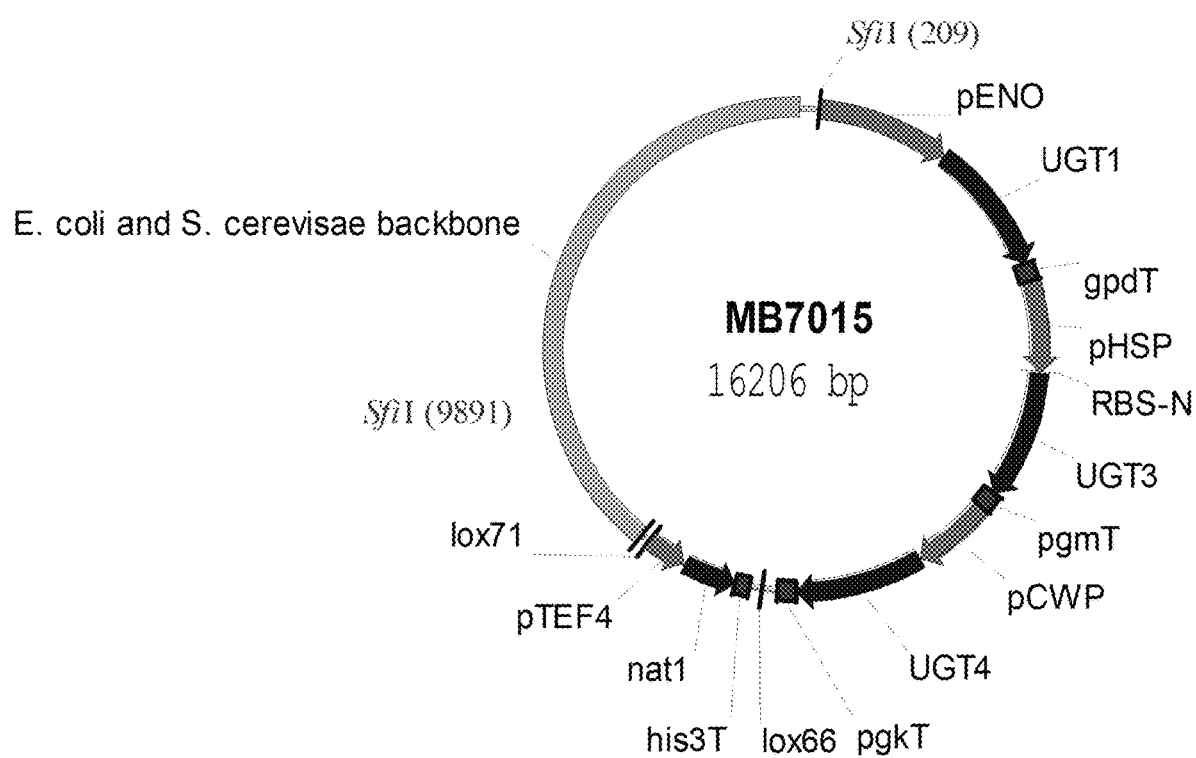
FIG. 18 sets out the map of plasmid MB7015, carrying genes UGT1, UGT3 and UGT4

Step 2. Strain ML13462 was transformed with a 9.7 kb fragment isolated by gel purification following SfiI digestion of plasmid MB7015 (FIG. 18). This construct encodes a synthetic construct for the overexpression of UGT1 (SEQ ID NO: 77) linked to the pENO (SEQ ID NO: 65) promoter and gpdT terminator (SEQ ID NO: 71), UGT3 (SEQ ID NO: 78) linked to the pHSP promoter (SEQ ID NO: 63) and pgmT terminator (SEQ ID NO: 72), UGT4 (SEQ ID NO: 79) linked to the pCWP (SEQ NO: 66) promoter and pgkT terminator (SEQ ID NO: 73), and the lox-flanked nourseothricin resistance marker (NAT). Note that placement of lox sites allows for subsequent removal of nourseothricin resistance via CRE recombinase mediated recombination. A nourseothricin resistant isolate was denoted ML13500.

Figure 19:
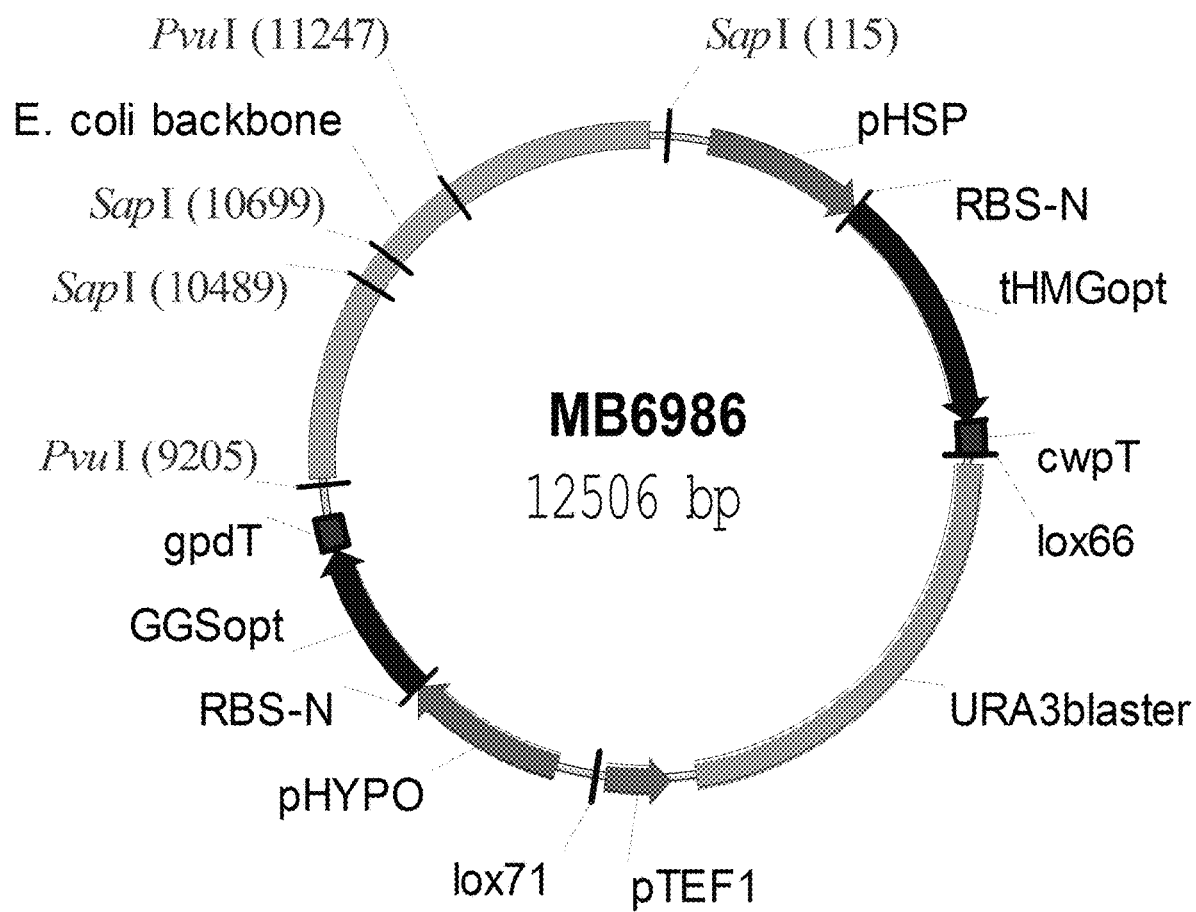
FIG. 19 sets out the map of plasmid MB6986, carrying genes tHMG and GGS

Step 3. Strain ML13500 was transformed with a 9.1 kb fragment isolated by gel purification following PvuI/SapI digestion of plasmid MB6986 (FIG. 19). This construct encodes tHMGopt (SEQ ID NO: 75) linked to the pHSP promoter (SEQ ID NO: 63) and cwpT terminator (SEQ ID NO: 70), the lox-flanked URA3blaster prototrophic marker, and GGSopt (SEQ ID NO: 76) linked to the pHYPO promoter (SEQ ID NO: 64) and gpdT terminator (SEQ ID NO: 71). Transformants were selected on minimal medium lacking uracil. One selected uracil prototroph was denoted ML13723.

Figure 20:
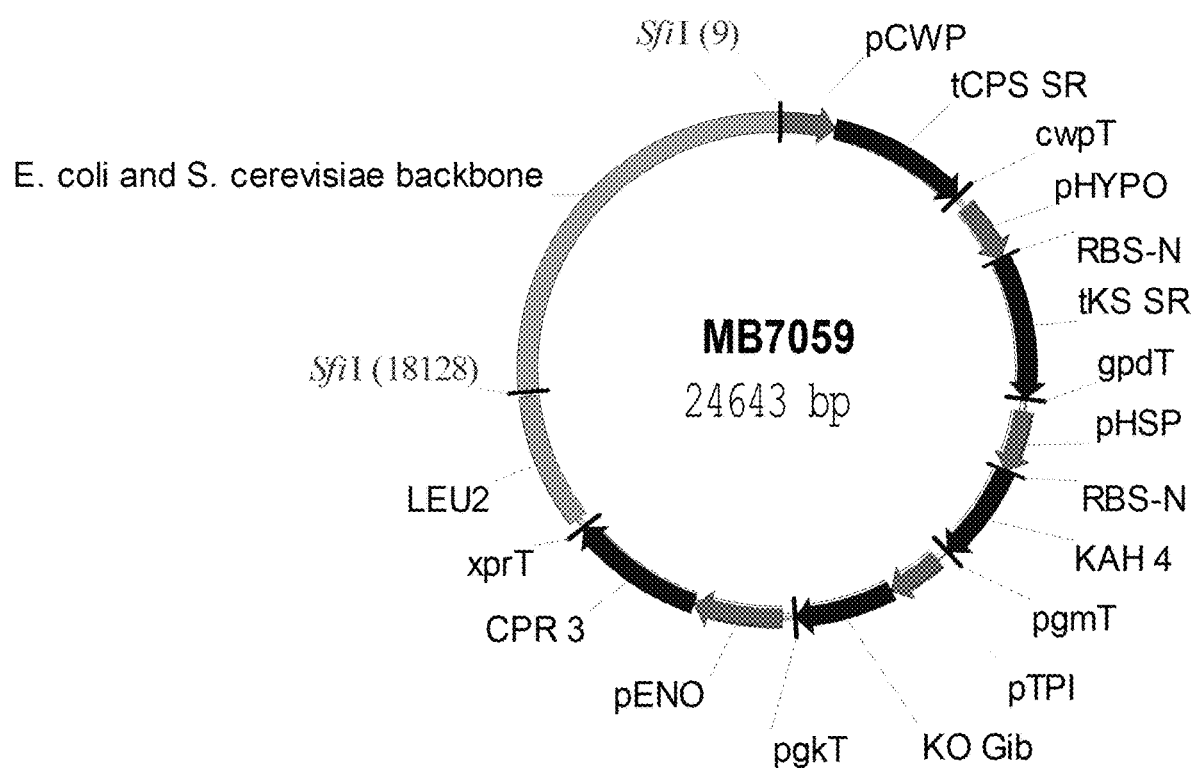
FIG. 20 sets out the map of plasmid MB7059, carrying genes tCPS_SR, tKS_SR, KAH_4, KO_Gib and CPR_3.

Step 4. Strain ML13723 was transformed with an 18.1 kb fragment isolated by gel purification following SfiI digestion of plasmid MB7059 (FIG. 20). MB7059 encodes the tCPS_SR (SEQ ID NO: 80) linked to pCWP promoter (SEQ ID NO: 66) and cwpT terminator (SEQ ID NO: 70), the tKS_SR (SEQ ID NO: 81) linked to the pHYPO promoter (SEQ ID NO: 64) and gpdT terminator (SEQ ID NO: 71), the KAH_4 (SEQ ID NO: 92) linked to the pHSP promoter (SEQ ID NO: 63) and pgmT terminator (SEQ ID NO: 72), the KO_Gib (SEQ ID NO: 83) linked to the pTPI promoter (SEQ ID NO: 67) and pgkT terminator (SEQ ID NO: 73), the CPR_3 (SEQ ID NO: 84) linked to the pENO promoter (SEQ ID NO: 65) and xprT terminator (SEQ ID NO: 69) and the native *Y. lipolytica* LEU2 locus. One selected rebaudioside A-producing transformant was denoted ML14032.

Step 5. Strain ML14032 was struck to YPD and grown overnight and then struck to 5-FOA plates to allow for recombination mediated loss of the URA3 marker introduced in Step 3. One selected 5-FOA resistant transformant was denoted ML14093.

Figure 21:
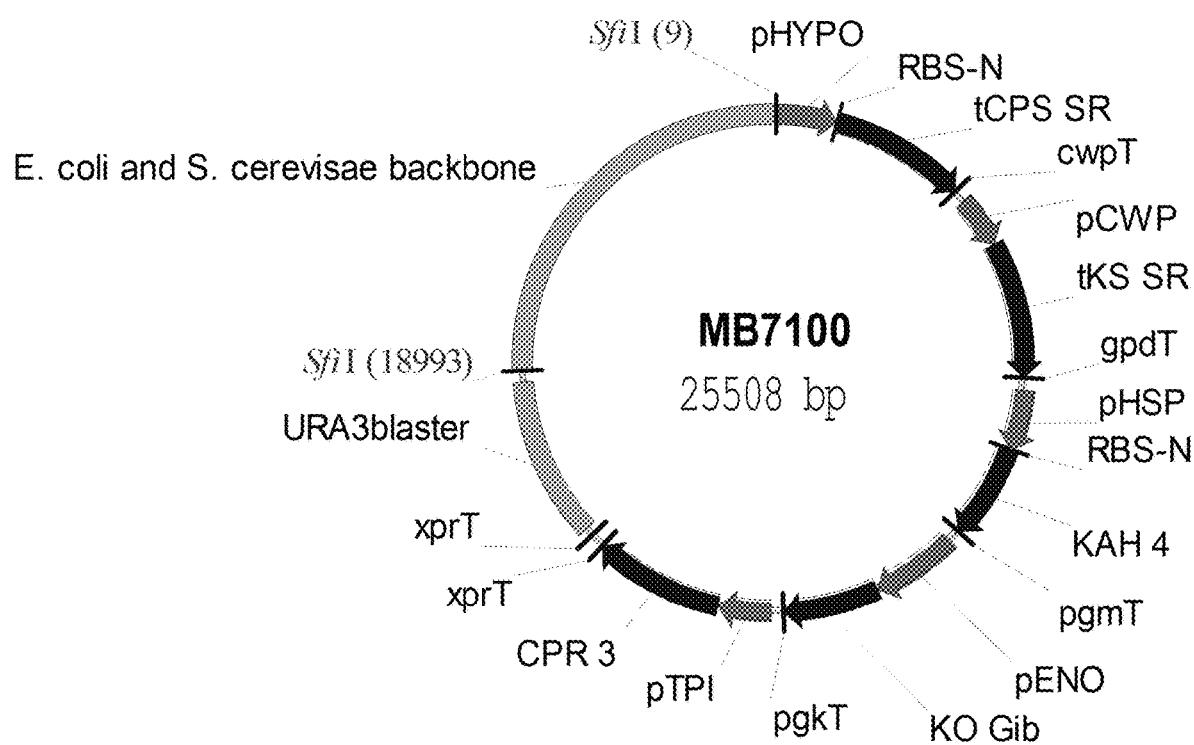
FIG. 21 sets out the map of plasmid MB7100, carrying genes tCPS_SR, tKS_SR, KAH_4, KO_Gib and CPR_3.

Step 6. Strain ML14093 was transformed with a 19.0 kb fragment isolated by gel purification following SfiI digestion of plasmid MB7100 (FIG. 21). MB7100 encodes the tCPS_SR (SEQ ID NO: 80) linked to the pHYPO promoter (SEQ ID NO: 64) and cwpT terminator (SEQ ID NO: 70), the tKS_SR (SEQ ID NO: 81) linked to the pCWP promoter (SEQ ID NO: 66) and gpdT terminator (SEQ ID NO: 71), the KAH_4 (SEQ ID NO: 82) linked to the pHSP promoter (SEQ ID NO: 63) and pgmT terminator (SEQ ID NO: 72), the KO_Gib (SEQ ID NO: 83) linked to the pENO promoter (SEQ ID NO: 65) and pgkT terminator (SEQ ID NO: 73), the CPR_3 (SEQ ID NO: 84) linked to the pTPI promoter (SEQ ID NO: 67) and xprT terminator (SEQ ID NO: 69) and URA3blaster prototrophic marker. Transformants were selected on minimal medium lacking uracil. One selected rebaudioside A producing uracil prototroph was denoted ML14094.

Example 12. Description of Steviol Glycoside Production Strain ML14087 (MAT-B Lineage)

Step 1. Strain ML13206 (MAT-B, ade1-, ure2-, leu2-) was transformed with 5 defined DNA fragments. All transformations were carried out via a lithium acetate/PEG fungal transformation protocol method and transformants were selected on minimal medium, YPD+100 ug/ml nourseothricin or YPD+100 ug/ml hygromycin, as appropriate.

1) a 7.0 kb DNA fragment isolated by gel purification following HindIII/NotI digestion of plasmid MB6969 (FIG. 13). This construct encodes a synthetic construct for the overexpression of the codon pair optimized (CpO) ORF of UGT2_1a (SEQ ID NO: 29) linked to the pPGM (SEQ ID NO: 62) promoter and xprT terminator (SEQ ID NO: 69) and the HPH hygromycin resistance gene, together flanked by lox sites (Güldener et al, 1996, Lambert et al, 2007), and a synthetic construct for the overexpression of the codon optimized *Y. lipolytica* hydroxymethylglutaryl-coenzyme A reductase open reading frame lacking the 5' membrane anchor sequence (tHMGopt: SEQ ID NO: 75) linked to the pHSP promoter (SEQ ID NO: 63) and cwpT terminator (SEQ ID NO: 70).

2) a 2.7 kb DNA fragment isolated by gel purification following HindIII/SspI digestion of MB6856 (FIG. 14). This construct encodes tHMGopt (SEQ ID NO: 75) linked to the pHYPO promoter (SEQ ID NO: 64) and gpdT terminator (SEQ ID NO: 71).

3) a 2.5 kb DNA fragment isolated by gel purification following SspI digestion of MB6857 (FIG. 15). This construct encodes tHMGopt (SEQ ID NO: 75) linked to the pHSP promoter (SEQ ID NO: 63) and cwpT terminator (SEQ ID NO: 70). 4) a 2.0 kb DNA fragment isolated by gel purification following SspI digestion of MB6948 (FIG. 16). This construct encodes a synthetic construct for the overexpression of the codon optimized *Y. lipolytica* geranyl-geranyl-pyrophosphate synthetase (GGSopt: SEQ ID NO: 76) linked to the pHSP promoter (SEQ ID NO: 63) and cwpT terminator (SEQ ID NO: 70).

5) a 2.2 kb DNA fragment isolated by gel purification following HindIII/SspI digestion of MB6958 (FIG. 17). This construct encodes GGSopt (SEQ ID NO: 76) linked to the pHYPO (SEQ ID NO: 64) promoter and gpdT terminator (SEQ ID NO: 71). The resulting strain was denoted ML13465.

Step 2. Strain ML13465 was transformed with 2 defined DNA fragments:

1). a 9.7 kb fragment isolated by gel purification following SfiI digestion of plasmid MB7015 (FIG. 18). This construct encodes a synthetic construct for the overexpression of UGT1 (SEQ ID NO: 77) linked to the pENO promoter (SEQ Id NO: 65) and gpdT (SEQ ID NO: 71) terminator, UGT3 (SEQ ID NO: 78) linked to the pHSP promoter (SEQ ID NO: 63) and pgmT terminator (SEQ ID NO: 72), UGT4 (SEQ ID NO: 79) linked to the pCWP promoter (SEQ ID NO: 66) and pgkT terminator (SEQ ID NO: 73), and the lox-flanked nourseothricin resistance marker (NAT). Note that placement of lox sites allows for subsequent removal of nourseothricin resistance via CRE recombinase mediated recombination.

Figure 22:
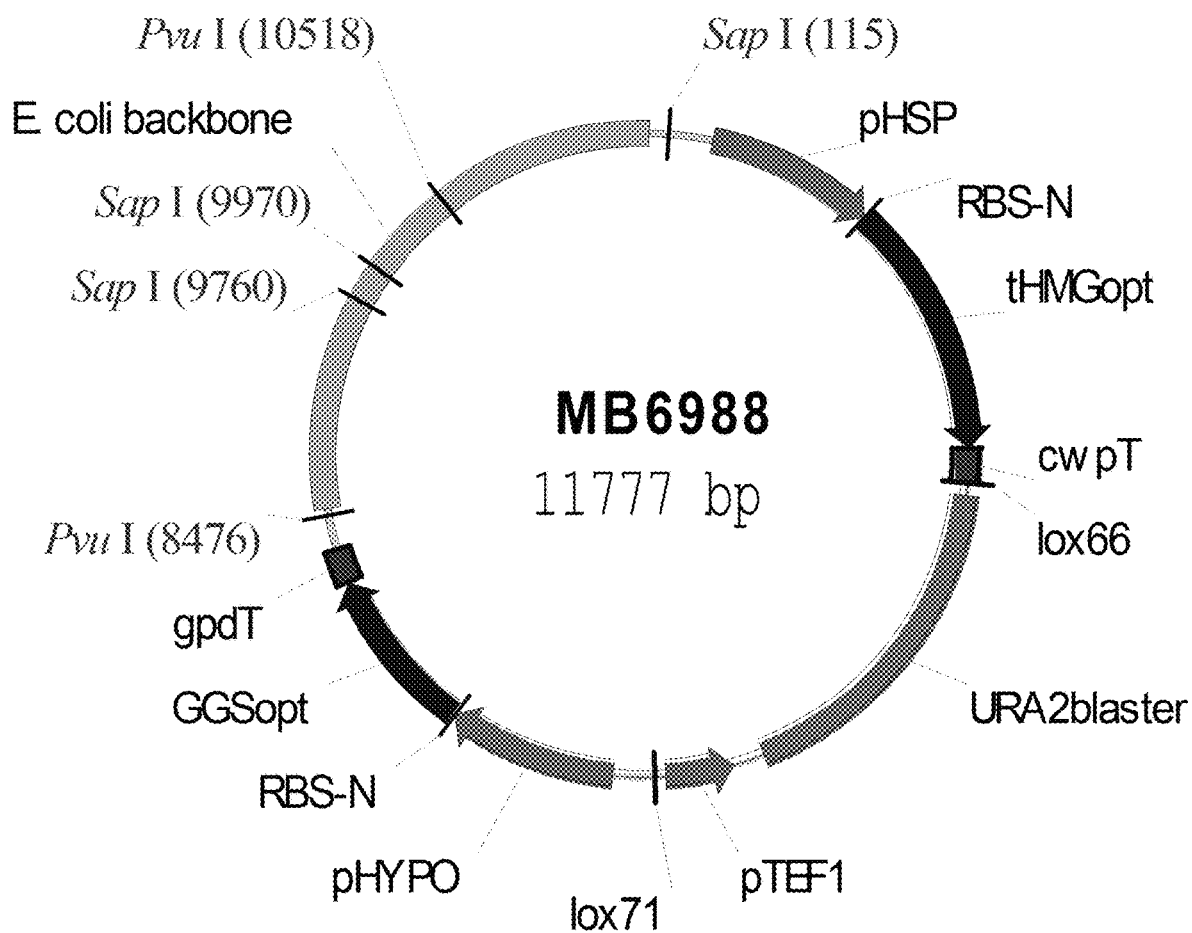
FIG. 22 sets out the map of plasmid MB6988, carrying genes tHMG and GGS

2). a 9.1 kb fragment isolated by gel purification following PvuI/SapI digestion of plasmid MB6988 (FIG. 22). This construct encodes tHMGopt (SEQ ID NO: 75) linked to the pHSP promoter (SEQ ID NO: 63) and cwpT terminator (SEQ ID NO: 70), the lox-flanked URA2blaster prototrophic marker, and GGSopt (SEQ ID NO: 76) linked to the pHYPO promoter (SEQ ID NO: 64) and gpdT terminator (SEQ ID NO: 71). Strains were selected on YPD+100 ug/ml nourseothricin and replica plated to minimal medium lacking uracil. A nourseothricin resistant, uracil prototrophic isolate was denoted ML13490

Step 3. Strain ML13490 was struck to YPD and grown overnight and then struck to 5-FOA plates to allow for recombination mediated loss of the URA2 marker introduced in step 3 above. One selected 5-FOA resistant transformant was denoted ML13501.

Step 4. Strain ML13501 was transformed with a 9.1 kb fragment isolated by gel purification following PvuI/SapI digestion of plasmid MB6988 (FIG. 22). Transformants were selected on minimal medium lacking uracil. One selected uracil prototroph was denoted ML13724.

Figure 23:
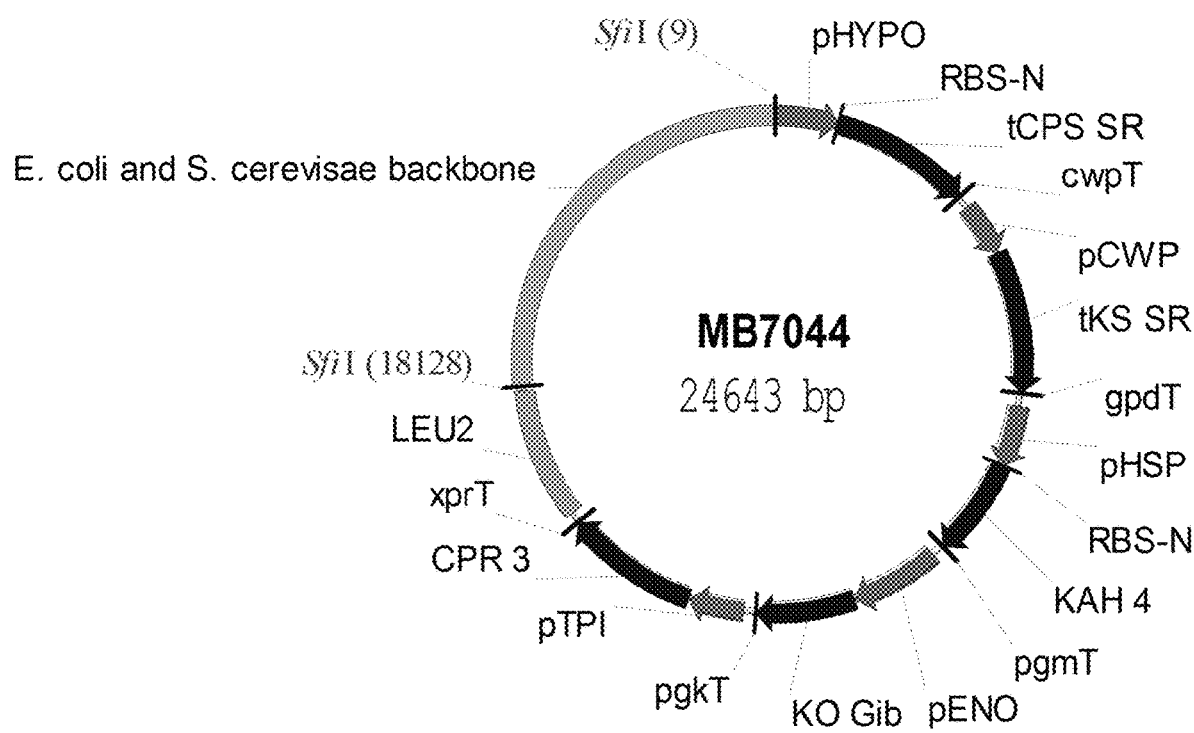
FIG. 23 sets out the map of plasmid MB7044, carrying genes tCPS_SR, tKS_SR, KAH_4, KO_Gib and CPR_3.

Step 5. Strain ML13724 was transformed with an 18.1 kb fragment isolated by gel purification following SfiI digestion of plasmid MB7044 (FIG. 23). MB7044 encodes the tCPS_SR (SEQ ID NO: 80) linked to the pHYPO promoter (SEQ ID NO: 64) and cwpT terminator (SEQ ID NO: 70), the tKS_SR (SEQ ID NO: 81) linked to the pCWP promoter (SEQ ID NO: 66) and gpdT terminator (SEQ ID NO: 70), the KAH_4 (SEQ ID NO: 82) linked to the pHSP promoter (SEQ ID NO: 63) and pgmT terminator (SEQ ID NO: 72), the KO_Gib (SEQ ID NO: 83) linked to the pENO promoter (SEQ ID NO: 65) and pgkT terminator (SEQ ID NO: 73), the CPR_3 (SEQ ID NO: 84) linked to the pTPI promoter (SEQ ID NO: 67) and xprT terminator (SEQ ID NO: 69) and the LEU2 locus. One selected rebaudioside A-producing transformant was denoted ML14044.

Step 6. Strain ML14044 was struck to YPD and grown overnight and then struck to 5-FOA plates to allow for recombination mediated loss of the URA2 marker introduced in Step 4 above. One selected 5'-FOA resistant transformant was denoted ML14076.

Figure 24:
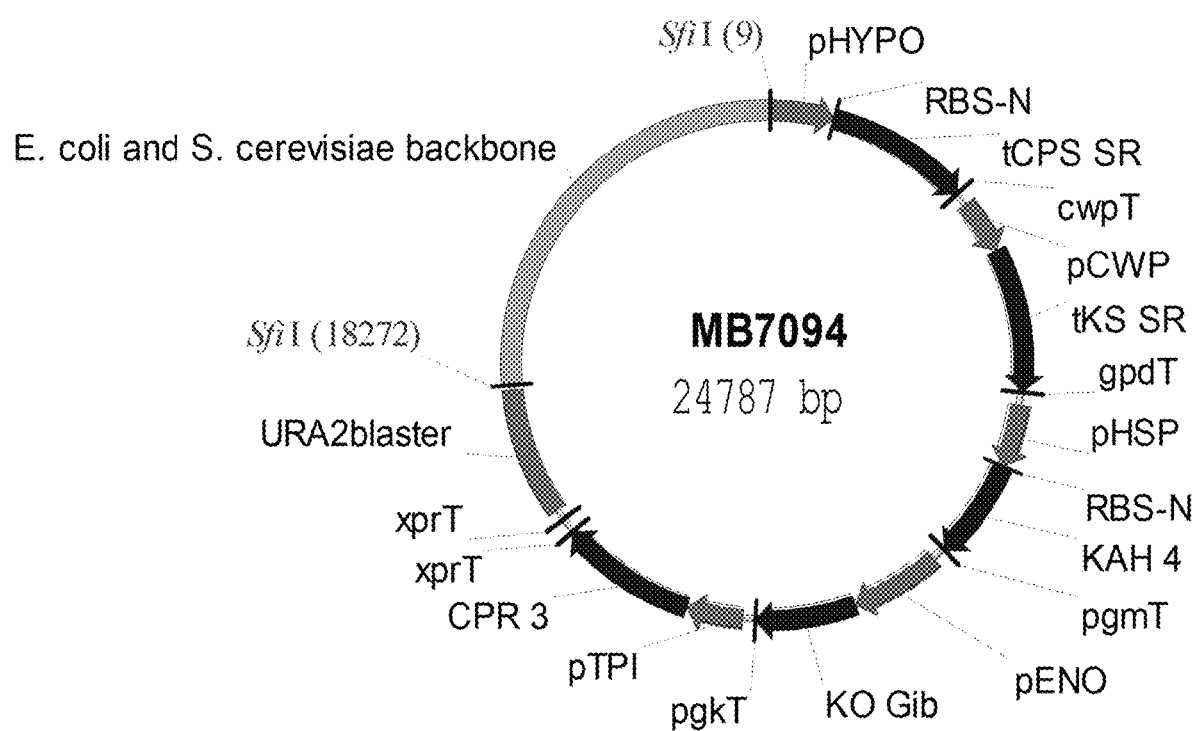
FIG. 24 sets out the map of plasmid MB7094, carrying genes tCPS_SR, tKS_SR, KAH_4, KO_Gib and CPR_3.

Step 7. Strain ML14076 was transformed with a 19.0 kb fragment isolated by gel purification following SfiI digestion of plasmid MB7094 (FIG. 24). MB7094 encodes the tCPS_SR (SEQ ID NO: 80) linked to the pHYPO promoter (SEQ ID NO: 64) and cwpT terminator (SEQ ID NO: 70), the tKS_SR (SEQ ID NO: 81) linked to the pCWP promoter (SEQ ID NO: 66) and gpdT terminator (SEQ ID NO: 71), the KAH_4 (SEQ ID NO: 82) linked to the pHSP promoter (SEQ ID NO: 63) and pgmT terminator (SEQ ID NO: 72), the KO_Gib (SEQ ID NO: 83) linked to the pENO promoter (SEQ ID NO: 65) and pgkT terminator (SEQ ID NO: 73), the CPR_3 (SEQ ID NO: 84) linked to the pTPI promoter (SEQ ID NO: 67) and xprT terminator (SEQ ID NO: 69) and URA2blaster prototrophic marker. Transformants were selected on minimal medium lacking uracil. One selected rebaudioside A producing uracil prototroph was denoted ML14087.

Example 13. Mating MATA and MATB Lineage and Selecting Steviol Glycoside-Producing Progeny Strains of opposite mating types (ML14094 and ML14087) with complementary nutritional deficiencies (ADE1+lys1- and ade1-LYS1+) were allowed to mate and then plated on selective media that would allow only diploids to grow (minimal media lacking both adenine and lysine). Diploid cells (ML14143) were then induced to undergo meiosis and sporulation by starvation, and the resulting haploid progenies were replica-plated to identify prototrophic isolates with hygromycin and nourseothricin resistance. One selected rebaudioside A-producing strain was denoted ML14737

Example 14. Making the Strain UGT2_1a-free

Figure 25:
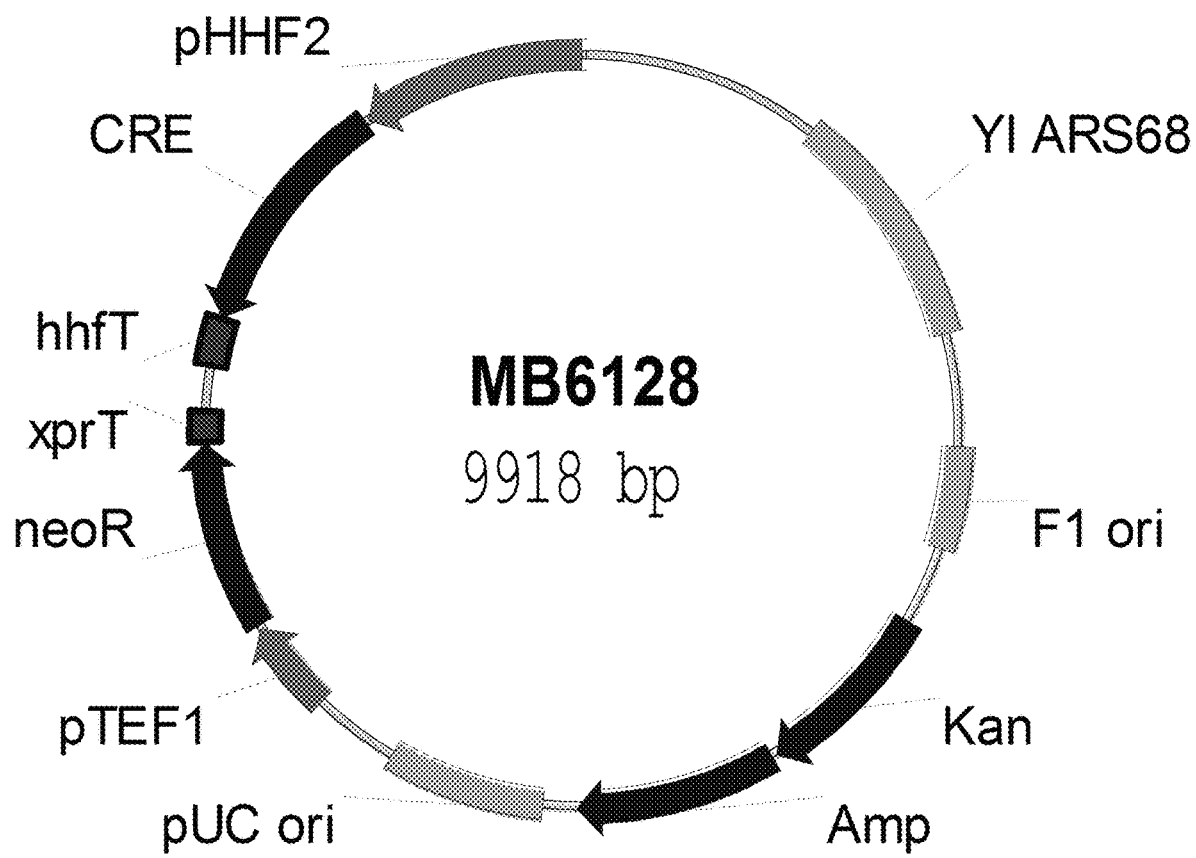
FIG. 25 sets out the map of plasmid MB6128, carrying CRE gene, which is used for removal of the antibiotic marker.

The hygromycin antibiotic marker and the nourseothricin antibiotic marker were removed from strain ML14737 after transformation with MB6128 (FIG. 25) which encodes a construct for constitutive overexpression of the CRE recombinase. CRE recombinase deletes the antibiotics markers by recombination over the Lox66 and Lox71 sites. An inactive Lox72 site is left in the genome (Güldener et al, 1996, Lambert et al, 2007). Plasmid MB6128 is a CEN plasmid which replicates episomally in *Yarrowia lipolytica* and which contains the CRE recombinase coding region under control of the native *Yarrowia lipolytica* pHHF promoter and hhfT terminator, and a neoR (encoding for G418 resistance) under the control of the native *Yarrowia lipolytica* pTEF1 promoter and xprT terminator. After selection of MB6128 transformants on YPD+G418 and screening for transformants that lost hygromycin and nourseothricin resistance by successful Cre-Lox recombination, the sensitive colonies were grown on non-selective medium to remove the MB6128 CEN plasmid (spontaneous loss of the CEN plasmid). The resulting antibiotic marker-free variant is denoted ML14869. This strain no longer produces rebaudioside A due to the loss of UGT2_1a along with the hygromycin resistance and produces the intermediate rubusoside instead.

Example 15. Transformation of UGT2 Genes

Figure 26:
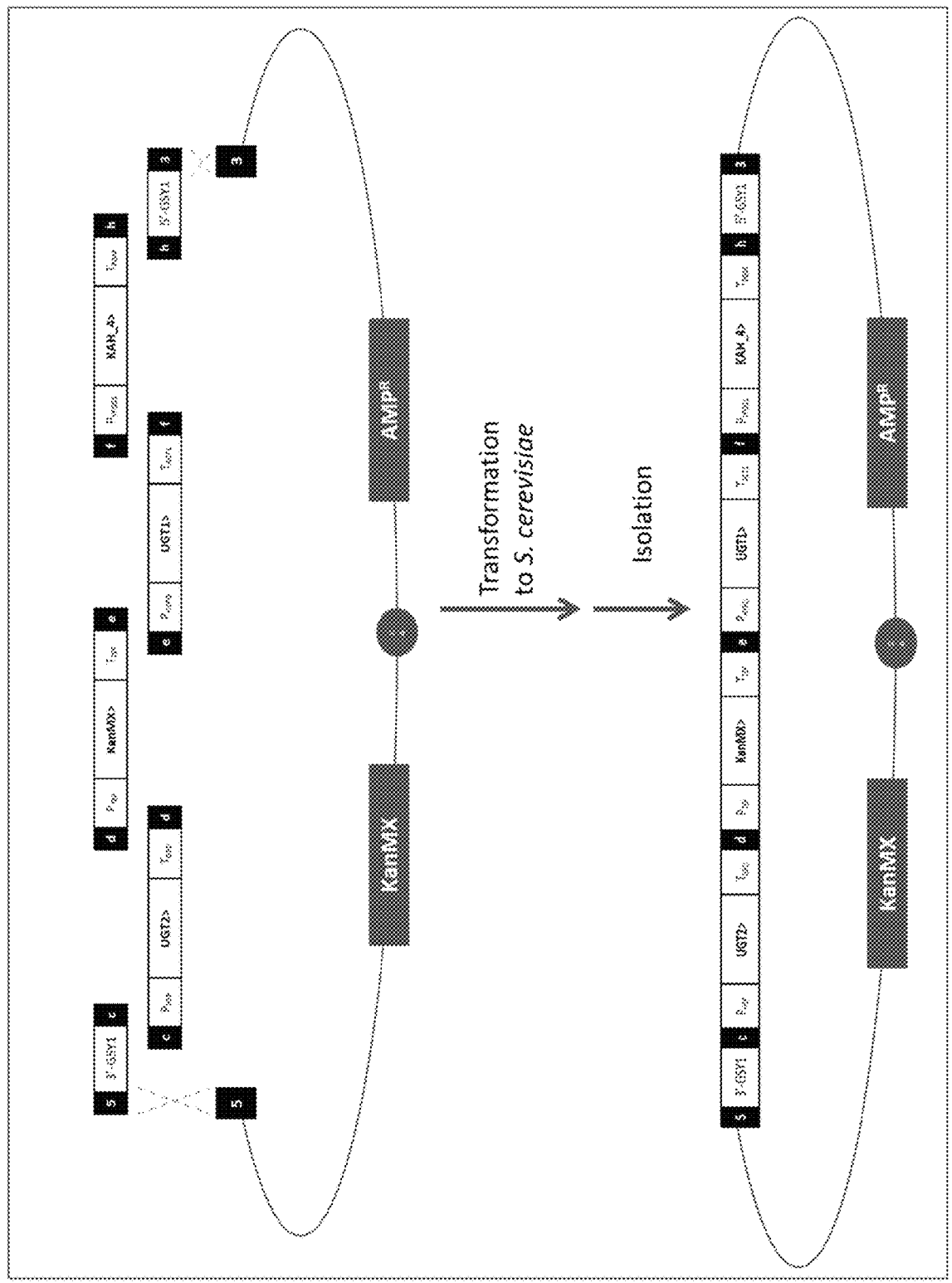
FIG. 26 sets out the method of assembly in a plasmid of genes UGT2, KanMX, UGT1 and KAH_4, flanked by gsyl integration flanks.

The UGT2 gene variants and UGT2_1a as control, were placed behind the *Yarrowia lipolytica* pHSP promoter (SEQ ID NO: 63) and combined with *Yarrowia lipolytica* terminator gpdT (SEQ ID NO: 71). Together with UGT1 (SEQ ID NO: 77), KAH_4 (SEQ ID NO: 82), the lox-flanked G418 resistance marker (KanMX) and *Yarrowia lipolytica* GSY1 integration flanks, each UGT2 was assembled into a construct on the CEN plasmid p417[5-3] in *Saccharomyces cerevisiae* (see FIG. 26).

TABLE 10

Promoters, ORFs and Terminators used in construction of strains with UGT2 variants

| Promoter | ORF | Terminator |
|---|---|---|
| pHSP (SEQ ID NO: 63) | UGT2 (SEQ ID NO: 5, 8, 13, 16, 19, 24, 26 and 29) | gpdT (SEQ ID NO: 71) |
| Ag_TEF1 | KanMX | Ag_TEF1 |
| pHYPO (SEQ ID NO: 64) | UGT1 (SEQ ID NO: 77) | act1T (SEQ ID NO: 74) |
| pYP001 (SEQ ID NO: 68) | KAH_4 (SEQ ID NO: 82) | pgmT (SEQ ID NO: 72) |

Figure 27:
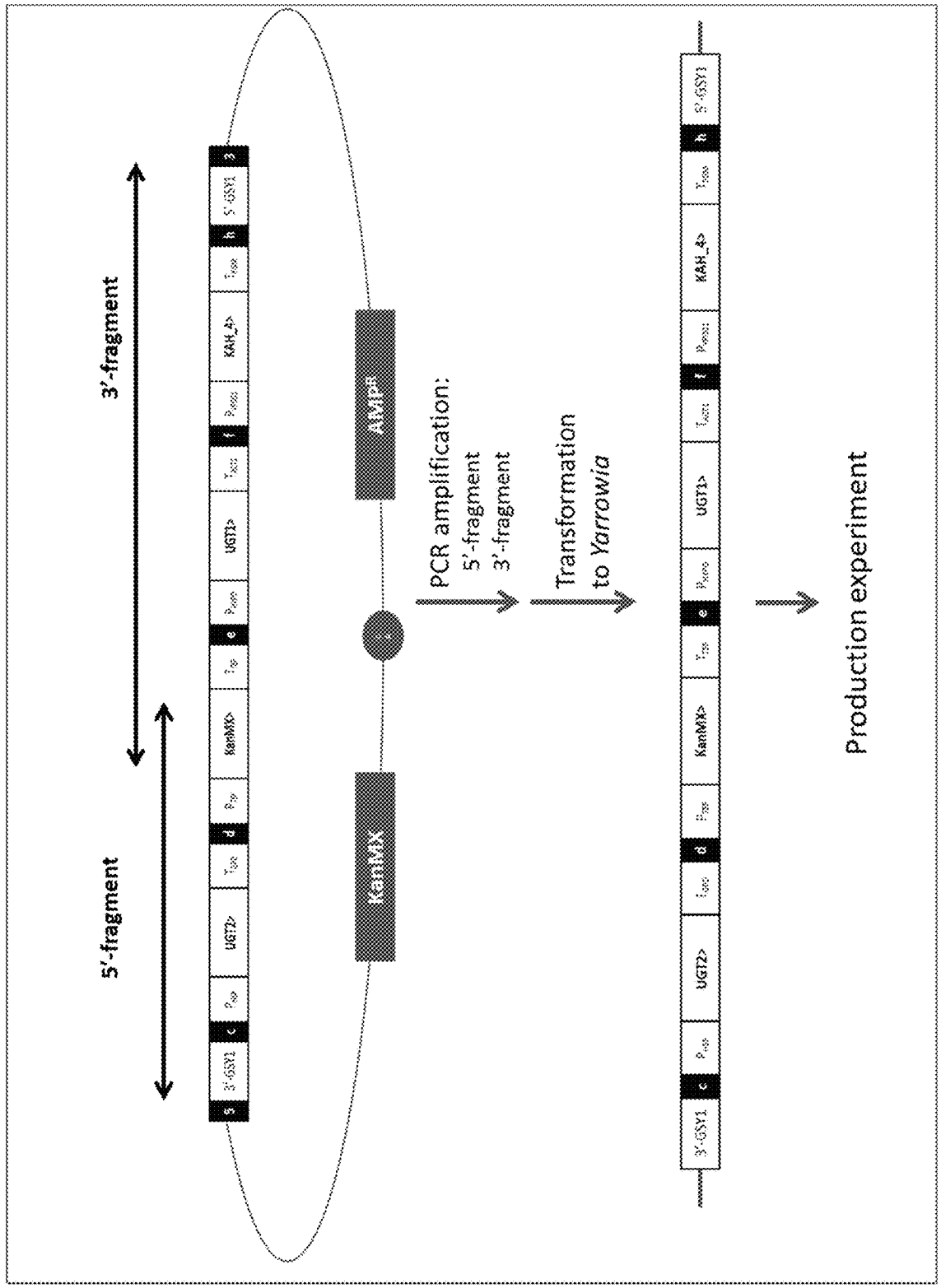
FIG. 27 sets out the method of amplification of the plasmid of FIG. 26, and transformation to *Yarrowia*.

These constructs, one for each UGT2, were used as template in PCRs to amplify the 5'-part and the 3'-part (see FIG. 27). This 5'-part consists of everything between the beginning of the 3'-GSY1 integration flank and the end of the KanMX open reading frame. The 3'-part consists of everything between the second codon of the KanMX open reading frame and the end of the 5'-GSY1 integration flank.

For the UGT2 testing each 5'-part and 3'-part combination was transformed to strain ML14869. Transformants were selected on YPD medium containing G418. From each transformation 12 colonies were selected for a production experiment.

Example 16. Production of RebA with *Y. lipolytica*

A pre-culture was inoculated with colony material from YEPh-D agar. The pre-culture was grown in 200 µl YEP with glucose as carbon source. The pre-culture was incubated 72 hours in an Infors incubator at 27° C., 750 rpm and 80% humidity. 40 µl of pre-culture was used to inoculate 2.5 ml YEP with glucose as carbon source. The main cultures were incubated 120 hours in an Infors incubator at 27° C., 550 rpm, 80% humidity. After 120 h the main culture was spun down at 2750 rpm for 10 min. From the supernatant 100 µl was taken and diluted 2.5 times in 55% acetonitrile. Further dilutions were made in 33% acetonitrile.

Figure 28:
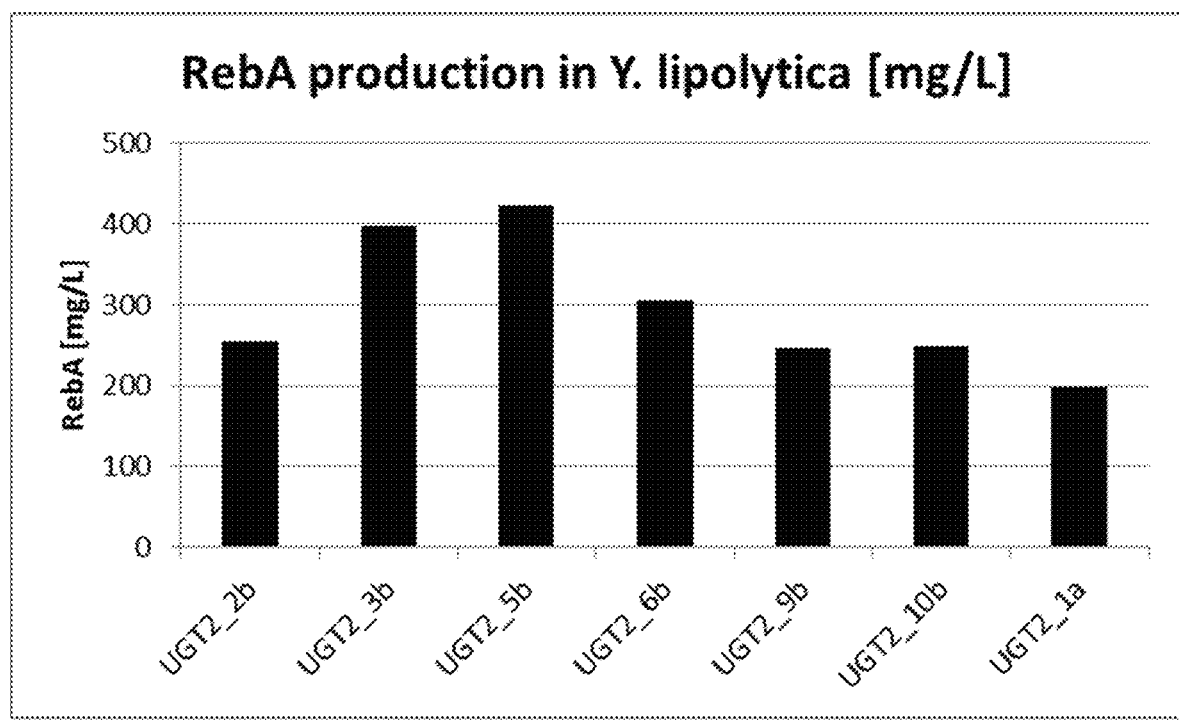
FIG. 28 sets out the production of rebaudioside A in *Yarrowia* strains expressing different variants of UGT2.

The results are set out in in FIG. 28 and Table 11. It can be seen that the strains that express the variant UGT2s produce higher titers of RebA.

TABLE 11

Rebaudioside A production in *Yarrowia* strains expressing UGT2 variant enzymes

| Sample | RebA (mg/L) |
|---|---|
| UGT2_2b | 254 |
| UGT2_3b | 396 |
| UGT2_5b | 422 |
| UGT2_9b | 246 |
| UGT2_10b | 249 |
| UGT2_1a | 198 |

Example 17. Production of RebM with *Y. lipolytica*

A pre-culture was inoculated with colony material from YEPh-D agar. The pre-culture was grown in 200 µl YEP with glucose as carbon source. The pre-culture was incubated 72 hours in an Infors incubator at 27° C., 750 rpm and 80% humidity. 40 µl of pre-culture was used to inoculate 2.5 ml YEP with glucose as carbon source. The main cultures were incubated 120 hours in an Infors incubator at 27° C., 550 rpm, 80% humidity. After 120 h the main culture was spun down at 2750 rpm for 10 min. From the supernatant 100 μl was taken and diluted 2.5 times in 55% acetonitrile. Further dilutions were made in 33% acetonitrile.

Figure 29:
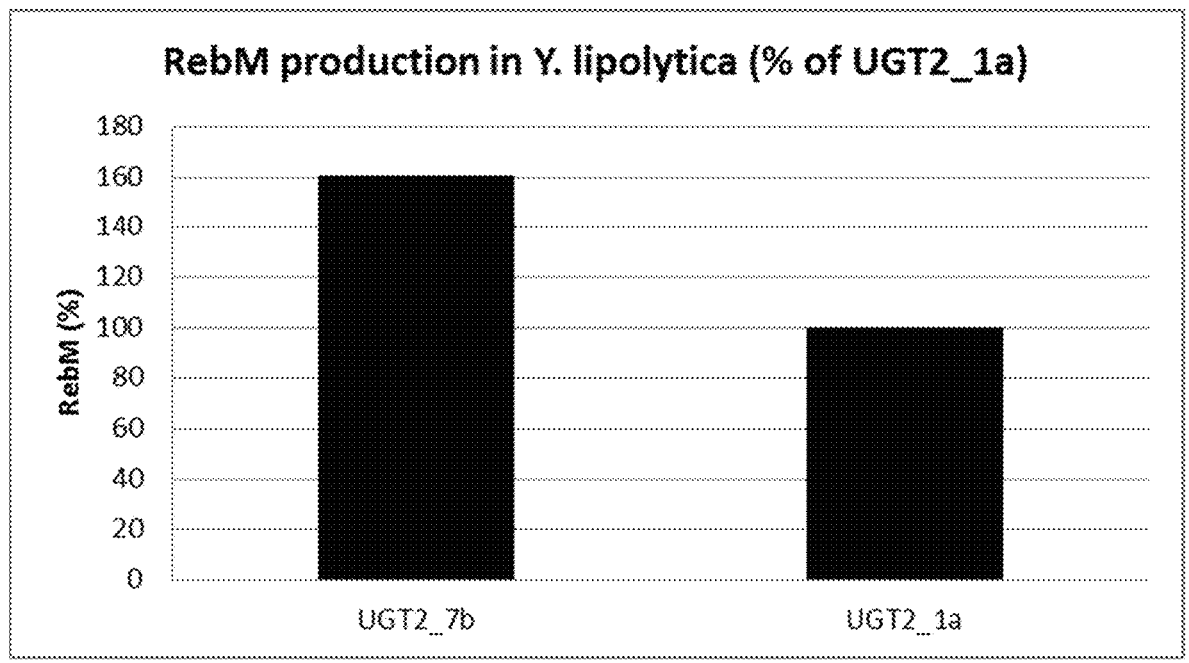

The results are set out in in FIG. 29 and Table 12. It can be seen that the strains that express the variant UGT2s produce higher titers of RebM.

TABLE 12

Rebaudioside M production in *Yarrowia* strains expressing UGT2 variant enzymes

| Sample | RebM (mg/L) |
|---|---|
| UGT2_7b | 37.5 |
| UGT2_1a | 23.3 |

Example 18

In order to evaluate the effect of different variants of UGT2 on steviol glycoside production in bioreactors, two of the strains described in example 15 were selected. One strain expresses UGT2_6b and the other strain expresses UGT2_7b. The fermentation protocol applied was a fed-batch fermentation and whole broth samples were taken daily for the analysis of steviol glycosides with LC/MS.

Figure 30:
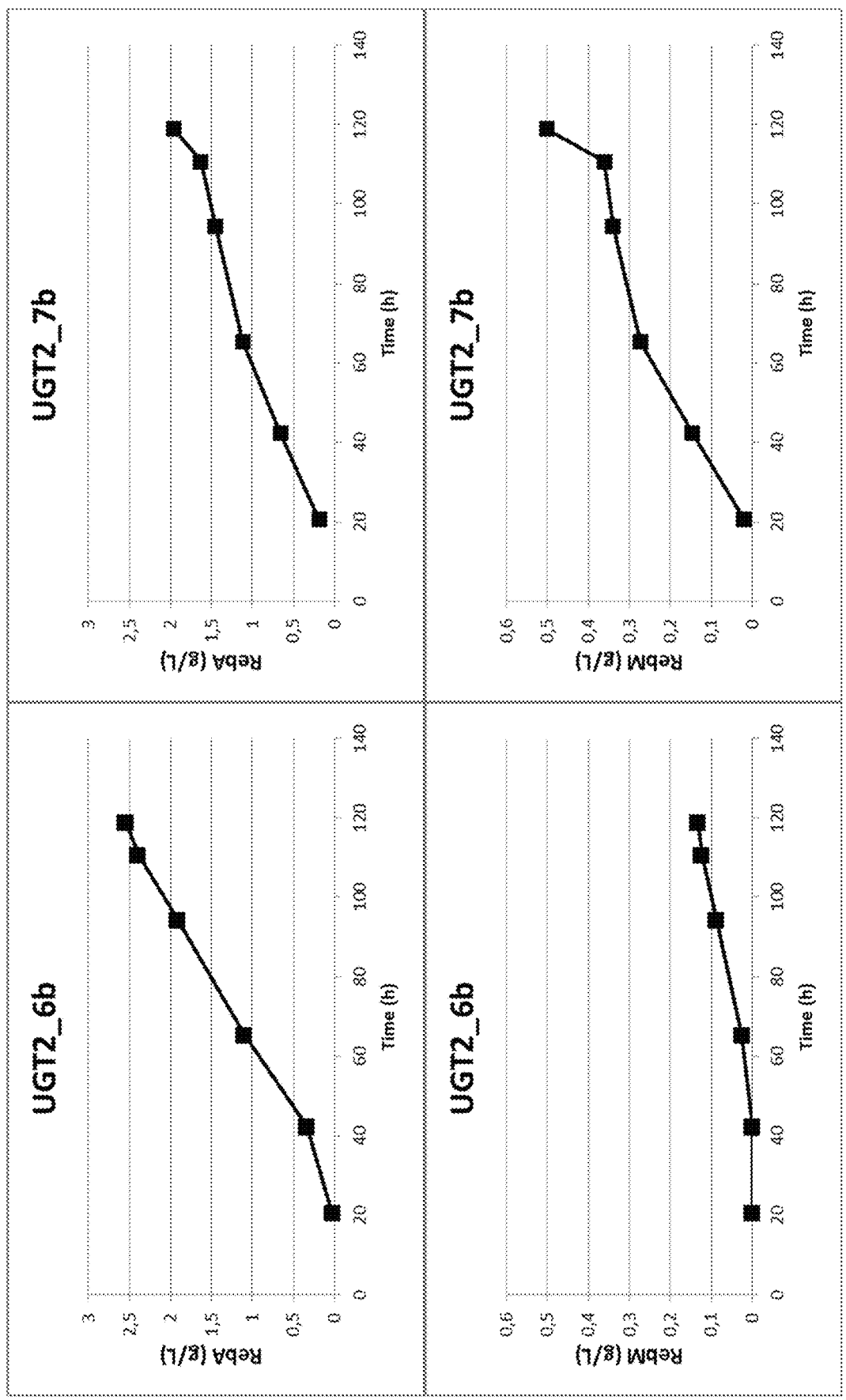
FIG. 30. RebA (top panels) and RebM (bottom panels) production in strains expressing either UGT2_6b (left panels) or UGT2_7b (right panels).

As can be seen in FIG. 30, the strain expressing UGT2_6b makes more RebA compared to the strain expressing the UGT2_7b. However, the strain expressing the UGT2_7b produces substantially more RebM compared to the strain expressing the UGT2_6b. Both strains make more RebA than RebM. At the end of the fermentation, with the strain expressing UGT2_6b the RebA concentration is 20 fold higher than the RebM concentration, whereas in the strain expressing the UGT2_7b, this is four fold higher. The different product ratio's reflect the intrinsic differences of the UGT2 properties, where the UGT2_7b has a higher activity of glycosylation of the glucose on the 19-position compared to the UGT2_6b. Products of the glycosylation reaction on the 19-position, such as RebE and RebD, from stevioside and RebA respectively, are further converted to RebM by the activity of UGT4, see FIG. 32.

This illustrates that production can be effectively steered to the product of interest by using the different variants of UGT2 here described.

TABLE 13

Description of the sequence listing

| SEQ ID NO | Description |
|---|---|
| SEQ ID NO: 1 | UGT2_1b amino acid |
| SEQ ID NO: 2 | UGT2_1b CpO for *S. cerevisiae* |
| SEQ ID NO: 3 | UGT2_2b amino acid |
| SEQ ID NO: 4 | UGT2_2b CpO for *S. cerevisiae* |
| SEQ ID NO: 5 | UGT2_2b CpO for *Y. lipolitica* |
| SEQ ID NO: 6 | UGT2_3b amino acid |
| SEQ ID NO: 7 | UGT2_3b CpO for *S. cerevisiae* |
| SEQ ID NO: 8 | UGT2_3b CpO for *Y. lipolitica* |
| SEQ ID NO: 9 | UGT2_4b amino acid |
| SEQ ID NO: 10 | UGT2_4b CpO for *S. cerevisiae* |
| SEQ ID NO: 11 | UGT2_5b amino acid |
| SEQ ID NO: 12 | UGT2_5b CpO for *S. cerevisiae* |
| SEQ ID NO: 13 | UGT2_5b CpO for *Y. lipolitica* |
| SEQ ID NO: 14 | UGT2_6b amino acid |
| SEQ ID NO: 15 | UGT2_6b CpO for *S. cerevisiae* |
| SEQ ID NO: 16 | UGT2_6b CpO for *Y. lipolitica* |
| SEQ ID NO: 17 | UGT2_7b amino acid |
| SEQ ID NO: 18 | UGT2_7b CpO for *S. cerevisiae* |
| SEQ ID NO: 19 | UGT2_7b CpO for *Y. lipolitica* |
| SEQ ID NO: 20 | UGT2_8b amino acid |

TABLE 13-continued

Description of the sequence listing

| SEQ ID NO | Description |
|---|---|
| SEQ ID NO: 21 | UGT2_8b CpO for *S. cerevisiae* |
| SEQ ID NO: 22 | UGT2_9b amino acid |
| SEQ ID NO: 23 | UGT2_9b CpO for *S. cerevisiae* |
| SEQ ID NO: 24 | UGT2_9b CpO for *Y. lipolitica* |
| SEQ ID NO: 25 | UGT2_10b amino acid |
| SEQ ID NO: 26 | UGT2_10b CpO for *Y. lipolitica* |
| SEQ ID NO: 27 | UGT2_1a amino acid |
| SEQ ID NO: 28 | UGT2_1a CpO for *S. cerevisiae* |
| SEQ ID NO: 29 | UGT2_1a CpO for *Y. lipolitica* |
| SEQ ID NO: 30 | Eno2 promoter from *S. cerevisiae* |
| SEQ ID NO: 31 | ERG20 nucleic acid from *S. cerevisiae* |
| SEQ ID NO: 32 | Adh1 terminator from *S. cerevisiae* |
| SEQ ID NO: 33 | Fba1 promoter from *S. cerevisiae* |
| SEQ ID NO: 34 | tHMG nucleic acid from *S. cerevisiae* |
| SEQ ID NO: 35 | Adh2 terminator from *S. cerevisiae* |
| SEQ ID NO: 36 | Tef1 promoter from *S. cerevisiae* |
| SEQ ID NO: 37 | BTS1 nucleic acid from *S. cerevisiae* |
| SEQ ID NO: 38 | Gmp1 terminator from *S. cerevisiae* |
| SEQ ID NO: 39 | Pgk1 promoter from *S. cerevisiae* |
| SEQ ID NO: 40 | Kl prom 12 promoter |
| SEQ ID NO: 41 | trCPS from *S. rebaudiana* CpO for *S. cerevisiae* |
| SEQ ID NO: 42 | trKS from *S. rebaudiana* CpO for *S. cerevisiae* |
| SEQ ID NO: 43 | TAL1 terminator from *S. cerevisiae* |
| SEQ ID NO: 44 | KO from *Giberella fujikuroi* CpO for S. |
| SEQ ID NO: 45 | Tpi1 terminator from *S. cerevisiae* |
| SEQ ID NO: 46 | Ag lox_TEF1.pro nucleic acid construct |
| SEQ ID NO: 47 | KANMX ORF CpO for *S. cerevisiae* |
| SEQ ID NO: 48 | Ag Tef1_lox.ter nucleic acid construct |
| SEQ ID NO: 49 | KAH_4 from *Arabidopsis thaliana* CpO for *S. cerevisiae* |
| SEQ ID NO: 50 | Kl prom 6.pro promoter |
| SEQ ID NO: 51 | CPR_3 from *Arabidopsis thaliana* CpO for *S. cerevisiae* |
| SEQ ID NO: 52 | Pdc1 terminator from *S. cerevisiae* |
| SEQ ID NO: 53 | Kl prom3 promoter |
| SEQ ID NO: 54 | UGT1 from *S. rebaudiana* CpO for *S. cerevisiae* |
| SEQ ID NO: 55 | Tdh1 terminator from *S. cerevisiae* |
| SEQ ID NO: 56 | Kl prom 2 promoter |
| SEQ ID NO: 57 | UGT3 from *S. rebaudiana* CpO for *S. cerevisiae* |
| SEQ ID NO: 58 | UGT4 from *S. rebaudiana* CpO for *S. cerevisiae* |
| SEQ ID NO: 59 | Eno1 terminator from *S. cerevisiae* |
| SEQ ID NO: 60 | Eno1 promoter from *S. cerevisiae* |
| SEQ ID NO: 61 | Gap1T promoter from *K. lactis* |
| SEQ ID NO: 62 | PGM promoter from *Y. lipolitica* |
| SEQ ID NO: 63 | HSP promoter from *Y. lipolitica* |
| SEQ ID NO: 64 | HYPO promoter from *Y. lipolitica* |
| SEQ ID NO: 65 | ENO promoter from *Y. lipolitica* |
| SEQ ID NO: 66 | CWP promoter from *Y. lipolitica* |
| SEQ ID NO: 67 | TPI promoter from *Y. lipolitica* |
| SEQ ID NO: 68 | YP001 promoter from *Y. lipolitica* |
| SEQ ID NO: 69 | Xpr terminator from *Y. lipolitica* |
| SEQ ID NO: 70 | Cwp terminator from *Y. lipolitica* |
| SEQ ID NO: 71 | Gpd terminator from *Y. lipolitica* |
| SEQ ID NO: 72 | Pgm terminator from *Y. lipolitica* |
| SEQ ID NO: 73 | Pgk terminator from *Y. lipolitica* |
| SEQ ID NO: 74 | act1T terminator from *Y. lipolitica* |
| SEQ ID NO: 75 | tHMG CpO for *Y. lipolitica* |
| SEQ ID NO: 76 | GGS CpO for *Y. lipolitica* |
| SEQ ID NO: 77 | UGT1 CpO for *Y. lipolitica* |
| SEQ ID NO: 78 | UGT3 CpO for *Y. lipolitica* |
| SEQ ID NO: 79 | UGT4 CpO for *Y. lipolitica* |
| SEQ ID NO: 80 | tCPS from *S. rebaudiana* CpO for *Y. lipolitica* |
| SEQ ID NO: 81 | tKS from *S. rebaudiana* CpO for *Y. lipolitica* |
| SEQ ID NO: 82 | KAH_4 CpO for *Y. lipolitica* |
| SEQ ID NO: 83 | KO from *Gibberella fujikori* CpO for *Y. lipolitica* |
| SEQ ID NO: 84 | CPR_3CpO for *Y. lipolitica* |

The invention claimed is:

1. A recombinant host comprising a recombinant nucleic acid sequence encoding a polypeptide having at least 90% sequence identity to the amino acid sequence set forth in SEQ ID NO:25.

2. The recombinant host of claim 1 which is capable of producing a glycosylated diterpene.

3. The recombinant host of claim 1, further comprising one or more recombinant nucleotide sequence(s) encoding:
   a polypeptide having ent-copalyl pyrophosphate synthase activity;
   a polypeptide having ent-Kaurene synthase activity;
   a polypeptide having ent-Kaurene oxidase activity; and
   a polypeptide having kaurenoic acid 13-hydroxylase activity.

4. The recombinant host of claim 1, which comprises a recombinant nucleic acid sequence encoding a polypeptide having NADPH-cytochrome p450 reductase activity.

5. The recombinant host of claim 1 which comprises a recombinant nucleic acid sequence encoding one or more of:
   (i) a polypeptide having UGT74G1 (UGT3) activity;
   (ii) a polypeptide having UGT85C2 (UGT1) activity; and
   (iii) a polypeptide having UGT76G1 (UGT4) activity.

6. The recombinant host of claim 1 which comprises a recombinant nucleic acid sequence encoding an additional polypeptide having UGT2 activity.

7. The recombinant host of claim 1, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma*, or *Escherichia*.

8. The recombinant host of claim 7, wherein the recombinant host is a *Saccharomyces cerevisiae* cell, a *Yarrowia lipolytica* cell, a *Candida krusei* cell, an *Issatchenkia orientalis* or an *Escherichia coli* cell.

9. The recombinant host of claim 1, wherein the ability of the host to produce geranylgeranyl diphosphate (GGPP) is upregulated.

10. The recombinant host of claim 1, comprising one or more recombinant nucleic acid sequence(s) encoding hydroxymethylglutaryl-CoA reductase, farnesyl-pyrophosphate synthetase and geranylgeranyl diphosphate synthase.

11. The recombinant host of claim 1 which comprises a nucleic acid sequence encoding one or more of:
   a polypeptide having hydroxymethylglutaryl-CoA reductase activity;
   a polypeptide having farnesyl-pyrophosphate synthetase activity; and
   a polypeptide having geranylgeranyl diphosphate synthase activity.

12. A process for the preparation of a glycosylated diterpene which comprises fermenting the recombinant host of claim 2 in a suitable fermentation medium, and optionally recovering the glycosylated diterpene.

13. The process of claim 12 for the preparation of a glycosylated diterpene, wherein the process is carried out on an industrial scale.

14. A method for converting a first glycosylated diterpene into a second glycosylated diterpene, which method comprises:
   contacting said first glycosylated diterpene with the recombinant host of claim 1, a cell free extract derived from such a recombinant host or an enzyme preparation derived from either thereof;
   thereby to convert the first glycosylated diterpene into the second glycosylated diterpene.

15. The method of claim 14, wherein the second glycosylated diterpene is steviol-19-diside, steviolbioside, stevioside, RebE, RebD or 13-[(β-D-glucopyranosyl)oxy)kaur-16-en-18-oic acid 2-O-β-D-glucopyranosyl-β-D-glucopyranosyl ester.

16. The method of claim 15, wherein the first glycosylated diterpene is steviol-13-monoside, steviol-19-monoside, rubusoside, stevioside, rebaudioside A or 13-[(β-D-glucopyranosyl)oxy)kaur-16-en-18-oic acid 2-O-β-D-glucopyranosyl-β-D-glucopyranosyl ester and the second glycosylated diterpene is steviol-19-diside, steviolbioside, stevioside, RebE, RebD or 13-[(β-D-glucopyranosyl)oxy)kaur-16-en-18-oic acid 2-O-β-D-glucopyranosyl-β-D-glucopyranosyl ester.

17. A nucleic acid construct comprising a polynucleotide sequence encoding a polypeptide having at least 90% sequence identity with the amino acid sequence of SEQ ID NO:25.

18. The nucleic acid construct of claim 17 which is an expression vector, wherein the polynucleotide sequence is operably linked to at least one control sequence for the expression of the polynucleotide sequence in a host cell.

19. A method of producing the nucleic acid construct of claim 17, comprising:
   (a) cultivating a recombinant host cell comprising a recombinant nucleic acid sequence encoding a polypeptide having at least 90% sequence identity to the amino acid sequence set forth in SEQ ID NO:25 under conditions conducive to the production of the nucleic acid construct by the host cell, and optionally,
   (b) recovering the nucleic acid construct.

* * * * *